US008407010B2

(12) United States Patent
Hofstadler et al.

(10) Patent No.: US 8,407,010 B2
(45) Date of Patent: *Mar. 26, 2013

(54) METHODS FOR RAPID FORENSIC ANALYSIS OF MITOCHONDRIAL DNA

(75) Inventors: Steven A. Hofstadler, Oceanside, CA (US); Thomas A. Hall, Oceanside, CA (US); David J. Ecker, Encinitas, CA (US); Lawrence B. Blyn, Mission Viejo, CA (US); Mark W. Eshoo, Solana Beach, CA (US); Vivek Samant, Encinitas, CA (US); Neill White, Encinitas, CA (US)

(73) Assignee: Ibis Biosciences, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/049,949

(22) Filed: Mar. 17, 2008

(65) Prior Publication Data

US 2009/0125245 A1     May 14, 2009

Related U.S. Application Data

(63) Continuation of application No. 10/853,660, filed on May 25, 2004, now abandoned.

(51) Int. Cl.
*G06F 7/00* (2006.01)

(52) U.S. Cl. ............. 702/19; 702/20; 703/11; 703/12; 707/700; 435/6.1; 536/24.5

(58) Field of Classification Search .................. None
See application file for complete search history.

(56) References Cited

U.S. PATENT DOCUMENTS

| | | |
|---|---|---|
| 4,075,475 A | 2/1978 | Risby et al. |
| 4,683,195 A | 7/1987 | Mullis et al. |
| 4,683,202 A | 7/1987 | Mullis |
| 4,965,188 A | 10/1990 | Mullis et al. |
| 5,015,845 A | 5/1991 | Allen et al. |
| 5,072,115 A | 12/1991 | Zhou |
| 5,143,905 A | 9/1992 | Sivasubramanian et al. |
| 5,213,961 A | 5/1993 | Bunn et al. |
| 5,219,727 A | 6/1993 | Wang et al. |
| 5,288,611 A | 2/1994 | Kohne |
| 5,436,129 A | 7/1995 | Stapleton |
| 5,451,500 A | 9/1995 | Stapleton |
| 5,472,843 A | 12/1995 | Milliman |
| 5,476,774 A | 12/1995 | Wang et al. |
| 5,484,808 A | 1/1996 | Grinnell |
| 5,484,908 A | 1/1996 | Froehler et al. |
| 5,502,177 A | 3/1996 | Matteucci et al. |
| 5,503,980 A | 4/1996 | Cantor |
| 5,504,327 A | 4/1996 | Sproch et al. |
| 5,504,329 A | 4/1996 | Mann et al. |
| 5,523,217 A | 6/1996 | Lupski et al. |
| 5,527,669 A | 6/1996 | Resnick et al. |
| 5,527,675 A | 6/1996 | Coull et al. |
| 5,527,875 A | 6/1996 | Yokoyama et al. |
| 5,547,835 A | 8/1996 | Koster |
| 5,567,587 A | 10/1996 | Kohne |
| 5,576,204 A | 11/1996 | Blanco et al. |
| 5,580,733 A | 12/1996 | Levis et al. |
| 5,605,798 A | 2/1997 | Koster |
| 5,608,217 A | 3/1997 | Franzen et al. |
| 5,612,179 A | 3/1997 | Simons |
| 5,622,824 A | 4/1997 | Koster |
| 5,625,184 A | 4/1997 | Vestal et al. |
| 5,639,606 A | 6/1997 | Willey |
| 5,641,632 A | 6/1997 | Kohne |
| 5,645,985 A | 7/1997 | Froehler et al. |
| 5,645,994 A | 7/1997 | Huang |
| 5,683,869 A | 11/1997 | Ramsay Shaw et al. |
| 5,686,242 A | 11/1997 | Bruice et al. |
| 5,691,141 A | 11/1997 | Koster |
| 5,700,642 A | 12/1997 | Monforte et al. |
| 5,702,895 A | 12/1997 | Matsunaga et al. |
| 5,705,332 A | 1/1998 | Roll |
| 5,707,802 A | 1/1998 | Sandhu et al. |
| 5,712,125 A | 1/1998 | Uhlen |
| 5,716,825 A | 2/1998 | Hancock et al. |
| 5,727,202 A | 3/1998 | Kucala |
| 5,745,751 A | 4/1998 | Nelson et al. |
| 5,747,246 A | 5/1998 | Pannetier et al. |
| 5,747,251 A | 5/1998 | Carson et al. |
| 5,753,467 A | 5/1998 | Jensen et al. |
| 5,753,489 A | 5/1998 | Kistner et al. |
| 5,759,771 A | 6/1998 | Tilanus |
| 5,763,169 A | 6/1998 | Sandhu et al. |
| 5,763,588 A | 6/1998 | Matteucci et al. |
| 5,770,367 A | 6/1998 | Southern et al. |
| 5,777,324 A | 7/1998 | Hillenkamp |
| 5,814,442 A | 9/1998 | Natarajan et al. |
| 5,822,824 A | 10/1998 | Dion |
| 5,828,062 A | 10/1998 | Jarrell et al. |
| 5,830,653 A | 11/1998 | Froehler et al. |
| 5,830,655 A | 11/1998 | Monforte et al. |
| 5,830,853 A | 11/1998 | Backstrom et al. |
| 5,832,489 A | 11/1998 | Kucala |
| 5,834,255 A | 11/1998 | Van Gemen et al. |
| 5,845,174 A | 12/1998 | Yasui et al. |
| 5,849,492 A | 12/1998 | Rogan |

(Continued)

FOREIGN PATENT DOCUMENTS

| | | |
|---|---|---|
| CN | 1202204 A | 12/1998 |
| DE | 19732086 A1 | 1/1999 |

(Continued)

OTHER PUBLICATIONS

Torroni et al. 1996 Genetics 144: 1835-1850.*

(Continued)

*Primary Examiner* — Mary Zeman
(74) *Attorney, Agent, or Firm* — Casimir Jones S.C.; Christopher C. Sappenfield

(57) ABSTRACT

The present invention provides methods for rapid forensic analysis of mitochondrial DNA by amplification of a segment of mitochondrial DNA containing restriction sites, digesting the mitochondrial DNA segments with restriction enzymes, determining the molecular masses of the restriction fragments and comparing the molecular masses with the molecular masses of theoretical restriction digests of known mitochondrial DNA sequences stored in a database.

66 Claims, 10 Drawing Sheets

U.S. PATENT DOCUMENTS

| | | |
|---|---|---|
| 5,849,497 A | 12/1998 | Steinman |
| 5,849,901 A | 12/1998 | Mabilat et al. |
| 5,851,765 A | 12/1998 | Koster |
| 5,856,174 A | 1/1999 | Lipshutz et al. |
| 5,864,137 A | 1/1999 | Becker et al. |
| 5,866,429 A | 2/1999 | Bloch |
| 5,869,242 A | 2/1999 | Kamb |
| 5,871,697 A | 2/1999 | Rothberg et al. |
| 5,872,003 A | 2/1999 | Koster |
| 5,876,936 A | 3/1999 | Ju |
| 5,876,938 A | 3/1999 | Stolowitz et al. |
| 5,885,775 A | 3/1999 | Haff et al. |
| 5,900,481 A | 5/1999 | Lough et al. |
| 5,928,905 A | 7/1999 | Stemmer et al. |
| 5,928,906 A | 7/1999 | Koster et al. |
| 5,965,363 A | 10/1999 | Monforte et al. |
| 5,965,383 A | 10/1999 | Vogel et al. |
| 5,972,693 A | 10/1999 | Rothberg et al. |
| 5,976,798 A | 11/1999 | Parker et al. |
| 5,981,176 A | 11/1999 | Wallace |
| 5,981,178 A | 11/1999 | Tsui et al. |
| 5,981,190 A | 11/1999 | Israel |
| 5,994,066 A | 11/1999 | Bergeron et al. |
| 6,001,564 A | 12/1999 | Bergeron et al. |
| 6,001,584 A | 12/1999 | Karin et al. |
| 6,005,096 A | 12/1999 | Matteucci et al. |
| 6,007,690 A | 12/1999 | Nelson et al. |
| 6,007,992 A | 12/1999 | Lin et al. |
| 6,015,666 A | 1/2000 | Springer et al. |
| 6,018,713 A | 1/2000 | Coli et al. |
| 6,024,925 A | 2/2000 | Little et al. |
| 6,028,183 A | 2/2000 | Lin et al. |
| 6,043,031 A | 3/2000 | Koster et al. |
| 6,046,005 A | 4/2000 | Ju et al. |
| 6,051,378 A | 4/2000 | Monforte et al. |
| 6,054,278 A | 4/2000 | Dodge et al. |
| 6,055,487 A | 4/2000 | Margery et al. |
| 6,060,246 A | 5/2000 | Summerton et al. |
| 6,061,686 A | 5/2000 | Gauvin et al. |
| 6,063,031 A | 5/2000 | Cundari et al. |
| 6,074,823 A | 6/2000 | Koster |
| 6,074,831 A | 6/2000 | Yakhini et al. |
| 6,090,558 A | 7/2000 | Butler et al. |
| 6,104,028 A | 8/2000 | Hunter et al. |
| 6,110,710 A | 8/2000 | Smith et al. |
| 6,111,251 A | 8/2000 | Hillenkamp |
| 6,133,436 A | 10/2000 | Koster et al. |
| 6,140,053 A | 10/2000 | Koster |
| 6,146,144 A | 11/2000 | Fowler et al. |
| 6,146,854 A | 11/2000 | Koster et al. |
| 6,153,389 A | 11/2000 | Haarer et al. |
| 6,159,681 A | 12/2000 | Zebala |
| 6,180,339 B1 | 1/2001 | Sandhu et al. |
| 6,180,372 B1 | 1/2001 | Franzen |
| 6,187,842 B1 | 2/2001 | Kobayashi et al. |
| 6,194,144 B1 | 2/2001 | Koster |
| 6,197,498 B1 | 3/2001 | Koster |
| 6,214,555 B1 | 4/2001 | Leushner et al. |
| 6,218,118 B1 | 4/2001 | Sampson et al. |
| 6,221,587 B1 | 4/2001 | Ecker et al. |
| 6,221,598 B1 | 4/2001 | Schumm et al. |
| 6,221,601 B1 | 4/2001 | Koster et al. |
| 6,221,605 B1 | 4/2001 | Koster |
| 6,225,450 B1 | 5/2001 | Koster |
| 6,235,476 B1 | 5/2001 | Bergmann et al. |
| 6,235,478 B1 | 5/2001 | Koster |
| 6,235,480 B1 | 5/2001 | Shultz et al. |
| 6,238,871 B1 | 5/2001 | Koster |
| 6,238,927 B1 | 5/2001 | Abrams et al. |
| 6,239,159 B1 | 5/2001 | Brown et al. |
| 6,258,538 B1 | 7/2001 | Koster et al. |
| 6,261,769 B1 | 7/2001 | Everett et al. |
| 6,265,716 B1 | 7/2001 | Hunter et al. |
| 6,265,718 B1 | 7/2001 | Park et al. |
| 6,266,131 B1 | 7/2001 | Hamada et al. |
| 6,266,144 B1 | 7/2001 | Li |
| 6,268,129 B1 | 7/2001 | Gut et al. |
| 6,268,131 B1 | 7/2001 | Kang et al. |
| 6,268,144 B1 | 7/2001 | Koster |
| 6,268,146 B1 | 7/2001 | Shultz et al. |
| 6,270,973 B1 | 8/2001 | Lewis et al. |
| 6,270,974 B1 | 8/2001 | Shultz et al. |
| 6,274,726 B1 | 8/2001 | Laugharn, Jr. et al. |
| 6,277,573 B1 | 8/2001 | Koster |
| 6,277,578 B1 | 8/2001 | Shultz et al. |
| 6,277,634 B1 | 8/2001 | McCall et al. |
| 6,300,076 B1 | 10/2001 | Koster |
| 6,303,297 B1 | 10/2001 | Lincoln et al. |
| 6,312,893 B1 | 11/2001 | Van Ness et al. |
| 6,312,902 B1 | 11/2001 | Shultz et al. |
| 6,322,970 B1 | 11/2001 | Little et al. |
| 6,361,940 B1 | 3/2002 | Van Ness et al. |
| 6,372,424 B1 | 4/2002 | Brow et al. |
| 6,389,428 B1 | 5/2002 | Rigault et al. |
| 6,391,551 B1 | 5/2002 | Shultz et al. |
| 6,393,367 B1 | 5/2002 | Tang et al. |
| 6,419,932 B1 | 7/2002 | Dale |
| 6,423,966 B2 | 7/2002 | Hillenkamp et al. |
| 6,428,955 B1 | 8/2002 | Koster et al. |
| 6,428,956 B1 | 8/2002 | Crooke et al. |
| 6,432,651 B1 | 8/2002 | Hughes et al. |
| 6,436,635 B1 | 8/2002 | Fu et al. |
| 6,436,640 B1 | 8/2002 | Simmons et al. |
| 6,453,244 B1 | 9/2002 | Oefner |
| 6,458,533 B1 | 10/2002 | Felder et al. |
| 6,468,743 B1 | 10/2002 | Romick et al. |
| 6,468,748 B1 | 10/2002 | Monforte et al. |
| 6,475,143 B2 | 11/2002 | Iliff |
| 6,475,736 B1 | 11/2002 | Stanton, Jr. |
| 6,475,738 B2 | 11/2002 | Shuber et al. |
| 6,479,239 B1 | 11/2002 | Anderson et al. |
| 6,500,621 B2 | 12/2002 | Koster |
| 6,553,317 B1 | 4/2003 | Lincoln et al. |
| 6,558,902 B1 | 5/2003 | Hillenkamp |
| 6,563,025 B1 | 5/2003 | Song et al. |
| 6,566,055 B1 | 5/2003 | Monforte et al. |
| 6,568,055 B1 | 5/2003 | Tang et al. |
| 6,582,916 B1 | 6/2003 | Schmidt et al. |
| 6,586,584 B2 | 7/2003 | McMillian et al. |
| 6,589,485 B2 | 7/2003 | Koster |
| 6,602,662 B1 | 8/2003 | Koster et al. |
| 6,605,433 B1 | 8/2003 | Fliss et al. |
| 6,610,492 B1 | 8/2003 | Stanton, Jr. et al. |
| 6,613,509 B1 | 9/2003 | Chen |
| 6,613,520 B2 | 9/2003 | Ashby |
| 6,623,928 B2 | 9/2003 | Van Ness et al. |
| 6,638,714 B1 | 10/2003 | Linnen et al. |
| 6,680,476 B1 | 1/2004 | Hidalgo et al. |
| 6,682,889 B1 | 1/2004 | Wang et al. |
| 6,705,530 B2 | 3/2004 | Kiekhaefer |
| 6,706,530 B2 | 3/2004 | Hillenkamp |
| 6,783,939 B2 | 8/2004 | Olmsted et al. |
| 6,800,289 B2 | 10/2004 | Nagata et al. |
| 6,813,615 B1 | 11/2004 | Colasanti et al. |
| 6,836,742 B2 | 12/2004 | Brekenfeld |
| 6,852,487 B1 | 2/2005 | Barany et al. |
| 6,856,914 B1 | 2/2005 | Pelech |
| 6,875,593 B2 | 4/2005 | Froehler et al. |
| 6,906,316 B2 | 6/2005 | Sugiyama et al. |
| 6,906,319 B2 | 6/2005 | Hoyes |
| 6,914,137 B2 | 7/2005 | Baker |
| 6,977,148 B2 | 12/2005 | Dean et al. |
| 6,994,962 B1 | 2/2006 | Thilly |
| 7,022,835 B1 | 4/2006 | Rauth et al. |
| 7,024,370 B2 | 4/2006 | Epler et al. |
| 7,108,974 B2 | 9/2006 | Ecker et al. |
| 7,198,893 B1 | 4/2007 | Köster et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 7,285,422 B1 | 10/2007 | Little et al. |
| 7,312,036 B2 | 12/2007 | Sampath et al. |
| 7,321,828 B2 | 1/2008 | Cowsert et al. |
| 7,349,808 B1 | 3/2008 | Kreiswirth et al. |
| 7,390,458 B2 | 6/2008 | Burow et al. |
| 7,419,787 B2 | 9/2008 | Köster |
| 7,501,251 B2 | 3/2009 | Köster et al. |

| Patent Number | Date | Inventor |
|---|---|---|
| 7,666,588 B2 | 2/2010 | Ecker et al. |
| 7,718,354 B2 | 5/2010 | Ecker et al. |
| 7,741,036 B2 | 6/2010 | Ecker et al. |
| 7,781,162 B2 | 8/2010 | Ecker et al. |
| 7,956,175 B2 | 6/2011 | Sampath et al. |
| 8,017,322 B2 | 9/2011 | Ecker et al. |
| 8,017,358 B2 | 9/2011 | Ecker et al. |
| 8,017,743 B2 | 9/2011 | Ecker et al. |
| 8,026,084 B2 | 9/2011 | Ecker et al. |
| 8,046,171 B2 | 10/2011 | Ecker et al. |
| 8,057,993 B2 | 11/2011 | Ecker et al. |
| 8,071,309 B2 | 12/2011 | Ecker et al. |
| 8,073,627 B2 | 12/2011 | Ecker et al. |
| 8,158,354 B2 | 4/2012 | Hofstadler et al. |
| 2001/0039263 A1 | 11/2001 | Matthes et al. |
| 2002/0006611 A1 | 1/2002 | Portugal et al. |
| 2002/0028923 A1 | 3/2002 | Cowsert et al. |
| 2002/0042112 A1 | 4/2002 | Koster et al. |
| 2002/0042506 A1 | 4/2002 | Kristyanne et al. |
| 2002/0045178 A1 | 4/2002 | Cantor et al. |
| 2002/0055101 A1 | 5/2002 | Bergeron et al. |
| 2002/0090320 A1 | 7/2002 | Burow et al. |
| 2002/0120408 A1 | 8/2002 | Kreiswirth et al. |
| 2002/0137057 A1 | 9/2002 | Wold et al. |
| 2002/0138210 A1 | 9/2002 | Wilkes et al. |
| 2002/0150903 A1 | 10/2002 | Koster |
| 2002/0150927 A1 | 10/2002 | Matray et al. |
| 2002/0168630 A1 | 11/2002 | Fleming et al. |
| 2002/0187490 A1 | 12/2002 | Tiedje et al. |
| 2003/0017487 A1 | 1/2003 | Xue et al. |
| 2003/0027135 A1 | 2/2003 | Ecker et al. |
| 2003/0039976 A1 | 2/2003 | Haff |
| 2003/0050470 A1 | 3/2003 | An et al. |
| 2003/0064483 A1 | 4/2003 | Shaw et al. |
| 2003/0073112 A1 | 4/2003 | Zhang et al. |
| 2003/0082539 A1 | 5/2003 | Ecker et al. |
| 2003/0084483 A1 | 5/2003 | Simpson et al. |
| 2003/0101172 A1 | 5/2003 | De La Huerga |
| 2003/0104410 A1 | 6/2003 | Mittmann |
| 2003/0104699 A1 | 6/2003 | Minamihaba et al. |
| 2003/0113738 A1 | 6/2003 | Liu et al. |
| 2003/0113745 A1 | 6/2003 | Monforte et al. |
| 2003/0119018 A1 | 6/2003 | Omura et al. |
| 2003/0124556 A1 | 7/2003 | Ecker et al. |
| 2003/0125192 A1 | 7/2003 | Moon |
| 2003/0129589 A1 | 7/2003 | Koster et al. |
| 2003/0134312 A1 | 7/2003 | Burgoyne |
| 2003/0148281 A1 | 8/2003 | Glucksmann |
| 2003/0148284 A1 | 8/2003 | Vision et al. |
| 2003/0167133 A1 | 9/2003 | Ecker et al. |
| 2003/0167134 A1 | 9/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0175729 A1 | 9/2003 | Van Eijk et al. |
| 2003/0186247 A1 | 10/2003 | Smarason et al. |
| 2003/0187588 A1 | 10/2003 | Ecker et al. |
| 2003/0187593 A1 | 10/2003 | Ecker et al. |
| 2003/0187615 A1 | 10/2003 | Epler et al. |
| 2003/0190605 A1 | 10/2003 | Ecker et al. |
| 2003/0190635 A1 | 10/2003 | McSwiggen |
| 2003/0194699 A1 | 10/2003 | Lewis et al. |
| 2003/0203398 A1 | 10/2003 | Bramucci et al. |
| 2003/0220844 A1 | 11/2003 | Marnellos et al. |
| 2003/0224377 A1 | 12/2003 | Wengel et al. |
| 2003/0225529 A1 | 12/2003 | Ecker et al. |
| 2003/0228571 A1 | 12/2003 | Ecker et al. |
| 2003/0228597 A1 | 12/2003 | Cowsert et al. |
| 2003/0228613 A1 | 12/2003 | Bornarth et al. |
| 2004/0005555 A1 | 1/2004 | Rothman et al. |
| 2004/0006611 A1 | 1/2004 | Yi |
| 2004/0013703 A1 | 1/2004 | Ralph et al. |
| 2004/0014957 A1 | 1/2004 | Eldrup et al. |
| 2004/0023207 A1 | 2/2004 | Polansky |
| 2004/0023209 A1 | 2/2004 | Jonasson |
| 2004/0029129 A1 | 2/2004 | Wang et al. |
| 2004/0038206 A1 | 2/2004 | Zhang et al. |
| 2004/0038208 A1 | 2/2004 | Fisher et al. |
| 2004/0038234 A1 | 2/2004 | Gut et al. |
| 2004/0038385 A1 | 2/2004 | Langlois et al. |
| 2004/0081993 A1 | 4/2004 | Cantor et al. |
| 2004/0101809 A1 | 5/2004 | Weiss et al. |
| 2004/0110169 A1 | 6/2004 | Ecker et al. |
| 2004/0111221 A1 | 6/2004 | Beattie et al. |
| 2004/0117129 A1 | 6/2004 | Ecker et al. |
| 2004/0117354 A1 | 6/2004 | Azzaro et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0126764 A1 | 7/2004 | Lasken et al. |
| 2004/0137013 A1 | 7/2004 | Katinger et al. |
| 2004/0161770 A1 | 8/2004 | Ecker et al. |
| 2004/0180328 A1 | 9/2004 | Ecker et al. |
| 2004/0185438 A1 | 9/2004 | Ecker |
| 2004/0191769 A1 | 9/2004 | Marino et al. |
| 2004/0202997 A1 | 10/2004 | Ecker et al. |
| 2004/0209260 A1 | 10/2004 | Ecker et al. |
| 2004/0219517 A1 | 11/2004 | Ecker et al. |
| 2004/0253583 A1 | 12/2004 | Ecker et al. |
| 2004/0253619 A1 | 12/2004 | Ecker et al. |
| 2005/0009053 A1 | 1/2005 | Boecker et al. |
| 2005/0026147 A1 | 2/2005 | Walker et al. |
| 2005/0026641 A1 | 2/2005 | Hokao |
| 2005/0027459 A1 | 2/2005 | Ecker et al. |
| 2005/0065813 A1 | 3/2005 | Mishelevich et al. |
| 2005/0130196 A1 | 6/2005 | Hofstadler et al. |
| 2005/0130216 A1 | 6/2005 | Becker et al. |
| 2005/0142584 A1 | 6/2005 | Willson et al. |
| 2005/0250125 A1 | 11/2005 | Novakoff |
| 2005/0266397 A1 | 12/2005 | Ecker et al. |
| 2005/0266411 A1 | 12/2005 | Hofstadler et al. |
| 2006/0020391 A1 | 1/2006 | Kreiswirth et al. |
| 2006/0057605 A1 | 3/2006 | Sampath et al. |
| 2006/0121520 A1 | 6/2006 | Ecker et al. |
| 2006/0172330 A1 | 8/2006 | Osborn et al. |
| 2006/0205040 A1 | 9/2006 | Sampath |
| 2006/0240412 A1 | 10/2006 | Hall et al. |
| 2006/0259249 A1 | 11/2006 | Sampath et al. |
| 2006/0275788 A1 | 12/2006 | Ecker et al. |
| 2007/0048735 A1 | 3/2007 | Ecker et al. |
| 2007/0218467 A1 | 9/2007 | Ecker et al. |
| 2008/0160512 A1 | 7/2008 | Ecker et al. |
| 2008/0311558 A1 | 12/2008 | Ecker et al. |
| 2009/0004643 A1 | 1/2009 | Ecker et al. |
| 2009/0023150 A1 | 1/2009 | Koster et al. |
| 2009/0042203 A1 | 2/2009 | Koster |
| 2009/0092977 A1 | 4/2009 | Koster |
| 2009/0148829 A1 | 6/2009 | Ecker et al. |
| 2009/0148836 A1 | 6/2009 | Ecker et al. |
| 2009/0148837 A1 | 6/2009 | Ecker et al. |
| 2009/0182511 A1 | 7/2009 | Ecker et al. |
| 2009/0239224 A1 | 9/2009 | Ecker et al. |
| 2009/0280471 A1 | 11/2009 | Ecker et al. |
| 2010/0070194 A1 | 3/2010 | Ecker et al. |
| 2010/0145626 A1 | 6/2010 | Ecker et al. |
| 2010/0184035 A1 | 7/2010 | Hall et al. |
| 2011/0172925 A1 | 7/2011 | Ecker et al. |

FOREIGN PATENT DOCUMENTS

| | | |
|---|---|---|
| DE | 19802905 A1 | 7/1999 |
| DE | 19824280 A1 | 12/1999 |
| DE | 19852167 A1 | 5/2000 |
| DE | 19943374 A1 | 3/2001 |
| DE | 10132147 B4 | 2/2003 |
| EP | 281390 A2 | 9/1988 |
| EP | 0620862 A1 | 10/1994 |
| EP | 633321 A1 | 1/1995 |
| EP | 620862 B1 | 4/1998 |
| EP | 1035219 A1 | 9/2000 |

| | | | | | | |
|---|---|---|---|---|---|---|
| EP | 1138782 | A2 | 10/2001 | WO | WO0127857 A2 | 4/2001 |
| EP | 1234888 | A2 | 8/2002 | WO | WO0132930 A1 | 5/2001 |
| EP | 1308506 | A1 | 5/2003 | WO | WO0140497 A2 | 6/2001 |
| EP | 1310571 | A2 | 5/2003 | WO | WO0146404 A1 | 6/2001 |
| EP | 1333101 | A1 | 8/2003 | WO | WO0151661 A2 | 7/2001 |
| EP | 1364064 | A2 | 11/2003 | WO | WO0151662 A1 | 7/2001 |
| EP | 1365031 | A1 | 11/2003 | WO | WO0157263 A1 | 8/2001 |
| EP | 1234888 | A3 | 1/2004 | WO | WO0157518 A2 | 8/2001 |
| EP | 1748072 | A1 | 1/2007 | WO | WO0173119 A2 | 10/2001 |
| FR | 2811321 | A1 | 1/2002 | WO | WO0173199 A1 | 10/2001 |
| GB | 2325002 | A | 11/1998 | WO | WO0177392 A2 | 10/2001 |
| GB | 2339905 | A | 2/2000 | WO | WO0196388 A2 | 12/2001 |
| JP | 5276999 | A2 | 10/1993 | WO | WO0202811 A2 | 1/2002 |
| JP | 11137259 | A | 5/1999 | WO | WO0210186 A1 | 2/2002 |
| JP | 24024206 | A2 | 1/2004 | WO | WO0210444 A1 | 2/2002 |
| JP | 2004000200 | A2 | 1/2004 | WO | WO0218641 A2 | 3/2002 |
| JP | 24201641 | A2 | 7/2004 | WO | WO0221108 A2 | 3/2002 |
| JP | 24201679 | A2 | 7/2004 | WO | WO0222873 A1 | 3/2002 |
| WO | WO8803957 A1 | | 6/1988 | WO | WO0224876 A2 | 3/2002 |
| WO | WO9015157 A1 | | 12/1990 | WO | WO0250307 A1 | 6/2002 |
| WO | WO9205182 A1 | | 4/1992 | WO | WO02057491 A2 | 7/2002 |
| WO | WO9208117 A1 | | 5/1992 | WO | WO02070664 A2 | 9/2002 |
| WO | WO9209703 A1 | | 6/1992 | WO | WO02070728 A2 | 9/2002 |
| WO | WO9219774 A1 | | 11/1992 | WO | WO02070737 A2 | 9/2002 |
| WO | WO9303186 A1 | | 2/1993 | WO | WO02077278 A2 | 10/2002 |
| WO | WO9305182 A1 | | 3/1993 | WO | WO02099034 A2 | 12/2002 |
| WO | WO9308297 A1 | | 4/1993 | WO | WO02099095 A2 | 12/2002 |
| WO | WO9416101 A2 | | 7/1994 | WO | WO02099129 A2 | 12/2002 |
| WO | WO9419490 A1 | | 9/1994 | WO | WO02099130 A2 | 12/2002 |
| WO | WO9421822 A1 | | 9/1994 | WO | WO03001976 A2 | 1/2003 |
| WO | WO9504161 A1 | | 2/1995 | WO | WO03002750 A2 | 1/2003 |
| WO | WO9511996 A1 | | 5/1995 | WO | WO03008636 A2 | 1/2003 |
| WO | WO9513395 A1 | | 5/1995 | WO | WO03012058 A2 | 2/2003 |
| WO | WO9513396 A2 | | 5/1995 | WO | WO03012074 A2 | 2/2003 |
| WO | WO9531997 A1 | | 11/1995 | WO | WO03014382 A2 | 2/2003 |
| WO | WO9606187 A1 | | 2/1996 | WO | WO03016546 A1 | 2/2003 |
| WO | WO9616186 A1 | | 5/1996 | WO | WO03018636 A2 | 3/2003 |
| WO | WO9629431 A2 | | 9/1996 | WO | WO03020890 A2 | 3/2003 |
| WO | WO9632504 A2 | | 10/1996 | WO | WO03033732 A2 | 4/2003 |
| WO | WO9635450 A1 | | 11/1996 | WO | WO03054162 A2 | 7/2003 |
| WO | WO9637630 A1 | | 11/1996 | WO | WO03054755 A2 | 7/2003 |
| WO | WO9733000 A1 | | 9/1997 | WO | WO03060163 A2 | 7/2003 |
| WO | WO9734909 A1 | | 9/1997 | WO | WO03075955 A1 | 9/2003 |
| WO | WO9737041 A2 | | 10/1997 | WO | WO03088979 A2 | 10/2003 |
| WO | WO9747766 A1 | | 12/1997 | WO | WO03093506 A2 | 11/2003 |
| WO | WO9803684 A1 | | 1/1998 | WO | WO03097869 A2 | 11/2003 |
| WO | WO9812355 A1 | | 3/1998 | WO | WO03100035 A2 | 12/2003 |
| WO | WO9814616 A1 | | 4/1998 | WO | WO03100068 A1 | 12/2003 |
| WO | WO9815652 A1 | | 4/1998 | WO | WO03102191 A1 | 12/2003 |
| WO | WO9820020 A2 | | 5/1998 | WO | WO03104410 A2 | 12/2003 |
| WO | WO9820157 A2 | | 5/1998 | WO | WO03106635 A2 | 12/2003 |
| WO | WO9820166 A2 | | 5/1998 | WO | WO2004003511 A2 | 1/2004 |
| WO | WO9826095 A1 | | 6/1998 | WO | WO2004009849 A1 | 1/2004 |
| WO | WO9831830 A1 | | 7/1998 | WO | WO2004011651 A1 | 2/2004 |
| WO | WO9835057 A1 | | 8/1998 | WO | WO2004013357 A2 | 2/2004 |
| WO | WO9840520 A1 | | 9/1998 | WO | WO2004040013 A1 | 5/2004 |
| WO | WO9854571 A1 | | 12/1998 | WO | WO2004044123 A2 | 5/2004 |
| WO | WO9854751 A1 | | 12/1998 | WO | WO2004044247 A2 | 5/2004 |
| WO | WO9905319 A2 | | 2/1999 | WO | WO2004052175 A2 | 6/2004 |
| WO | WO9912040 A2 | | 3/1999 | WO | WO2004052175 A3 | 6/2004 |
| WO | WO9913104 A1 | | 3/1999 | WO | WO2004053076 A2 | 6/2004 |
| WO | WO9914375 A2 | | 3/1999 | WO | WO2004053141 A2 | 6/2004 |
| WO | WO9929898 A2 | | 6/1999 | WO | WO2004053164 A1 | 6/2004 |
| WO | WO9931278 A1 | | 6/1999 | WO | WO2004060278 A2 | 7/2004 |
| WO | WO9957318 A2 | | 11/1999 | WO | WO2004070001 A2 | 8/2004 |
| WO | WO9958713 A2 | | 11/1999 | WO | WO2004072230 A2 | 8/2004 |
| WO | WO9960183 A1 | | 11/1999 | WO | WO2004072231 A2 | 8/2004 |
| WO | WO0032750 A1 | | 6/2000 | WO | WO2004101809 A2 | 11/2004 |
| WO | WO0038636 A1 | | 7/2000 | WO | WO2005003384 A1 | 1/2005 |
| WO | WO0063362 A1 | | 10/2000 | WO | WO2005009202 A2 | 2/2005 |
| WO | WO0066762 A2 | | 11/2000 | WO | WO2005012572 A1 | 2/2005 |
| WO | WO0066789 A2 | | 11/2000 | WO | WO2005024046 A2 | 3/2005 |
| WO | WO0077260 A1 | | 12/2000 | WO | WO2005036369 A2 | 4/2005 |
| WO | WO0100828 A2 | | 1/2001 | WO | WO2005053141 A1 | 6/2005 |
| WO | WO0107648 A1 | | 2/2001 | WO | WO2005054454 A1 | 6/2005 |
| WO | WO0112853 A1 | | 2/2001 | WO | WO2005075686 A1 | 8/2005 |
| WO | WO0120018 A2 | | 3/2001 | WO | WO2005086634 A2 | 9/2005 |
| WO | WO0123604 A2 | | 4/2001 | WO | WO2005091971 A2 | 10/2005 |
| WO | WO0123608 A2 | | 4/2001 | WO | WO2005098047 A2 | 10/2005 |

| WO | WO2005116263 | A2 | 12/2005 |
| WO | WO2006089762 | A1 | 8/2006 |
| WO | WO2006094238 | A2 | 9/2006 |
| WO | WO2006116127 | A2 | 11/2006 |
| WO | WO2006135400 | A2 | 12/2006 |
| WO | WO2007014045 | A2 | 2/2007 |
| WO | WO2007086904 | A2 | 8/2007 |
| WO | WO2008104002 | A2 | 8/2008 |
| WO | WO2008118809 | A1 | 10/2008 |

OTHER PUBLICATIONS

Alves-Silva et al. Am J Hum Genet. 67 :444-461. 2000.*
Stoneking et al. Am J Hum Genet. 48:370-382, 1991.*
Aaserud et al. J Am Soc Mass Spectrom 1996; 7, 1266-1269.*
Alba M.M., et al., "VIDA: A Virus Database System for the Organization of Animal Virus Genome Open Reading Frames," Nucleic Acids Research, 2001, vol. 29 (1), pp. 133-136.
BLAST Search results, Mar. 7, 2006.
Butler J.M., et al., High Throughput Genotyping of Forensic STRs and SNPs using Time-of-Flight Mass Spectrometry, 9th International Symposium on Human Identification, 1998, Orlando FL.
Certificate of Correction mailed Jan. 6, 2009 for U.S. Appl. No. 10/660,996, filed Sep. 12, 2003.
Certificate of Correction mailed Dec. 12, 2006 for U.S. Appl. No. 10/156,608, filed May 24, 2002.
Certificate of Correction mailed Jul. 17, 2007 for U.S. Appl. No. 09/891,793, filed Jun. 26, 2001.
Co-pending U.S. Appl. No. 10/318,463, filed Dec. 13, 2002.
Co-pending U.S. Appl. No. 10/323,186, filed Dec. 18, 2002.
Co-pending U.S. Appl. No. 10/323,187, filed Dec. 18, 2002.
Co-pending U.S. Appl. No. 10/324,721, filed Dec. 18, 2002.
Co-pending U.S. Appl. No. 10/521,662, filed Jul. 21, 2003.
Co-pending U.S. Appl. No. 10/754,415, flied Jan. 9, 2004.
Co-pending U.S. Appl. No. 10/807,019, filed Mar. 23, 2004.
Co-pending U.S. Appl. No, 10/845,052, filed May 12, 2004.
Co-pending U.S. Appl. No. 10/964,571, filed Oct. 12, 2004.
Co-pending U.S. Appl. No. 11/209,439, flied Aug. 23, 2005.
Co-pending U.S. Appl. No. 11/233,630, filed Sep. 21, 2005.
Co-pending U.S. Appl. No. 11/674,538, filed Feb. 13, 2007.
Co-pending U.S. Appl. No. 11/682,259, filed Mar. 5, 2007.
Co-pending U.S. Appl. No. 11/929,910, flied Oct. 30, 2007.
Co-pending U.S. Appl. No. 11/930,741, filed Oct. 31, 2007.
Co-pending U.S. Appl. No. 90/010,209, filed Jun. 27, 2008.
Co-pending U.S. Appl. No. 90/010,210, filed Jun. 27, 2008.
Co-pending U.S. Appl. No. 90/010,447, flied Apr. 9, 2009.
Co-pending U.S. Appl. No. 90/010,448, filed Apr. 9, 2009.
Co-pending U.S. Appl. No. 60/639,068, filed Dec. 22, 2004.
Co-pending U.S. Appl. No. 60/648,188, filed Jan. 28, 2005.
Co-pending U.S. Appl. No. 60/369,405, filed Apr. 1, 2002.
Co-pending U.S. Appl. No. 60/397,365, filed Jul. 19, 2002.
Co-pending U.S. Appl. No. 60/431,319.
Co-pending U.S. Appl. No. 60/443,443, filed Jan. 29, 2003.
Co-pending U.S. Appl. No. 60/443,788.
Co-pending U.S. Appl. No. 60/447,529, filed Feb. 14, 2003.
Co-pending U.S. Appl. No. 60/453,607, filed Mar. 10, 2003.
Co-pending U.S. Appl. No. 60/461,494.
Co-pending U.S. Appl. No. 60/470,175, filed May 12, 2003.
Co-pending U.S. Appl. No. 60/501,926, filed Sep. 11, 2003.
Co-pending U.S. Appl. No. 60/509,911.
Co-pending U.S. Appl. No. 60/604,329, filed Aug. 24, 2004.
Co-pending U.S. Appl. No. 60/615,387.
Co-pending U.S. Appl. No. 60/701,404, filed Jul. 21, 2005.
Co-pending U.S. Appl. No. 60/705,631, filed Aug. 3, 2005.
Co-pending U.S. Appl. No. 60/720,843, filed Sep. 27, 2005.
Co-pending U.S. Appl. No. 60/747,607, filed May 18, 2006.
Co-pending U,S, Appl. No. 60/771,101, filed Feb. 6, 2006.
Co-pending U.S. Appl. No. 60/773,124, filed Feb. 13, 2006.
Co-pending U.S. Appl. No. 60/891,479.
Co-pending U.S. Appl. No. 60/941,641.
Deyde V.M., et al., "Genomic Signature-Based Identification of Influenza A Viruses Using RT-PCR/Electro-Spray Ionization Mass Spectrometry (ESI-MS) Technology," PLoS One, 2010, vol. 5(10), pp. e13293.

European Search Report for Application No. EP10175659.1, mailed on Feb. 9, 2011, 4 pages.
Ex Parte Re-Examination Certificate for U.S. Appl. No. 90/010,447 mailed Feb. 15, 2011.
Examiner Interview Summary mailed Oct. 3, 2005 for U.S. Appl. No. 10/326,046, filed Dec. 18, 2002.
Examiner Interview Summary mailed Nov. 6, 2008 for U.S. Appl. No. 10/728,486, filed Dec. 5, 2003.
Examiner Interview Summary mailed Jun. 7, 2011 for U.S. Appl. No. 11/930,108, filed Oct. 31, 2007.
Examiner Interview Summary mailed Aug. 10, 2004, for U.S. Appl. No. 09/798,007, filed Mar. 2, 2001.
Examiner Interview Summary mailed Aug. 10, 2004 for U.S. Appl. No. 09/891,793, filed Jun. 26, 2001.
Examiner Interview Summary mailed Aug. 10, 2004 for U.S. Appl. No. 10/156,608, filed May 24, 2002.
Examiner Interview Summary mailed Aug. 10, 2004 for U.S. Appl. No. 10/326,642, filed Dec. 18, 2002.
Examiner Interview Summary mailed Oct. 24, 2008 for U.S. Appl. No. 11/582,859, filed Oct. 17, 2006.
Examiner Interview Summary mailed Feb. 27, 2006 for U.S. Appl. No. 10/326,644, filed Dec. 18, 2002.
Examiner Interview Summary mailed Jan. 27, 2006 for U.S. Appl. No. 10/323,211, filed Dec. 18, 2002.
Examiner Interview Summary mailed May 28, 2008 for U.S. Appl. No. 10/660,998, filed Sep. 12, 2003.
Examiner Interview Summary mailed Oct. 28, 2008 for U.S. Appl. No. 11/331,987, filed Jan. 13, 2006.
Examiner Interview Summary mailed Oct. 29, 2008 for U.S. Appl. No. 11/331,978, filed Jan. 13, 2006.
Examiner Interview Summary mailed Oct. 29, 2009 for U.S. Appl. No. 10/660,122, filed Sep. 11, 2003.
Examiner Interview Summary mailed Jul. 31, 2006 for U.S. Appl. No. 10/326,643, filed Dec. 18, 2002.
Extended European Search Opinion for Application No. EP10175659.1, mailed on Feb. 21, 2011, 5 pages.
Extended European Search Report for Application No. EP10179789.2, mailed on Mar. 22, 2011, 9 pages.
Extended European Search Report for Application No. EP10179791.8, mailed on Mar. 17, 2011, 7 pages.
Extended European Search Report for Application No. EP10179795.9, mailed on Mar. 22, 2011, 9 pages.
Final Office Action mailed Aug. 6, 2010 for U.S. Appl. No. 11/929,910, filed Oct. 30, 2007.
Final Office Action mailed Jul. 8, 2010 for U.S. Appl. No. 12/326,800, filed Dec. 2, 2008.
Final Office Action mailed May 12, 2010 for U.S. Appl. No. 11/674,538, filed Feb. 13, 2007.
Final Office Action mailed Jun. 14, 2011 for U.S. Appl. No. 12/616,422, filed Nov. 11, 2009.
Final Office Action mailed Oct. 14, 2009 for U.S. Appl. No. 10/943,344, filed Sep. 17, 2004.
Final Office Action mailed Nov. 17, 2009 for U.S. Appl. No. 11/582,875, filed Oct. 17, 2006.
Final Office Action mailed Feb. 18, 2010 for U.S. Appl. No. 10/754,415, filed Jan. 9, 2004.
Final Office Action mailed Nov. 20, 2009 for U.S. Appl. No. 11/331,987, filed Jan. 13, 2006.
Final Office Action mailed Jun. 23, 2010 for U.S. Appl. No. 11/930,017, filed Oct. 30, 2007.
Final Office Action mailed Feb. 26, 2009 for U.S. Appl. No. 11/582,863, filed Oct. 17, 2006.
Final Office Action mailed Jul. 28, 2011 for U.S. Appl. No. 11/930,108, filed Oct. 31, 2007.
Final Office Action mailed Jan. 30, 2009 for U.S. Appl. No. 10/844,938, filed May 12, 2004.
GENBANK, "Mouse Hepatitis Virus Strain MHV-A59 C12 Mutant, Complete Genome," Accession No. AF029248, Jul. 25, 2000.
International Preliminary Report on Patentability and Written Opinion for Application No. PCT/US04/007236, mailed on Mar. 16, 2006, 7 pages.
International Preliminary Report on Patentability for Application No. PCT/US2005/018031, mailed on Nov. 29, 2006, 1 page.

Lubman D.M., Application for Continuation Grant by David Mitchell Lubman dated Jun. 4, 1996 and Jun. 14, 1996.
Lubman D.M., Application for Continuation Grant by David Mitchell Lubman dated Jun. 10, 1994 and Jun. 24, 1994.
Lubman D.M., Application for Grant by David Mitchell Lubman dated Sep. 1, 1994 and Sep. 27, 1994.
Lubman D.M., Application for Grant by David Mitchell Lubman dated Oct. 25, 1992 and Oct. 29, 1992.
Non-Final Office Action mailed Feb. 2, 2007 for U.S. Appl. No. 10/844,938, filed May 12, 2004.
Non-Final Office Action mailed Oct. 2, 2009 for U.S. Appl. No. 11/929,707, filed Oct. 30, 2007.
Non-Final Office Action mailed Apr. 6, 2009 for U.S. Appl. No. 11/331,987, filed Jan. 13, 2006.
Non-Final Office Action mailed Apr. 7, 2006 for U.S. Appl. No. 10/964,571, filed Oct. 12, 2004.
Non-Final Office Action mailed Aug. 7, 2007 for U.S. Appl. No. 10/844,938, filed May 12, 2004.
Non-Final Office Action mailed Jun. 10, 2009 for U.S. Appl. No. 10/844,938, filed May 12, 2004.
Non-Final Office Action mailed Jan. 12, 2010 for U.S. Appl. No. 11/491,376, filed Jul. 21, 2006.
Non-Final Office Action mailed Oct. 13, 2010 for U.S. Appl. No. 10/754,415, filed Jan. 9, 2004.
Non-Final Office Action mailed Sep. 16, 2009 for U.S. Appl. No. 11/233,630, filed Sep. 21, 2005.
Non-Final Office Action mailed Apr. 17, 2009 for U.S. Appl. No. 12/211,641, filed Sep. 16, 2008.
Non-Final Office Action mailed Nov. 19, 2003 for U.S. Appl. No. 09/798,007, filed Mar. 2, 2001.
Non-Final Office Action mailed Aug. 20, 2007 for U.S. Appl. No. 11/582,863, filed Oct. 17, 2006.
Non-Final Office Action mailed May 20, 2008 for U.S. Appl. No. 10/844,938, filed May 12, 2004.
Non-Final Office Action mailed Oct. 20, 2004 for U.S. Appl. No. 09/891,793, filed Jun. 26, 2001.
Non-Final Office Action mailed Feb. 23, 2009 for U.S. Appl. No. 10/660,122, filed Sep. 11, 2003.
Non-Final Office Action mailed May 26, 2010 for U.S. Appl. No. 11/869,449, filed Oct. 9, 2007.
Non-Final Office Action mailed Jul. 27, 2006 for U.S. Appl. No. 11/209,439, filed Aug. 8, 2005.
Non-Final Office Action mailed Jun. 28, 2010 for U.S. Appl. No. 11/930,002, filed Oct. 30, 2007.
Non-Final Office Action mailed Sep. 28, 2009 for U.S. Appl. No. 11/930,017, filed Oct. 30, 2007.
Non-Final Office Action mailed Dec. 29, 2010 for U.S. Appl. No. 12/616,422, filed Nov. 11, 2009.
Non-Final Office Action mailed Apr. 30, 2010 for U.S. Appl. No. 11/930,108, filed Oct. 31, 2007.
Notice of Allowance and Examiner Interview Summary mailed Jul. 21, 2011 for U.S. Appl. No. 10/754,415, filed Jan. 9, 2004.
Notice of Allowance mailed Apr. 1, 2011 for U.S. Appl. No. 11/233,630, filed Sep. 21, 2005.
Notice of Allowance mailed Jun. 3, 2009 for U.S. Appl. No. 11/331,978, filed Jan. 13, 2006.
Notice of Allowance mailed Aug. 5, 2010 for U.S. Appl. No. 11/233,630, filed Sep. 21, 2005.
Notice of Allowance mailed Aug. 6, 2009 for U.S. Appl. No. 10/728,486, filed Dec. 5, 2003.
Notice of Allowance mailed Aug. 9, 2011 for U.S. Appl. No. 11/930,002, filed Oct. 30, 2007.
Notice of Allowance mailed Jun. 9, 2011 for U.S. Appl. No. 11/331,987, filed Jan. 13, 2006.
Notice of Allowance mailed Jun. 9, 2011 for U.S. Appl. No. 11/491,376, filed Jul. 21, 2006.
Notice of Allowance mailed Dec. 10, 2010 for U.S. Appl. No. 11/233,630, filed Sep. 21, 2005.
Notice of Allowance mailed Dec. 10, 2010 for U.S. Appl. No. 11/491,376, filed Jul. 21, 2006.
Notice of Allowance mailed Nov. 12, 2009 for U.S. Appl. No. 10/728,486, filed Dec. 5, 2003.
Notice of Allowance mailed Dec. 15, 2008 for U.S. Appl. No. 11/331,978, filed Jan. 13, 2006.
Notice of Allowance mailed Sep. 18, 2009 for U.S. Appl. No. 10/660,998, filed Sep. 12, 2003.
Notice of Allowance mailed Nov. 24, 2009 for U.S. Appl. No. 11/331,978, filed Jan. 13, 2006.
Notice of Allowance mailed May 25, 2011 for U.S. Appl. No. 11/929,707, filed Oct. 30, 2007.
Notice of Allowance mailed Oct. 29, 2009 for U.S. Appl. No. 10/660,122, filed Sep. 11, 2003.
Office Action mailed Apr. 1, 2004 for U.S. Appl. No. 10/156,608, filed May 24, 2002.
Office Action mailed May 1, 2006 for U.S. Appl. No. 10/660,998, filed Sep. 12, 2003.
Office Action mailed Feb. 2, 2011 for U.S. Appl. No. 11/869,449, filed Oct. 9, 2007.
Office Action mailed Jan. 2, 2009 for U.S. Appl. No. 11/060,135, filed Feb. 17, 2005.
Office Action mailed Jun. 2, 2006 for U.S. Appl. No. 10/933,928, filed Sep. 3, 2004.
Office Action mailed Jun. 2, 2008 for U.S. Appl. No. 11/331,978, filed Jan. 13, 2006.
Office Action mailed Oct. 2, 2008 for U.S. Appl. No. 11/233,630, filed Sep. 21, 2005.
Office Action mailed Oct. 2, 2009 for Japanese Application No. 2005508560 filed Dec. 5, 2003.
Office Action mailed Aug. 3, 2006 for U.S. Appl. No. 10/660,998, filed Sep. 12, 2003.
Office Action mailed Aug. 3, 2009 for U.S. Appl. No. 11/754,174, filed May 25, 2007.
Office Action mailed Dec. 3, 2003 for U.S. Appl. No. 10/325,527, filed Dec. 18, 2002.
Office Action mailed Feb. 3, 2011 for U.S. Appl. No. 12/326,800, filed Dec. 2, 2008.
Office Action mailed Nov. 3, 2008 for U.S. Appl. No. 10/728,486, filed Dec. 5, 2003.
Office Action mailed Apr. 4, 2008 for U.S. Appl. No. 10/829,826, filed Apr. 22, 2004.
Office Action mailed Dec. 4, 2006 for Indian Application No. 1136KOLNP2003 filed Mar. 4, 2002.
Office Action mailed Feb. 4, 2009 for U.S. Appl. No. 11/404,561, filed Apr. 12, 2006.
Office Action mailed Jun. 4, 2009 for U.S. Appl. No. 10/754,415, filed Jan. 9, 2004.
Office Action mailed May 4, 2010 for U.S. Appl. No. 90/010,447, filed Apr. 9, 2009.
Office Action mailed May 4, 2010 for U.S. Appl. No. 90/010,448, filed Apr. 9, 2009.
Office Action mailed Nov. 4, 2009 for European Application No. 02709785.6 filed Mar. 4, 2002.
Office Action mailed Sep. 4, 2008 for Australian Application No. 2003297687 filed Dec. 5, 2003.
Office Action mailed Aug. 5, 2010 for European Application No. 02709785.6 filed Mar. 4, 2002.
Office Action mailed Sep. 5, 2006 for U.S. Appl. No. 10/660,996 filed Sep. 12, 2003.
Office Action mailed Jan. 6, 2011 for Israel Application No. 157661 filed Mar. 4, 2002.
Office Action mailed Jul. 6, 2006 for U.S. Appl. No. 10/660,122, filed Sep. 11, 2003.
Office Action mailed Jul. 6, 2007 for U.S. Appl. No. 10/829,826, filed Apr. 22, 2004.
Office Action mailed Mar. 6, 2009 for U.S. Appl. No. 11/233,630, filed Sep. 21, 2005.
Office Action mailed Nov. 6, 2002 for U.S. Appl. No. 09/798,007, filed Mar. 2, 2001.
Office Action mailed Apr. 7, 2009 for Canadian Application No. 2525498 filed May 13, 2004.
Office Action mailed Apr. 7, 2009 for European Application No. 07760292.8 filed Apr. 6, 2007.
Office Action mailed Apr. 7, 2009 for U.S. Appl. No. 10/660,998, filed Sep. 12, 2003.

Office Action mailed Aug. 7, 2007 for U.S. Appl. No. 10/660,998, filed Sep. 12, 2003.
Office Action mailed Feb. 7, 2008 for European Application No. 03796752.8, filed Dec. 5, 2003.
Office Action mailed Jun. 7, 2010 for European Application No. 06800205.4 filed Jul. 27, 2006.
Office Action mailed Jan. 8, 2003 for U.S. Appl. No. 09/798,007, filed Mar. 2, 2001.
Office Action mailed Jan. 8, 2007 for U.S. Appl. No. 09/891,793, filed Jun. 26, 2001.
Office Action mailed Mar. 8, 2005 for U.S. Appl. No. 09/891,793, filed Jun. 26, 2001.
Office Action mailed Mar. 8, 2007 for U.S. Appl. No. 11/060,135, filed Feb. 17, 2005.
Office Action mailed Sep. 8, 2006 for Chinese Application No. 02809122.1 filed Mar. 4, 2002.
Office Action mailed Dec. 9, 2004 for U.S. Appl. No. 10/156,608, filed May 24, 2002.
Office Action mailed Dec. 9, 2009 for U.S. Appl. No. 90/010,210, filed Jun. 27, 2008.
Office Action mailed Dec. 9, 2009 for U.S. Appl. No. 90/010,447, filed Apr. 9, 2009.
Office Action mailed Dec. 9, 2009 for U.S. Appl. No. 90/010,448, filed Apr. 9, 2009.
Office Action mailed Feb. 9, 2007 for Chinese Application No. 02809122.1 filed Mar. 4, 2002.
Office Action mailed Jan. 9, 2008 for Japanese Application No. 2002570692 filed Mar. 4, 2002.
Office Action mailed Jul. 9, 2008 for U.S. Appl. No. 10/660,122, filed Sep. 11, 2003.
Office Action mailed Jul. 9, 2008 for U.S. Appl. No. 11/331,987, filed Jan. 13, 2006.
Office Action mailed Mar. 9, 2004 for U.S. Appl. No. 09/891,793, filed Jun. 26, 2001.
Office Action mailed Nov. 9, 2010 for U.S. Appl. No. 11/331,987, filed Jan. 13, 2006.
Office Action mailed Dec. 10, 2008 for U.S. Appl. No. 10/829,826, filed Apr. 22, 2004.
Office Action mailed Dec. 10, 2009 for U.S. Appl. No. 11/929,910, filed Oct. 30, 2007.
Office Action mailed Feb. 10, 2005 for U.S. Appl. No. 09/798,007, filed Mar. 2, 2001.
Office Action mailed Feb. 10, 2006 for Australian Application No. 2002244250 filed Mar. 4, 2002.
Office Action mailed Jun. 10, 2009 for U.S. Appl. No. 90/010,210, filed Jun. 27, 2008.
Office Action mailed Jun. 10, 2010 for U.S. Appl. No. 90/010,447, filed Apr. 9, 2009.
Office Action mailed Jun. 10, 2007 for U.S. Appl. No. 90/010,448, filed Apr. 9, 2009.
Office Action mailed Oct. 10, 2007 for U.S. Appl. No. 10/754,415, filed Jan. 9, 2004.
Office Action mailed Sep. 10, 2008 for Australian Application No. 2003302236 filed Dec. 5, 2003.
Office Action mailed Aug. 11, 2005 for U.S. Appl. No. 09/891,793, filed Jun. 26, 2001.
Office Action mailed Aug. 11, 2010 for U.S. Appl. No. 90/010,447, filed Apr. 9, 2009.
Office Action mailed Aug. 11, 2010 for U.S. Appl. No. 90/010,448, filed Apr. 9, 2009.
Office Action mailed Dec. 11, 2007 for U.S. Appl. No. 10/660,998, filed Sep. 12, 2003.
Office Action mailed Jul. 11, 2003 for U.S. Appl. No. 09/798,007, filed Mar. 2, 2001.
Office Action mailed Jun. 11, 2010 for U.S. Appl. No. 90/010,210, filed Jun. 27, 2008.
Office Action mailed Mar. 11, 2005 for U.S. Appl. No. 10/325,527, filed Dec. 18, 2002.
Office Action mailed May 11, 2007 for U.S. Appl. No. 10/728,486, filed Dec. 5, 2003.
Office Action mailed Jul. 12, 2006 for U.S. Appl. No. 09/891,793, filed Jun. 26, 2001.
Office Action mailed Jul. 12, 2006 for U.S. Appl. No. 10/660,996, filed Sep. 12, 2003.
Office Action mailed Jun. 12, 2008 for U.S. Appl. No. 10/754,415, filed Jan. 9, 2004.
Office Action mailed Jun. 12, 2009 for Chinese Application No. 200480016187.9 filed May 13, 2004.
Office Action mailed May 12, 2002 for U.S. Appl. No. 09/798,007, filed Mar. 2, 2001.
Office Action mailed Aug. 13, 2009 for U.S. Appl. No. 11/674,538, filed Feb. 13, 2007.
Office Action mailed Jul. 13, 2004 for U.S. Appl. No. 09/891,793, filed Jun. 26, 2001.
Office Action mailed Jul. 13, 2007 for U.S. Appl. No. 11/233,630, filed Sep. 21, 2005.
Office Action mailed Jul. 13, 2010 for U.S. Appl. No. 11/929,930, filed Oct. 30, 2007.
Office Action mailed Mar. 13, 2006, for U.S. Appl. No. 10/754,415, filed Jan. 9, 2004.
Office Action mailed Nov. 13, 2003 for U.S. Appl. No. 09/891,793, filed Jun. 26, 2001.
Office Action mailed Sep. 13, 2006 for U.S. Appl. No. 09/891,793, filed Jun. 26, 2001.
Office Action mailed Jul. 14, 2004 for U.S. Appl. No. 10/326,642, filed Dec. 18, 2002.
Office Action mailed Jun. 14, 2004 for U.S. Appl. No. 09/891,793, filed Jun. 26, 2001.
Office Action mailed Mar. 14, 2011 for U.S. Appl. No. 11/930,002, filed Oct. 30, 2007.
Office Action mailed Aug. 15, 2008 for U.S. Appl. No. 11/331,978, filed Jan. 13, 2006.
Office Action mailed Dec. 15, 2008 for Israel Application No. 157661 filed Mar. 4, 2002.
Office action mailed Dec. 15, 2010 for Canadian Application No. 2508726 filed Dec. 5, 2003.
Office Action mailed Jan. 15, 2008 for Israel Application No. 157661 filed Mar. 4, 2002.
Office Action mailed Jul. 15, 2009 for U.S. Appl. No. 11/060,135, filed Feb. 17, 2005.
Office Action mailed Mar. 15, 2010 for European Application No. 08730682.5 filed Feb. 25, 2008.
Office Action mailed Nov. 15, 2007 for U.S. Appl. No. 11/331,978, filed Jan. 13, 2006.
Office Action mailed Sep. 15, 2005 for U.S. Appl. No. 10/156,608, filed May 24, 2002.
Office Action mailed Apr. 16, 2002 for U.S. Appl. No. 09/798,007, filed Mar. 2, 2001.
Office Action mailed Apr. 16, 2008 for U.S. Appl. No. 11/233,630, filed Sep. 21, 2005.
Office Action mailed Apr. 16, 2009 for U.S. Appl. No. 90/010,210, filed Jun. 27, 2008.
Ofice Action mailed Aug. 16, 2004 for U.S. Appl. No. 10/325,527, filed Dec. 18, 2002.
Office Action mailed Aug. 16, 2010 for U.S. Appl. No. 11/929,707, filed Oct. 30, 2007.
Office Action mailed Feb. 16, 2011 for U.S. Appl. No. 11/929,910, filed Oct. 30, 2007.
Office Action mailed Jul. 16, 2007 for U.S. Appl. No. 11/331,987, filed Jan. 13, 2006.
Office Action mailed Mar. 16, 2006 for U.S. Appl. No. 09/891,793, filed Jun. 26, 2001.
Office Action mailed Mar. 16, 2010 for Canadian Application No. 2616281 filed Jul. 21, 2006.
Office Action mailed May 16, 2008 for U.S. Appl. No. 11/404,561, filed Apr. 12, 2006.
Office Action mailed Nov. 16, 2009 for Japanese Application No. 2005508488 filed Dec. 5, 2003.
Office Action mailed Jun. 17, 2008 for U.S. Appl. No. 11/582,863, filed Oct. 17, 2006.
Office Action mailed Mar. 17, 2006 for U.S. Appl. No. 10/660,122, filed Sep. 11, 2003.
Office Action mailed Nov. 17, 2006 for U.S. Appl. No. 10/754,415, filed Jan. 9, 2004.

Office Action mailed Oct. 17, 2007 for U.S. Appl. No. 10/728,486, filed Dec. 5, 2003.
Office Action mailed Oct. 17, 2008 for U.S. Appl. No. 11/331,978, filed Jan. 13, 2006.
Office Action mailed Sep. 17, 2008 for European Application No. 03796752.8 filed Dec. 5, 2003.
Office Action mailed Sep. 17, 2008 for U.S. Appl. No. 10/660,122, filed Sep. 11, 2003.
Office Action mailed Feb. 18, 2010 for European Application No. 03814656.9 filed Dec. 5, 2003.
Office Action mailed Jan. 18, 2011 for U.S. Appl. No. 11/930,108, filed Oct. 31, 2007.
Office Action mailed May 18, 2005 for New Zealand Application No. 527857 filed Mar. 4, 2002.
Office Action mailed Sep. 18, 2006 for U.S. Appl. No. 10/660,997, filed Sep. 12, 2003.
Office Action mailed Sep. 18, 2006 for Australian Application No. 2003298030 filed Dec. 5, 2003.
Office Action mailed Sep. 18, 2008 for U.S. Appl. No. 10/660,998, filed Sep. 12, 2003.
Office Action mailed Jan. 19, 2007 for U.S. Appl. No. 11/059,776, filed Feb. 17, 2005.
Office Action mailed May 19, 2005 for U.S. Appl. No. 09/891,793, filed Jun. 26, 2001.
Office Action mailed Nov. 19, 2004 for U.S. Appl. No. 10/156,608, filed May 24, 2002.
Office Action mailed Oct. 19, 2007 for U.S. Appl. No. 11/210,516, filed Aug. 24, 2005.
Office Action mailed Sep. 19, 2006 for U.S. Appl. No. 10/660,122, filed Sep. 11, 2003.
Office Action mailed Sep. 19, 2007 for U.S. Appl. No. 10/660,122, filed Sep. 11, 2003.
Office Action mailed Apr. 20, 2007 for U.S. Appl. No. 10/660,122, filed Sep. 11, 2003.
Office Action mailed Apr. 20, 2009 for U.S. Appl. No. 10/891,337, filed Jul. 14, 2004.
Office Action mailed Dec. 20, 2006 for U.S. Appl. No. 10/728,486, filed Dec. 5, 2003.
Office Action mailed Jul. 20, 2005 for U.S. Appl. No. 10/156,608, filed May 24, 2002.
Office Action mailed Jun. 20, 2002 for U.S. Appl. No. 09/798,007, filed Mar. 2, 2001.
Office Action mailed Nov. 20, 2003 for U.S. Appl. No. 10/323,438, filed Dec. 18, 2002.
Office Action mailed Nov. 20, 2006 for U.S. Appl. No. 09/891,793, filed Jun. 26, 2001.
Office Action mailed Nov. 20, 2006 for European Application No. 02709785.6 filed Mar. 4, 2002.
Office Action mailed Sep. 20, 2010 for U.S. Appl. No. 90/010,447, filed Apr. 9, 2009.
Office Action mailed Sep. 20, 2010 for U.S. Appl. No. 90/010,448, filed Apr. 9, 2009.
Office Action mailed Apr. 21, 2009 for U.S. Appl. No. 90/010,209, filed Jun. 27, 2008.
Office Action mailed Mar. 21, 2008 for U.S. Appl. No. 10/660,122, filed Sep. 11, 2003.
Office Action mailed May 21, 2008 for U.S. Appl. No. 10/943,344, filed Sep. 17, 2004.
Office Action mailed Nov. 21, 2003 for U.S. Appl. No. 10/326,642, filed Dec. 18, 2002.
Office Action mailed Nov. 21, 2006 for U.S. Appl. No. 10/660,997, filed Sep. 12, 2003.
Office Action mailed Oct. 21, 2005 for U.S. Appl. No. 10/326,641, filed Dec. 18, 2002.
Office Action mailed Oct. 21, 2009 for U.S. Appl. No. 12/326,800, filed Dec. 2, 2008.
Office Action mailed Apr. 22, 2009 for U.S. Appl. No. 11/491,376, filed Jul. 21, 2006.
Office Action mailed Jul, 22, 2008 for U.S. Appl. No. 90/010,209, filed Jun. 27, 2008.
Office Action mailed Jul. 22, 2008 for U.S. Appl. No. 90/010,210, filed Jun. 27, 2008.
Office Action mailed Nov. 22, 2006 for U.S. Appl. No. 10/660,996, filed Sep. 12, 2003.
Office Action mailed Oct. 22, 2007 for U.S. Appl. No. 11/331,987, filed Jan. 13, 2006.
Office Action mailed Sep. 22, 2003 for U.S. Appl. No. 09/798,007, filed Mar. 2, 2001.
Office Action mailed Sep. 22, 2010 for Canadian Application No. 2510007 filed Dec. 5, 2003.
Office Action mailed Apr. 23, 2010 for U.S. Appl. No. 90/010,210, filed Jun. 27, 2008.
Office Action mailed Feb. 23, 2009 for U.S. Appl. No. 10/943,344, filed Sep. 17, 2004.
Office Action mailed Jan. 23, 2008 for U.S. Appl. No. 10/728,486, filed Dec. 5, 2003.
Office Action mailed Jan. 23, 2008 for U.S. Appl. No. 11/059,776, filed Feb. 17, 2005.
Office Action mailed May 23, 2003 for U.S. Appl. No. 09/891,793, filed Jun. 26, 2001.
Office Action mailed May 23, 2005 for U.S. Appl. No. 10/156,608, filed May 24, 2002.
Office Action mailed Oct. 23, 2003 for New Zealand Application No. 527857, filed Mar. 4, 2002.
Office Action mailed Apr. 24, 2009 for U.S. Appl. No. 90/010,447, filed Apr. 9, 2009.
Office Action mailed Apr. 24, 2009 for U.S. Appl. No. 90/010,448, filed Apr. 9, 2009.
Office Action mailed Aug. 24, 2010 for U.S. Appl. No. 90/010,210, filed Jun. 27, 2008.
Office Action mailed Dec. 24, 2004 for New Zealand Application No. 527857 filed Mar. 4, 2002.
Office Action mailed Feb. 24, 2004 for U.S. Appl. No. 10/326,642, filed Dec. 18, 2002.
Office Action mailed Jan. 24, 2005 for U.S. Appl. No. 10/326,642, filed Dec. 18, 2002.
Office Action mailed Jan. 24, 2007 for U.S. Appl. No. 10/660,998, filed Sep. 12, 2003.
Office Action mailed Jul. 24, 2007 for Mexican Application No. PAA2003007927 filed Sep. 2, 2003.
Office Action mailed Jul, 24, 2007 for U.S. Appl. No. 11/060,135, filed Feb. 17, 2005.
Office Action mailed Jul. 24, 2009 for U.S. Appl. No. 11/754,182, filed May 25, 2007.
Office Action mailed Jun. 24, 2008 for European Application No. 06800205.4 filed Jul. 27, 2006.
Office Action mailed Mar. 24, 2011 for U.S. Appl. No. 11/929,930, filed Oct. 30, 2007.
Office Action mailed Nov. 24, 2009 for U.S. Appl. No. 90/010,210, filed Jun. 27, 2008.
Office Action mailed Sep. 24, 2009 for U.S. Appl. No. 90/010,210, filed Jun. 27, 2008.
Office Action mailed Aug. 25, 2009 for U.S. Appl. No. 11/754,169, filed May 25, 2007.
Office Action mailed Jun. 25, 2009 for U.S. Appl. No. 11/869,449, filed Oct. 9, 2007.
Office Action mailed Jun. 25, 2009 for U.S. Appl. No. 90/010,210, filed Jun. 27, 2008.
Office Action mailed Mar. 25, 2008 for U.S. Appl. No. 11/060,135, filed Feb. 17, 2005.
Office Action mailed Aug. 26, 2003 for U.S. Appl. No. 09/891,793, filed Jun. 26, 2001.
Office Action mailed Aug. 26, 2010 for Canadian Application No. 2508584 filed Dec. 5, 2003.
Office Action mailed Jul. 26, 2004 for U.S. Appl. No. 10/323,438, filed Dec. 18, 2002.
Office Action mailed May 26, 2005 for U.S. Appl. No. 10/156,608, filed May 24, 2002.
Office Action mailed May 26, 2006 for U.S. Appl. No. 10/660,997, filed Sep. 12, 2003.
Office Action mailed Feb. 27, 2003 for U.S. Appl. No. 09/798,007, filed Mar. 2, 2001.
Office Action mailed Feb. 27, 2007 for U.S. Appl. No. 10/754,415, filed Jan. 9, 2004.

Office Action mailed Feb. 27, 2007 for U.S. Appl. No. 10/943,344, filed Sep. 17, 2004.
Office Action mailed Jul. 27, 2006 for U.S. Appl. No. 10/728,486, filed Dec. 5, 2003.
Office Action mailed Jul. 27, 2009 for Canadian Application No. 2439655 filed Mar. 4, 2002.
Office Action mailed Aug. 28, 2006 for U.S. Appl. No. 10/754,415, filed Jan. 9, 2004.
Office Action mailed Feb. 28, 2006 for U.S. Appl. No. 10/660,996, filed Sep. 12, 2003.
Office Action mailed Jul. 28, 2009 for U.S. Appl. No. 11/754,163, filed May 25, 2007.
Office Action mailed Jul. 28, 2010 for U.S. Appl. No. 90/010,210, filed Jun. 27, 2008.
Office Action mailed May 28, 2003 for U.S. Appl. No. 09/798,007, filed Mar. 2, 2001.
Office Action mailed Mar. 29, 2010 for Australian Application No. 2006272776 filed Jul. 21, 2006.
Office Action mailed May 29, 2007 for U.S. Appl. No. 11/059,776, filed Feb. 17, 2005.
Office Action mailed Oct. 29, 2009 for U.S. Appl. No. 90/010,447, filed Apr. 9, 2009.
Office Action mailed Oct. 29, 2009 for U.S. Appl. No. 90/010,448, filed Apr. 9, 2009.
Office Action mailed Aug. 30, 2007 for U.S. Appl. No. 10/754,415, filed Jan. 9, 2004.
Office Action mailed Jul. 30, 2008 for Australian Application No. 2004248107 filed Apr. 23, 2004.
Office Action mailed Jul. 30, 2009 for Japanese Application No. 2002570692 filed Mar. 4, 2002.
Office Action mailed Jun. 30, 2004 for U.S. Appl. No. 09/798,007, filed Mar. 2, 2001.
Office Action mailed Jun. 30, 2010 for U.S. Appl. No. 90/010,210, filed Jun. 27, 2008.
Office Action mailed Jun. 30, 2010 for U.S. Appl. No. 90/010,447, filed Apr. 9, 2009.
Office Action mailed Jun. 30, 2010 for U.S. Appl. No. 90/010,448, filed Apr. 9, 2009.
Office Action mailed May 30, 2006 for U.S. Appl. No. 10/660,996, filed Sep. 12, 2003.
Office Action mailed Nov. 30, 2009 for U.S. Appl. No. 10/660,122, filed Sep. 11, 2003.
Office Action mailed Sep. 30, 2005 for Chinese Application No. 02809122.1 filed Mar. 4, 2002.
Office Action mailed Jan. 31, 2003 for U.S. Appl. No. 09/798,007, filed Mar. 2, 2001.
Office Action mailed Jan. 31, 2007 for Philippines Application No. PH12003500824 filed Mar. 4, 2002.
Ross P., et al., "High Level Multiplex Genotyping by MALDI-TOF Mass Spectrometry," Nature Biotechnology, 1998, vol. 16 (13), pp. 1347-1351.
Co-pending U.S. Appl. No. 13/174,254, filed Jun. 30, 2011.
Co-pending U.S. Appl. No. 13/243,960, filed Sep. 23, 2011.
Ecker Supporting Information [online], May 23, 2005 [retrieved on Jul. 31, 2011]. Retrieved from the Internet:<URL: http://www.pnas.org/content/102/22/8012/suppl/DC1>.
Final Office Action mailed Oct. 19, 2011 for U.S. Appl. No. 12/326,800, filed Dec. 2, 2008.
Klijn N., et al., "Identification of Mesophilic Lactic Acid Bacteria by using Polymerase Chain Reaction-Amplified Variable Regions of 16S rRNA and Specific DNA Probes," Applied and Environmental Microbiology, 1991, vol. 57 (11), pp. 3390-3393.
Krenke B.E., et al., "Validation of a 16-Locus Fluorescent Multiplex System," Journal of Forensic Sciences, 2002, vol. 47 (4), pp. 773-785.
Non-Final Office Action mailed Oct. 11, 2011 for U.S. Appl. No. 12/605,628, filed Oct. 26, 2009.
Non-Final Office Action mailed Dec. 13, 2011 for U.S. Appl. No. 12/326,800, filed Dec. 2, 2008.
Non-Final Office Action mailed Oct. 13, 2011 for U.S. Appl. No. 11/929,930, filed Oct. 30, 2007.
Non-Final Office Action mailed Dec. 14, 2011 for U.S. Appl. No. 11/682,259, filed Mar. 5, 2007.
Non-Final Office Action mailed Jan. 27, 2012 for U.S. Appl. No. 11/929,930, filed Oct. 30, 2007.
Notice of Allowance mailed Nov. 21, 2011 for U.S. Appl. No. 12/326,800, filed Dec. 2, 2008.
Office Action mailed Dec. 2, 2011 for European Application No. 10179791.8 filed Mar. 4, 2002.
Office Action mailed Aug. 3, 2011 for Canadian Application No. 2439655 filed Mar. 4, 2002.
Office Action mailed Aug. 3, 2011 for European Application No. 08730682.5 filed Feb. 25, 2008.
Office Action mailed Jul. 5, 2011 for Mexican Application No. PAa2003007927 filed Sep. 2, 2003.
Office Action mailed Dec. 6, 2011 for Australian Application No. 2010200893 filed Mar. 10, 2010.
Office Action mailed Oct. 20, 2011 for European Application No. 02709785.6 filed Mar. 4, 2002.
Office Action mailed Nov. 30, 2011 for Australian Application No. 2010202418 filed Jun. 10, 2010.
Office Action mailed Sep. 30, 2011 for U.S. Appl. No. 10/754,415, filed Jan. 9, 2004.
Aaserud D.J., et al., "DNA Sequencing with Balckbody Infrared Radioactive Dissociation of Electrosprayed Ions," International Journal of Mass Spectrometry and Icon Processes, 1997, vol. 167-168, pp. 705-712.
Adam E., et al., "Characterization of Intertype Specific Epitopes on Adenovirus Hexons," Archives of Virology, 1998, vol. 143 (9), pp. 1669-1682.
Adam E., et al., "Intertype Specific Epitope Structure of Adenovirus Hexon," Acta Microbiologica et Immunologica Hungarica, 1998, vol. 45 (3-4), pp. 311-316.
Adam E., et al., "Molecular Structure of the Two-Dimensional Hexon Crystalline Array and of Adenovirus Capsid," Acta Microbiologica et Immunologica Hungarica, 1998, vol. 45 (3-4), pp. 305-310.
Adrian T., et al., "DNA Restriction Analysis of Adenovirus Prototypes 1 to 41," Archives of Virology, 1986, vol. 91 (3-4), pp. 277-290.
Adzhar A., et al., "Universal Oligonucleotides for the Detection of Infectious Bronchitis Virus by Thepolymerase Chain Reaction," Avian Pathology : Journal of the W.V.P.A, 1996, vol. 25 (4), pp. 817-836.
Agostini H.T., et al., "Complete Genome of a JC Virus Genotype Type 6 from the Brain of an African American with Progressive Multifocal Leukoencephalopathy," Journal of Human Virology, 1998, vol. 1 (4), pp. 267-272.
Aires De Sousa M., et al., "Bridges from Hospitals to the Laboratory: Genetic Portraits of Methicillin-Resistant Staphylococcus aureus Clones," FEMS Immunology and Medical Microbiology, 2004, vol. 40 (2), pp. 101-111.
Akalu A., et al., "Rapid Identification of Subgenera of Human Adenovirus by Serological and PCR Assays," Journal of Virological Methods, 1998, vol. 71 (2), pp. 187-196.
Alba M.M., et al., "VIDA: A Virus Database System for the Organization of Animal Virus Genome Open Reading Frames," Nucleic Acids Research, vol. 29 (1), pp. 133-136.
Allaouchiche B., et al., "Clinical Impact of Rapid Oxacillin Susceptibility Testing Using a PCR Assay in Staphylococcus aureus Bactaeremia," The Journal of Infection, 1999, vol. 39 (3), pp. 198-204.
Allawi H.T., et al., "Thermodynamics and NMR of Internal G.T. Mismatches in DNA," Biochemistry, 1997, vol. 36 (34), pp. 10581-10594.
Altschuel S.F., et al., "Basic Local Alignment Search Tool," Journal of Molecular Biology, 1990, vol. 215 (3), pp. 403-410.
Altschuel S.F., et al., "Gapped BLAST and PSI-BLAST: A New Generation of Protein Database Search Programs," Nucleic Acids Research, 1997, vol. 25 (17), pp. 3389-3402.
Amano Y., et al., "Detection of Influenza Virus: Traditional Approaches and Development of Biosensors," Analytical and Bioanalytical Chemistry, 2005, vol. 381 (1), pp. 156-164.
Amexis G., et al., "Quantitative Mutant Analysis of Viral Quasispecies by Chip-Based Matrix Assisted LaserDesorption Ionization Time-of-Flight Mass Spectrometry," Proceedings of the National Academy of Sciences, 2001, vol. 98 (21), pp. 12097-12102.

Anderson M.L.M., "Quantitative Filter Hybridization" in: Nucleic Acid Hybridization, Hames B.D. ed., IRL Press, 1985, pp. 73-111.

Anderson S., et al., "Sequence and Organization of the Human Mitochondrial Genome," Nature, 1981, vol. 290 (5806), pp. 457-465.

Andreasson H., et al., "Mitochondrial Sequence Analysis for Forensic Identification Using Pyrosequencing Technology," BioTechniques, 2002, vol. 32 (1), pp. 124-133.

Anthony R.M., et al., "Use of the Polymerase Chain Reaction for Rapid Detection of High-Level Mupirocin Resistance in Staphylococci," European Journal of Clinical Microbiology & Infectious Diseases, 1999, vol. 18 (1), pp. 30-34.

Arbique J., et al., "Comparison of the Velogene Rapid MRSA Identification Assay, Denka MRSAScreen Assay, and BBL Crystal MRSA ID System for Rapid Identification of Methicillin-Resistant Staphylococcus aureus," Diagnositic Microbiology and Infectious Diseases, 2001, vol. 40 (1-2), pp. 5-10.

Archer G.L., et al., "Detection of Methicillin Resistance in Staphylococci by Using a DNA Probe," Antimicrobial Agents and Chemotherapy, 1990, vol. 34 (9), pp. 1720-1724.

Armstrong P., et al., "Sensitive and Specific Colorimetric Dot Assay to Detect Eastern Equine Encephalomyelitis Viral RNA in Mosquitoes After PCR Amplification," Journal of Medicinal Entomology, 1995, vol. 32 (1), pp. 42-52.

Arnal C., et al., "Quantification of Hepatitis A virus in shellfish by competitive reverse transcription PCRwith coextraction of standard RNA," Applied and Environmental Microbiology, 1999, vol. 65 (1), pp. 322-326.

Aronsson F., et al., "Persistence of the influenza A/WSN/33 virus RNA at midbrain levels of immunodefective mice," Journal of Neurovirology, 2001, vol. 7 (2), pp. 117-124.

Ausubel F.M., et al., eds., Current Protocols in Molecular Biology, vol. 1, John Wiley & Sons Inc., 2004, Table of Contents.

Ausubel F.M., et al., eds., Short Protocols in Molecular Biology: A Compendium of Methods from Current Protocols in Molecular Biology, 2nd Edition, John Wiley & Sons, 1992, Units 2.9, 3.4-3.17, 4.6-4.10, and 10.8.

Ausubel F.M., et al., "Unit 2.11 "Synthesis and Purification of Oligonucleotides," in: Current Protocols in Molecular Biology," 1998, John Wiley & Sons, Inc., pp. 2.11-2.11.21.

Avellon A., et al., "Rapid and Sensitive Diagnosis of Human Adenovirus Infections by a Generic Polymerase Chain Reaction," Journal of Virological Methods, 2001, vol. 92 (2), pp. 113-120.

Azevedo A.M., et al., "Detection of Influenza, Parainfluenza, Adenovirus and Respiratory Syncytial Virus during Asthma Attacks in Children Older than 2 Years Old," Allergologia Immunopathologia, 2003, vol. 31 (6), pp. 311-317.

Baba T., et al., "Genome and Virulence Determinants of High Virulence Community-Acquired MRSA," Lancet, 2002, vol. 359 (9320), pp. 1819-1827.

Bahrmahd A.R., et al., "Polymerise Chain Reaction of Bacterial Genomes with Single Universal Primer: Application to Distinguishing Mycobacteria Species," Molecular and Cellular Probes, 1996, vol. 10 (2), pp. 117-122.

Bahrmahd A.R., et al., "Use of Restriction Enzyme Analysis of Amplified DNA Coding for the hsp65 Gene and Polymerase Chain Reaction with Universal Primer for Rapid Differtiation of Mycobacterium Species in the Clinical Laboratory," Scandinavian Journal of Infectious Diseases, 1998, vol. 30 (5), pp. 477-480.

Bai J., et al., "Matrix-Assisted Laser Desorption/Ionization Mass Spectrometry of Restriction Enzyme-Digested Plasmid DNA Using an Active Nafion Substrate," Rapid Communications in Mass Spectrometry, 1994, vol. 8 (9), pp. 687-691.

Baker G.C., et al., "Review and Re-Analysis of Domain-Specific 16S Primers," Journal of Microbiological Methods, 2003, vol. 55 (3), pp. 541-555.

Banik U., et al., "Multiplex PCR Assay for Rapid Identification of Oculopathogenic Adenoviruses by Amplification of the Fiber and Hexon Genes," Journal of Clincal Microbiology, 2005, vol. 43 (3), pp. 1064-1068.

Barbour A.G., et al., "Identification of an Uncultivatable Borrelia Species in the hard tick Amblyomma americanum: Possible Agent of a Lyme disease-like illness," The Journal of Infectious Diseases, 1996, vol. 173 (2), pp. 403-409.

Barns S.M., et al., "Detection of Diverse New Francisella-like Bacteria in Environmental Samples," Applied and Environmental Microbiology, 2005, vol. 71 (9), pp. 5494-5500.

Baron E.J., "Genetic Aspects of Methicillin Resistance in Staphylococcus aureus and MethodsUsed for its Detection in Clinical Laboratories in the United States," Journal of Chemotherapy, 1995, vol. 7 (Supl.3), pp. 87-92.

Barr I.G., et al., "An Influenza A(H3) Reassortant Was Epidemic in Australia and New Zealand in 2003," Journal of Medical Virology, 2005, vol. 76 (3), pp. 391-397.

Barski P., et al., "Rapid Assay for Detection of Methicillin-Resistant Staphylococcus aureus Using Multiplex PCR," Molecular and Cellular Probes, 1996, vol. 10 (6), pp. 471-475.

Bastia T., et al., "Organelle DNA Analysis of Solanum and Brassica Somatic Hybrids by PCR with Universal Primers," Theoretical and Applied Genetics, 2001, vol. 102 (8), pp. 1265-1272.

Batey R.T., et al., "Preparation of Isotopically Labeled Ribonucleotides for Multidimensional NMR Spectroscopy of RNA," Nucleic Acids Research, 1992, vol. 20 (17), pp. 4515-4523.

Baumer A., et al., "Age-Related Human mtDNA Deletions: A Heterogeneous Set of Deletions Arising at aSingle Pair of Directly Repeated Sequences," American Journal of Human Jenetics, 1994, vol. 54 (4), pp. 618-630.

Beall B., et al., "Sequencing emm-Specific PCR Products for Routine andAccurate Typing of Group A Streptococci," Journal of Clincal Microbiology, 1996, vol. 34 (4), pp. 953-958.

Beall B., et al., "Survey of emm Gene Sequences and T-Antigen Types fromSystemic Streptococcus pyogenes Infection Isolates Collected in San Francisco, California; Atlanta, Georgia; and Connecticut in 1994 and 1995," Journal of Clincal Microbiology, 1997, vol. 35 (5), pp. 1231-1235.

Benko, M. et al., "Family Adenoviridae," Virus taxonomy. VIIIth report of the International Committee on Taxonomy of Viruses, 2004, Academic Press, New York, pp. 213-228.

Benson D.A., et al., "GenBank," Nucleic Acids Research, 1999, vol. 27 (1), pp. 12-17.

Benson L.M., et al, "Advantages of Thermococcus kodakaraenis (KOD) DNA polymerase for PCR-mass spectrometry based analyses," American Society for Mass Spectrometry, 2003, vol. 14 (6), pp. 601-604.

Berencsi G., et al., "Molecular Biological Characterization of Adenovirus DNA," Acta Microbiologica et Immunologica Hungarica, 1998, vol. 45 (3-4), pp. 297-304.

Bishop M.J., et al., "Molecular Sequence Databases" in: Nucleic Acid and Protein Sequence Analysis, 4th Chapter, Bishop M.J., et al., eds, IRL Press, 1987, pp. 83-113.

Bisno A.L., "Streptococcus Pyogenes in Infectious Diseases and Their Etiologic Agents "Principles and Practice of Infectious Diseases, 1995, vol. 2, pp. 1786-1799.

Black R.M., et al., "Detection of Trace Levels of Tricothecene Mycotoxins in Human Urineby Gas Chromatography-Mass Spectrometry," Journal of Chromatography, 1986, vol. 367 (1), pp. 103-115.

Blaiotta G., et al., "PCR Detection of Staphylococcal Enterotoxin Genes in Staphyiococcus Spp. Strains Isolated from Meat and Dairy Products. Evidence for New Variants of seG and Sel in S. aureus AB-8802," Journal of Applied Microbiology, 2004, vol. 97 (4), pp. 719-730.

BLAST Search results, Mar. 2006.

Boivin-Jahns V., et al., "Bacterial Diversity in a Deep-Subsurface Clay Environment," Applied and Environmental Microbiology, 1996, vol. 62 (9), pp. 3405-3412.

Bolton E.T., et al., "A general method for the isolation of RNA complementary to DNA," Proceedings of the National Academy of Sciences of the USA, 1962, vol. 48, pp. 1390-1397.

Bonk T., et al., "Matrix-Assisted Laser Desorption/Ionization Time-of-Flight Mass Spectrometry-Based Detection of Microsatellite Instabilities in Coding DNA Sequences: A Novel Approach to Identify DNA-Mismatch Repair-Deficient Cancer Cells," Clinical Chemistry, 2003, vol. 49 (4), pp. 552-561.

Borrow R., et al., "SiaD PCR Elisa for Confirmation and Identification of Serogroup Y and W135 Meningococcal Infections," FEMS Microbiology Letters, 1998, vol. 159 (2), pp. 209-214.

Boubaker K., et al., "Panton-Valentine Leukocidin and *Staphylococcal* Skin Infections in Schoolchildren," Emerging Infectious Diseases, 2004, vol. 10 (1), pp. 121-124.

Bowen J.E., et al., "The Native Virulence Plasmid Combination Affects the Segregational Stability of a Thetareplicating Shuttle Vector in *Bacillus anthracis* Var," Journal of Applied Microbiology, 1999, vol. 87 (2), pp. 270-278.

Bowers K.M., et al., "Screening for Methicillin Resistance in *Staphylococars aureus* and Coagulasenegative *Staphylococci*: Evaluation of Three Selective and Mastalex-MRSA latex Agglutination," British Journal of Biomedical Science, 2003, vol. 60 (2), pp. 71-74.

Brakstad O.G., et al., "Direct Identification of *Staphylococcus aureus* in Blood Cultures Bydetection of the Gene, Encoding the Thermostable Nuclease or the Gene Product," Acta Pathologica, Microbiologica et Immunologica Scandinavica, 1995, vol. 103 (3), pp. 209-218.

Brakstad O.G., et al., "Multiplex Polymerase Chain Reaction for Detection of Genes for *Staphylococcus aureus* Themonuclease and Methicillin Resistance and Correlation with Oxacillin Resistance," Acta Pathologica, Microbiologica et Immunologica Scandinavica, 1993, vol. 101 (9), pp. 681-688.

Brandt C.D., et al., "Infections in 18,000 Infants and Children in a Controlled Study of Respiratory Tract Disease. I. Adenovirus Pathogenicity in Relation to Serologic Type and Illness Syndrome," American Journal of Epidemiology, 1969, vol. 90 (6), pp. 484-500.

Brayshaw D.P., "Methicillin-Resistant *Staphylococcus aureus*: Evaluation of Detection Techniques on Laboratory-Passaged Organisms," British Journal of Biomedical Science, 1999, vol. 56 (3), pp. 170-176.

Brightwell G., et al., "Development of Internal Controls for PCR Detection of *Bacillus anthracis*," Molecular and Cellular Probes, 1998, vol. 12 (6), pp. 367-377.

Brightwell G., et al., "Genetic Targets for the Detection and Identifiaction of Venezuelan Equine Encephalitis Viruses," Archives of Virology, 1998, vol. 143 (4), pp. 731-742.

Bronzoni R.V.M., et al., "Duplex Reverse Transcription-PCR Followed by Nested PCR Assays for Detection and Identification of Brazilian Alphaviruses and Flaviviruses," Journal of Clincal Microbiology, 2005, vol. 43 (2), pp. 696-702.

Bronzoni R.V.M., et al., "Multiplex Nested PCR for Brazilian Alphavirus Diagnosis," Transactions of the Royal Society of Tropical Medicine and Hygiene, 2004, vol. 98 (8), pp. 456-461.

Brown I.H., "Advances in Molecular Diagnostics for Avian Influenza," Developments in Biologicals, 2006, vol. 124, pp. 93-97.

Brownstein M.J., et al., "Modulation of Non-Templated Nucleotide Addition by Taq DNA Polymerase: Primer Modifications that Facilitate Genotyping," BioTechniques, 1996, vol. 20 (6), pp. 1004-1010.

Brunaud V., et al., "T-DNA Integration into the *Arabidopsis* Genome Depends on Sequence of Pre-Insertion Sites," EMBO Reports, 2002, vol. 3 (12), pp. 1152-1157.

Buck G.A., et al., "Design Strategies and Performance of Custom DNA Sequencing Primers," BioTechniques, 1999, vol. 27 (3), pp. 528-536.

Buetow K.H., et al., "High-Throughput Development and Characterization of a Genomewide Collection of Gene-Based Single Nucleotide Polymorphism Markers by Chip-Based Matrix-Assisted Laser Desorption/Ionization Time-of-Flight Mass Spectrometry," Proceedings of the National Academy of Sciences, 2001, vol. 98 (2), pp. 581-584.

Butel J.S., et al., "Cell and Molecular Biology of Simian Virus 40: Implications for Human Infections and Disease," Journal of the National Cancer Institute, 1999, vol. 91 (2), pp. 119-134.

Butler J., "DNA Profiling and Quantitation of Human DNA," CCQM Bio Analysis Working Group, 2005.

Campbell W.P., et al., "Detection of California serogroup Bunyavirus in tissue culture and mosquito pools by PCR," Journal of Virological Methods, 1996, vol. 57 (2), pp. 175-179.

Carracedo A., et al., "DNA Commission of the International Society for Forensic Genetics: Guidelines Formitochondrial DNA Typing," Forensic Science International, 2000, vol. 110 (2), pp. 79-85.

Carroll K.C., et al., "Rapid Detection of the Staphylococcal mecA Gene from BACTEC BloodCulture Bottles by the Polymerase Chain Reaction," American Journal of Clincal Pathology, 1996, vol. 106 (5), pp. 600-605.

Case J.T., et al., "Maternal Inheritance of Mitochondria! DNA Polymorphisms in Cultured Human Fibroblasts," Somatic Cell Genetics, 1981, vol. 7 (1), pp. 103-108.

Cattoli G., et al., "Comparison of Three Rapid Detection Systems for Type A Influenza Virus on Tracheal Swabs of Experimentally and Naturally Infected Birds," Avian Pathology, 2004, vol. 33 (4), pp. 432-437.

Cavassini M., et al., "Evaluation of MRSA-Screen, a Simple Anti-PBP 2a Slide Latex AgglutinationKit, for Rapid Detection of Methicillin Resistance in *Staphylococcus aureus*," Journal of Clincal Microbiology, 1999, vol. 37 (5), pp. 1591-1594.

Certificate of Correction mailed Mar. 31, 2008 for U.S. Appl. No. 09/891,793, filed Jun. 26, 2001.

Certificate of Correction mailed Mar. 31, 2008 for U.S. Appl. No. 10/156,608, filed May 24, 2002.

Certificate of Correction mailed Mar. 31, 2008 for U.S. Appl. No. 10/660,997, filed Sep. 12, 2003.

Cespedes A., et al., "Polymerase Chain Reaction-Restriction Fragment Length Polymorphism Analysis of a Short Fragment of the Cytochrome b Gene for Identification of *Flatfish* Species," Journal of Food Protection, 1998, vol. 61 (12), pp. 1684-1685.

Chamberlin M., et al., "New RNA Polymerase from *Escerichia coli* Infected with Bacteriophage T7," Nature, 1970, vol. 228 (5268), pp. 227-231.

Chandra S., et al., "Virus Reduction in the Preparation and Intravenous Globulin: In Vitro Experiments," Transfusion, 1999, vol. 39 (3), pp. 249-257.

Chang P.K., et al., "aflT, a MFS Transporter-Encoding Gene Located in the Aflatoxin Gene Cluster, does not have a Significant Role in Aflatoxin Secretion," Fungal Genetics and Biology, 2004, vol. 41 (10), pp. 911-920.

Chaves F., et al., "Molecular Characterization of Resistance to Mupirocin in Methicillin- Susceptible and -Resistant Isolates of *Staphylococcus aureus* from Nasal Samples," Journal of Clincal Microbiology, 2004, vol. 42 (2), pp. 822-824.

Chelly J., et al., "Transcription of the Dystrophin Gene in Human Muscle and Non-Muscle Tissue," Nature, 1988, vol. 333 (6176), pp. 858-860.

Chen C.A., et al., "Universal Primers for Amplification of Mitochondria! small Subunit Ribosomal RNA-Encoding Gene in Scleractinian Corals," Marine Biotechnology, 2000, vol. 2 (2), pp. 146-153.

Chen C.H., et al., Laser Desorption Mass Spectrometry for FastDNA Sequencing [online], Nov. 1994, Retrieved from the Internet< URL:http://www.ornl.gove/sci/techresources/Human_ Genome/publicat/94SANTA/sequencing/seqtoc.shtml>.

Chen J., et al., "A universal PCR Primer to Detect Members of the *Potyviridae* and its use to Examine the Taxonomic Status of Several Members of the Family," Archives of Virology, 2001, vol. 146 (4), pp. 757-766.

Chen N., et al., "The Genomic Sequence of Ectromelia Virus, the Causative Agent of Mousepox," Virology, 2003, vol. 317 (1), pp. 165-186.

Chen R., et al., "Trapping, Detection, and Charge and Mass Measurement of Large Individual Ions (up to 1.1 X 108 Daltons) by Electrospray Ionization FTICR MS," 42nd ASMS Conference on Mass Spectrometry, 1994.

Chen Y.Z., et al., "A BAC-Based STS-Content Map Spanning a 35-MB Region of Human Chromosome 1p35-36," Genomics, 2001, vol. 74 (1), pp. 55-70.

Chen Z., et al., "Genetic Mapping of the Cold-Adapted Phenotype of B/Ann Arbor/1/66, the Master Donor Virus for Live Attenuated Influenza Vaccines (FluMist)," Virology, 2006, vol. 345 (2), pp. 416-423.

Chinese Application No. CN1202204 filed Dec. 16, 1998, Sequenom Inc.

Chiu N.H., et al., "Mass Spectrometry of Single-Stranded Restriction Fragments Captured by an Undigested Complementary Sequence," Nucleic Acids Research, 2000, vol. 28 (8), E31.

Chmielewicz B., et al., "Development of a PCR-Based Assay for Detection, Quantification, and Genotyping of Human Adenoviruses," Clinical Chemistry, 2005, vol. 51 (8), pp. 1365-1373.
Cho M., et al., "Application of the Ribonuclease P (RNaseP) RNA Gene Sequence for Phylogenetic Analysis of the Genus *Saccharomonospora*," International Journal of Systematic Bacteriology, 1998, vol. 48 (4), pp. 1223-1230.
Choi S., et al., "Real-Time PCR Quantification of Human Adenoviruses in Urban Rivers Indicates Genome Prevalence but Low Infectivity," Applied and Environmental Microbiology, 2005, vol. 71 (11), pp. 7426-7433.
Choi Y.K., et al., "Detection and Subtying of Swine Influenza H1N1, H1 N2 and H3N2 Viruses in Clinical Samples Using Two Multiplex RT-PCR Assays," Journal of Virological Methods, 2002, vol. 102 (1-2), pp. 53-59.
Christel L.A., et al., "Rapid, Automated Nucleic Acid Probe Assays Using Silicon Microstructures forNucleic Acid Concentration," Journal of Biomechanical Engineering, 1999, vol. 121 (1), pp. 22-27.
Claas E.C., et al., "Internally Controlled Real-Time PCT Monitoring of Adenovirus DNA Load inSerum or Plasma of Transplant Recipients," Journal of Clincal Microbiology, 2005, vol. 43 (4), pp. 1738-1744.
Cloney L., et al., "Rapid Detection of mecA in Methicillin Resistant *Staphylococcus aureus* Using Cycling Probe Technology," Molecular and Cellular Probes, 1999, vol. 13 (13), pp. 191-197.
Collins D.W., et al., "Numerical Classification of Coding Sequences," Nucleic Acids Research, 1992, vol. 20 (6), pp. 1405-1410.
Conrads G., et al., "16S-23S rDNA Internal Transcribed Spacer Sequences for Analysis of the Phylogenetic Relationships Among Species of the Genus *Fusobacterium*," International Journal of Systematic and Evolutionary Microbiology, 2002, vol. 52 (2), pp. 493-499.
Contreras-Salazar B., et al., "Up Regulation of the Epstein-Barr Virus (EBV)-Encoded Membrane Protein LMP in the Burkitt's Lymphoma Line Daudi after Exposure to N-Butyrate and after EBV Superinfection," Journal of Virology, 1990, vol. 64 (11), pp. 5441-5447.
Co-pending U.S. Appl. No. 10/318,463.
Co-pending U.S. Appl. No. 10/318,681.
Co-pending U.S. Appl. No. 10/323,186.
Co-pending U.S. Appl. No. 10/323,187.
Co-pending U.S. Appl. No. 10/324,721.
Co-pending U.S. Appl. No. 10/521,662.
Co-pending U.S. Appl. No. 10/754,415.
Co-pending U.S. Appl. No. 10/807,019.
Co-pending U.S. Appl. No. 10/845,052.
Co-pending U.S. Appl. No. 10/964,571.
Co-pending U.S. Appl. No. 11/209,439.
Co-pending U.S. Appl. No. 11/674,538.
Co-pending U.S. Appl. No. 11/682,259.
Co-pending U.S. Appl. No. 11/929,910.
Co-pending U.S. Appl. No. 11/930,108.
Co-pending U.S. Appl. No. 11/930,741.
Co-pending U.S. Appl. No. 90/010,209.
Co-pending U.S. Appl. No. 90/010,210.
Co-pending U.S. Appl. No. 90/010,447.
Co-pending U.S. Appl. No. 90/010,448.
Co-pending U.S. Appl. No. 11/233,630, filed Sep. 25, 2005.
Co-pending U.S. Appl. No. 60/632,862, filed Dec. 3, 2004.
Cornel A.J., et al., "Polymerase Chain Reaction Species Diagnostic Assay for *Anopheles quadrimaculatus* Cryptic Species (*Diptera:Culicidae*) Based on Ribosomal DNA ITS2 Sequences," Journal of Medical Entomology, 1996, vol. 33 (1), pp. 109-116.
Couto I., et al., "Development of Methicillin Resistance in Clinical Isolates of *Staphylococcus sciuri* by Transcriptional Activation of the mecA Homologue Native to the Species," Journal of Bacteriology, 2003, vol. 185 (2), pp. 645-653.
Crain P.F., et al., "Applications of Mass Spectrometry to the Characterization of Oligonucleotides and Nucleic Acids," Annual Biochemistry, 1998, vol. 9 (1), pp. 25-34.
Crawford-Miksza L., et al., "Analysis of 15 Adenovirus Hexon Proteins Reveals the Location and Structure of Seven Hypervariable Regions Containing Serotype-Specific Residues," Journal of Virology, 1996, vol. 70 (3), pp. 1836-1844.
Crawford-Miksza L.K., et al., "Adenovirus Serotype Evolution is Driven by Illegitimate Recombination in the Hypervariable Regions of the Hexon Protein," Virology, 1996, vol. 224 (2), pp. 357-367.
Crawford-Miksza L.K., et al., "Strain Variation in Adenovirus Serotypes 4 and 7a Causing Acute Respiratory Disease," Journal of Clincal Microbiology, 1999, vol. 37 (4), pp. 1107-1112.
Crespillo M., et al., "Mitochondrial DNA Sequences for 118 Individuals from Northeastern Spain," International Journal of Legal Medicine, 2000, vol. 114 (1-2), pp. 130-132.
Cui L., et al., "Contribution of a Thickened Cell Wall and Its Glutamine Nonamidated Component to the Vancomycin Resistance Expressed by *Staphylococcus aureus Mu50*," Antimicrobial Agents and Chemotherapy, 2000, vol. 44 (9), pp. 2276-2285.
Dasen G., et al., "Classification and Identification of Propiolbacteria based on Ribosomal RNA Genes and PCR," Systematic and Applied Microbiology, 1998, vol. 21 (2), pp. 251-259.
De Jong J.C., et al., "Adenoviruses from Human Immunodeficiency Virus-Infected Individuals,Including Two Strains That Represent New Candidate Serotypes Ad50 and Ad51 of Species B1 and D, Respectively," Journal of Clincal Microbiology, 1999, vol. 37 (12), pp. 3940-3945.
De La Puente-Redondo V.A., et al., "Comparison of Different PCR Approaches for Typing of *Francisella tularensis* Strains," Journal of Clinical Microbiology, 2000, vol. 38 (3), pp. 1016-1022.
Deforce D.L.D., et al., "Characterization of DNA Oligonudeotides by Coupling of Capillary zone Electrophoresis to Electrospray Ionization Q-TOF Mass Spectrometry," Analytical Chemistry, 1998, vol. 70 (14), pp. 3060-3068.
Deforce D.L. et al., "Analysis of Oligonucleotides by ESI-MS," Advances in Chromatography (New York), 2000, vol. 40, pp. 539-566.
Del Blanco Garcia N., et al., "Genotyping of *Francisella tularensis* Strains by Pulsed-field gel Electrophoresis, Amplified Fragment Length Polymorphism Fingerprinting, and 16S rRNA gene Sequencing," Journal of Clinical Microbiology, 2002, vol. 40 (8), pp. 2964-2972.
Del Vecchio V.G., et al., "Molecular Genotyping of Methicillin-Resistant *Staphylococcus aureus* via Fluorophore-Enhanced Repetitive-Sequence PCR," Journal of Clincal Microbiology, 1995, vol. 33 (8), pp. 2141-2144.
Demesure B., et al., "A set of Universal Primers for Amplification of Polymorphic Non-coding Regions of Mitochondrial and Chioroplast DNA in plants," Molecular Ecology, 1995, vol. 4, pp. 129-131.
Denis M., et al., "Development of a Semiquantitative PCR Assay Using Internal Standard and Colorimetricdetection on Microwell Plate for Pseudorabies Virus," Molecular and Cellular Probes, 1997, vol. 11 (6), pp. 439-448.
Deurenberg R.H., et al., "Rapid Detection of Panton-Valentine Leukocidin from Clinical Isolates of *Staphylococcus aureus* Strains by Real-Time PCR," FEMS Microbiology Letters, 2004, vol. 240 (2), pp. 225-228.
Deurenberg R.H., et al., "The Prevalence of the *Staphylococcus aureus* tst Gene among Community- and Hospital-Acquired Strains and Isolates from Wegener's Granulomatosis Patients," FEMS Microbiology Letters, 2005, vol. 245 (1), pp. 185-189.
Di Guilmi A.M., et al., "Human Adenovirus Serotype 3 (Ad3) and the Ad3 fiber Protein Bind to a 130-kDa Membrane Protein on HLa Cells," Virus Research, 1995, vol. 38 (1), pp. 71-81.
Dias Neto E., et al., "Shotgun Sequencing of the Human Transcriptome with ORF Expressed Sequence Tags," Proceedings of the National Academy of Sciences, 2000, vol. 97 (7), pp. 3491-3496.
Diep B.A., et al., "Complete Genome Sequence of USA300, an Epidemic Clone of Community Acquired Meticillin-Resistant *Staphylococcus aureus*," Lancet, 2006, vol. 367 (9512), pp. 731-739.
Dinauer D.M., et al., "Sequence-based typing of HLA class II DQB1," Tissue Antigens, 2000, vol. 55 (4), pp. 364-368.
Ding C., et al., "A High-Throughput Gene Expression Analysis Technique using Compettiive PCR and Matrixassisted Laser Desorption Ionization time-of-Flight MS," Proceedings of the National Academy of Sciences, 2003, vol. 100 (6), pp. 3059-3064.

Donehower L.A., et al., "The Use of Primers from Highly Conserved Pol Regions to Identify Uncharacterized Retroviruses by the Polymerase Chain Reaction," Journal of Virological Methods, 1990, vol. 28 (1), pp. 33-46.

Donofrio J.C., et al., "Detection of Influenza A and B in Respiratory Secretions with the Polymerase Chain Reaction," PCR Methods and Applications, 1992, vol. 1 (4), pp. 263-268.

Doty P., et al., "Strand Separation and Specific Recombination in Deoxyribonucleic Acids: Physical Chemical Studies," Proceedings of the National Academy of Sciences of USA, 1960, vol. 46 (4), pp. 461-476.

Drosten C., et al., "Identification of a Novel Coronavirus in Patients with Severe Acute Respiratory Syndrome," New England Journal of Medicine, 2003, vol. 348 (20), pp. 1967-1976.

Dubernet S., et al., "A PCR-based Method for Identification of *Lactobacilli* at to Genus Level," FEMS Microbiology Letters, 2002, vol. 214 (2), pp. 271-275.

Ebner K., et al., "Molecular Detection and Quantitative Analysis of the Entire Spectrum of Human Adenoviruses by a Two-Reaction Real-Time PCR Assay," Journal of Clinical Microbiology, 2005, vol. 43 (7), pp. 3049-3053.

Ebner K., et al., "Typing of Human Adenoviruses in Specimens from Immunosuppressed Patients by PCR-Fragment Length Analysis and Real-Time Quantitative PCR," Journal of Clinical Microbiology, 2006, vol. 44 (8), pp. 2808-2815.

Echavarria M., et al., "Detection of Adenoviruses (AdV) in Culture-Negative EnvironmentalSamples by PCR During an AdV-Associated Respiratory Disease Outbreak," Journal of Clinical Microbiology, 2000, vol. 38 (8), pp. 2982-2984.

Echavarria M., et al., "PCR Method for Detection of Adenovirus in Urine of Healthy and Human Immunodeficiency Virus-Infected Individuals," Journal of Clinical Microbiology, 1998, vol. 36 (11), pp. 3323-3326.

Echavarria M., et al., "Prediction of Severe Disseminated Adenovirus Infection by Serum PCR," Lancet, 2001, vol. 358 (9279), pp. 384-385.

Echavarria M., et al., "Rapid Detection of Adenovirus in Throat Swab Specimens by PCR DuringRespiratory Disease Outbreaks among Military Recruits," Journal of Clinical Microbiology, 2003, vol. 41 (2), pp. 810-812.

Echavarria M., et al., "Use of PCR to Demonstrate Presence of Adenovirus Species B, C, or F as Well as Coinfection with Two Adenovirus Species in Children with Flu-Like Symptoms," Journal of Clinical Microbiology, 2006, vol. 44 (2), pp. 625-627.

Ecker D. J., et al., "Rapid Identification and Strain-Typing of Respiratory Pathogens for Epidemic Surveillance," Proceedings of the National Academy of Sciences, 2005, vol. 102 (22), pp. 8012-8017.

Ecker D. J., et al., "The Ibis T5000 Universal Biosensor. An Automated Platform for Pathogen Identification and Strain Typing," Journal of the Association for Laboratory Automation, 2006, vol. 11 (6), pp. 341-351.

Ecker D.J., et al., "Ibis T5000: a universal biosensor approach for microbiology," Nature Reviews Microbiology, 2008, vol. 6 (7), pp. 553-558.

Edwards K.M., et al., "Adenovirus Infections in Young Children," Pediatrics, 1985, vol. 76 (3), pp. 420-424.

Ellis J. S., et al., "Molecular Diagnosis of Influenza," Reviews in Medical Virology, 2002, vol. 12 (6), pp. 375-389.

Ellis J.S., et al., "Multiplex Reverse Transcription-PCR for Surveillance of Influenza A and B Viruses in England and Wales in 1995 and 1996," Journal of Clinical Microbiology, 1997, vol. 35(8), pp. 2076-2082.

Elnifro E.M., et al., "PCR and Restriction Endonuclease Analysis for Rapid Identification of *Adenovirus subgenera*," Journal of Clinical Microbiology, 2000, vol. 38 (6), pp. 2055-2061.

Elsayed S., et al., "Development and Validation of a Molecular Beacon Probe-Based Real-Time Polymerase Chain Reaction Assay for Rapid Detection of Methicillin Resistance in *Staphylococcus aureus*," Archives of pathology and laboratory medicine, 2003, vol. 127 (7), pp. 845-849.

EMBL "*Arabidopsis thaliana* T-DNA flanking sequence, left border, clone 346C06," Accession No. AJ552897, Mar. 29, 2003.

EMBL "Dog (Clone: CXX.147) primer for STS 147, 3' end, sequence tagged site," Accession No. L15697, Mar. 4, 2000.

EMBL "Human, muscle, Mitochondrial Mutant, 22 nt, segment 2 of 2," Accession No. S90302, Sep. 1, 2004.

EMBL "Sequence 10 from patent US 6563025," Accession No. AR321656, Aug. 31, 2006.

EMBL, "Synthetic construct DNA, reverse primer for human STS sts-AA031654 at 1p36", Accession No. AB068711, May 21, 2003.

Enright M.C., et al., "A multilocus sequence typing scheme for *Streptococcus pneumoniae*: identification of clones associated with serious invasive disease," Microbiology, 1998, vol. 144 (Pt 11), pp. 3049-3060.

Enright M.C., et al., "Multilocus Sequence Typing for Characterization of Methicillin-Resistant and Methicillin-Susceptible Clones of *Staphylococcus aureus*," Journal of Clinical Microbiology, 2000, vol. 38(3), pp. 1008-1015.

Enright M.C., et al., "Multilocus Sequence Typing of *Streptococcus pyogenes* and theRelationships between Emm Type and Clone," Infection and Immunity, 2001, vol. 69 (4), pp. 2416-2427.

Enright M.C., et al., "The Evolutionary History of Methicillin-Resistant *Staphylococcus aureus*(MRSA)," Proceedings of the National Academy of Sciences of USA, 2002, vol. 99 (11), pp. 7687-7692.

Enright M.C., "The Evolution of a Resistant Pathogen—the Case of MRSA," Current Opinion in Pharmacology, 2003, vol. 3 (5), pp. 474-479.

Eremeeva M.E., et al., "Evaluation of a PCR Assay for Quantitation of *Rickettsia rickettsii* and Closely Related Spotted Fever Group Rickettsiae," Journal of Clinical Microbiology, 2003, vol. 41 (12), pp. 5466-5472.

Erlich H.A., ed., PCR Technology: Principles and Applications for DNA Amplification, W.H. Freeman and Company, 1989.

Esmans E.L., et al., "Liquid Chromatography-Mass Spectrometry in Nucleoside, Nucleotide and Modified Nucleotide Characterization," Journal of Chromatography, 1998, vol. 794, pp. 109-127.

Eugene-Ruellan G., et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization," Journal of Clinical Microbiology, 1998, vol. 36 (3), pp. 796-801.

Evans P., et al., "Practical Algorithms for Universal DNA Primer Design: An Exercise in Algorithm Engineering," Currents in Computational Molecular Biology, 2001, Les Publications CRM, pp. 25-26.

Ex Parte Re-Examination Certificate for U.S. Appl. No. 90/010,209 mailed Jul. 7, 2009.

Ex Parte Re-Examination Certificate for U.S. Appl. No. 90/010,210, mailed Dec. 28, 2010.

Examiner Interview Summary Record mailed Oct. 29, 2009 for U.S. Appl. No. 10/660,122, filed Sep. 11, 2003.

Examiner Interview Summary Record mailed Nov. 30, 2009 for U.S. Appl. No. 10/660,122, filed Sep. 11, 2003.

Facklam R., et al., "Emm Typing and Validation of Provisional M Types for Group A *Streptococci*," Emerging Infectious Diseases, 1999, vol. 5 (2), pp. 247-253.

Fang H., et al., "Rapid Screening and Identification of Methicillin-Resistant *Staphylococcus aureus* from Clinical Samples by Selective-Broth and Real-Time PCR Assay," Journal of Clinical Microbiology, 2003, vol. 41 (7), pp. 2894-2899.

Farlow J., et al., "*Francisella tularensis* Strain Typing Using Multiple-Locus, Variable-Number Tandem Repeat Analysis," Journal of Critical Microbiology, 2001, vol. 39 (9), pp. 3186-3192.

Farrell D. J., "The Reliability of Microscan Conventional and Rapid Panels to Identify *Staphylococcus aureus* and Detect Methicillin Resistance: An Evaluation Using the Tube Coagulase Test and mecA PCR," Pathology, 1997, vol. 29 (4), pp. 406-410.

Fedele C.G., et al., "Multiplex Polymerase Chain Reaction for the Simultaneous Detection and Typing of Polyomavirus JC, BK and SV40 DNA in Clinical Samples," Journal of Virological Methods, 1999, vol. 82 (2), pp. 137-144.

Fedele C.G., et al., "Quantitation of Polyomavirus DNA by a Competitive Nested Polymerase Chain Reaction," Journal of Virological Methods, 2000, vol. 88 (1), pp. 51-61.

Feng P., "Impact of Molecular Biology on the Detection of Food Pathogens," Molecular Biotechnology, 1997, vol. 7 (3), pp. 267-278.

Figueiredo L.M., et al., "Identification of Brazilian Flavivirus by a simplified reverse transcription-polymerase chain reaction method using Flavivirus universal primers," American Journal of Tropical Medicine and Hygiene, 1998, vol. 59 (3), pp. 357-362.

Final Office Action mailed Jul. 23, 2009 for U.S. Appl. No. 11/070,632, filed Mar. 2, 2005.

Final Office Action mailed Jun. 30, 2008 for U.S. Appl. No. 11/070,632, filed Mar. 2, 2005.

Final Rejection mailed Oct. 14, 2009 for U.S. Appl. No. 10/943,344, filed Sep. 17, 2004.

Flora J.W., et al, "Dual-Micro-ESI Source for Precise Mass Determination on a Quadrupole time-of-Flight Mass Spectrometer for Genomic and Proteomic Applications," Annual Biochemistry, 2002, vol. 373 (7), pp. 538-546.

Fong W.K., et al., "Rapid Solid-Phase Immunoassay for Detection of Methicillin-Resistant*Staphylococcus aureus* Using Cycling Probe Technology," Journal of Clinical Microbiology, 2000, vol. 38 (7), pp. 2525-2529.

Fox A., et al., "Identification and Detection of Bacteria: Electrospray MS-MS Versus Derivatization/GC-MS," Proceedings of the ERDEC Scientific Conference on Chemical and Biological Defense Research, Aberdeen Proving Ground, MD, Nov. 15-18, 1994, pp. 39-44.

Fox A., et al., "Report of the Bioterrorism Workshop," Journal of Microbiological Methods, 2002, vol. 51 (3), pp. 247-254.

Fox J.P., et al., "The Virus Watch Program: A Continuing Surveillance of Viral Infections in Metropolitan New York Families," American Journal of Epidemiology, 1969, vol. 89 (1), pp. 25-50.

Fox K.F., et al., "Identification of *Brucella* by ribosomal-spacer-region PCR and differentiation of *Brucell canis* from other *Brucella* spp. pathogenic for humans by carbohydrate profiles," Journal of Clinical Microbiology, 1998, vol. 36 (11), pp. 3217-3222.

Francois J-C., et al., "Sequence-Specific Recognition and Cleavage of Duplex DNA via Triple-Helix Formation by Oligonucleotides Covalently Linked to a Phenanthroline-Copper Chelate," Proceedings of the National Academy of Sciences of USA, 1989, vol. 86 (24), pp. 9702-9706.

Francois P., et al., "Rapid Detection of Methicillin-Resistant *Staphylococcus aureus* Directly from Sterile or Nonsterile Clinical Samples by a New Molecular Assay," Journal of Clinical Microbiology, 2003, vol. 41 (1), pp. 254-260.

Fraser C.M., et al., "The Mimimal Gene Complement of Mycoplasma Genitalium," Science, 1995, vol. 270 (5235), pp. 397-403.

Freiberg C., et al., "Genome-Wide mRNA Profiling: Impact on Compound Evaluation and Target Identification in Anti-Bacterial Research," Targets, 2002, vol. 1 (1), pp. 20-29.

Freymuth F., et al., "Comparison of Multiplex PCR Assays and Conventional Techniques for the Diagnostic of Respiratory Virus Infections in Children Admitted to Hospital With an Acute Respiratory Illness," Journal of Medical Virology, 2006, vol. 78 (11), pp. 1498-1504.

Freymuth F., et al., "Detection of Respiratory Syncytial Virus, Parainfluenzavirus 3, Adenovirus Andrhinovirus Sequences in Respiratory Tract of Infants by Polymerase Chain Reaction and Hybridization," Clinical and Diagnostic Virology, 1997, vol. 8 (1), pp. 31-40.

Fuerstenau S.D., et al., "Molecular Weight Determination of Megadalton DNA Electrospray Ions Using Charge Detection Time-of-flight Mass Spectrometry," Rapid Communications in Mass Spectrometry, 1995, vol. 9 (15), pp. 1528-1538.

Fujimoto T., et al., "Single-Tube Multiplex. PCR for Rapid and Sensitive Diagnosis of Subgenus B and Other Subgenera Adenoviruses in Clinical Samples," Microbiology and Immunology, 2000, vol. 44 (10), pp. 821-826.

Fujimura S., et al., "Characterization of the mupA Gene in Strains of Methicillin-Resistant *Staphylococcus aureus* with a Low Level of Resistance to Mupirocin," Antimicrobial Agents and Chemotheraphy, 2001, vol. 45 (2), pp. 641-642.

Fujimura S., et al., "Isoleucyl-tRNA Synthetase Mutations in *Staphylococcus aureus* ClinicalIsolates and In Vitro Selection of Low-Level Mupirocin-Resistant Strains," Antimicrobial Agents and Chemotheraphy, 2003, vol. 47 (10), pp. 3373-3374.

Fujioka S., et al., "Analysis of Enterovirus Genotypes using Single-Strand Conformation Polymorphisms of Polymerase Chain Reaction Product," Journal of Virological Methods, 1995, vol. 51 (2-3), pp. 253-258.

Gabriel M.N., et al., "Improved mtDNA Sequence Analysis of Forensic Remains using a "Mini-Primer Set" Amplification Strategy," Journal of Forensic Sciences, 2001, vol. 46 (2), pp. 247-253.

Gall J. G. D., et al., "Construction and Characterization of Hexon-Chimeric Adenoviruses: Specification of Adenovirus Serotype," Journal of Virology, 1998, vol. 72 (12), pp. 10260-10264.

Gammelin M., et al., "Two Subtypes of Nucleoproteins (NP) of Influenza A Viruses," Virology, 1989, vol. 170 (1), pp. 71-80.

Garcia S., et al., "Quantitative Real-Time PCR Detection of Rift Valley Fever Virus and Its Application to Evaluation of Antiviral Compounds," Journal of Clinical Microbiology, 2001, vol. 39 (12), pp. 4456-4461.

Garcia-Martinez J., et al., "Use of the 16s-23s Ribosomal Genes Spacer Region in Studies of Prokaryotic Diversity," Journal of Microbiological Methods, 1999, vol. 36 (1-2), pp. 55-64.

Gattermann N., et al., "Heteroplasmic Point Mutations of Mitochondria! DNA Affecting Subunit I of Cytochrome c Oxidise in Two Patients with Acquired Idiopathic Siderblastic Anemia," Blood, 1997, vol. 90 (12), pp. 4961-4972.

Gaydos C.A., et al., "Adenovirus Vaccines in the U.S. Military," Military Medicine, 1995, vol. 160 (6), pp. 300-304.

Geha D.J., et al., "Multiplex PCR for Identification of Methicillin-Resistant *Staphylococci* in the Clinical Laboratory," Journal of Clinical Microbiology, 1994, vol. 32 (7), pp. 1768-1772.

Genbank, "{Deletion 6} [Human, Muscle, Mitochondrial Mutant, 22 nt, Segment 2 of 2]," Accession No. S90302.1, Jun. 10, 1992.

Genbank "*Acinetobacter genomosp*. 10 strain CIP 70.12 RNA polymerase subunit B (rpoB) gene, complete cds," Accession No. 78099429, Mar. 11, 2006.

Genbank, "Bovine parainfluenza virus 3 strain Shipping Fever, complete genome," Accesion No. AF178655, Sep. 19, 2000.

Genbank, "*Clostridium tetani* E88, complete genome," Accession No. AE015927.1, Feb. 4, 2003.

Genbank "*E. coli* operon rpoBC coding for the beta- and beta'-subunits of RNA polymerase (genes rpoC and rpoB), and genes rplL, rlpJ, rplA, and rplK coding for 50S ribosomal subunit proteins L7/L12, L10, L1, and L11, respectively. (Map position 89-90 min.)," Accession No. 42813, Feb. 28, 1992.

Genbank, "*E.coli* 16S ribosomal RNA," Accession No. 174375, Aug. 11, 1995.

Genbank, "*E.coli* Open Reading Frame Upstream of Leu Operon," Accession No. M21150, Sep. 15, 1990.

Genbank "*E.coli* rRNA operon (rrnB) coding for Glu-tRNA-2, 5S, 16S and 23S rRNA," Accession No. 147581, Sep. 14, 1992.

Genbank, "*Enterococcus malodoratus* strain ATCC43197 elongation factor Tu (tufA) gene, partial cds," Accession No. AF274728, Dec. 11, 2000.

Genbank "*Escherichia Coli* str. K-12 substr. MG1655, Complete Genome," Accession No. NC000913, Oct. 15, 2001.

Genbank, "*Homo sapiens* Haplotype V Mitochondrion, Complete Genome", Accession No. AF381990.1, Dec. 28, 2001.

Genbank, "Human Adenovirus Type 4 Hexon Gene," for Accession No. X84646, Jun. 30, 1995.

Genbank, "Human coronavirus 229E, complete genome," Accession No. AF304460, Jul. 11, 2001.

Genbank, "Human Isolate L34 Mitochondrion D-loop Region", Accession No. U08081.1, Aug. 16, 1994.

GenBank, "il11b08.y1 Human insulinoma *Homo sapiens* cDNA clone Image:6029534 5- similar to SW:COX3_Human P00414 Cytochrome C Oxidase Polypeptide III ;, mRNA sequence", Accession No. BQ581956.1, Jun. 20, 2002.

Genbank, "Influenza B Virus B/Panama/45/90 Polymerase (PB2) mRNA, Complete Cds", Accession No. AF005737, pp. 1-3, Oct. 4, 1997.

Genbank, "Mastadenovirus h7 hexon gene," Accession No. Z48571, Apr. 18, 2005.

GenBank, "or72a01.s1 NCI_CGAP_Lu5 *Homo sapiens* cDNA Clone Image:16013523- similar to SW:COX1_HUMAN P00395 CYTOCHROME C OXIDASE POLYPEPTIDE i ;, mRNA Sequence", Accession No. AI002209.1, Jun. 10, 1998.

Genbank "*Staphylococcus aureus* RN4220 ErmC gene, partial cds," Accession No. 18542231, Sep. 16, 2003.

Genbank "*Staphylococcus aureus* Strain MSSA476, Complete Genome," Accession No. BX571857.1, Jun. 24, 2004.

Genbank, "*Staphylococcus aureus* subsp. *aureus* Mu50, complete genome," Accession No. 15922990, Oct. 4, 2001.

Genbank "*Staphylococcus aureus* Subsp. *aureus* MW2, Complete Genome," Accession No. 21281729, May 31, 2002.

Genbank, "*Staphylococcus epidermidis* ATCC 12228, complete genome," Accession No. AE015929.1, Jan. 2, 2003.

Genbank "*Streptococcus agalactiae* 2603V/R, complete genome," Accession No. AE009948.1, Aug. 28, 2002.

Genbank, "*Streptococcus anginosus* Elongation Factor Tu (tuf) Gene, Partial cds," Accession No. AF276257.1, Jul. 1, 2001.

Genbank "*Streptococcus pneumoniae* isolate 95.11n00S DNA gyrase subunit B (gyrB) gene, complete cds," Accession No. 73916349, Sep. 30, 2005.

Genbank, "*Streptococcus pyogenes* strain MGAS8232, complete genome," Accession No. AE009949.1, Apr. 3, 2002.

Genbank, "Venezuelan equine encephalitis virus nonstructural polyprotein and structural polyprotein genes, complete cds," Accession No. AF375051.1, Jun. 26, 2001.

Gendel S.M., "Computational Analysis of the Specificity of 16S rRNA-Derived Signature Sequencesfor Identifying Food-Related Microbes," Food Microbiology, 1996, vol. 13, pp. 1-15.

Gibb T.R., et al., "Development and Evaluation of a 5' Fluorogenic Nuclease Assay to Detect and Differentiate Between Ebola Virus Subtypes Zaire and Sudan," Journal of Clinical Microbiology, 2001, vol. 39 (11), pp. 4125-4130.

Gilbert N., et al., "Comparison of Commercial Assays for the Quantitation of HBV DNA Load in Healthcare Workers: Calibration Differences," Journal of Virological Methods, 2002, vol. 100 (1-2), pp. 37-47.

Giles R.E., et al., "Maternal Inheritance of Human Mitochondrial DNA," Proceedings of the National Academy of Sciences, 1980, vol. 77 (11), pp. 6715-6719.

Gill S.R., et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidemidis* Strain," Journal of Bacteriology, 2005, vol. 187 (7), pp. 2426-2438.

Gilliland G., et al., "Analysis of Cytokine mRNA and DNA: Detection and Quantitation by Competitive Polymerase Chain Reaction," Proceedings of the National Academy of Sciences of USA, 1990, vol. 87 (7), pp. 2725-2729.

Ginther C., et al., "Identifying Individuals by Sequencing Mitochondrial DNA from Teeth," Nature Genetics, 1992, vol. 2 (2), pp. 135-138.

Gjoen K.V., et al., "Specific Detection of Coxsackie Viruses a by the Polymerase Chain Reaction," Clinical and Diagnostic Virology, 1997, vol. 8 (3), pp. 183-188.

Golden M. R., et al., "Pilot Study of COBAS PCR and Ligase Chain Reaction for Detection of Rectal Infections Due to *Chlamydia trachomatis*," Journal of Clinical Microbiology, 2003, vol. 41 (5), pp. 2174-2175.

Goto K., et al., "Applications of the Partial 16S rDNA Sequence as an Index for Rapid Identification of Species in the Genus *Bacillus*," Journal of General and Applied Microbiology, 2000, vol. 46 (1), pp. 1-8.

Gravet A., et al., "Characterization of a Novel Structural Member, LukE-LukD, of the Bi-Component *Staphylococcal leucotoxins* Family," FEBS Letters, 1998, vol. 436 (2), pp. 202-208.

Gray G.C., et al., "Adult Adenovirus Infections: Loss of Orphaned Vaccines Precipitates Military Respiratory Disease Epidemics," Clinical Infectious Diseases, 2000, vol. 31, pp. 663-670.

Greenberg B.D., et al., "Intraspecific Nucleotide Sequence Variability Surrounding the Origin of Replicationin Human Mitochondrial DNA," Gene, 1983, vol. 21, pp. 33-49.

Griffey, et al., "Detection of base pair mismatches in duplex DNA and RNA oligonucleotides using electrospray mass spectrometry," SPIE, 1997, vol. 2985, pp. 82-86.

Griffin T.J., et al., "Direct genetic analysis by matrix-assisted laseer desorption/ionization mass spectrometry," PNAS, 1999, vol. 96 (11), pp. 6301-6306.

Griffin T.J., et al., "Single-Nucleotide Polymorphism Analysis by Maldi-TOF Mass Spectrometry," Trends in Biotechnology, 2000, vol. 18 (2), pp. 77-84.

Grondahl B., et al., "Rapid Identification of Nine Microorganisms Causing Acute Respiratory TractInfections by Single-Tube Multiplex Reverse Transcription—PCR: Feasibility Study," Journal of Clinical Microbiology, 1999, vol. 37 (1), pp. 1-7.

Grundmann H., et al., "Emergence and Resurgence of Meticillin-Resistant *Staphylococcus aureus* as a Public-Health Threat," Lancet, 2006, vol. 368 (9538), pp. 874-885.

Grzybowski T., et al., "Extremely High Levels of Human Mitochondrial DNA Heteroplasmy in Single Hair Roots," Electrophoresis, 2000, vol. 21 (3), pp. 548-553.

Gu Z., et al., "Multiplexed, Real-Time PCR for Quantitative Detection of Human Adenovirus," Journal of Clinical Microboilogy, 2003, vol. 41 (10), pp. 4636-4641.

Guatelli J.C., et al., "Nucleic Acid Amplification In Vitro: Detection of Sequences with Low Copy Numbers and Application to Diagnosis of Human Immunodeficiency Virus Type 1 Infection," Clinical Microbiology Reviews, 1989, vol. 2 (2), pp. 217-226.

Haff L.A., et al., "Multiplex Genotyping of PCR Products with Mass Tag-Labeled Primers," Nucleic Acids Research, 1997, vol. 25 (18), pp. 3749-3750.

Hahner S., et al., "Analysis of Short Tandem Repeat Polymorphisms by Electrospray Ion Trap Mass Spectrometry," Nucleic Acids Research, 2000, vol. 28 (18), pp. E82.1-E82.8.

Haines J.D., et al., "Medical Response to Bioterrorism: Are we Prepared," Journal of Oklahoma State Medical Association, 2000, vol. 93, pp. 187-196.

Hall T.A., et al., "Base Composition Analysis of Human Mitochondrial DNA Using Electrospray Ionization Mass Spectrometry: A Novel Tool for the Identification and Differentiation of Humans," Analytical Biochemistry, 2005, vol. 344 (1), pp. 53-69.

Hamdad F., et al., "Detection of Methicillin/Oxacillin Resistance and Typing in Aminoglycoside-Susceptible Methicillin-Resistant and Kanamycin-TobramycinResistant Methicillin-Susceptible," Microbial Drug Resistance, 2006, vol. 12 (3), pp. 177-185.

Hamel S., et al., "Consensus PCR and Microarray for Diagnosis of the Genus *Staphylococcus*, Species, and Methicillin Resistance," Biotechniques, 2001, vol. 31 (6), pp. 1364-1372.

Hammerle T., et al., "A Sensitive PCR Assay System for the Quantitation of Viral Genome Equivalents:Hepatitis C Virus (HCV),"Archives of Virology, 1996, vol. 141 (11), pp. 2103-2114.

Hannis J.C., et al., "Accurate Characterization of the Tyrosine Hydroxylase Forensic Allele 9.3 through Development of Electrospray Ionization Fourier Transform Ion Cyclotron Resonance Mass Spectrometry," Rapid Communications in Mass Spectrometry, 1999, vol. 13 (10), pp. 954-962.

Hannis J.C., et al., "Detection of Double-Stranded PCR Amplicons at the Attomole Level Electrosprayed from Low Nanomolar Solutions using FT-ICR Mass Spectrometry," Journal of Analytical Chemistry, 2001, vol. 369 (3-4), pp. 246-251.

Hannis J.C., et al., "Genotyping Complex Short Tandem Repeats Using Electrospray Ionzation Fourier Transform Ion Cyclotron Resonance Multi-Stage Mass Spectrometry," Proceedings of SPIE, 2000, vol. 3926, pp. 36-47.

Hannis J.C., et al., "Genotyping Short Tandem repeats using flow Injection and Electrospray Ionization , Fourier Transform ion Cyclotron Resonance Mass Spectrometry," Rapid Communications in Mass Spectrometry, 2001, vol. 15 (5), pp. 348-350.

Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.

Hanssen A.M., et al., "*Sccmecin staphylococci*: Genes on the Move," FEMS Immuol Medical Microbiol, 2006, vol. 46, pp. 8-20.

Hasebe F. et al., "Combined Detection and Genotyping of Chikungunya Virus by a Specific Reverse Transcription-Polymerase Chain Reaction," Journal of Medical Virology, 2002, vol. 67 (3), pp. 370-374.

Hassan A.A., et al., "Inter- and Intraspecies Variations of the 16S-23S rDNA Intergenic Spacer Region of Various *Streptococcal* Species," Systematic and Applied Microbiology, 2003, vol. 26 (1), pp. 97-103.

Haugland R.A., et al., "Identification of Putative Sequence Specific PCR Primers for Detection of the Toxygenic Fungal Species *Stachybotrys chartarum*," Molecular and Cellular Probes, 1998, vol. 12 (6), pp. 387-396.

Hayashi H., et al., "Phylogenetic Analysis of the Human gut Microbiota using 16S rDNA clone Libraries and Strictly Anaerobic Culture-based Methods," Journal of Microbiology, Immunology, 2002, vol. 46 (8), pp. 535-548.

He L., et al, "Development of a Capillary High-performance Liquid Chromatography Tandem Mass Spectrometry System Using SWIFT Technology in an Ion Trap/Reflectron Time-of-flight Mass Spetrometer," Biochemical and Biophysical Research Communications, 1997, vol. 11, pp. 1739-1748.

Heim A., et al., "Rapid and Quantitative Detection of Human Adenovirus DNA by Real-Time PCR," Journal of Medical Viral, 2003, vol. 70, pp. 228-239.

Henchal E.A., et al., "Sensitivity and Specificity of a Universal Primer set for the Rapid Diagnosis of Dengue Virus Infections by Polymerase Chain Reaction and Nucleic acid Hybridization," American Journal of Tropical Medicine and Hygiene, 1991, vol. 45 (4), pp. 418-428.

Herrmann B., et al., "Differentiation of *Chiamydia* spp. by Sequence Determination and Restriction Endonuclease Cleavage of RNase P Rna Genes," Journal of Clinical Microbiology, 1996, vol. 34 (8), pp. 1897-1902.

Higgins G.S., et al., "Competitive Oligonucleotide Single-base Extension Combined with Mass Spectrometric Detection for Mutation Screening," Biotechniques, 1997, vol. 23 (4), pp. 710-714.

Higgins J.A., et al., "Sensitive and Rapid Identification of Biological Threat Agents," Annals of the New York Academy of Sciences, 1999, vol. 894, pp. 130-148.

Hill F., et al., "Polymerase Recognition of Synthetic Oligodeoxyribonucleotides Incorporating Degenerate Pyrimidine and Purine Bases," Proceedings of the National Academy of Sciences, 1998, vol. 95, pp. 4258-4263.

Hiramatsu K., et al., "The Emergence and Evolution of Methicillin-Resistant *Staphylococcusaureus*," Trends Microbiology, 2001, vol. 9 (10), pp. 486-493.

Hodgson J.E., et al., "Molecular Characterization of the Gene Encoding High-Level Mupirocin Resistancein *Staphylococcus aureus* J2870," Antimicrobial Agents and Chemotherapy, 1994, vol. 38 (5), pp. 1205-1208.

Hoffman E., et al., "Rescue of Influenza B Virus from Eight Plasmids," Proceedings of the National Academy of Sciences, 2002, vol. 99 (17), pp. 11411-11416.

Hoffmann E., et al., "Universal Primer Set for the Full-Length Amplification of all Influenza A Viruses.," Archives of Virology, 2001, vol. 146 (12), pp. 2275-2289.

Hofstadler S.A., et al., "TIGER: The Universal Biosensor," International Journal of Mass Spectrometry, 2005, vol. 242, pp. 23-41.

Holden M.T., et al., "Complete Genomes of Two Clinical *Staphylocuccus aureus* Strain: Evidence for the Rapid Evolution of Virulence and Drug Resistance," Proceedings of the National Academy of Sciences, 2004, vol. 101 (26), pp. 9786-9791.

Holland M.M., et al., "Mitochondria! DNA Sequence Analysis of Human Skeletal Remains: Identification of Remains from the Vietnam War," Journal of Forensic Sciences, 1993, vol. 38 (3), pp. 542-553.

Holland M.M., et al., "Mitochondrial DNA Sequence Analsysis—Validation and Use for Forensic Casework," Forensic Science Review, 1999, vol. 11 (1), pp. 22-50.

Holm L., et al., "Removing Near-Neighbour Redundancy from Large Protein Sequence Collections," Bioinformatics, 1998, vol. 14 (5), pp. 423-429.

Holmes E.C., et al., "Whole-Genome Analysis of Human Influenza A Virus Reveals Multiple Persistent Lineages and Reassortment among Recent H3N2 Viruses," Public Library of Science Biology, 2005, vol. 3 (9), pp. 1579-1589.

Honda K., et al., "Universal Method of Hypersensitive Nested PCR Toward Forensic DNA typing," International Congress Series, 1998, vol. 7, pp. 28-30.

Hongoh Y., et al., "Evaluation of Primers and PCR Conditions for the Analysis of 16s rRNA Genes from a Naturalenvironment," FEMS Microbiology Letters, 2003, vol. 221 (2), pp. 299-304.

Hood E., et al., "Chemical and Biological Weapons: New Questions, New Answers," Environmental Health Perspectives, 1999, vol. 107 (12), pp. 931-932.

Houng H.S., et al., "Rapid Type-Specific Diagnosis of Adenovirus Type 4 Infection Using a Hexon-Based Quantitative Fluorogenic PCR," Diagnostic Microbiology and Infectious Disease, 2002, vol. 42 (4), pp. 227-236.

Howell N., et al., "Persistent Heteroplasmy of a Mutation in the Human Mtdna Control Region: Hypermutation As an Apparent Consequence of Simple-Repeat Expansion/Contraction," American Journal of Human Genetics, 2000, vol. 66 (5), pp. 1589-1598.

Huber C.G., et al., "On-Line Cation Exchange for Suppression of Adduct Formation in Negative-Ion Electrospray Mass Spectrometry of Nucleic Acids," Analytical Chemistry, 1998, vol. 70 (24), pp. 5288-5295.

Huletsky A., et al., "New Real-Time PCR Assay for Rapid Detection of Methicillin-Resistant*Staphylococcus aureus* Directly from Specimens Containing a Mixture of *Staphylococci*," Journal of Clinical Microbiology, 2004, vol. 42 (5), pp. 1875-184.

Hunag C., et al., "Detection of Arboviral RNA Directly from Mosquito Homogenates by Reverse Transcription-Polymerase Chain Reaction," Journal of Virological Methods, 2001, vol. 94 (1-2), pp. 121-128.

Hung E.C., et al., "Detection of SARS coronavirus RNA in the cerebrospinal fluid of a patient with severe acute respiratory syndrome," Clinical Chemistry, 2003, vol. 49 (12), pp. 2108-2109.

Hurdle J.G., et al., "Analysis of Mupirocin Resistance and Fitness in *Staphylococcus aureus* by Molecular Genetic and Structural Modeling Techniques," Antimicrobial Agents and Chemotherapy, 2004, vol. 48 (11), pp. 4366-4376.

Hurst G.B., et al., "Detection of Bacterial DNA Polymerase Chain Reaction Products by Matrix-Assisted Laser Desorptionfionization Mass Spectrometry," Rapid Communications in Mass Spectrometry, 1996, vol. 10 (3), pp. 377-382.

Hurst G.B., et al., "MALDI-TOF Analysis of Polymerase Chain Reaction Products from Methanotrophic Bacteria," Analytical Chemistry, 1998, vol. 70 (13), pp. 2693-2698.

Hutchison C.A., et al., "Maternal Inheritance of Mammalian Mitochondrial DNA," Nature, 1974, vol. 251 (5475), pp. 536-538.

Hyde-Deruyscher R., et al., "Polyomavirus Early-Late Switch is not Regulated at the Level of Transcription Initiation and is associated with changes in RNA Processing," Proceedings of the National Academy of Sciences, 1988, vol. 85, pp. 8993-8997.

Ieven M., et al., "Rapid Detection of Methicillin Resistance in Coagulase-Negative *Staphylococci* by Commercially Available Fluorescence Test," Journal of Clinical Microbiology, 1995, vol. 33 (8), pp. 2183-2185.

Ihle O., et al., "Efficient Purification of DNA Fragments using a Protein Binding Membrane," Nucleic Acids Research, 2000, vol. 28 (16), pp. e76.

Inglis T.J., et al., "Rapid Genotypic Confirmation of Methicillin Resistance," Pathology, 1996, vol. 28 (3), pp. 259-261.

Ingman M., et al., "Mitochondrial Genome Variation and the Origin of Modern Humans," Nature, 2000, vol. 408 (6813), pp. 708-713.

International Preliminary Examination Report and Written Opinion for Application No. PCT/US2005/00386, mailed on May 9, 2006, 6 pages.

International Preliminary Examination Report for Application No. PCT/US2002/06763, mailed on Jun. 11, 2003, 6 pages.

International Preliminary Examination Report for Application No. PCT/US2003/09802, mailed on Apr. 8, 2005, 7 pages.

International Preliminary Examination Report for Application No. PCT/US2003/22835, mailed on Mar. 5, 2005, 4 pages.

International Preliminary Examination Report for Application No. PCT/US2003/38505, mailed on Mar. 3, 2006, 5 pages.
International Preliminary Examination Report for Application No. PCT/US2003/38757, mailed on Feb. 2, 2007, 5 pages.
International Preliminary Examination Report for Application No. PCT/US2003/38761, mailed on Jun. 27, 2006, 6 pages.
International Preliminary Report on Patentability and Written Opinion for Application No. PCT/US2005/030058, mailed on Aug. 20, 2007, 6 pages.
International Preliminary Report on Patentability and Written Opinion for Application No. PCT/US2005/033707, mailed on Mar. 20, 2007, 6 pages.
International Preliminary Report on Patentability for Application No. PCT/US2002/20336, mailed on May 12, 2004, 8 pages.
International Preliminary Report on Patentability for Application No. PCT/US2004/033742, mailed on Jun. 20, 2006, 1 page.
International Preliminary Report on Patentability for Application No. PCT/US2006/028397, mailed on Jan. 22, 2008, 1 page.
International Preliminary Report on Patentability for Application No. PCT/US2008/054926, mailed on Aug. 26, 2009, 1 page.
International Preliminary Report on Patentability, Written Opinion and International Search Report for Application No. PCT/US2004/015123, mailed on Oct. 3, 2005, 8 pages.
International Search Report and Written Opinion for Application No. PCT/US2005/018031, mailed on Jun. 28, 2006, 14 pages.
International Search Report and Written Opinion for Application No. PCT/US2006/007747, mailed on Sep. 5, 2006, 13 pages.
International Search Report and Written Opinion for Application No. PCT/US2006/015160, mailed on Oct. 10, 2006, 13 pages.
International Search Report and Written Opinion for Application No. PCT/US2006/028397, mailed on Mar. 5, 2007, 14 pages.
International Search Report and Written Opinion for Application No. PCT/US2006/040747, mailed on Mar. 17, 2009, 19 pages.
International Search Report and Written Opinion for Application No. PCT/US2006/061307, mailed on Jan. 9, 2008, 21 pages.
International Search Report and Written Opinion for Application No. PCT/US2007/20045 mailed on Jan. 8, 2009, 18 pages.
International Search Report and Written Opinion for Application No. PCT/US2008/054926, mailed on Jan. 26, 2009, 15 pages.
International Search Report and Written Opinion for Application No. PCT/US2008/057717, mailed on Jan. 13, 2009, 18 pages.
International Search Report and Written Opinion for Application No. PCT/US2008/057901, mailed on Aug. 28, 2008, 14 pages.
International Search Report for Application No. PCT/US02/20336, mailed on Feb. 3, 2002, 4 pages.
International Search Report for Application No. PCT/US2002/06763, mailed on Oct. 23, 2002, 4 pages.
International Search Report for Application No. PCT/US2003/009802, mailed on Aug. 3, 2004, 2 pages.
International Search Report for Application No. PCT/US2003/038505 mailed on Apr. 12, 2005.
International Search Report for Application No. PCT/US2003/038830, mailed on Aug. 25, 2004, 4 pages.
International Search Report for Application No. PCT/US2003/22835, mailed on Dec. 12, 2003, 1 page.
International Search Report for Application No. PCT/US2003/38505, mailed on Apr. 12, 2005, 2 pages.
International Search Report for Application No. PCT/US2003/38757, mailed on Jun. 24, 2004, 2 pages.
International Search Report for Application No. PCT/US2003/38761, mailed on Dec. 30, 2005, 5 pages.
International Search Report for Application No. PCT/US2003/38795, mailed on Apr. 19, 2004, 3 pages.
International Search Report for Application No. PCT/US2004/011877, mailed on Apr. 20, 2006, 4 pages.
International Search Report for Application No. PCT/US2004/012671, mailed on Sep. 28, 2007, 2 pages.
International Search Report for Application No. PCT/US2004/015123, mailed on Oct. 3, 2005, 2 pages.
International Search Report for Application No. PCT/US2004/015196, mailed on Jul. 1, 2005, 3 pages.
International Search Report for Application No. PCT/US2004/028869, mailed on Jul. 17, 2006, 4 pages.
International Search Report for Application No. PCT/US2004/033742, mailed on May 15, 2006, 2 pages.
International Search Report for Application No. PCT/US2005/000386, mailed on May 9, 2006, 3 pages.
International Search Report for Application No. PCT/US2005/005356, mailed on Aug. 7, 2007, 5 pages.
International Search Report for Application No. PCT/US2005/006133, mailed on Jul. 26, 2007, 4 pages.
International Search Report for Application No. PCT/US2005/007022, mailed on Oct. 20, 2006, 1 page.
International Search Report for Application No. PCT/US2005/009557, mailed on Sep. 19, 2005, 1 page.
International Search Report for Application No. PCT/US2005/018337, mailed on Oct. 10, 2006, 2 pages.
International Search Report for Application No. PCT/US2005/024799, mailed on Dec. 28, 2006, 4 pages.
International Search Report for Application No. PCT/US2005/030058, mailed on Aug. 20, 2007, 1 page.
International Search Report for Application No. PCT/US2005/033707, mailed on Feb. 6, 2006, 3 pages.
International Search Report for Application No. PCT/US2007/066194, mailed on Jan. 15, 2008, 5 pages.
International Search Report for Application No. PCT/US2007/087091, mailed on Jan. 15, 2008, 13 pages.
International Search Report for Application No. PCT/US2008/057901, mailed on Jun. 29, 2009, 15 pages.
International Search Report for Application No. PCT/US2008/064891, mailed on Aug. 28, 2008.
International Search Report for Application No. PCT/US2008/065332, mailed on Nov. 28, 2008, 5 pages.
International Search Report for Application No. PCT/US2009/045635, mailed on Oct. 7, 2009, 9 pages.
International Search Report for Application No. PCT/USO4/007236, mailed on Feb. 24, 2006, 3 pages.
Interview Summary Report mailed May 19, 2003 for U.S. Appl. No. 09/891,793, filed Jun. 26, 2001.
Inyaku K., et al., "Rapid Detection and Identification of Mycobacteria in Sputum Samples by NestedPolymerase Chain Reaction and Restriction Fragment Length Polymorphisms of dnaJ Heat ShockProtein Gene," Journal of Medical Sciences, 1993, vol. 42 (1), pp. 21-31.
Iqbal S.S., et al., "A Review of Molecular Recognition Technologies for Detection of Biological Threat Agents," Biosensors & Bioelectronics, 2000, vol. 15 (11-12), pp. 549-578.
Isola N. R., et al., "MALDI-TOF mass spectrometric method for detection of hybridized DNA oligomers," Analytical Chemistry, 2001, vol. 73 (9), pp. 2126-2131.
Ito T., et al., "Insights on Antibiotic Resistance of *Staphylococcus aureus* from its Whole Genome: Genomic Island Scc," Drug Resistance Updates, 2003, vol. 6 (1), pp.
Iteman I., et al., "Comparison of Conserved Structural and Regulatory Domains within Divergent 16S rRNA-23S rRNA Spacer Sequences of Cyanobacteria," Microbiology, vol. 146 (Pt 6), pp. 1275-1286.
Ito T., et al., "Insights on Antibiotic Resistance of *Staphylococcus aureus* from its Whole Genome: Genomic Island Scc," Drug Resistance Updates, 2003, vol. 6 (1), pp. 41-52.
Ito T., et al., "Structural Comparison of Three Types of Staphylococcal Cassette Chromosome mecIntegrated in the Chromosome in Methicillin-Resistant *Staphylococcus aureus*," Antimicrobial Agents and Chemotherapy, 2001, vol. 45 (5), pp. 1323-1336.
Jackson P.E., et al., "Mass Spectrometry for Genotyping: an Emerging Tool for Molecular Medicine," Molecular Medicine Today, 2000, vol. 6 (7), pp. 271-276.
James A.M., et al., "Borelia Lonestari Infection after a Bite by an *Amblyomma americanum* Tick," The Journal of Infectious Diseases, 2001, vol. 183 (12), pp. 1810-1814.
Jankowski K., et al., "Mass Spectrometry of DNA. Part 2 Quantitative Estimation of Base Composition," European Journal of Mass Spectrometry, 1980, vol. 1 (1), pp. 45-52.
Jansen R.C., et al., "Genotype-by-environment Interaction in Genetic Mapping of Multiple Quantitative Trait Loci," Theoretical and Applied Genetics, 1995, vol. 91, pp. 33-37.

Jaulhac B., et al., "Specific Detection of the Toxic Shock Syndrome Toxin-1 Gene Using the Polymerase Chain Reaction," Molecular and Cellular Probes, 1991, vol. 5, pp. 281-284.

Jaulhac B., et al., "Synthetic DNA Probes for Detection of Genes for Enterotoxins A, B, C, D, E and for Tsst-1 in Staphylococcal Strains," Journal of Applied Bacterial, 1992, vol. 72 (5), pp. 386-392.

Jensen M.A., et al., "Rapid Identification of Bacteria on the Basis of Polymcrase Chain Reaction-Amplified Ribosomal DNA Spacer Polymorphisms," Applied and Environmental Microbiology, 1993, vol. 59 (4), pp. 945-952.

Jeong J., et al., "Early Screening of Oxacillin-Resistant Staphylococcus aureus and Staphylococcus epidermidis From Blood Culture," Journal of Korean Medical Science, 2002, vol. 17, pp. 168-172.

Jiang C., et al., "Multiple Trait Analysis of Genetic Mapping for Quantitative Trait Loci Genetics," Genetics, 1995, vol. 140 (3), pp. 1111-1127.

Jiang Y., et al., "A Highly Efficient and Automated Method for Purifying and Desalting PCR Products for Analysis by Electrospray Ionization Mass Spectrometry," Analytical Biochemistry, 2003, vol. 316 (1), pp. 50-57.

Johansson A., et al., "Evaluation of PCR-based Methods for Discrimination of Francisella species and Subspecies and Development of a Specific PCR that Distinguishes the two Major Subspecies of Francisella tularensis," Journal of Clinical Microbiology, 2000, vol. 38 (11), pp. 4180-4185.

Johnson W.M., et al., "Detection of Genes for Enterotoxins, Exfoliative Toxins, and Toxic Shock Syndrome Toxin 1 in Staphylococcus aureus by the Polymerase Chain Reaction," Journal of Clinical Microbiology, 1991, vol. 29 (3), pp. 426-430.

Johnson Y.A., et al., "Precise Molecular Weight Determination of PCR Products of the rRNA Intergenic Spacer Region Using Electrospray Quadrupole Mass Spectrometry for Differentiation of B. subtilis and B. atrophaeus, Closely Related Species of Bacilli," Journal of Microbiological Methods, 2000, vol. 40 (3), pp. 241-254.

Jonas D., et al., "Rapid PCR-Based Identification of Methicillin-Resistant Staphylococcus aureusfrom Screening Swabs," Journal of Clinical Microbiology, 2002, vol. 40 (5), pp. 1821-1823.

Jurinke C., et al., "Application of Nested PCR and Mass Spectrometry for DNA Based Virus Detection: HBV-DNA Detected in the Majority of Isolated Anti-Hbc Positive Sera," Genetic Analysis: Biomolecular Engineering, 1998, vol. 14 (3), pp. 97-102.

Jurinke C., et al., "Detection of Hepatitis B: Virus DNA in Serum Samples Via Nested PCR and MALDI-TOF Mass Spectrometry," Genetic Analysis: Biomolecular Engineering, 1996, vol. 13 (3), pp. 67-71.

Jurinke C., et al., "MALDI-TOF Mass Spectrometry. A Versatile Tool for High-Performance DNA Analysis," Molecular Biotechnology, 2004, vol. 26 (2), pp. 147-163.

Kacian D.L., et al., "A Replicating RNA Molecule Suitable for a Detailed Analysis of Extracellular Evolution and Replication," Proceeding of the National Academy of Sciences, 1972, vol. 69 (10), pp. 3038-3042.

Kageyama A., et al. "Rapid Detection of Human Fecal Eubacterium Species and Related Genera by Tested PCR Method," Journal of Microbiology, Immunology, 2001, vol. 45 (4), pp. 315-318.

Kajon A.E., et al., "Genome Type Analysis of Brazilian Adenovirus Strains of Serotypes 1, 2, 3, 5,and 7 Collected Between 1976 and 1995," Journal of Medical, 1999, vol. 58 (4), pp. 408-412.

Kasai H., et al., "Construction of the gyrB Database for the Identification and Classification of Bacteria," Genome Informatics. Workshop on Genome Informatics, 1998, pp. 13-21.

Katano H., et al., "Identification of Adeno-Associated Virus Contamination in Cell and Virus Stocks by PCR," Biotechniques, 2004, vol. 36 (4), pp. 676-680.

Katayama Y., et al., "Genetic Organization of the Chromosome Region Surrounding mecA inClinical Staphylococcal Strains: Role of IS431-Mediated mecl Deletion in Expression of Resistance inmed-Canying, Low-Level Methicillin-Resistant Staphylococcus haemolyticus," Antimicrobial Agents and Chemotherapy, 2001, vol. 45 (7), pp. 1955-1963.

Ke D., et al., "Development of a PCR Assay for Rapid Detection of Enterococci," Journal of Clinical Microbiology, 1999, vol. 37 (11), pp. 3497-3503.

Kearns A.M., et al., "Rapid Detection of Methicillin-Resistant Staphylococci by Multiplex PCR," The Journal of Hospital Inspection, 1999, vol. 43 (1), pp. 33-37.

Keller A., et al., "Empirical Statistical Model to Estimate the Accuracy of Peptide Identifications Made by MS/MS and Database Search," Analytical Chemistry, 2002, vol. 74 (20), pp. 5383-5392.

Khan A.S., et al., "An Outbreak of Crimean-Congo Haemorrhagic Fever in the United Arab Emirates, 1994-1995," The American Journal of Tropical Medicine and Hygiene, 1997, vol. 57 (5), pp. 519-525.

Khan S.A., et al., "Simultaneous Detection of Erythromycin-Resistant Methylase Genes ermA and ermC from Staphylococcus Spp. By Multiplex-PCR," Molecular and Cellular Probes, 1999, vol. 13 (5), pp. 381-387.

Kidd A.H., et al., "Rapid Subgenus Identification of Human Adenovirus Isolates by a General PCR," Journal of Clinical Microbiology, 1996, vol. 34 (3), pp. 622-627.

Kidd-Ljunggren K., et al., "The hepatitis B virus X gene: analysis of functional domain variation and gene phylogeny using multiple sequences," Journal of General Virology, 1995, vol. 76 (pt 9), pp. 2119-2130.

Kikuchi K., et al., "Restriction Fragment Length Polymorphism Analysis of Clinical Isolates of Mycobacterium haemophilum," Journal of Clinical Microbiology, vol. 32 (7), pp. 1763-1767.

Kilbourne E.D., "Influenza Pandemics of the 20th Century," Emerging Infectious Diseases Journal, 2006, vol. 12 (1), pp. 9-14.

Kilbourne E.D., "Influenza Pandemics: Can We Prepare for the Unpredictable," Viral Immunology, 2004, vol. 17 (3), pp. 350-357.

Kilpatrick D.R., et al., "Group-Specific Identification of Polioviruses by PCR Using Primer Containing Mixed-Base or Deoxyinosine Residues at Positions of Codon Degeneracy," Journal of Clinical Microbiology, 1996, vol. 34 (12), pp. 2990-2996.

Kim B.J., et al., "Identification of Mycobacterial Species by Comparative Sequence Analysis of the RNA Polymerase Gene (rpoB)," Journal of Clinical Microbiology, 1999, vol. 37 (6), pp. 1714-1720.

Kinney R.M., et al., "Nucleotide Sequences of the 26S mRNAs of the Viruses Defining the Venezuelan Equine Encephalitis Antigenic Complex," The American Journal of Tropical Medicine and Hygiene, 1998, vol. 59 (6), pp. 952-964.

Kirpekar F., et al., "Matrix Assisted Laser Desorption/Ionization Mass Spectrometry of Enzymatically Synthesized RNA up to 150 kDa," Nucleic Acids Research, vol. 22 (19), pp. 3866-3870.

Kitagawa Y., et al., "Rapid Diagnosis of Methicillin-Resistant Staphylococcus aureus bacteremia by Nested Polymerase Chain Reaction," Annals of Surgery, 1996, vol. 224 (5), pp. 665-671.

Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.

Kolbert C.P., et al., "Branched-DNA Assay for Detection of the mecA Gene in Oxacillin-Resistant and Oxacillin-Sensitive Staphylococci," Journal of Clinical Microbiology, 1998, vol. 36 (9), pp. 2640-2644.

Kowalak J.A., et al., "A Novel Method for the Determination of Post-Transcriptional Modification in RNA by Mass Spectrometry," Nucleic Acids Research, 1993, vol. 21 (19), pp. 4577-4585.

Krafft A.E., et al., "Evaluation of PCR Testing of Ethanol-Fixed Nasal Swab Specimens as anAugmented Surveillance Strategy for Influenza Virus and Adenovirus Identification," Journal of Clincal Microbiology, 2005, vol. 43 (4), pp. 1768-1775.

Krahmer M.T., et al., "Electrospray Quadrupole Mass Spectrometry Analysis of Model Oligonucleotides and Polymerase Chain Reaction Products: Determination of Base Substitutions, Nucleotide Additions/Deletions, and Chemical Modifications," Analytical Chemistry, 1999, vol. 71 (14), pp. 2893-2900.

Krahmer M.T., et al, "MS for Identification of Single Nucleotide Polymorphisms and MS/MS for Discrimination of Isomeric PCR Products," Analytical Chemistry, 2000, vol. 72 (17), pp. 4033-4040.

Kramer L.D., et al., "Dection of Encephalitis Viruses in Mosquitoes (Diptera: Culicidea) and Avian Tissues," Journal of Medical Entomology, 2002, vol. 39 (2), pp. 312-323.

Kramer L.D., et al., "Dection of St. Louis Encephalitis and Western Equine Encephalomyelitis RNAin Mosquitoes Tested Without Maintainance of a Cold Chain," Journal of the American Mosquito Control Association, 2001, vol. 17 (4), pp. 213-215.

Kresken M., et al., "Prevalence of Mupirocin Resistance in Clinical Isolates of *Staphylococccus aureus* and *Staphylococcus epidermidis*: Results of the Antimicrobial Resistance Surveillance Study of the Paul-Ehrlich-Society for Chemotherapy, 2001," International Journal of Antimicrobial Agents, 2004, vol. 23 (6), pp. 577-581.

Krishnan P.U., et al., "Detection of Methicillin and Mupirocin Resistance in *Staphylococcus aureusisolates* Using Conventional and Molecular Methods: A Descriptive Study from a Burns Unit with Highprevalence of MRSA," Journal of Clinical Pathology, 2002, vol. 55 (10), pp. 745-748.

Kroes I., et al., "Bacterial Diversity Within the Human Subgingival Crevice," Proceeding of the National Academy of Sciences, 1999, vol. 96 (25), pp. 14547-14552.

Krossoy B., et al., "The Putative Polymerase Sequence of Infectious Salmon Anemia Virus Suggests a New Genus within the Orthomyxoviridae," Journal of Virology, 1999, vol. 73 (3), pp. 2136-2142.

Ksiaxek T.G., et al., "A Novel Coronavirus Associated with Severe Acute Respiratory. Syndrome," The New England Journal of Medicine, 2003, vol. 348 (20), pp. 1953-1966.

Kupke T., et al., "Molecular Characterization of Lantibiotic-Synthesizing Enzyme EpiD Reveals a Function for Bacterial Dfp Proteins in Coenzyme A Biosynthesis," Journal of Biological Chemistry, 2000, vol. 275 (41), pp. 31838-31846.

Kuroda M., et al., "Whole Genome Sequencing of Meticillin-Resistant *Staphylococcus aureus*," The Lancet, 2001, vol. 357 (9264), pp. 1225-1240.

Kwok S., et al., "Avoiding False Positives with PCR," Nature, 1989, vol. 339 (6221), pp. 237-238.

Labandeira-Rey, M. et al., "*Staphylococcus aureus* Panton Valentine Leukocidin CausesNecrotizing Pneumonia," Sciencexpress, 2007, pp. 1-8.

Lacroix J.M., et al, "PCR-Based Technique for the Detection of Bacteria in Semen and Urine," Journal of Microbiological Methods, 1996, vol. 26, pp. 61-71.

Lacroix L., et al., "Triplex Formation by Oligonucleotides Containing 5-(1-Propynyl)-2-deoxyuridine: Decreased Magnesium Dependence and Improved Intracellular Gene Targeting," Biochemistry, 1999, vol. 38 (6), pp. 1893-1901.

Laken S.J., et al., "Genotyping by Mass Spectrometric Analysis of Short DNA Fragments," Nature Biotechnology, 1998, vol. 16 (13), pp. 1352-1356.

Lamb R.A., et al., "Sequence of Interrupted and Uninterrupted mRNAs and Cloned DNA Coding for the Two Overlapping Nonstructural Proteins of Influenza Virus," Cell, 1980, vol. 21 (2), pp. 475-485.

Lambert A.J., et al., "Detection of North American Eastern and Western Equine EncephalitisViruses by Nucleic Acid Amplification Assays," Journal of Clinical Microbiology, 2003, vol. 41 (1), pp. 379-385.

Lau L.T., et al, "A Real-Time PCR for SARS-Coronavirus Incorporating Target Gene Pre-Amplification," Biochemical and Biophysical Research Communications, 2003, vol. 312 (4), pp. 1290-1296.

Lau L.T., et al., "Nucleic Acid Sequence-Based Amplification Methods to Detect Avian Influenza Virus," Biochemical and Biophysical Research Communications, 2004, vol. 313 (2), pp. 336-342.

Le Cann P., et al., "Quantification of Human Astroviruses in Sewage Using Real-Time RT-PCR," Research in Microbiology, 2004, vol. 155 (1), pp. 11-15.

Lebedev Y., et al., "Oligonucleotides Containing 2-Aminoadenine and 5-Methycytosine are More Effective as Primers for PCR Amplification than their Nonmodified Counterparts," Genetic Analysis: Biomolecular Engineering, 1996, vol. 13 (1), pp. 15-21.

Lednicky J.A., et al., "Polyomaviruses and Human Tumors: A Brief Review of Current Concenpts and Interpretations," Frontiers Bioscience, 1999, vol. 4, pp. D153-D164.

Lee J.A., et al., "Rapid Identification of Human Adenovirus Types 3 and 7 from Respiratory Specimens via Multiplex Type-Specific PCR," Journal of Clinical Microbiology, 2005, vol. 43 (11), pp. 5509-5514.

Lee J.H., et al., "Simultaneous Detection of Three Mosquito-Borne Encephalitis Viruses (Eastern equine, La Crosse, and St. Louis) with a Single-Tube Multiplex Reverse Transcriptase Polymerase Chaine Reaction Assay," Journal of the American Mosquito Control Association, 2002, vol. 18 (1), pp. 26-31.

Leif H., et al., "Isolation and Characterization of the Proton-Translocating NADH: Ubiqu None Oxidoreductase from *Escherichia coli*," European Journal of Biochemistry, 1995, vol. 230 (2), pp. 538-548.

Lengyel A., et al., "Characterization of the Main Protein Components of Adenovirus Virion and itsPossible Use in Laboratory Diagnostics," Acta Microbiologica Immunologica Hungarica, 1998, vol. 43 (3-4), pp. 281-283.

Leroy E.M., et al., "Diagnosis of Ebola Haemorrhagic Fever by RT-PCR in an Epidemic Setting," Journal of Medicinal Virology, 2000, vol. 60 (4), pp. 463-467.

Levi K., et al., "Evaluation of an Isothermal Signal Amplification Method for Rapid Detection of Methicillin-Resistant *Staphylococcus aureus* from Patient-Screening Swabs," Journal of Clinical Microbiology, 2003, vol. 41 (7), pp. 3187-3191.

Levine S.M., et al., "PCR-Based Detection of *Bacillus anthracis* in Formalin-Fixed Tissue from a Patient Receiving Ciprofloxacin," Journal of Clinical Microbiology, 2002, vol. 40 (11), pp. 4360-4362.

Levison P.R., et al., "Recent Developments of Magnetic Beads for Use in Nucleic Acid Purification," Journal of Chromatography, 1998, vol. A816, pp. 107-111.

Lewers K.S., et al., "Detection of Linked QTL for Soybean Brown Stem Rot Resistance in "BSR 101" asExpressed in a Growth Chamber Environment," Molecular Breeding, 1999, vol. 5, pp. 33-42.

Li C., et al., "Evolution of H9N2 Influenza Viruses from Domestic Poultry in Mainland China," Virology, 2005, vol. 340 (1), pp. 70-83.

Li J., et al., "Single Nucleotide Polymorphism Determination Using Primer Extension and Time-of-Flight Mass Spectrometry," Electrophoresis, 1999, vol. 20 (6), pp. 1258-1265.

Li Q., et al., "Genetic Variability of Hexon Loops 1 and 2 between Seven Genome Types of Adenovirus Serotype 7," Archives of Virology, 1999, vol. 144 (9), pp. 1739-1749.

Li Q., et al., "Screening of the High Yield Influenza B Virus on MDCK c14d Cloning of its Whole Genome," International Congress Series, 2004, pp. 610-614.

Li Q.G., et al., "Analysis of 15 Different Genome Types of Adenovirus Type 7 Isolated on FiveContinents," Journal of Virology, 1986, vol. 60 (1), pp. 331-335.

Li Q.G., et al., "Comparison of 17 Genome Types of Adenovirus Type 3 Identified among Strains Recovered from Six Continents," Journal of Clinical Microbiology, 1988, vol. 26 (5), pp. 1009-1015.

Liebermann H., et al., "Mapping of Epitopes on the Fiber Knobs of Human Adenovirus Serotypes 8 and 15," Intervirology, 2002, vol. 45 (1), pp. 59-66.

Liebermann H., et al., "Mapping of Linear Epitopes on Fibre Knob of Human Adenovirus Serotype 5," Virus Research, 2001, vol. 73 (2), pp. 145-151.

Lim L.P., et al., "The MicroRNAs of *Caenorhabditis elegans*," Genes and Development, 2003, vol. 17 (8), pp. 991-1008.

Limbach P.A., et al., "Enzymatic Sequencing of Oligonucleotides with Electrospray Mass Spectrometry," 42nd ASMS Conference on Mass Spectrometry, 1994.

Limoncu M.H., et al., "Emergence of Phenotypic Resistance to Ciprofloxacin and Levofloxacin Inmethicillin-Resistant and Methicillin-Sensitive *Staphylococcus aureus* Strains," International Journal of Antimicrobial Agents, 2003, vol. 21 (5), pp. 420-424.

Lin B., et al., "Use of Oligonucleotide Microarrays for Rapid Detection and Serotyping of Acute Respiratory Disease-Associated Adenoviruses," Journal of Clinical Microbiology, 2004, vol. 42 (7), pp. 3232-3239.

Lin P.H., et al., "Oxidative Damage to Mitochondrial DNA in Atrial Muscle of Patients with Atrial Fibrillation," Free Radical Biology and Medicine, 2003, vol. 35 (10), pp. 1310-1318.

Lina G., et al., "Bacterial Competition for Human Nasal Cavity Colonization: Role of *Staphylococcalagr alleles*," Applied and Environmental Microbiology, 2003, vol. 69 (1), pp. 18-23.

Lina G., et al., "Involvement of Panton-Valentine Leukocidin-Producing *Staphylococcus aureus* in Primary Skin Infections and Pneumonia," Clinical Infectious Diseases, 1999, vol. 29 (5), pp. 1128-1132.

Linssen B., et al., "Development of Reverse Transcription-PCR Assays Specific for Detection of Equine Encephalitis Viruses," Journal of Clinical Microbiology, 2000, vol. 38 (4), pp. 1527-1535.

Little D.P., et al., "MALDI on a Chip: Analysis of Arrays of Low-Femtomole to Subfemtomole Quantities of Synthetic Oligonucleotides and DNA Diagnostic Products Dispensed by a Piezoelectric Pipet," Analytical Chemistry, 1997, vol. 69, pp. 4540-4546.

Little D.P., et al, "Rapid Sequencing of Oligonucleotides by High-Resolution Mass Spectrometry," Journal of the American Chemical Society, 1994, vol. 116 (11), pp. 4893-4897.

Liu C., et al., "Improving the Microdialysis Procedure for Electrospray Ionization Mass Spectrometry of Biological Samples," Journal of Mass Spectrometry, 1997, vol. 32 (4), pp. 425-431.

Liu J.H., et al., "Interregional Transmission of the Internal Protein Genes of H2 Influenza Virus in Migratory Ducks from North America to Eurasia," Virus Genes, 2004, vol. 29 (1), pp. 81-86.

Liu Y., et al., "An Unusual Gene Arrangement for the Putative Chromosome Replication Origin and Circadianexpression of dnaN in *Synechococcus* sp. Strain PCC 7942," Gene, 1996, vol. 172 (1), pp. 105-109.

Livermore D.M., "The Threat from the Pink Corner," Annals of Medicine, 2003, vol. 35 (4), pp. 226-234.

Loakes D., et al., "Nitroindoles as Universal Bases," Nucleosides and Nucleotides, 1995, vol. 14 (3-5), pp. 1001-1003.

Loo J.A., et al., "Applying Charge Discrimination with Electrospray Ionization-Mass Spectrometry to Protein Analysis," Journal of American Society for Mass Spectrometry, 1995, vol. 6, pp. 1098-1104.

Lott T.J., et al., "Nucleotide Sequence Analysis of the 5-8s rDNA and Adjacent ITS2 Region of *Candidaalbicans* and Related Species," Yeast, 1993, vol. 9, pp. 1199-1206.

Louie L., et al., "Evaluation of Three Rapid Methods for Detection of Methicillin Resistance in *Staphylococcus aureus*," Journal of Clinical Microbiology, 2000, vol. 38 (6), pp. 2170-2173.

Love B.C., et al., "Cloning and Sequence of the GroESL Heat-Shock Operon of *Pasteurella multocida*," Gene, 1995, vol. 166 (1), pp. 179-180.

Lovseth A., et al., "Modified Multiplex PCR Method for Detection of Pyrogenic Exotoxin Genes in Staphylococcal Isolates," Journal of Clinical Microbiology, 2004, vol. 42 (8), pp. 3869-3872.

Lowe T., et al., "A Computer Program for Selection of Oligonucleotide Primers for Polymerase Chain Reactions," Nucleic Acids Research, 1990, vol. 18 (7), pp. 1757-1761.

Lu X., et al., "Molecular Typing of Human Adenoviruses by PCR and Sequencing of a Partial Region of the Hexon Gene," Archives of Virology, 2006, vol. 151 (8), pp. 1587-1602.

Lubman D.M., Application for Continuation Grant by David Mitchell Lubmann dated Jun. 4, 1996 and Jun. 14, 1996.

Lubman D.M., Application for Continuation Grant by David Mitchell Lubmann dated Jun. 10, 1994 and Jun. 24, 1994.

Lubman D.M., Application for Grant by David Mitchell Lubmann dated Sep. 1, 1994 and Sep. 27, 1994.

Lubman D.M., Application for Grant by David Mitchell Lubmann dated Oct. 25, 1992 and Oct. 29, 1992.

Ludwig S.L., et al., "Prevalence of Antibodies to Adenovirus Serotypes 4 and 7 among Unimmunized US Army Trainees: Results of a Retrospective Nationwide Seroprevalence Survey," The Journal of Infectious Diseases, 1998, vol. 178 (6), pp. 1776-1778.

Ludwig W., et al., "Bacterial Phylogeny Based on 16S and 23S rRNA Sequence Analysis," FEMS Microbiolofy Reviews, 1994, vol. 15 (2-3), pp. 155-173.

Lukashov V.V., et al., "Evolutionary Relationships among Parvoviruses: Virus-Host Coevolution among Autonomous Primate Parvoviruses and Links between Adeno-Associated and Avian Parvoviruses," Journal of Virology, 2001, vol. 75 (6), pp. 2729-2740.

Ma X.X., et al., "Novel Type of Staphylococcal Cassette Chromosome mec Identified in Community-Acquired Methicillin-Resistant *Staphylococcus aureus* Strains," Antimicrobial Agents and Chemotherapy, 2002, vol. 46 (4), pp. 1147-1152.

Mack D.H., et al., "A Sensitive Method for the Identification of Uncharacterized Viruses Related Toknown Virus Groups: Hepadnavirus Model System," Proceedings of the National Academy of Sciences, 1988, vol. 85 (18), pp. 6977-6981.

Magnuson V.L., et al., "Substrate Nucleotide-Determined Non-Templated Addition of Adenine by TagDNA Polymerase: Implications for PCR-Based Genotyping and Cloning," BioTechniques, 1996, vol. 21 (4), pp. 700-709.

Maiwald M., et al., "Characterization of Contaminating DNA in Taq Polymerase which Occurs During Amplification with a Primer Set for Legionella 5S Ribosomal RNA," Molecular and Cellular Probes, 1994, vol. 8 (1), pp. 11-14.

Malasig M.D., et al., "Simplified Microneutralization Test for Serotyping Adenovirus Isolates," Journal of Clinical Microbiology, 2001, vol. 39 (8), pp. 2984-2986.

Mangrum J.D., et al., "Solution Composition and Thermal Denaturation for the Production of Single-Stranded PCR Amplicons: Piperidine-Induced Destabilization of the DNA Duplex," Journal of the American Society for Mass Spectrometry, 2002, vol. 13 (3), pp. 232-240.

Manian F.A., "Asymptomatic Nasal Carriage of Mupirocin-Resistant, Methicillin-Resistant *Staphylococcus aureus* (MRSA) in a Pet Dog Associated with MRSA Infection in Household Contacts," Clinical Infectious Diseases, 2003, vol. 36 (2), pp. e26-e28.

Marks F., et al., "Genotyping of Plasmodium Falciparum Pyrimethamine Resistance by Matrix-Assisted Laser Desorption-Ionization Time-of-Flight Mass Spectrometry," Antimicrobial Agents and Chemotherapy, 2004, vol. 48 (2), pp. 466-472.

Marmur J., et al., "Strand Separation and Specific Recombination in Deoxyribonucleic Acids: Biological Studies," Proceedings of the National Academy of Sciences, 1960, vol. 46 (4), pp. 453-461.

Martemyanov K.A., et al., "Extremely Thermostable Elongation Factor (3 from *Aquifer aeolicus*: Cloning, Expression, Purification, and Characterization in a Heterologous Translation System," Protein Expression and Purification, 2000, vol. 18 (3), pp. 257-261.

Martineau F., et al., "Development of a PCR Assay for Identification of Staphylococci at Genus andSpecies Levels," Journal of Clinical Microbiology, 2001, vol. 39 (7), pp. 2541-2547.

Martineau F., et al., "Species-Specific and Ubiquitous-DNA-Based Assays for Rapid Identification of *Staphylococcus aureus*," Journal of Clinical Microbiology, 1998, vol. 36 (3), pp. 618-623.

Martin-Lopez J.V., et al., "Simultaneous PCR Detection of ica Cluster and Methicillin and Mupirocinresistance Genes in Catheter-Isolated Staphylococcus," International Microbiology, 2004, vol. 7 (1), pp. 63-66.

Mason V.P., et al., "Diversity and linkage of Replication and Mobilisation Genes in Bacillus Rolling Irclereplicating Plasmids from Diverse Geographical Origins," FEMS Microbiology Ecology, 2002, vol. 42 (2), pp. 235-241.

Matray T.J., et al., "Synthesis and Properties of RNA Analogs-Oligoribonucleotide N3→p5 Phosphoramidates," Nucleic Acids Research, 1999, vol. 27 (20), pp. 3976-3985.

Matsuoka M., et al., "Characteristic Expression of Three Genes, msr(A), mph(C) and erm(Y), Thatconfer Resistance to Macrolide Antibiotics on *Staphylococcus aureus*," FEMS Microbiology Letters, 2003, vol. 220 (2), pp. 287-293.

May A.C., "Percent Sequence Identity: The Need to be Explicit," Structure, 2004, vol. 12 (5), pp. 737-738.

McCabe K.M., et al., "Bacterial species identification after DNA amplification with a universal primer pair," Molecular Genetics and Metabolism, 1999, vol. 66 (3), pp. 205-211.

McLafferty F.W., et al., "Comparison of Algorithms and Databases for Matching Unknown Mass Spectra," Journal of the American Society for Mass Spectrometry, 1998, vol. 9 (1), pp. 92-95.

McLuckey S.A., et al., "Ion Trap Tandem Mass Spectrometry Applied to Small Multiply Charged Oligonucleotides with a Modified Base," Journal of the American Society for Mass Spectrometry, 1994, vol. 5, pp. 740-747.

Mehrotra M., et al., "Multiplex PCR for Detection of Genes for *Staphylococcus aureus* Enterotoxins, Exfoliative Toxins, Toxic Shock Syndrome Toxin 1, and Methicillin Resistance," Journal of Clinical Microbiology, 2000, vol. 38 (3), pp. 1032-1035.

Meiyu F., et al., "Detection of Flaviviruses by Reverse Transcriptase-Polymerase Chain Reaction with the Universal Primer Set," Microbiology and Immunology, 1997, vol. 41 (3), pp. 209-213.

Mellor J., et al., "Genotype Dependence of Hepatitis C Virus Load Measurement in Commercially Available Quantitative Assays," Journal of Clinical Microbiology, 1999, vol. 37 (8), pp. 2525-2532.

Merlino J., et al., "New Chromogenic Identification and Detection of *Staphylococcus aureus* andMethicillin-Resistant *S. aureus*," Journal of Clinical Microbiology, 2000, vol. 38 (6), pp. 2378-2380.

Merlino J., et al., "Rapid Detection of Non-Multidrug-Resistant and Multidrug-Methicillin-Resistant *Staphylococcus aureus* Using Cycling Probe Technology for the mecA Gene," European Journal of Clinical Microbiology & Infectious Diseases, 2003, vol. 22 (5), pp. 322-323.

Messmer T.O., et al., "Discrimination of *Streptococcus pneumoniae* from Other Upper respiratory tract Streptococci by arbitrary primed PCR," Clinical Biochemistry, 1995, vol. 28 (6), pp. 567-572.

Metzgar D., et al., "PCR Analysis of Egyptian Respiratory Adenovirus Isolates, Including Identification of Species, Serotypes and Coinfections," Journal of Clinical Microbiology, 2005, vol. 43 (11), pp. 5743-5752.

Miller K.W., et al., "A Compendium of Human Mitochondrial DNA Control Region: Development of an International Standard Forensic Database," Croatian Medical Journal, 2001, vol. 42 (3), pp. 315-327.

Miragaia M., et al., "Genetic Diversity among Methicillin-Resistant *Staphylococcus epidemidis*(MRSE," Microbial Drug Resistance, 2005, vol. 11 (2), pp. 83-93.

Miura-Ochiai R., et al., "Quantitative Detection and Rapid Identification of Human Adenoviruses," Journal of Clinical Microbiology, 2007, vol. 45 (3), pp. 958-967.

Mollet C., et al., "rpoB Sequence Analysis as a Novel Basis for Bacterial Identification," Molecular Microbiology, 1997, vol. 26 (5), pp. 1005-1011.

Monroy A.M., et al., "Exvaluation of Reverse Transcriptase Polymerase Chain Reaction for theDetection of Eastern Equine Encephalumyelitis Virus during Vector Surveillance," Journal of Medical Entomology, 1996, vol. 33 (3), pp. 449-457.

Moore C., et al., "Development and Evaluation of a Real-Time Nucleic Acid Sequence Based Amplification Assay for Rapid Detection of Influenza A," Journal of Medical Virology, 2004, vol. 74 (4), pp. 619-628.

Moricca S., et al., "Detection of *Fusarium oxysporum f.*sp. Vasinfectum in Cotton Tissue by Polymerase Chain Reaction," Plant Pathology, 1998, vol. 47 (4), pp. 486-494.

Morinaga N., et al., "Purification, Cloning and Charactarizarion of Variant LukE-LukD with Strong Leukocidal Activity of Staphylococcal Bi-Component Leukotoxin Family," Microbiology and Immunology, 2003, vol. 47 (1), pp. 81-90.

Morse R., et al., "Nucleotide Sequence of Part of the ropC Gene Encoding the B Subunit of DNADependentRNA Polymerase from some Gram-Positive Bacteria and Comparative Amino AcidSequence Analysis," Systematic and Applied Microbiology, 1996, vol. 19, pp. 150-157.

Muddiman D.C., et al., "Application of Secondary Ion and Matrix-Assisted Laser Desorption-Ionization Time-of-Flight Mass Spectrometry for the Quantitative Analysis of Biological Molecules," Mass Spectrometry Reviews, 1995, vol. 14 (6), pp. 383-429.

Muddiman D.C., et al., "Characterization of PCR Products from Bacilli Using Electrospray Ionization FTICR Mass Spectrometry," Analytical Chemistry, 1996, vol. 68 (21), pp. 3705-3712.

Muddiman D.C., et al., "Important Aspects Concerning the Quantification of Biomolecules by Time-of-Flight Secondaryion Mass Spectrometry," Applied Spectrometry, 1996, vol. 50 (2), pp. 161-166.

Muddiman D.C., et al., "Length and Base Composition of PCR-Amplified Nucleic Acids Using Mass Measurements from Electrospray Ionization Mass Spectrometry," Analytical Chemistry, 1997, vol. 69 (8), pp. 1543-1549.

Muddiman D.C., et al., "Precise Mass Measurement of a Double-Stranded 500 Base-(309 kDa) Polymerase Chain Reaction Product by Negative Ion Electrospray Ionization Fourier Transform Ion Cyclotron Resonance Mass Spectrometry," Rapid Communications in Mass Spectrometry, 1999, vol. 13 (2), pp. 1201-1204.

Muddiman D.C., et al., "Sequencing and Characterization of Larger Oligonucleotides by Electrospray Ionization Fourier Transform Ion Cyclotron Resonance Mass Spectrometry," Reviews in Analytical Chemistry, 1998, vol. 17 (1), pp. 1-68.

Muhammed W.T., et al., "Electrospray Ionization Quadrupole Time-of-Flight Mass Spectrometry and Guadrupole Mass Spectrometry for Genotyping Single Nucleotide Substitutions in Intact Polymerase Chain Reaction Products in K-Ras and p53," Rapid Communications in Mass Spectrometry, 2002, vol. 16 (24), pp. 2278-2285.

Murakami K., et al., "Identification of Methicillin-Resistant Strains of Staphylococci by PolymeraseChain Reaction," Journal of Clinical Microbiology, 1991, vol. 29 (10), pp. 2240-2244.

Mushegian A.R., et al., "A Minimal Gene Set for Cellular Life Derived by Comparison of Complete Bacterial Genomes," Proceedings of the National Academy of Science, 1996, vol. 93 (19), pp. 10268-10273.

Na B.K., et al., "Detection and Typing of Respiratory Adenoviruses in a Single-Tube Multiplex Polymerase Chain Reaction," Journal of Medical Virology, 2002, vol. 66 (4), pp. 512-517.

Nagpal M.L., et al., "Utility of 16S-23S rRNA Spacer Region Methodology: How Similar are Interspace Regions within a Genome and Between Strains for Closely Related Organisms?," Journal of Microbiological Methods, 1998, vol. 33, pp. 211-219.

Nagy M., et al., "Sequence Analysis of Porcine Adenovirus Serotype 5 Fibre Gene: Evidence for Recombination," Virus Genes, 2002, vol. 24 (2), pp. 181-185.

Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.

Nakagawa S., et al., "Gene sequences and specific detection for Panton-Valentine leukocidin," Biochemical and Biophysical Research Communications, 2005, vol. 328 (4), pp. 995-1002.

Nakao H., et al., "Development of a Direct PCR Assay for Detection of the Diphtheria Toxin Gene," Journal of Clinical Microbiology, 1997, vol. 35 (7), pp. 1651-1655.

Narita S., et al., "Phage conversion of Panton-Valentine leukocidin in *Staphylococcus aureus*: molecular analysis of a PVL-converting phage, cpSLT," Gene, 2001, vol. 268 (1-2), pp. 195-206.

Naumov G.I., et al., "Discrimination between the soil yeast species *Williopsis saturnus* and *Williopsis suaveolens* by the polymerase chain reaction with the universal primer N21," Microbiology, 2000, vol. 69 (2), pp. 229-233.

NEB Catalog. 1998/1999 pp. 1, 79, 121 and 284.

Neumann G., et al., "Host Range Restriction and Pathogenicity in the Context of Influenza Pandemic," Emerging Infectious Diseases, 2006, vol. 12 (6), pp. 881-886.

Newcombe J., et al., "PCR of Peripheral Blood for Diagnosis of Meningococcal Disease," Journal of Clinical Microbiology, 1996, vol. 34 (7), pp. 1637-1640.

Ng E.K., et al., "Quantitative Analysis an Prognostic Implication of SARS Coronavirus RNA in the Plasma and Serum of Patients with Severe Acute Respiratory Syndrome," Clinical Chemistry, 2003, vol. 49 (12), pp. 1976-1980.

Ng E.K., et al., "Serial Analysis of the Plasma Concentration of SARS Coronavirus RNA in Pediatric Patients with Severe Acute Respiratory Syndrome," Clinical Chemistry, 2003, vol. 49 (12), pp. 2085-2088.

Ni J., et al., "Interpretation of Oligonucleotide Mass Spectra for Determinationof Sequence Using Electrospray Ionization and Tandem Mass Spectrometry," Analytical Chemistry, 1996, vol. 68 (13), pp. 1989-1999.

Nilsson M., et al., "Evaluation of Mitochondrial DNA Coding Region Assays for Increased Discrimination in Forensic Analysis," Forensic Science International: Genetics, 2008, vol. 2 (1), pp. 1-8.

Nishikawa T., et al., "Reconstitution of Active Recombinant Ship Toxin (Stc)1 from Recombinant Stxl-A and Sbtl-B Subunits Independently Produced by *E. coli* Clones," FEMS Microbiol Letters, 1999, vol. 178 (1), pp. 13-18.

Non-Final Office Action mailed Oct. 6, 2008 for U.S. Appl. No. 11/070,632, filed Mar. 2, 2005.

Non-Final Office Action mailed Jun. 10, 2005 for U.S. Appl. No. 10/844,938, filed May 12, 2004.

Non-Final Office Action mailed Jul. 28, 2010 for U.S. Appl. No. 11/930,002, filed Oct. 30, 2007.

Norder H., et al., "Typing of Hepatitis B Virus Genomes by a Simplified Polymerase Chain Reaction," Journal of Medical Virology, 1990, vol. 31 (3), pp. 215-221.

Nordhoff E., et al., "Matrix Assisted Laser Desorption/Ionization Mass Spectrometry of Nucleic Acids with Wavelengths in the Ultraviolet and Infrared," Rapid Communications in Mass Spectrometry, 1992, vol. 6 (12), pp. 771-776.

Nubel U.,et al., "PCR primers to amplify 16S rRNA genes from Cyanobacteria," Applied andEnvironmental Microbiology, 1997, vol. 63 (8), pp. 3327-3332.

Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.

Null A.P., et al., "Determination of a Correction to Improve Mass Measurement Accuracy of Isotopically Unresolved Polymerase Chain Reaction Amplicons by Electrospray Ionization Fourier Transform Ion Cyclotron Resonance Mass Spectrometry," Rapid Communications in Mass Spectrometry, 2003, vol. 17 (15), pp. 1714-1722.

Null A.P., et al., "Evaluation of Sample Preparation Techniques for Mass Measurements of PCR Products Using ESIFT-ICR Mass Spectrometry," The American Society for Mass Spectrometry, 2002, vol. 13 (4), pp. 338-344.

Null A.P., et al., "Genotyping of Simple and Compound Short Tandem Repeat Loci Using Electrospray Ionization Fourier Transform Ion Cyclotron Resonance Mass Spectrometry," Analytical Chemistry, 2001, vol. 73 (18), pp. 4514-4521.

Null A.P., et al., "Implications of Hydrophobicity and Free Energy of Solvation for Characterization of Nucleic Acids by Electrospray Ionization Mass Spectrometry," Analytical Chemistry, 2003, vol. 75 (6), pp. 1331-1339.

Null A.P., et al., "Perspectives on the Use of Electrospray Ionization Fourier Transform Ion Cyclotron Resonance Mass Spectrometry for Short Tandem Repeat Genotyping in the Post Genome Era," Journal of Mass Spectrometry, 2001, vol. 36 (6), pp. 589-606.

Null A.P., et al., "Preparation of Single-Stranded PCR Products for Electrospray Ionization Mass Spectrometry Using the DNA Repair Enzyme Lambda Exonuclease," Analyst, 2000, vol. 125 (4), pp. 619-626.

Nunes E.L., et al., "Detection of ileS-2 Gene Encoding Mupirocin Resistance in Methicillin-Resistant*Staphylococcus aureus* by Multiplex PCR," Diagnostic Microbiology and Infectious Disease, 1999, vol. 34 (2), pp. 77-81.

Nygren M., et al., "Quantification of HIV-1 Using Multiple Quantitative Polymerase Chain ReactionStandards and Bioluminometric Detection," Analytical Biochemistry, 2001, vol. 288 (1), pp. 28-38.

Oberacher H., et al., "Analysis of Polymerase Chain Reaction Products by On-Line Liquid Chromatography Mass Spectrometry for Genotyping of Polymeric Short tandem Repeat Loci," Analytical Chemistry, 2001, vol. 73 (21), pp. 5109-5115.

Oberacher H., et al., "Increased foresnic efficiency of DNA fingerprints through simultaneous resolution of length and nucleotide variability by high-performance mass spectrometry," Human Mutation, 2008, vol. 29 (3), pp. 427-432.

Oberste M.S., et al., "Improved molecular identification of enteroviruses by RT-PCR and amplicon sequencing," Journal of Medical Virology, 2003, vol. 26 (3), pp. 375-377.

Oberste M.S., et al., "Molecular epidemiology and type-specific detection of echovirus 11 isolates fromthe Americas, Europe, Africa, Australia, southern Asia and the Middle East," Virus Research, 2003, vol. 91 (2), pp. 241-248.

Oberste M.S., et al., "Molecular phylogeny and proposed classification of the Simian picornaviruses," Journal of Virology, 2002, vol. 76 (3), pp. 1244-1251.

Office Action mailed Mar. 23, 2009 for U.S. Appl. No. 10/418,514, filed Apr. 18, 2003.

Office Action mailed Jul. 1, 2008 for U.S. Appl. No. 10/418,514, filed Apr. 18, 2003.

Office Action mailed Feb. 2, 2007 for U.S. Appl. No. 09/891,793, filed Jun. 26, 2001.

Office Action mailed Jul. 2, 2009 for U.S. Appl. No. 11/582,930, filed Oct. 17, 2006.

Office Action mailed May 2, 2008 for U.S. Appl. No. 11/582,930, filed Oct. 17, 2006.

Office Action mailed Apr. 3, 2002 for U.S. Appl. No. 09/891,793, filed Jun. 26, 2001.

Office Action mailed Jun. 3, 2009 for U.S. Appl. No. 11/331,978, filed Jan. 13, 2006.

Office Action mailed Oct. 3, 2005 for U.S. Appl. No. 10/326,046, filed Dec. 18, 2002.

Office Action mailed Jan. 4, 2002 for U.S. Appl. No. 09/891,793, filed Jun. 26, 2001.

Office Action mailed Aug. 5, 2010 for U.S. Appl. No. 11/233,630, filed Sep. 21, 2005.

Office Action mailed Sep. 5, 2006 for U.S. Appl. No. 10/660,996, filed Sep. 12, 2003.

Office Action mailed Aug. 6, 2009 for U.S. Appl. No. 10/728,486, filed Dec. 5, 2003.

Office Action mailed Dec. 6, 2007 for U.S. Appl. No. 10/418,514, filed Apr. 18, 2003.

Office Action mailed Jan. 6, 2009 for U.S. Appl. No. 10/660,996, filed Sep. 12, 2003.

Office Action mailed Nov. 6, 2008 for U.S. Appl. No. 10/728,486, filed Dec. 5, 2003.

Office Action mailed Oct. 6, 2009 for European Application No. 08730682.5 filed Feb. 25, 2008.

Office Action mailed Aug. 7, 2007 for U.S. Appl. No. 10/660,997, filed Sep. 12, 2003.

Office Action mailed Feb. 7, 2008 for European Application No. 03796752.8 filed Dec. 5, 2003.

Office Action mailed Jun. 8, 2007 for U.S. Appl. No. 11/210,516, filed Aug. 24, 2005.

Office Action mailed Dec. 9, 2004 for U.S. Appl. No. 10/156,608, filed May, 24, 2002.

Office Action mailed Feb. 9, 2009 for Chinese Application No. 02809122.1 filed Mar. 4, 2002.

Office Action mailed Mar. 9, 2004 for U.S. Appl. No. 09/891,793, filed Jun. 6, 2001.

Office Action mailed Aug. 10,1 2004 for U.S. Appl. No. 09/891,793, filed Jun. 26, 2001.

Office Action mailed Aug. 10, 2004 for U.S. Appl. No. 09/798,007, filed Mar. 2, 2001.

Office Action mailed Aug. 10, 2004 for U.S. Appl. No. 10/156,608, filed May 24, 2002.

Office Action mailed Aug. 10, 2004 for U.S. Appl. No. 10/326,642, filed Dec. 18, 2002.

Office Action mailed Aug. 10, 2005 for European Application No. 03796752.8 filed Dec. 5, 2003.

Office Action mailed Dec. 10, 2010 for U.S. Appl. No. 11/233,630, filed Sep. 21, 2005.

Office Action mailed Dec. 10, 2010 for U.S. Appl. No. 11/491,376, filed Jul. 21, 2006.

Office Action mailed Feb. 10, 2003 for U.S. Appl. No. 09/891,793, filed Jun. 26, 2001.

Office Action mailed Jun. 10, 2010 for U.S. Appl. No. 90/010,448, filed Apr. 9, 2009.

Office Action mailed Dec. 12, 2006 for U.S. Appl. No. 10/156,608, filed May 24, 2002.

Office Action mailed Feb. 12, 2009 for U.S. Appl. No. 11/136,134, filed May 24, 2005.

Office Action mailed Mar. 12, 2008 for European Application No. 06849755.1 filed Apr. 12, 2006.

Office Action mailed Nov. 12, 2009 for U.S. Appl. No. 10/728,486, filed Dec. 5, 2003.

Office Action mailed Jul. 13, 2004 for U.S Appl. No. 09/891,793, filed Jun. 26, 2001.

Office Action mailed Mar. 13, 2006 for U.S. Appl. No. 10/754,415, filed Jan. 9, 2004.

Office Action mailed Sep. 14, 2007 for U.S. Appl. No. 11/582,930, filed Oct. 17, 2006.

Office Action mailed Apr. 15, 2008 for U.S. Appl. No. 10/418,514, filed Apr. 18, 2003.

Office Action mailed Dec. 15, 2008 for U.S. Appl. No. 11/331,978, filed Jan. 13, 2006.

Office Action mailed Apr. 16, 2008 for U.S. Appl. No. 11/409,535, filed Apr. 21, 2006.
Office Action mailed Aug. 16, 2004 for U.S. Appl. No. 10/325,527, filed Dec. 18, 2002.
Office Action mailed Jan. 16, 2009 for U.S. Appl. No. 11/582,930, filed Oct. 17, 2006.
Office Action mailed Nov. 16, 2009 for Japanese Application No. 2005508560 filed Dec. 5, 2003.
Office Action mailed Feb. 17, 2010 for U.S. Appl. No. 10/660,122, filed Sep. 11, 2003.
Office Action mailed Jul. 17, 2007 for U.S. Appl. No. 09/891,793, filed Jun. 26, 2001.
Office Action mailed Aug. 18, 2009 for U.S. Appl. No. 11/685,598, filed Mar. 13, 2007.
Office Action mailed Feb. 18, 2010 for European Application No. 03814656 filed Dec. 5, 2003.
Office Action mailed Mar. 18, 2010 for U.S. Appl. No. 11/331,978, filed Jan. 13, 2006.
Office Action mailed Sep. 18, 2008 for Australian Application No. 2003298030 filed Dec. 5, 2003.
Office Action mailed Sep. 18, 2009 for U.S. Appl. No. 10/660,998, filed Sep. 12, 2003.
Office Action mailed Jun. 20, 2007 for U.S. Appl. No. 11/136,134, filed May 24, 2005.
Office Action mailed Dec. 21, 2006 for U.S. Appl. No. 11/060,135, filed Feb. 17, 2005.
Office Action mailed May 21, 2009 for U.S. Appl. No. 11/136,134, filed May 24, 2005.
Office Action mailed Oct. 21, 2008 for U.S. Appl. No. 11/582,859, filed Oct. 17, 2006.
Office Action mailed Jul. 22, 2008 for U.S. Appl. No. 90/010,209, filed Jun. 27, 2008.
Office Action mailed Jul. 23, 2009 for U.S. Appl. No. 11/070,634, filed Mar. 2, 2005.
Office Action mailed Oct. 23, 2003 for New Zealand Application No. 527857 filed Mar. 4, 2002.
Office Action mailed Aug. 24, 2010 for U.S. Appl. No. 90/010,210, filed Jun. 27, 2008,
Office Action mailed Feb. 24, 2010 for U.S. Appl. No. 10/728,486, filed Dec. 5, 2003.
Office Action mailed Jul. 24, 2007 for U.S. Appl. No. 11/060,135, filed Feb. 17, 2005.
Office Action mailed Jul. 24, 2009 for U.S. Appl. No. 11/754,182, filed May, 25, 2007.
Office Action mailed Nov. 24, 2009 for U.S. Appl. No. 11/331,978, filed Jan. 13, 2006.
Office Action mailed Oct. 24, 2008 for U.S. Appl. No. 11/582,930, filed Oct. 17, 2006.
Office Action mailed Mar. 26, 2008 for U.S. Appl. No. 11/136,134, filed May 24, 2005.
Office Action mailed Feb. 27, 2006 for U.S. Appl. No. 10/326,644, filed Dec. 18, 2002.
Office Action mailed Feb. 27, 2006 for U.S. Appl. No. 10/418,514, filed Apr. 18, 2003.
Office Action mailed Jan. 27, 2006 for U.S. Appl. No. 10/323,211, filed Dec. 18, 2002.
Office Action mailed Mar. 27, 2007 for U.S. Appl. No. 10/418,514, filed Apr. 18, 2003.
Office Action mailed May 28, 2008 for U.S. Appl. No. 10/660,998, filed Sep. 12, 2003.
Office Action mailed Oct. 28, 2008 for U.S. Appl. No. 11/331,987, filed Jan. 13, 2006.
Office Action mailed Oct. 29, 2008 for U.S. Appl. No. 11/331,978, filed Jan. 13, 2006.
Office Action mailed Oct. 29, 2009 for U.S. Appl. No. 10/660,122, filed Sep. 11, 2003.
Office Action mailed Sep. 29, 2005 for U.S. Appl. No. 10/418,514, filed Apr. 18, 2003.
Office Action mailed Sep. 29, 2009 for U.S. Appl. No. 10/418,514, filed Apr. 18, 2003.
Office Action mailed Jan 31, 2007 for Philippines Application No. PH12003500824 filed Mar. 4, 2002.
Office Action mailed Jul. 31, 2006 for U.S. Appl. No. 10/326,643, filed Dec. 18, 2002.
Office Action mailed Oct. 31, 2007 for U.S. Appl. No. 11/409,535, filed Apr. 21, 2006.
Office Action mailed Oct. 31, 2008 for U.S. Appl. No. 11/136,134, filed May 24, 2005.
O'Guinn M.L., et al., "Field Detection of Eastern Equine Encephalitis Virus in the Amazon BasinRegion of Peru Using Reverse Transcription-Polymerase Chain Reaction Adapted for FieldIdentification of Arthropod-Borne Pathogens," American Journal of Tropical Medicine and Hygiene, 2004, vol. 70 (2), pp. 164-171.
Oizumi N., et al., "Relationship between mutations in the DNA gyrase and topoisomerase IV genes and nadifloxacin resistance in clinically isolated quinolone-resistant Staphylococcus aureus," Journal of Infection and Chemotherapy, 2001, vol. 7 (3), pp. 191-194.
Okada M., et al., "Detection and sequence-based typing of human adenoviruses using sensitiveuniversal primer sets for the hexon gene," Archives of Virology, 2007, vol. 152 (1), pp. 1-9.
Okuma K., et al., "Dissemination of New Methicillin-Resistant Staphylococcus aureus Clones in the Community," Journal of Clinical Microbiology, 2002, vol. 40 (11), pp. 4289-4294.
Oliveira D.C., et al., "Genetic Organization of the Downstream Region of the mecA Element inMethicillin-Resistant Staphylococcus aureus Isolates Carrying Different Polymorphisms of This Region," Antimicrobial Agents and Chemotherapy, 2000, vol. 44 (7), pp. 1906-1910.
Oliveira D.C., et al., "Multiplex PCR Strategy for Rapid Identification of Structural Types and Variants of the mec Element in Methicillin-Resistant Staphylococcus aureus," Antimicrobial Agents and Chemotherapy, 2002, vol. 46 (7), pp. 2155-2161.
Olsen B., et al., "Transhemispheric Exchange of Lyme Disease Spyrochetes by Seabirds," Journal of Clinical Microbiology, 1995, vol. 33 (12), pp. 3270-3274.
Osiowy C., et al., "Direct Detection of Respiratory Syncytial Virus, Parainfluenza Virus, and Adenovirus in Clinical Respiratory Specimens by a Multiplex Reverse Transcription-PCR Assay," Journal of Clinical Microbiology, 1998, vol. 36 (11), pp. 3149-3154.
Ostrander E.A., et al., "Identification and Characterization of Dinucleotide Repeat (CA)n Markers for Genetic Mapping in Dog," Genomics, 1993, vol. 16 (1), pp. 207-213.
Ounissi H., et al., "Gene Homogeneity for Aminoglycoside-Modifying Enzymes in Gram-PositiveCocci," Antimicrobial Agents and Chemotherapy, 1990, vol. 34 (11), pp. 2164-2168.
Palys T., et al., "Discovery and Classification of Ecological Diversity in the Bacterial World: the Role of DNA Sequence Data," International Journal of Systematic Bacteriology, vol. 47 (4), pp. 1145-1156.
Pan ZQ., et al., "Oligonucleotide-targeted degradation of U1 and U2 snRNAs reveals differential interactions of simian virus 40 pre-mRNAs with snRNPs," Nucleic Acids Research, 1989, vol. 17 (16), pp. 6553-6568.
Pannetier C., et al., "Quantitative Titration of Nucleic Acids by Enzymatic Amplification Reactions run to Saturation," Nucleic Acids Research, 1993, vol. 21 (3), pp. 577-583.
Parson W., et al., "Population Data for 101 Austrian Caucasian Mitochondrial DNA d-Loop Sequences: Application of mtDNA Sequence Analysis to a Forensic Case," International Journal of Legal Medicine, 1998, vol. 111 (3), pp. 124-132.
Partial European Search Report for Application No. EP01106974, mailed on Dec. 16, 2002, 2 pages.
Pastorino B., et al., "Development of a TaqMan PCR assay without RNA extraction step for the detection and quantification of African Chikungunya viruses," Journal of Virological Methods, 2005, vol. 124 (1-2), pp. 65-71.
Paterson A.H., et al., "Fine Mapping of Quantitative Trait Loci Using Selected Overlapping RecombinantChromosomes, in an Interspecies Cross of Tomato," Genetics, 1990, vol. 124 (3), pp. 735-742.
Pawa A., et al., "Co-transfer of plasmids in association with conjugative transfer of mupirocin or mupirocin and penicillin resistance in methicillin-resistant Staphylococcus aureus," Journal of Clinical Microbiology, 2000, vol. 49 (12), pp. 1103-1107.

Payne D., et al., "Antimicrobials: The Challenge of Antibiotic Resistant Bacterial Pathogens: The Medical Need, The Market and Prospects for New Antimicrobial Agents," Current Opinion in Microbiology, 2004, vol. 7, pp. 435-438.

Peng X., et al., "Rapid Detection of *Shigella* Species in Environmental Sewage by an Immunocapture PCR with Universal Primers," Applied and Environmental Microbiology, 2002, vol. 68 (5), pp. 2580-2583.

Perez-Roth E., et al., "Multiplex PCR for Simultaneous Identification of *Staphylococcus aureus* andDetection of Methicillin and Mupirocin Resistance," Journal of Clinical Microbiology, 2001, vol. 39 (11), pp. 4037-4041.

Peters S.E., et al., "Quantification of the detection of *Pneumocystis carinii* by DNA amplification," Molecular and Cellur Probes, 1992, vol. 6 (2), pp. 115-117.

Pfeffer M., et al., "Genus-Specific Detection of Alphaviruses by a Semi-Nested ReverseTranscription-Polymerase Chain Reaction," American Journal of Tropical Medicine and Hygiene, 1997, vol. 57 (6), pp. 709-718.

Pfeffer M., et al., "Specific Detection of Chikungunya Virus Using a RT-PCR/Nested PCR Combination," Journal of Veterinary Medicine B, 2002, vol. 49 (1), pp. 49-54.

Pieles U., et al., "Matrix-Assisted Laser Desorption Ionization Time-of-Flight Spectrometry: APowerful Tool for the Mass and Sequence Analysis of Natural and Modified Oligonucleotides, 787 reexamination," Nucleic Acids Research, 1993, vol. 21 (14), pp. 3191-3196.

Pillai S.D., et al., "Rapid molecular detection of microbial pathogens: breakthroughs and challenges," Archives of Virology, 1997, vol. 13, pp. 67-82.

Piper J., et al., "Commercially Available Technique for Rapid Laboratory Detection of MethicillinResistance Among *Staphylococcus aureus*," Diagnostic Microbiology and Infectious Disease, 1988, vol. 11 (3), pp. 177-180.

Poddar S.K., et al., "Detection of adenovirus using PCR and molecular beacon," Journal of Virological Methods, 1999, vol. 82 (1), pp. 19-26.

Pomerantz S.C., et al., "Determination of oligonucleotide composition from mass spectrometrically measured molecular weight," Journal of the American Society for Mass Spectrometry, 1993, vol. 4 (3), pp. 204-209.

Pring-Akerblom P., et al., "Multiplex Polymerase Chain Reaction for Subgenus-Specific Detection of Human Adenoviruses in Clinical Samples," Journal of Medical Virology, 1999, vol. 58 (1), pp. 87-92.

Pring-Akerblom P., et al., "PCR-based detection and typing of human adenoviruses in clinical samples," Research in Virology, 1997, vol. 148 (3), pp. 225-231.

Promega. T4 Polynucleotide Kinase, Technical Bulletin No. 519, 2002.

Puthavathana P., et al., "Molecular characterization of the complete genome of human influenza H5N1 virus Isolates from Thailand," Journal of General Virology, 2005, vol. 86 (2), pp. 423-433.

Qadri S.M., et al., "Rapid Detection of Methicillin-Resistant *Staphylococcus aureus* by CrystalMRSA ID System," Journal of Clinical Microbiology, 1994, vol. 32 (7), pp. 1830-1832.

Raaum R.L., et al., "Catarrhine Primate Divergence Dates Estimated from Complete Mitochondria Genomes: Concordance with Fossil and Nuclear DNA Evidence," Journal of Human Evolution, 2005, vol. 48 (3), pp. 237-257.

Ramisse V., et al., "Identification and characterization of *Bacillus anthracis* by multiplex PCR analysis of sequences on plasmids pX01 and pX02 and chromosomal DNA," FEMS Microbiology Letters, 1996, vol. 145 (1), pp. 9-16.

Reid S.M., et al., "Primary Diagnosis of Foot-and-Mouth Disease by Reverse Transcription Polymerase Chain Reaction," Journal of Virological Methods, 2000, vol. 89 (1-2), pp. 167-176.

Reilly K., et al., "Design and Use of 16s Ribosomal DNA-Directed Primers in Competitive PCRs to Enumerate Proteolytic Bacteria in the Rumen," Microbial Ecology, 2002, vol. 43 (2), pp. 259-270.

Reischl U., "Application of Molecular Biology-Based Methods to theDiagnosis of Infectious Diseases 1, e72-e77.," Frontiers in Bioscience, 1996, vol. 1 (1), pp. e72-e77.

Reischl U., et al., "Rapid Identification of Methicillin-Resistant *Staphylococcus aureus* and Simultaneous Species Confirmation Using Real-Time Fluorescence PCR," Journal of Clinical Microbiology, 2000, vol. 38 (6), pp. 2429-2433.

Roberts M.M., et al., "Three-Dimensional Structure of the Adenovirus Major Coat Protein Hexon," Science, 1986, vol. 232 (4754), pp. 1148-1151.

Roberts M.S., et al., "Recombination and Migration Rates in Natural Populations of *Bacillus subtilis* and *Bacillus mojavensis*," Evolution, 1995, vol. 49 (6), pp. 1081-1094.

Robinson D.A., et al., "Multilocus sequence typing and the evolution of methicillin-resistant*Staphylococcus aureus*," Clinical Microbiology and Infection, 2004, vol. 10, pp. 92-97.

Rong S., et al., "Design and Application of 60mer Oligonucleotide Microarray in SARS Coronavirus Detection," Chinese Science Bulletin, 2003, vol. 48 (12), pp. 1165-1169.

Ross P.L., et al., "Analysis of DNA Fragments from Conventional and Microfabricated PCR Devices Using Delayed Extraction MALDI-TOF Mass Spectrometry," Analytical Chemistry, 1998, vol. 70 (10), pp. 2067-2073.

Ross P.L., et al., "Discrimination of Single-Nucleotide Polymorphisms in Human DNA Using Peptide Nucleic Acid Probes Detected by MALDI-TOF Mass Spectrometry," Analytical Chemistry, 1997, vol. 69 (20), pp. 4197-4202.

Rota P.A., et al., "Sequencing of a cDNA clone of the nucleoprotein gene of influenza B/Ann Arbor/1/86," Nucleic Acids Research, 1989, vol. 17 (9), pp. 3595.

Ruan Y., et al., "Comparative full-length genome sequence analysis of 14 SARS coronavirus isolates and common mutations associated with the putative origins of infection," The Lancet, 2003, vol. 361, pp. 1779-1785, 1832.

Ruest A., et al., "Comparison of the Directigen Flu A+B test, the QuickVue Influenza Test, and Clinical Case Definition to Viral Culture and Reverse Transcription-PCR for Rapid Diagnosis of Influenza Virus Infection," Journal of Clinical Microbiology, 2003, vol. 41 (8), pp. 3487-3493.

Rupf S., et al., "Quantitative determination of *Streptococcus mutans* by using competitive polymerasechain reaction," European Journal of Oral Sciences, 1999, vol. 107 (2), pp. 75-81.

Russell K.L., et al., "Transmission Dynamics and Prospective Environmental Sampling of Adenovirus in a Military Recruit Setting," Journal of Infectious Diseases, 2006, vol. 194 (7), pp. 877-885.

Sabat A., et al., "Comparison of PCR-Based Methods for Typing *Staphylococcus aureus* Isolates" Journal of Clinical Microbiology, 2006, vol. 44 (10), pp. 3804-3807.

Sackesen C., et al., "Use of polymerase chain reaction for detection of adenovirus in children withor without wheezing," Turkish Journal of Pediatrics, 2005, vol. 47 (3), pp. 227-231.

Sakai H., et al., "Simultaneous Detection of *Staphylococcus aureus* and Coagulase-Negative Staphylococci in Positive Blood Cultures by Real-Time PCR with Two Fluorescence Resonance Energy Transfer Probe Sets," Journal of Clinical Microbiology, 2004, vol. 42 (12), pp. 5739-5744.

Sala M., et al., "Ambiguous Base Pairing of the Purine Analogue 1-(2-Deoxy-B-D-Ribofuranosyl)-Imidazole-4-Carboxamide During PCR," Nucleic Acids Research, 1996, vol. 24 (17), pp. 3302-3306.

Sambrook J., et al., "Molecular Cloning—A Laboratory Manual," 1989, Cold Spring Harbor Laboratory Press, Table of Contents.

Sampath R., et al., "Global Surveillance of Emerging Influenza Virus Genotypes by Mass Spectrometry," Plos ONE, 2007, vol. 2 (5), pp. e489.

Sampath R., et al., "Rapid Identification of Emerging Infectious Agents using PCR and Electrospray Ionization Mass Spectrometry," Annals of the New York Academy of Science, 2007, vol. 1102, pp. 109-120.

Sampath R., et al., "Rapid Identification of Emerging Pathogens: Coronavirus," Emerging Infectious Diseases, 2005, vol. 11 (3), pp. 373-379.

Sanchez A., et al., "Detection and molecularcharacterization of Ebola viruses causing disease in human and nonhuman primates," Journal of Infectious Diseases, 1999, vol. 179 (1), pp. S164-S169.

Sanchez J.L., et al., "Epidemic of Adenovirus-Induced Respiratory Illness Among US Military Recruits: Epidemiologic and Immunologic Risk Factors in Healthy, Young adults," Journal of Medical Virology, 2001, vol. 65 (4), pp. 710-718.

Sanchez-Seco M.P., et al., "A Generic Nested-RT-PCR followed by Sequencing for Detection and Identification of Members of the *Alphavirus* Genus," Journal of Virological Methods, 2001, vol. 95 (1-2), pp. 153-161.

Santos S.R., et al., "Identification and phylogenetic sorting of bacterial lineages with universally conserved genes and proteins," Environmental Microbiology, 2004, vol. 6 (7), pp. 754-759.

Sarantis H., et al., "Comprehensive Detection and Serotyping of Human Adenoviruses by PCR and Sequencing," Journal of Clinical Microbiology, 2004, vol. 42 (9), pp. 3963-3969.

Sauer S., et al., "A Novel Procedure for Efficient Genotyping of Single Nucleotide Polymorphisms," Nucleic Acids Research, 2000, vol. 28 (5), pp. E13.1-E13.8.

Scaramozzino N., et al., "Comparison of Flavivirus universal Primer Pairs and Development of a Rapid, Highly Sensitive Heminested Reverse Transcription-PCR Assay for Detection of Flaviviruses Targeted to a Conserved Region of the NS5 Gene Sequences," Journal of Clinical Microbiology, 2001, vol. 39 (5), pp. 1922-1927.

Schabereiter-Gurtner C., et al., "Application of Broad-Range 16s rRNA PCR Amplification and DGGE Fingerprinting for Detection of Tick-Infecting Bacteria," The Journal of Microbiological Methods, 2003, vol. 52 (2), pp. 251-260.

Scheffner M., et al., "The E6 Oncoprotein Encoded by Human Papillomavirus Types 16 and 18 Promotes the Degradation of p53," Cell, 1990, vol. 63 (6), pp. 1129-1136.

Schena M., et al., "Genome Analysis with Gene Expression Microarrays," Bioessays, 1996, vol. 18 (5), pp. 427-431.

Scheuermann R.N., et al., "Polymerase chain-reaction-based mRNA quantification Using an internal standard: analysis of oncogene expression," Methods in Enzymology, 1993, vol. 218, pp. 446-473.

Schlecht N. F., et al., "Viral Load as a Predictor of the Risk of Cervical Intraepithelial Neoplasia," British Journal of Cancer, 2003, vol. 103 (4), pp. 519-524.

Schmidt T.M., et al., "Analysis of a marine pikoplankton community by 16s rRNA gene cloning and sequencing," Journal of Bacteriology, 1991, vol. 173 (14), pp. 4371-4378.

Schmitz F.J., et al., "Development of a Multiplex-PCR for Direct Detection of the Genes for Enterotoxin B and C, and Toxic Shock Syndrome Toxin-1 in *Staphylococcus aureus* Isolates," Journal of Medical Microbiology, 1998, vol. 47 (4), pp. 335-340.

Schmitz F.J., et al., "Development of Resistance to Ciprofloxacin, Rifampin, and Mupirocin inMethicillin-Susceptible and -Resistant *Staphylococcus aureus* Isolates," Antimicrobial Agents and Chemotherapy, 2000, vol. 44 (11), pp. 3229-3231.

Schmitz F.J., et al., "Specific information concerning taxonomy, pathogenicity and methicillin esistance of staphylococci obtained by a multiplex PCR," Journal of Medical Microbiology, 1997, vol. 46 (9), pp. 773-778.

Schram K.H., et al., "Mass Spectrometry of Nucleic Acid Components," Methods of Biochemical Analysis, 1990, vol. 34, pp. 203-280.

Schultz J.C., et al., "Polymerise Chain Reaction Products Analyzed by Charge Detection Mass Spectrometry," Rapid Communications in Mass Spectrometry, 1999, vol. 13 (1), pp. 15-20.

Schwartz M., et al., "Prenatal Diagnosis of Alpha-1-Antitrypsin Deficiency Using Polymerase Chainreaction (PCR). Comparison of Conventional RFLP Methods with PCR used in Combination with Allelespecific Oligonucleotides or RFLP analysis, 787 Reexamination," Clinical Genetics, 1989, vol. 36 (6), pp. 419-426.

Schweiger B., et al., "Application of a Fluorogenic PCR Assay for Typing and Subtyping of Influenza Viruses in Respiratory Samples," Journal of Clinical Microbiology, 2000, vol. 38 (4), pp. 1552-1558.

Sciacchitano C.J., "Analysis of Polymerase Chain Reaction-Amplified DNA Fragments of *Clostridium botulinum* Type E Neurotoxin Gene by High Performance Capillary Electrophoresis," Journal of Liquid Chromatography & Related Technologies, 1996, vol. 19 (13), pp. 2165-2178.
Scott-Taylor T.H., et al., "Conserved Sequences of the Adenovirus Genome for Detection of all Human Adenovirus Types by Hybridization," Journal of Clinical Microbiology, 1992, vol. 30 (7), pp. 1703-1710.
Seifarth W., et al., "Rapid identification of all known retroviral reverse transcriptase sequences with a novel versatile detection assay," AIDS Research and Human Retroviruses, 2000, vol. 16 (8), pp. 721-729.
Sellner L., et al., "A Single-Tube Nested RT-PCR for the Detection of Ross River Virus," Methods in Molecular Biology, 1998, vol. 92, pp. 145-152.
Sellner L.N., et al., "Sensitive detection of Ross River virus—a one-tube nested RT-PCR," Journal ofVirological Methods, 1994, vol. 49 (1), pp. 47-58.
Senko M.W., et al., "Determination of Monoisotopic Masses and Ion Populations for Large Biomoleculesfrom Resolved Isotopic Distributions," Journal of the American Society for Mass Spectrometry, 1995, vol. 6, pp. 229-233.
Seshadri R., et al., "Differential Expression of Translational Elements by Life Cycle Variants of *Coxiella burnetii*," Infection and Immunity, 1999, vol. 67 (11), pp. 6026-6033.
Shadan F.F., et al., "n-Butyrate, a Cell Cycle Blocker, Inhibits the Replication of Polyomaviruses and Papillomaviruses but Not That of Adenoviruses and Herpesviruses," Journal of Virology, 1994, vol. 68 (8), pp. 4785-4796.
Shaver Y.J., et al., "Restriction Fragment Length Polymorphism of rRNA Operons for Discrimination and Intergenic Spacer Sequences for Cataloging of *Bacilus subtilis* Sub-Groups," Journal of Microbiological Methods, 2002, vol. 50 (2), pp. 215-223.
Shaver Y.J., et al., "Variation in 16s-23s rRNA Intergenic Spacer Regions Among *Bacilus subtilis* 168 Isolates," Molecular Microbiology, 2001, vol. 42 (1), pp. 101-109.
Shimaoka M., et al., "Detection of the gene for toxic shock syndrome toxin 1 in *Siaphylococcusaureus* by enzyme-labelled oligonucleotideprobes," Journal of Medical Microbiology, 1996, vol. 44 (3), pp. 215-218.
Shimaoka M., et al., "Development of Enzyme-Labeled Oligonucleotide Probe for Detection of mecA gene in Methicillin-Resistant *Staphylococcus aureus*," Journal of Clinical Microbiology, 1994, vol. 32 (8), pp. 1866-1869.
Shrestha N. K., et al., "Rapid Identification of *Staphylococcus aureus* and the mecA Gene from BacT/ALERT Blood Culture Bottles by Using the Lightcycler System," Journal of Clinical Microbiology, 2002, vol. 40 (7), pp. 2659-2661.
Simonsen L., et al., "The Impact of Influenza Epidemics on Hospitalizations," Journal of Infectious Diseases, 2000, vol. 181 (3), pp. 831-837.
Skov R.L., et al., "Evaluation of a new 3-h hybridization method for detecting the mecA gene in *Staphylococcus aureus* and comparison with existing genotypic and phenotypic susceptibility testing methods," Journal of Antimicrobial Chemotherapy, 1999, vol. 43 (4), pp. 467-475.
Smirnov I.P., et al., "Application of DNA-binding polymers for preparation of DNA for analysis by matrix-assisted laser desorption/ionization mass spectrometry," Rapid Communications in Mass Spectrometry, 2001, vol. 15 (16), pp. 1427-1432.
Smith T.F., "Comparison of Biosequences," Advances in Applied Mathematics, 1981, vol. 2, pp. 482-489.
Song F., et al., "Identification of cry11-type Genes from *Bacilus thuringiensis* Strains and Characterization of a Novel Cry11-Type Gene," Applied and Environmental Microbiology, 2003, vol. 69, pp. 5207-5211.
Spackman E., et al., "Development of a real-time reverse transcriptase PCR assay for type a influenzavirus and the avian H5 and H7 hemagglutinin subtypes," Journal of Clinical Microbiology, 2002, vol. 40 (9), pp. 3256-3260.
Spiess L., et al., "Trehalose is a potent PCR enhancer: Lowering of DNA melting temperature and thermal stabilization of Taq polymerase by the disaccharide trehalose," Clinical Chemistry, 2004, vol. 50 (7), pp. 1256-1259.
Srinivasan J.R., et al., "Matrix-Assisted Laser Desorption/lonization Time-of-Flight Mass Spectrometry as a Rapid Screening Method to Detect Mutations Causing Tay-Sachs Disease," Rapid Communications in Mass Spectrometry, 1997, vol. 11 (10), pp. 1144-1150.
Steffens D.L., et al., "Sequence Analysis of Mitochondrial DNA Hypervariable Regions Using Infrared Fluorescence Detection," BioTechniques, 1998, vol. 24 (6), pp. 1044-1046.

Stephensen C.B., et al., "Phylogenetic analysis of a highly conserved region of the poymerase gene from 11 coronaviruses and development of a consensus poymerase chain reaction assay," Virus Research, 1999, vol. 60 (2), pp. 181-189.

Stone B., et al., "Rapid detection and simultaneous subtype differentiation of influenza a viruses by real time PCR," Journal of Virological Methods, 2004, vol. 117 (2), pp. 103-112.

Stratagene Catalog. 1988, p. 39.

Strommenger B., et al., "Multiplex PCR Assay for Simultaneous Detection of Nine Clinically Relevant Antibiotic Resistance Genes in *Staphylococcus aureus*," Journal of Clinical Microbiology, 2003, vol. 41 (9), pp. 4089-4094.

Studdert M.J., et al., "Polymerase Chain Reaction Tests for the Identification of Ross River, Kunjin and Murray Valley Encephalitis Virus Infections in Horses," Australian Veterinary Journal, 2003, vol. 81 (1-2), pp. 76-80.

Stuhlmeier R., et al., "Fast, Simultaneous, and Sensitive Detection of Staphylococci," Journal of Clinical Pathology, 2003, vol. 56 (10), pp. 782-785.

Sumner J.W., et al., "PCR Amplification and Comparison of Nucleotide Sequences from the groESL Heat Shock Operon of *Ehrlichia* Species," Journal of Critical Microbiology, 1997, vol. 35 (8), pp. 2087-2092.

Sundsfjord A., et al., "Genetic Methods for Detection of Antimicrobial Resistance," APMIS : Acta Pathologica, Microbiologica, et Immunologica Scandinavica, 2004, vol. 112 (11-12), pp. 815-837.

Supplementary European Search Report for Application No. EP02709785.6, mailed Sep. 1, 2005, 5 pages.

Supplementary European Search Report for Application No. EP02709785.6, mailed on Oct. 12, 2005, 17 pages.

Supplementary European Search Report for Application No. EP03796752.8, mailed on Aug. 7, 2007, 3 pages.

Supplementary European Search Report for Application No. EP03810055.8, mailed on Jun. 8, 2007, 4 pages.

Supplementary European Search Report for Application No. EP03814656, mailed on Oct. 16, 2007, 2 pages.

Supplementary European Search Report for Application No. EP04752257.8, mailed on Feb. 15, 2006, 2 pages.

Supplementary European Search Report for Application No. EP05753037, mailed on Aug. 21, 2009, 2 pages.

Supplementary European Search Report for European Application No. 04775904.8, mailed on Jul. 7, 2008, 8 pages.

Supplementary Partial European Search Report for Application No. EP05751872.2, mailed on Jan. 28, 2008, 8 pages.

Supplementary Partial European Search Report for Application No. EP05856582.1, mailed on Oct. 27, 2008, 10 pages.

Swaminathan B., et al., "PulseNet: The Molecular Subtyping Network for Foodborne Bacterial Disease Surveillance, United States," Emerging Infectious Diseases, 2001, vol. 7 (3), pp. 382-389.

Swanborg R.H., et al., "Human Herpesvirus 6 and *Chlamydia pneumoniae* as Etiologic Agents in Multiplesclerosis—a Critical Review," Microbes and Infection / Institut Pasteur, 2002, vol. 4 (13), pp. 1327-1333.

Swenson J.M., et al., "Performance of Eight Methods, Including Two New Rapid Methods, for Detection of Oxacillin Resistance in a Challenge Set of *Staphylococcus aureus* Organisms," Journal of Clinical Microbiology, 2001, vol. 39 (10), pp. 3785-3788.

Takagaki Y., et al., "Four Factors are Required for 3'-End Cleavage of Pre-mRNAs," Genes and Development, 1989, vol. 3 (11), pp. 1711-1724.

Takahashi H., et al., "Characterization of gryA, gryB, grlA and grlB mutations in fluoroquinolone-resistant clinical isolates of *Staphylococcus aureus*," The Journal of Antimicrobial Chemotherapy, 1998, vol. 41 (1), pp. 49-57.

Takahata M., et al., "Mutations in the GyrA and Gr1A Genes of Quinolone-Resistant Clinical Isolates of Methicillin-Resistant *Staphylococcus aureus*," The Journal of Antimicrobial Chemotherapy, 1996, vol. 38 (3), pp. 543-546.

Takayama R., et al., "Quantification of Adenovirus Species B and C Viremia by Real-Time PCR in Adults and Children Undergoing Stem Cell Transplantation," Journal of Medical Virology, 2007, vol. 79 (3), pp. 278-284.

Takeuchi S., et al., "Serotyping of Adenoviruses on Conjunctival Scrapings by PCR and Sequence Analysis," Journal of Clinical Microbiology, 1999, vol. 37 (6), pp. 1839-1845.

Talaat A.M., et al., "Genome-Directed Primers for Selective Labeling of Bacterial Transcripts for DNA Microarray Analysis," Nature Biotechnology, 2000, vol. 17, pp. 679-682.

Tan T.Y., "Use of Molecular Techniques for the Detection of Antibiotic Resistance in Bacteria," Expert review of Molecular diagnostics, 2003, vol. 3 (1), pp. 93-103.

Tanabe F., et al., "The Properties and Mec A Gene of the Methicillin-Resistant *Staphylococcus aureus* Isolated in Fukushima Medical College Hospital," Fukushima Journal of Medical Science, 1993, vol. 39 (1), pp. 35-42.

Tang K., et al., "Detection of 500-Nucleotide DNA by Laser Desorption Mass Spectrometry," Rapid Communications in Mass Spectrometry, 1994, vol. 8 (9), pp. 727-730.

Tang K., et al., Double-Stranded DNA Analysis by Matrix Assisted Laser Desorption/Ionization, 42nd ASMS Conference on Mass Spectrometry, 1994.

Tang K., et al., "Matrix-Assisted Laser Desorption/Ionization of Restriction Enzyme-Digested DNA," Rapid Communications in Mass Spectrometry, 1994, vol. 8 (2), pp. 183-186.

Tang K., et al., "Matrix-Assisted Laser Desorption/Ionization Mass Spectrometry of Oligonucleotides," Dissertation submitted to the Faculty of Vanderbilt University, 1994.

Tarassishin L., et al., "Adenovirus Core Protein VII Displays a Linear Epitope Conserved in a Range of Human Adenoviruses," Journal of General Virology, 1999, vol. 80 (Pt 1), pp. 47-50.

Tarassishin L., et al., "An Epitope on the Adenovirus Fibre Tail is Common to all Human Subgroups," Archives of Virology, 2000, vol. 145 (4), pp. 805-811.

Tatuch Y., et al., "Heteroplasmic mtDNA Mutation (T-G) at 8993 Can Cause Leigh Disease When the Percentage of Abnormal mtDNA is High," The American Journal of Human Genetics, 1992, vol. 50 (4), pp. 852-858.

Taubenberger J.K., et al., "Characterization of the 1918 Influenza Virus Polymerase Genes," Nature, 2005, vol. 437 (7060), pp. 889-893.

Taylor L.H., et al., "Risk Factors for Human Disease Emergence," Philosophical Transactions of the Royal Society of London Series B, Biological Sciences, 2001, vol. 356 (1411), pp. 983-989.

Tenover F.C., et al., "Characterization of a Strain of Community-Associated Methicillin-Resistant*Slaphylococcus aureus* Widely Disseminated in the United States," Journal of Clinical Microbiology, 2006, vol. 44 (1), pp. 108-118.

Teramura T., et al., "Quantitative Detection of Serum Adenovirus in a Transplant Recipient," Lancet, 2002, vol. 359 (9321), pp. 1945.

Thiel V., et al., "Infectious RNA Transcribed in Vitro from a cDNA Copy of the Human Coronavirus Genome Cloned in Vaccinia Virus," The Journal of General Virology, 2001, vol. 82 (Pt 6), pp. 1273-1281.

Thompson J.D., et al., "Clustal W: Improving the Sensitivity of Progressive Multiple Sequence Alignmen Through Sequence Weighting, Position-Specific Gap Penalties and Weight Matrix Choice," Nucleic Acids Research, 1994, vol. 22 (22), pp. 4673-4680.

Thompson W.W., et al., "Influenza-Associated Hospitalizations in the United States," The Journal of the American Medical Association, 2004, vol. 292 (11), pp. 1333-1340.

Tokue Y., et al., "Comparison of a Polymerase Chain Reaction Assay and a Conventional Microbiologic Method for Detection of Methicillin-Resistant *Slaphylococcus aureus*," Antimicrobial Agents and Chemotherapy, 1992, vol. 36 (1), pp. 6-9.

Tong J., et al., "Ligation Reaction Specificities of an Nad+-Dependent DNA Ligase from the Hyperthermophile *Aquifex aeolicus*," Nucleic Acids Research, 2000, vol. 28 (6), pp. 1447-1454.

Top FH Jr., "Control of Adenovirus Acute Respiratory Disease in U.S. Army Trainees," The Yale Journal of Biology and Medicine, 1975, vol. 48 (3), pp. 185-195.

Towner K.J., et al., "Development and Evaluation of a PCR-Based Immunoassay for the Rapid Detection of Methicillin-Resistant *Staphylococcus aureus*," Journal of Medical Microbiology, 1998, vol. 47 (7), pp. 607-613.

Tsuneyosh I, et al., "Mass Spectrometric Gene Diagnosis of One-Base Substitution from Polymerase Chain Reaction Amplified Human DNA," Rapid Communications in Mass Spectomerty, 1997, vol. 11 (7), pp. 719-722.

Tsunoda T., et al., "Time and Memory Efficient Algorithm for Extracting Palindromic and RepetitiveSubsequences in Nucleic Acid Sequences," Pacific Symposium on Biocomputing, 1999, vol. 4, pp. 202-213.

Udo E.E., et al., "A Chromosomal Location of the MupA Gene in *Staphylococcus aureus* Expressing High-Level Mupirocin Resistance," The Journal of Antimicrobial Chemotherapy, 2003, vol. 51 (5), pp. 1283-1286.

Udo E.E., et al., "Genetic Analysis of Methicillin-Resistant *Staphylococcus aureus* Expressing High-and Low-Level Mupirocin Resistance," Journal of Medical Microbiology, 2001, vol. 50 (10), pp. 909-915.

Udo E.E., et al., "Rapid Detection of Methicillin Resistance in Staphylococci Using a Slide Latex Agglutination Kit," International Journal of Antimicrobial Agents, 2000, vol. 15 (1), pp. 19-24.

Unal S., et al., "Detection of Methicillin-Resistant Staphylococci by Using the Polymerase Chain Reaction," Journal of Clinical Microbiology, 1992, vol. 30 (7), pp. 1685-1691.

Upton A., et al., "Mupirocin and *Staphylococcus aureus*: A Recent Paradigm of Emerging Antibiotic Resistance," The Journal of Antimicrobial Chemotherapy, 2003, vol. 51 (3), pp. 613-617.

U.S. Appl. No. 60/369,405.
U.S. Appl. No. 60/397,365.
U.S. Appl. No. 60/431,319.
U.S. Appl. No. 60/443,443.
U.S. Appl. No. 60/443,788.
U.S. Appl. No. 60/447,529.
U.S. Appl. No. 60/453,607.
U.S. Appl. No. 60/461,494.
U.S. Appl. No. 60/470,175.
U.S. Appl. No. 60/501,926.
U.S. Appl. No. 60/509,911.
U.S. Appl. No. 60/604,329.
U.S. Appl. No. 60/615,387.
U.S. Appl. No. 60/658,248.
U.S. Appl. No. 60/701,404.
U.S. Appl. No. 60/705,631.
U.S. Appl. No. 60/720,843.
U.S. Appl. No. 60/747,607.
U.S. Appl. No. 60/771,101.
U.S. Appl. No. 60/773,124.
U.S. Appl. No. 60/891,479.
U.S. Appl. No. 60/941,641.

Vabret A., et al., "Development of a PCR-and Hybridization-Based Assay (PCR Adenovirus Consensus) for the Detection and the Species Identification of Adenoviruses in Respiratory Specimens," Journal of Clinical Virology, 2004, vol. 31 (2), pp. 116-122.

Van Aerschot A., et al., "In Search of Acyclic Analogues as Universal Nucleosides in Degenerate Probes," Nucleosides and Nucleotides, 1995, vol. 14 (3-5), pp. 1053-1056.

Van Baar B.L., "Characterisation of Bacteria by Matrix-Assisted Laser Desorption/Ionisation and Electrospray Mass Spectrometry," FEMS Microbiology Reviews, 2000, vol. 24 (2), pp. 193-219.

Van Camp G., et al., "Amplification and Sequencing of Variable Regions in Bacterial 23s Ribosomal RNA Genes with Conserved Primer Sequences," Current Microbiology, 1993, vol. 27 (3), pp. 147-151.

Van Der Vossen J.M., et al., "DNA Based Typing Identification and Detection Systems for Food Spoilage Microorganisms: Development and Implementation," International Journal of Food Microbiology, 1996, vol. 33 (1), pp. 35-49.

Van Der Zee H., et al., "Rapid and Alternative Screening Methods for Microbiological Analysis," Journal of AOAC International, 1997, vol. 80 (4), pp. 934-940.

Van Dinten L.C., et al., "Proteolytic Processing of the Open Reading Frame Ib-EncodedPart of Arterivirus Replicase Is Mediated by nsp4 Serine Protease and is Essential for Virus Replication," Journal of Virology, 1999, vol. 73 (3), pp. 2027-2037.

Van Elden L.J., et al., "Clinical Diagnosis of Influenza Virus Infection: Evaluation of Diagnostic Tools in General Practice," The British Journal of General Practice, 2001, vol. 51 (469), pp. 630-634.

Van Elden L.J., et al., "Simultaneous Detection of Influenza Viruses A and B Using Real-Time Quantitative PCR," Journal of Clinical Microbiology, 2001, vol. 39 (1), pp. 196-200.

Van Ert M.N., et al., "Mass Spectrometry Provides Accurate Characterization of Two Genetic Marker Types in *Bacillus anthracis*," Bio Techniques, 2004, vol. 37 (4), pp. 642-651.

Van Leeuwen W.B., et al., "Multilocus Sequence Typing of *Staphylococcus aureus* with DNA Array Technology," Journal of Clinical Microbiology, 2003, vol. 41 (7), pp. 3323-3326.

Van Leeuwen W.B., et al., "Rapid Detection of Methicillin-Resistance in *Staphylococcus aureus* Isolates by the MRSA-Screen Latex Agglutination Test," Journal of Clinical Microbiology, 1999, vol. 37 (9), pp. 3029-3030.

Vanchiere J.A., et al., "Detection of BK Virus and Simian Virus 40 in the Urine of Healthy Children," Journal of Medical Virology, 2005, vol. 75 (3), pp. 447-454.

Vanderhallen H., et al. "Identification of Encephalomyocarditis Virus in Clinical Samples by ReverseTranscription-PCR Followed by Genetic Typing Using Sequence Analysis," Journal of Clinical Microbiology, 1998, vol. 36 (12), pp. 3463-3467.

Vannuffel P., et al., "Rapid and Specific Molecular Identification of Methicillin-Resistant *Staphylococcus aureus* in Endotracheal Aspirates from Mechanically Ventilated Patients," Journal of Clinical Microbiology, 1998, vol. 36 (8), pp. 2366-2368.

Vannuffel P., et al., "Specific Detection of Methicillin-Resistant *Staphylococcus* Species by Multiplex PCR," Journal of Clinical Microbiology, 1995, vol. 33 (11), pp. 2864-2867.

Verma S., et al., "Modified Oligonucleotides: Synthesis and Strategy for Users," Annual Review of Biochemistry, 1998, pp. 99-134.

Videla C., et al., "Genomic Analysis of Adenovirus Isolated from Argentinian Children with Acute Lower Respiratory Infections," Journal of Clinical Virology, 1999, vol. 14 (1), pp. 67-71.

Vilchez R.A. et al., "Detection of Polyomavirus Simian Virus 40 Tumor Antigen DNA in AIDS-Related Systemic Non-Hodgkin Lymphoma," Journal of Acquired Immune Deficiencysyndromes, 2002, vol. 29 (2), pp. 109-116.

Voelter C., et al., "Screening Human Tumor Samples with a Broad-Spectrum Polymerase Chain Reaction Method for the Detection of Polyomaviruses," Virology, 1997, vol. 237 (2), pp. 389-396.

Volokhov D., et al., "Microarray Analysis of Erythromycin Resistance Determinants," Journal of Applied Microbiology, 2003, vol. 95 (4), pp. 787-798.

Von Eiff C., et al., "Pathogenesis of Infections Due to Coagulase-Negative *Staphylococci*," The Lancet Infectious Diseases, 2002, vol. 2 (11), pp. 677-685.

Von Wintzingerode F., et al., "Base-Specific Fragmentation of Amplified 16S rRNA Genes Analyzed by Mass Spectrometry: A Tool for Rapid Bacterial Identification," Proceedings of the National Academy of Sciences, 2002, vol. 99 (10), pp. 7039-7044.

Walker E.S., et al., "A Decline in Mupirocin Resistance in Methicillin-Resistant *Staphylococcus aureus* Accompanied Administrative Control of Prescriptions," Journal of Clinical Microbiology, 2004, vol. 42 (6), pp. 2792-2795.

Wallace S.S., et al., "The Enigma of Endonuclease VIII," DNA Repair, 2003, vol. 2 (5), pp. 441-453.

Wallet F., et al., "Choice of a Routine Method for Detecting Methicillin-Resistance in *Staphylococci*," The Journal of Antimicrobial Chemotherapy, 1996, vol. 37 (5), pp. 901-909.

Walters J.J., et al., "Genotyping Single Nucleotide Polymorphisms Using Intact Polymerase Chain Reaction Products by Electrospray Quadrupole Mass Spectrometry," Rapid Communications in Mass Spectrometry, 2001, vol. 15 (18), pp. 1752-1759.

Wang G., et al., "Targeted Mutagenesis in Mammalian Cells Mediated by Intracellular Triple Helix Formation," Molecular and Cellular Biology, 1995, vol. 15 (3), pp. 1759-1768.

Ward C.L., et al., "Design and Performance Testing of Quantitative Real Time PCR Assays for Influenza A and B Viral Load Measurement," Journal of Clinical Virology, 2004, vol. 29 (3), pp. 179-188.

Watanabe K., et al., "ICB Database: the gyrB Database for Identification and Classification of Bacteria," Nucleic Acids Research, 2001, vol. 29 (1), pp. 344-345.

Weissenbacher M., et al., "Etiologic and Clinical Evaluation of Acute Lower Respiratory TractInfections in Young Argentinean Children: An Overview," Reviews of Infectious Diseases, 1990, vol. 12 (Suppl 8), pp. S889-S898.

Welham K.J., et al., "The Characterization of Micro-Organisms by Matrix-Assisted Laser Desorption/Lonization Time-of-Flight Mass Spectrometry," Rapid Communications in Mass Spectrometry, 1998, vol. 12 (4), pp. 176-180.

Wertheim H.F., et al., "Effect of Mupirocin Treatment on Nasal, Pharyngeal, and Perineal Carriage of Staphylococcus aureus in Healthy Adults," Antimicrobial Agents and Chemotherapy, 2005, vol. 49 (4), pp. 1465-1467.

Westermann P., et al., "Inhibition of Expression of SV40 Virus Large T-Antigen by Antisense Oligodeoxyribonucleotides," Biomedica Biochimica Acta, 1989, vol. 1, pp. 85-93.

Whiley D.M., et al., "Simultaneous Detection and Differentiation of Human Polyomaviruses JC and BK by a Rapid and Sensitive PCR-ELAHA Assay and a Survey of the JCV Subtypes within an Australian Population," Journal of Medical Virology, 2004, vol. 72 (3), pp. 467-472.

Wichelhaus T.A., et al., "Rapid Detection of Epidemic Strains of Methicillin-ResistantStaphylococcus aureus," Journal of Clinical Microbiology, 1999, vol. 37 (3), pp. 690-693.

Wickham T.J., "Targeting Adenovirus," Gene Therapy, 2000, vol. 7 (2), pp. 110-114.

Widjojoatmodjo M.N., et al., "Rapid Identification of Bacterial by PCR-SingleStrand Conformation Polymorphism," Journal of Clinical Microbiology, 1994, vol. 32 (12), pp. 3002-3007.

Widjojoatmodjo M.N., et al., "The Magnetic Immuno Polymerase Chain Reaction Assay for Direct Detection of Salmonellae in Fecal Samples," Journal of Clinical Microbiology, 1992, vol. 30 (12), pp. 3195-3199.

Winger B.E., et al., "High Resolution Accurate Mass Measurements of Biomolecules using a new Electrospray Ionization Ion Cyclotron Resonance Mass Spectrometer," Journal American Society for Mass Spectrometry, 1993, vol. 4 (7), pp. 566-577.

Wolter A., et al., "Negative ion FAB mass Spectrometric Analysis of non-Charged key Intermediates in Oligonucleotide Synthesis: Rapid Identification of Partially Protected Dinucleoside Monophosphates," Biomedical and Environmental Mass Spectrometry, 1987, vol. 14, pp. 111-116.

Woo T.H., et al., "Identification of Leptospira inadai by Continuous Monitoring of Fluorescence during Rapid Cycle PCR," Systematic and Applied Microbiology, 1998, vol. 21 (1), pp. 89-96.

Wood S.R., et al., "Rapid Detection and Serotyping of Adenovirus by Direct Immunofluorescence," Journal of Medical Virology, 1997, vol. 51 (3), pp. 198-201.

Wright K.E., et al., "Typing and Subtyping of Influenza Viruses in Clinical Samples by PCR," Journal of Clinical Microbiology, 1995, vol. 33 (5), pp. 1180-1184.

Written Opinion for Application No. PCT/US2004/33742, mailed on May 15, 2006, 5 pages.

Wu S., et al., "Genetic Organization of the mecA Region in Methicillin-Susceptible and Methicillin-Resistant Strains of Staphylococcus sciuri," The Journal of Bacteriology, 1998, vol. 180 (2), pp. 236-242.

Wu X., et al., "Establishment of a Fluorescent Polymerase Chain Reaction Method for the Detection of SARS-Associated Coronavhus and its Clinical Application," Chinese Medical Journal, 2003, vol. 116 (7), pp. 988-990.

Wunschel D., et al., "Discrimination Among the B. cereus Group, in Comparison to B. subtilis, by Structural Carbohydrate Profiles and Ribosomal RNA Spacer Region PCR," Systematic and Applied Microbiology, 1994, vol. 17, pp. 625-635.

Wunschel D.S., et al., "Analysis of Double-Stranded Polymerase Chain Reaction Products from the Bacilus cereus Group by Electrospray Lonization Fourier Transform Lon Cyclotron Resonance Mass Spectrometry," Rapid Communications in Mass Spectrometry, 1996, vol. 10 (1), pp. 29-35.

Wunschel, D.S., et al., "Heterogeneity in Bacillus cereus PCR Products Detected by ESI-FTICR Mass Spectrometry," Analytical Chemistry, 1998, vol. 70 (6), pp. 1203-1207.

Wunschel D.S., et al., "Mass spectrometric characterization of DNA for molecular biological applications: advances using MALDI and ESI," Advances in Mass Spectrometry, 1998, vol. 14, Elsevier, pp. 377-406.

Xu L., et al., "Electrospray Mass Tag Dideoxy DNA Sequencing," Analytical Chemistry, 1997, vol. 69 (17), pp. 3595-3602.

Xu W., et al., "Species-Specific Identification of Human Adenoviruses by a Multiplex PCR Assay," Journal of Clinical Microbiology, 2000, vol. 38 (11), pp. 4114-4120.

Xu W., et al., "Type-Specific Identification of Human Adenovirus, 3, 7, and 21 by a Multiplex PCR Assay," Journal of Medical Virology, 2001, vol. 64 (4), pp. 537-542.

Xu X., et al., "Intercontinental Circulation of Human Influenza A(H1N2) Reassortant Viruses During the 2001-2002 Influenza Season," The Journal of Infectious Diseases, 2002, vol. 186 (10), pp. 1490-1493.

Yao Z.P., et al., "Mass Spectrometry Based Proteolytic Mapping for Rapid Virus Identification," Analytical Chemistry, 2002, vol. 74 (11), pp. 2529-2534.

Yasui T., et al., "A Specific Oligonucleotide Primer for the Rapid Detection of Lactobacillus iindneri by Polymerase Chain Reaction," Canadian Journal of Microbiology, 1997, vol. 43 (2), pp. 157-163.

Ye K., et al., "Three Distinct Promoters Direct Transcription of Different 5' Untranslated Regions of the Human Interleukin 1 Type 1 Receptor. A Possible Mechanism for Control of Translation," Cytokine, 1996, vol. 8 (6), pp. 421-429.

Yun H.J., et al., "Increased Antibacterial Activity of OW286, A Novel Fluoronaphthyridone Antibiotic, Against Staphylococcus aureus Strains with Defined Mutations in DNA Gyrase and Toposiomerase IV," International Journal of Antimicrobial Agents, 2005, vol. 25 (4), pp. 334-337.

Zeng Z.B., "Precision Mapping of Quantitative Trait Loci," Genetics, 1994, vol. 136 (4), 1 pp. 1457-1468.

Zhang J., et al., "PowerBLAST: A New Network BLAST Application for Interactive or Automated Sequence Analysis and Annotation," Genome Research, 1997, vol. 7 (6), pp. 649-656.

Zhang K., et al., "New Quadriplex PCR Assay for Detection of Methicillin and Mupirocin Resistance and Simultaneous Discrimination of Staphylococcus aureus from Coagulase-Negative Staphylococci," Journal of Clinical Microbiology, 2004, vol. 42 (11), pp. 4947-4955.

Zhang W.D., et al., "Detection and Identification of Human Influenza Viruses by the Polymerase Chain Reaction," Journal of Virological Methods, 1991, vol. 33 (1-2), pp. 165-189.

Zhang Y.Q., et al., "Genome-Based Analysis of Virulence Genes in a Non-BiofilmForming Staphylococcus epidemidis Strain (ATCC 12228)," Molecular Microbiology, 2003, vol. 49 (6), pp. 1577-1593.

Final Office Action mailed Oct. 4, 2012 for U.S. Appl. No. 11/682,259, filed Mar. 5, 2007.

Notice of Allowance mailed Oct. 2, 2012 for U.S. Appl. No. 11/930,108, filed Oct. 31, 2007.

Office Action mailed Sep. 14, 2012 for Australian Application No. 2010200893 filed Mar. 10, 2010.

Office Action mailed Aug. 29, 2012 for Canadian Application No. 2439655 filed Mar. 4, 2002.

Co-pending U.S. Appl. No. 60/431,319, filed Dec. 6, 2002.
Co-pending U.S. Appl. No. 60/443,788, filed Jan. 30, 2003.
Co-pending U.S. Appl. No. 60/461,494, filed Apr. 9, 2003.
Co-pending U.S. Appl. No. 60/509,911, filed Oct. 9, 2003.
Co-pending U.S. Appl. No. 60/615,387, filed Sep. 4, 2003.
Co-pending U.S. Appl. No. 60/891,479, filed Feb. 23, 2007.
Co-pending U.S. Appl. No. 60/941,641, filed Jun. 1, 2007.

Iteman I., et al., "Comparison of Conserved Structural and Regulatory Domains within Divergent 16S rRNA-23S rRNA Spacer Sequences of Cyanobacteria," Microbiology, 2000, vol. 146 (Pt 6), pp. 1275-1286.

Kikuchi K., et al., "Restriction Fragment Length Polymorphism Analysis of Clinical Isolates of Mycobacterium Haemophilum," Journal of Clinical Microbiology, 1994, vol. 32 (7), pp. 1763-1767.

Kirpekar F., et al., "Matrix Assisted Laser Desorption/Ionization Mass Spectrometry of Enzymatically Synthesized RNA up to 150 kDa," Nucleic Acids Research, 1994, vol. 22 (19), pp. 3866-3870.
Non-Final Office Action mailed May 2, 2012 for U.S. Appl. No. 12/326,800, filed Dec. 2, 2008.
Non-Final Office Action mailed May 8, 2012 for U.S. Appl. No. 13/174,254, filed Jun. 30, 2011.
Non-Final Office Action mailed Feb. 16, 2012 for U.S. Appl. No. 11/674,538, filed Feb. 13, 2007.
Non-Final Office Action mailed Apr. 18, 2012 for U.S. Appl. No. 12/605,628, filed Oct. 26, 2009.
Non-Final Office Action mailed Mar. 21, 2012 for U.S. Appl. No. 12/616,422, filed Nov. 11, 2009.
Notice of Allowance mailed Apr. 9. 2012 for U.S. Appl. No. 11/929,910, filed Oct. 30, 2007.
Notice of Allowance mailed Mar. 19, 2012 for U.S. Appl. No. 11/930,017, filed Oct. 30, 2007.
Notice of Allowance mailed Mar. 22, 2012 for U.S. Appl. No. 11/930,108, filed Oct. 31, 2007.
Notice of Allowance mailed Mar. 22, 2012 for U.S. Appl. No. 12/326,800, filed Dec. 2, 2008.
Notice of Allowance mailed Feb. 29, 2012 for U.S. Appl. No. 11/929,910, filed Oct. 30, 2007.
Office Action mailed Feb. 2, 2012 for Israel Application No. 157661 filed Mar. 4, 2002.
Office Action mailed Feb. 6, 2012 for Australian Application No. 2010202418 filed Jun. 10, 2010.
Office Action mailed Feb. 6, 2012 for European Application No. 06800205.4 filed Jul. 21, 2006.
Notice of Allowance mailed May 23, 2012 for U.S. Appl. No. 12/326,800, filed Dec. 2, 2008.
Office Action mailed May 24, 2012 for European Application No. 10179791.8 filed Mar. 4, 2002.
Office Action mailed May 29, 2012 for Indian Application No. IN4504/KOLNP/2007 filed Nov. 22, 2007.
Office Action mailed May 31, 2012 for Canadian Application No. 2616281 filed Jul. 21, 2006.
Notice of Allowance mailed Aug. 3, 2012 for U.S. Appl. No. 11/674,538, filed Feb. 13, 2007.
Notice of Allowance mailed Jul. 24, 2012 for U.S. Appl. No. 11/930,017, filed Oct. 30, 2007.
Office Action mailed Jun. 12, 2012 for Mexican Application No. PAa2003007927 filed Sep. 2, 2003.
Office Action mailed Jul. 25, 2012 for European Application No. 06800205.4 filed Jul. 21, 2006.
Office Action mailed Nov. 21, 2012 for Israel Application No. 157661 filed Mar. 4, 2002.
Co-Pending U.S. Appl. No. 13/663,176, filed Oct. 29, 2012.
Final Office Action mailed Dec. 4, 2012 for U.S. Appl. No. 13/174,254, filed Jun. 30, 2011.
Final Office Action mailed Dec. 17, 2012 for U.S. Appl. No. 12/616,422, filed Nov. 11, 2009.
Non-Final Office Action mailed Dec. 20, 2012 for U.S. Appl. No. 11/930,741, filed Oct. 31, 2007.
Office Action mailed Dec. 6, 2012 for European Application No. 10179795.9 filed Mar. 4, 2002.
Office Action mailed Dec. 12, 2012 for European Application No. 10179789.2 filed Mar. 4, 2002.
Office Action mailed Oct. 15, 2012 for European Application No. 10175659.1 filed Dec. 5, 2003.
Office Action mailed Sep. 25, 2012 for Japanese Application No. 2008522997 filed Jul. 21, 2006.
Office Action mailed Jan. 10, 2012 for Japanese Application No. 2008522997 filed Jul. 21, 2006.
Office Action mailed Feb. 14, 2012 for Australian Application No. 2010200686 filed Feb. 25, 2010.
Office Action mailed Feb. 14, 2012 for European Application No. 10179789.2 filed Mar. 4, 2002.
Office Action mailed Jan. 19, 2012 for Canadian Application No. 2510007 filed Dec. 5, 2003.
Office Action mailed Mar. 21, 2012 for Japanese Application No. 2009245976 filed Oct. 26, 2009.

* cited by examiner

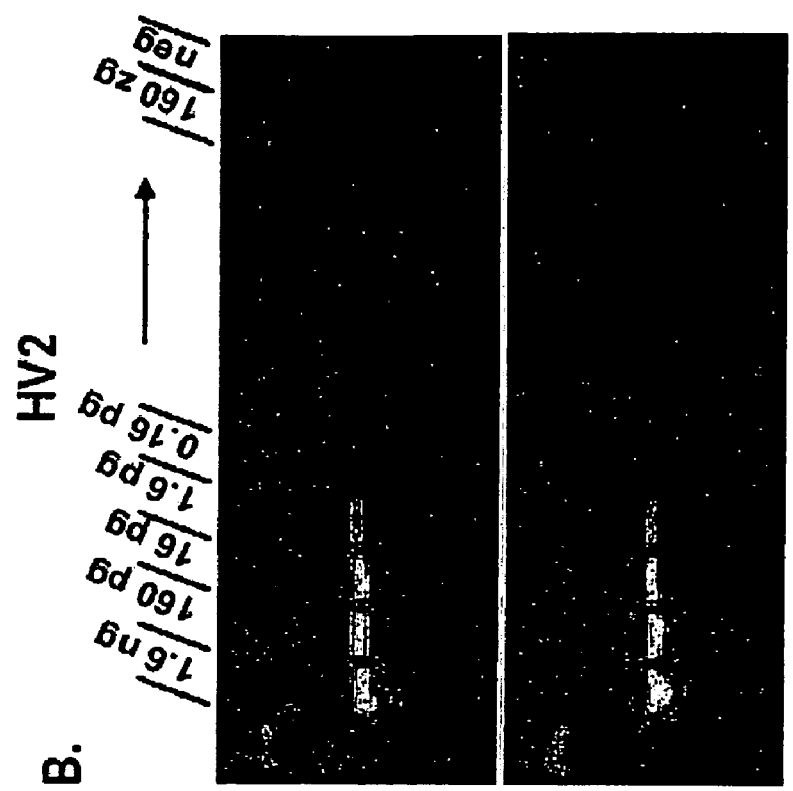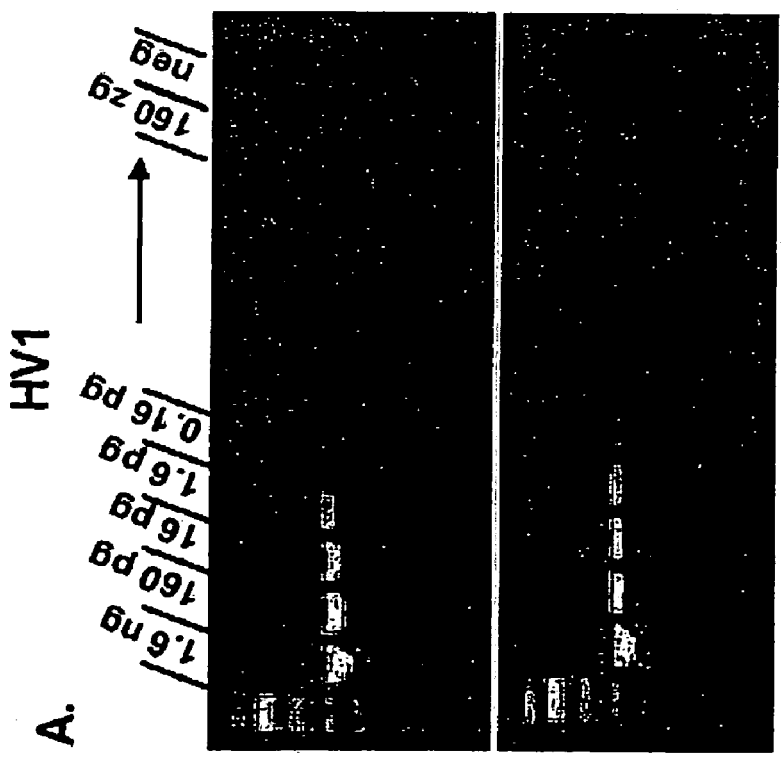
Fig 9

METHODS FOR RAPID FORENSIC ANALYSIS OF MITOCHONDRIAL DNA

RELATED APPLICATIONS

This application is a continuation of U.S. patent application Ser. No. 10/853,660 filed May 25, 2004, the disclosure of which is incorporated by reference in its entirety for any purpose.

STATEMENT OF GOVERNMENT SUPPORT

This invention was made with United States Government support under DARPA contract MDA-972-03C-112. The United States Government has certain rights in the invention.

FIELD OF THE INVENTION

This invention relates to the field of mitochondrial DNA analysis. The invention enables rapid and accurate forensic analysis by using mass spectrometry to characterize informative regions of mitochondrial DNA.

BACKGROUND OF THE INVENTION

Mitochondrial DNA (mtDNA) is found in eukaryotes and differs from nuclear DNA in its location, its sequence, its quantity in the cell, and its mode of inheritance. The nucleus of the cell contains two sets of 23 chromosomes, one paternal set and one maternal set. However, cells may contain hundreds to thousands of mitochondria, each of which may contain several copies of mtDNA. Nuclear DNA has many more bases than mtDNA, but mtDNA is present in many more copies than nuclear DNA. This characteristic of mtDNA is useful in situations where the amount of DNA in a sample is very limited. Typical sources of DNA recovered from crime scenes include hair, bones, teeth, and body fluids such as saliva, semen, and blood.

In humans, mitochondrial DNA is inherited strictly from the mother (Case J. T. and Wallace, D. C., *Somatic Cell Genetics*, 1981, 7, 103-108; Giles, R. E. et al. Proc. Natl. Acad. Sci. 1980, 77, 6715-6719; Hutchison, C. A. et al *Nature*, 1974, 251, 536-538). Thus, the mtDNA sequences obtained from maternally related individuals, such as a brother and a sister or a mother and a daughter, will exactly match each other in the absence of a mutation. This characteristic of mtDNA is advantageous in missing persons cases as reference mtDNA samples can be supplied by any maternal relative of the missing individual (Ginther, C. et al. *Nature Genetics*, 1992, 2, 135-138; Holland, M. M. et al. *Journal of Forensic Sciences*, 1993, 38, 542-553; Stoneking, M. et al. *American Journal of Human Genetics*, 1991, 48, 370-382).

The human mtDNA genome is approximately 16,569 bases in length and has two general regions: the coding region and the control region. The coding region is responsible for the production of various biological molecules involved in the process of energy production in the cell and includes about 37 genes (22 transfer RNAs, 2 ribosomal RNAs, and 13 peptides), with very little intergenic sequence and no introns. The control region is responsible for regulation of the mtDNA molecule. Two regions of mtDNA within the control region have been found to be highly polymorphic, or variable, within the human population (Greenberg, B. D. et al. Gene, 1983, 21, 33-49). These two regions are termed "hypervariable Region I" (HV1), which has an approximate length of 342 base pairs (bp), and "hypervariable Region II" (HV2), which has an approximate length of 268 bp. Forensic mtDNA examinations are performed using these two regions because of the high degree of variability found among individuals.

There exists a need for rapid identification of humans wherein human remains and/or biological samples are analyzed. Such remains or samples may be associated with war-related casualties, aircraft crashes, and acts of terrorism, for example. Analysis of mtDNA enables a rule-in/rule-out identification process for persons for whom DNA profiles from a maternal relative are available. Human identification by analysis of mtDNA can also be applied to human remains and/or biological samples obtained from crime scenes.

The process of human identification is a common objective of forensics investigations. As used herein, "forensics" is the study of evidence discovered at a crime or accident scene and used in a court of law. "Forensic science" is any science used for the purposes of the law, in particular the criminal justice system, and therefore provides impartial scientific evidence for use in the courts of law, and in a criminal investigation and trial. Forensic science is a multidisciplinary subject, drawing principally from chemistry and biology, but also from physics, geology, psychology and social science, for example.

Forensic scientists generally use two highly variable regions of human mtDNA for analysis. These regions are designated "hypervariable regions 1 and 2" (HV1 and HV2 which contain 341 and 267 base pairs respectively). These hypervariable regions, or portions thereof, provide one non-limiting example of mitochondrial DNA identifying amplicons.

A typical mtDNA analysis begins when total genomic DNA is extracted from biological material, such as a tooth, blood sample, or hair. The polymerase chain reaction (PCR) is then used to amplify, or create many copies of, the two hypervariable portions of the non-coding region of the mtDNA molecule, using flanking primers. Care is taken to eliminate the introduction of exogenous DNA during both the extraction and amplification steps via methods such as the use of pre-packaged sterile equipment and reagents, aerosol-resistant barrier pipette tips, gloves, masks, and lab coats, separation of pre- and post-amplification areas in the lab using dedicated reagents for each, ultraviolet irradiation of equipment, and autoclaving of tubes and reagent stocks. In casework, questioned samples are always processed before known samples and they are processed in different laboratory rooms. When adequate amounts of PCR product are amplified to provide all the necessary information about the two hypervariable regions, sequencing reactions are performed. These chemical reactions use each PCR product as a template to create a new complementary strand of DNA in which some of the nucleotide residues that make up the DNA sequence are labeled with dye. The strands created in this stage are then separated according to size by an automated sequencing machine that uses a laser to "read" the sequence, or order, of the nucleotide bases. Where possible, the sequences of both hypervariable regions are determined on both strands of the double-stranded DNA molecule, with sufficient redundancy to confirm the nucleotide substitutions that characterize that particular sample. At least two forensic analysts independently assemble the sequence and then compare it to a standard, commonly used, reference sequence. The entire process is then repeated with a known sample, such as blood or saliva collected from a known individual. The sequences from both samples, about 780 bases long each, are compared to determine if they match. The analysts assess the results of the analysis and determine if any portions of it need to be repeated. Finally, in the event of an inclusion or match, the SWGDAM mtDNA database, which is maintained by the FBI, is searched for the mitochondrial sequence that has been observed for the samples. The analysts can then report the number of observations of this type based on the nucleotide positions that have been read. A written report can be provided to the submitting agency.

Approximately 610 bp of mtDNA are currently sequenced in forensic mtDNA analysis. Recording and comparing mtDNA sequences would be difficult and potentially confusing if all of the bases were listed. Thus, mtDNA sequence information is recorded by listing only the differences with respect to a reference DNA sequence. By convention, human mtDNA sequences are described using the first complete published mtDNA sequence as a reference (Anderson, S. et al., *Nature*, 1981, 290, 457-465). This sequence is commonly referred to as the Anderson sequence. It is also called the Cambridge reference sequence or the Oxford sequence. Each base pair in this sequence is assigned a number. Deviations from this reference sequence are recorded as the number of the position demonstrating a difference and a letter designation of the different base. For example, a transition from A to G at Position 263 would be recorded as 263 G. If deletions or insertions of bases are present in the mtDNA, these differences are denoted as well.

In the United States, there are seven laboratories currently conducting forensic mtDNA examinations: the FBI Laboratory; Laboratory Corporation of America (LabCorp) in Research Triangle Park, North Carolina; Mitotyping Technologies in State College, Pa.; the Bode Technology Group (BTG) in Springfield, Va.; the Armed Forces DNA Identification Laboratory (AFDIL) in Rockville, Md.; BioSynthesis, Inc. in Lewisville, Tex.; and Reliagene in New Orleans, La.

Mitochondrial DNA analyses have been admitted in criminal proceedings from these laboratories in the following states as of April 1999: Alabama, Arkansas, Florida, Indiana, Illinois, Maryland, Michigan, New Mexico, North Carolina, Pennsylvania, South Carolina, Tennessee, Texas, and Washington. Mitochondrial DNA has also been admitted and used in criminal trials in Australia, the United Kingdom, and several other European countries.

Since 1996, the number of individuals performing mitochondrial DNA analysis at the FBI Laboratory has grown from 4 to 12, with more personnel expected in the near future. Over 150 mitochondrial DNA cases have been completed by the FBI Laboratory as of March 1999, and dozens more await analysis. Forensic courses are being taught by the FBI Laboratory personnel and other groups to educate forensic scientists in the procedures and interpretation of mtDNA sequencing. More and more individuals are learning about the value of mtDNA sequencing for obtaining useful information from evidentiary samples that are small, degraded, or both. Mitochondrial DNA sequencing is becoming known not only as an exclusionary tool but also as a complementary technique for use with other human identification procedures. Mitochondrial DNA analysis will continue to be a powerful tool for law enforcement officials in the years to come as other applications are developed, validated, and applied to forensic evidence.

Presently, the forensic analysis of mtDNA is rigorous and labor-intensive. Currently, only 1-2 cases per month per analyst can be performed. Several molecular biological techniques are combined to obtain a mtDNA sequence from a sample. The steps of the mtDNA analysis process include primary visual analysis, sample preparation, DNA extraction, polymerase chain reaction (PCR) amplification, post-amplification quantitation of the DNA, automated DNA sequencing, and data analysis. Another complicating factor in the forensic analysis of mtDNA is the occurrence of heteroplasmy wherein the pool of mtDNAs in a given cell is heterogeneous due to mutations in individual mtDNAs. There are two forms of heteroplasmy found in mtDNA. Sequence heteroplasmy (also known as point heteroplasmy) is the occurrence of more than one base at a particular position or positions in the mtDNA sequence. Length heteroplasmy is the occurrence of more than one length of a stretch of the same base in a mtDNA sequence as a result of insertion of nucleotide residues.

Heteroplasmy is a problem for forensic investigators since a sample from a crime scene can differ from a sample from a suspect by one base pair and this difference may be interpreted as sufficient evidence to eliminate that individual as the suspect. Hair samples from a single individual can contain heteroplasmic mutations at vastly different concentrations and even the root and shaft of a single hair can differ. The detection methods currently available to molecular biologists cannot detect low levels of heteroplasmy. Furthermore, if present, length heteroplasmy will adversely affect sequencing runs by resulting in an out-of-frame sequence that cannot be interpreted.

Mass spectrometry provides detailed information about the molecules being analyzed, including high mass accuracy. It is also a process that can be easily automated.

Several groups have described detection of PCR products using high resolution electrospray ionization-Fourier transform-ion cyclotron resonance mass spectrometry (ESI-FT-ICR MS). Accurate measurement of exact mass combined with knowledge of the number of at least one nucleotide allowed calculation of the total base composition for PCR duplex products of approximately 100 base pairs. (Aaserud et al., *J. Am. Soc. Mass Spec.*, 1996, 7, 1266-1269; Muddiman et al, *Anal Chem.*, 1997, 69, 1543-1549; Wunschel et al., *Anal. Chem.*, 1998, 70, 1203-1207; Muddiman et al., *Rev. Anal. Chem.*, 1998, 17, 1-68). Electrospray ionization-Fourier transform-ion cyclotron resistance (ESI-FT-ICR) MS may be used to determine the mass of double-stranded, 500 base-pair PCR products via the average molecular mass (Hurst et al., *Rapid Commun. Mass Spec.* 1996, 10, 377-382). The use of matrix-assisted laser desorption ionization-time of flight (MALDI-TOF) mass spectrometry for characterization of PCR products has been described. (Muddiman et al., *Rapid Commun. Mass Spec.*, 1999, 13, 1201-1204). However, the degradation of DNAs over about 75 nucleotides observed with MALDI limited the utility of this method.

U.S. Pat. No. 5,849,492 reports a method for retrieval of phylogenetically informative DNA sequences which comprise searching for a highly divergent segment of genomic DNA surrounded by two highly conserved segments, designing the universal primers for PCR amplification of the highly divergent region, amplifying the genomic DNA by PCR technique using universal primers, and then sequencing the gene to determine the identity of the organism.

U.S. Pat. No. 5,965,363 reports methods for screening nucleic acids for polymorphisms by analyzing amplified target nucleic acids using mass spectrometric techniques and to procedures for improving mass resolution and mass accuracy of these methods.

WO 99/14375 reports methods, PCR primers and kits for use in analyzing preselected DNA tandem nucleotide repeat alleles by mass spectrometry.

WO 98/12355 reports methods of determining the mass of a target nucleic acid by mass spectrometric analysis, by cleaving the target nucleic acid to reduce its length, making the target single-stranded and using MS to determine the mass of the single-stranded shortened target. Also reported are methods of preparing a double-stranded target nucleic acid for MS analysis comprising amplification of the target nucleic acid, binding one of the strands to a solid support, releasing the second strand and then releasing the first strand which is then analyzed by MS. Kits for target nucleic acid preparation are also reported.

PCT WO97/33000 reports methods for detecting mutations in a target nucleic acid by nonrandomly fragmenting the target into a set of single-stranded nonrandom length fragments and determining their masses by MS.

U.S. Pat. No. 5,605,798 reports a fast and highly accurate mass spectrometer-based process for detecting the presence of a particular nucleic acid in a biological sample for diagnostic purposes.

WO 98/20166 reports processes for determining the sequence of a particular target nucleic acid by mass spectrometry. Processes for detecting a target nucleic acid present in a biological sample by PCR amplification and mass spectrometry detection are disclosed, as are methods for detecting a target nucleic acid in a sample by amplifying the target with primers that contain restriction sites and tags, extending and cleaving the amplified nucleic acid, and detecting the presence of extended product, wherein the presence of a DNA fragment of a mass different from wild-type is indicative of a mutation. Methods of sequencing a nucleic acid via mass spectrometry methods are also described.

WO 97/37041, WO 99/31278 and U.S. Pat. No. 5,547,835 report methods of sequencing nucleic acids using mass spectrometry. U.S. Pat. Nos. 5,622,824, 5,872,003 and 5,691,141 report methods, systems and kits for exonuclease-mediated mass spectrometric sequencing.

There is a need for a mitochondrial DNA forensic analysis which is both specific and rapid, and in which no nucleic acid sequencing is required. The present invention addresses this need, among others.

SUMMARY OF THE INVENTION

The present invention is directed to methods of forensic analysis of mitochondrial DNA comprising: amplifying a segment of mitochondrial DNA containing a plurality of restriction sites and flanked by a pair of primers to produce an amplification product, digesting the amplification product with a plurality of restriction enzymes to produce a plurality of restriction digest products, determining the molecular mass of each member of the plurality of restriction digest products, generating a fragment coverage map from the molecular masses and comparing the fragment coverage map with a plurality of theoretical fragment coverage maps contained in a database stored on a computer readable medium.

The present invention is also directed to primer pair compositions used to amplify mitochondrial DNA for the forensic method and to isolated mitochondrial DNA amplicons obtained by amplification of mitochondrial DNA with the primer pair compositions.

BRIEF DESCRIPTION OF THE DRAWINGS

FIG. 9 is an agarose gel electrophoresis photo indicating the sensitivity of the HV1 and Hv2 primer pairs assessed against DNA isolated from human blood. A PCR product is detectable down to between 160 pg and 1.6 ng for both HV1 and HV2 primer pairs.

DESCRIPTION OF EMBODIMENTS

Figure 1:
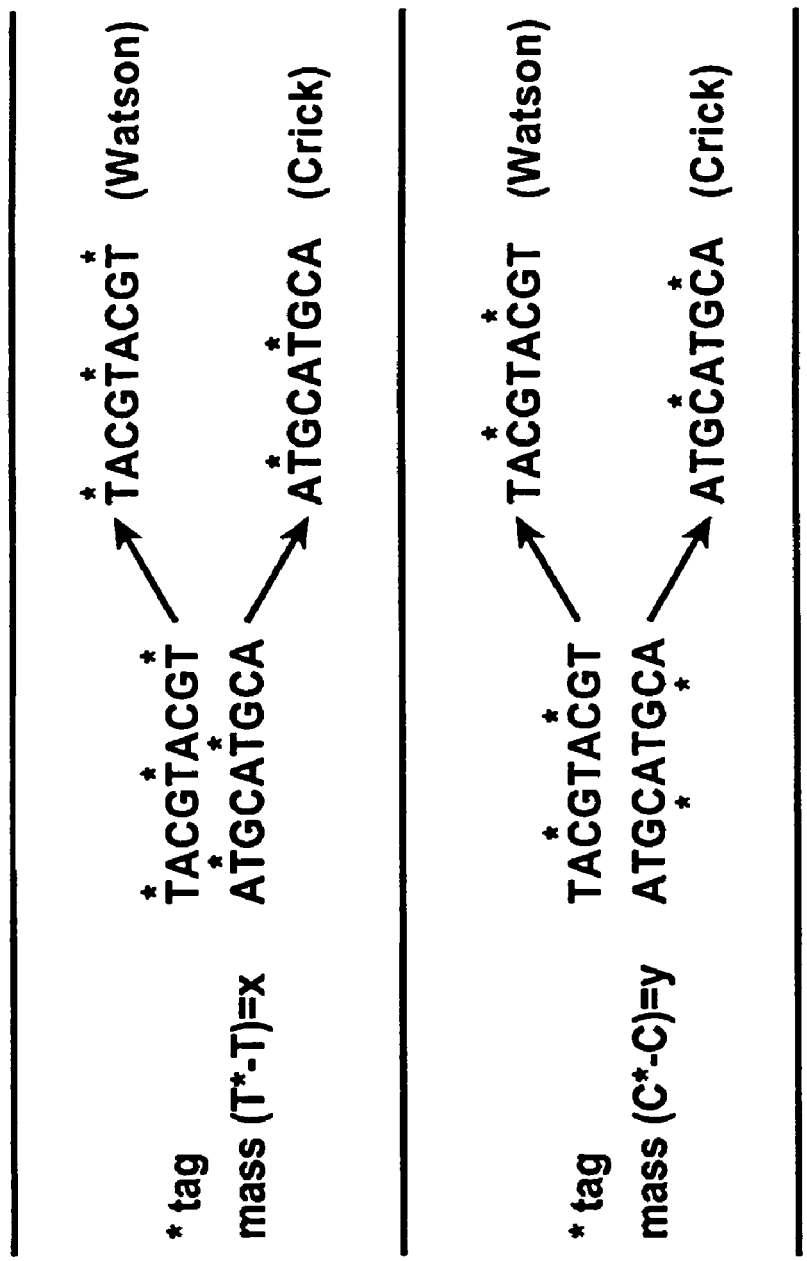
FIG. 1 is a schematic diagram of base composition determination using nucleotide analog "tags" to determine base compositions.

The present invention provides, inter alia, methods for forensic analysis of mitochondrial DNA. A region of mitochondrial DNA which contains on or more restriction sites is selected to provide optimal distinguishing capability which enables forensic conclusions to be drawn. A relational database of known mitochondrial DNA sequences is then populated with the results of theoretical restriction digestion reactions. One or more primer pairs are then selected to amplify the region of mitochondrial DNA and amplification product is digested with one or more restriction enzymes which are chosen to yield restriction fragments of up to about 150 base pairs that are amenable to molecular mass analysis. The molecular masses of all of the restriction fragments are then measured and the results are compared with the results calculated for the theoretical restriction digestions of all of the entries in the relational database. The results of the comparison enable a forensic conclusion to be drawn.

In one embodiment, more than one region can be analyzed to draw a forensic conclusion via a triangulation strategy. For example, it is possible that analysis of one region of DNA obtained from a crime scene yields several possible matches to entries in a relational database. In this case, depending on the objective of the individual forensic analysis, it may be advantageous to carry out one or more additional analyses of different mtDNA regions. Examples of such mtDNA regions include, but are not limited to a portion of, HV1, HV2, R1, R2, R3, R4, R5, R6, R7, R8, R9, R10, R1 and R12 (coordinates for each of these defined regions, relative to the Anderson Sequence are given in Table 2). Thus, in this embodiment, any combination of two or more regions of mtDNA are used to provide optimal distinguishing capability and provide an improved confidence level for the forensic analysis.

In another embodiment, the relational database of known mitochondrial DNA sequences is populated with base compositions of the theoretical restriction fragments obtained from theoretical digestion of each member of the database. Then the base compositions of each of the restriction fragments of the experimentally determined molecular masses are determined. The analysis may then end with a comparison of the experimentally determined base compositions with the base compositions of the theoretical digestions of each member of the database so that at least one base composition match or lack of a base composition match provides a forensic conclusion.

In another embodiment, one or more restriction enzymes which are chosen to yield restriction fragments of up to about 50 base pairs, of up to about 100 base pairs, of up to about 150 base pairs, of up to about 200 base pairs, or of up to about 250 base pairs that are amenable to molecular mass analysis.

In another embodiment, the molecular masses of all or most (i.e., about 75%, about 80%, about 90% about 99% or every fragment minus one fragment) of the restriction fragments are then measured and the results are compared with the results calculated for the theoretical restriction digestions of all of the entries in the relational database.

In some embodiments, the amplifying step is accomplished by using the polymerase chain reaction and a polymerase chain reaction is catalyzed by a polymerase enzyme whose function is modified relative to a native polymerase. In some embodiments the modified polymerase enzyme is exo (−) Pfu polymerase which catalyzes the addition of nucleotide residues to staggered restriction digest products to convert the staggered digest products to blunt-ended digest products.

Although the use of PCR is suitable, other nucleic acid amplification techniques may also be used, including ligase chain reaction (LCR) and strand displacement amplification (SDA).

Mass spectrometry (MS)-based detection of PCR products provides a means for determination of BCS which has several advantages. MS is intrinsically a parallel detection scheme without the need for radioactive or fluorescent labels, since every amplification product is identified by its molecular mass. The current state of the art in mass spectrometry is such that less than femtomole quantities of material can be readily analyzed to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons. Intact molecular ions can be generated from amplification products using one of a variety of ionization techniques to convert the sample to gas phase. These ionization methods include, but are not limited to, electrospray ionization (ES), matrix-assisted laser desorption ionization (MALDI) and fast atom bombardment (FAB). For example, MALDI of nucleic acids, along with examples of matrices for use in MALDI of nucleic acids, are described in WO 98/54751. The accurate measurement of molecular mass for large DNAs is limited by the adduction of cations from the PCR reaction to each strand, resolution of the isotopic peaks from natural abundance $^{13}$C and $^{15}$N isotopes, and assignment of the charge state for any ion. The cations are removed by in-line dialysis using a flow-through chip that brings the solution containing the PCR products into contact with a solution containing ammonium acetate in the presence of an electric field gradient orthogonal to the flow. The latter two problems are addressed by operating with a resolving power of >100,000 and by incorporating isotopically depleted nucleotide triphosphates into the DNA. The resolving power of the instrument is also a consideration. At a resolving power of 10,000, the modeled signal from the $[M-14H+]^{14-}$ charge state of an 84 mer PCR product is poorly characterized and assignment of the charge state or exact mass is impossible. At a resolving power of 33,000, the peaks from the individual isotopic components are visible. At a resolving power of 100,000, the isotopic peaks are resolved to the baseline and assignment of the charge state for the ion is straightforward. The [$^{13}$C,$^{15}$N]-depleted triphosphates are obtained, for example, by growing microorganisms on depleted media and harvesting the nucleotides (Batey et al., *Nucl. Acids Res.*, 1992, 20, 4515-4523).

While mass measurements of intact nucleic acid regions are believed to be adequate, tandem mass spectrometry (MS$^n$) techniques may provide more definitive information pertaining to molecular identity or sequence. Tandem MS involves the coupled use of two or more stages of mass analysis where both the separation and detection steps are based on mass spectrometry. The first stage is used to select an ion or component of a sample from which further structural information is to be obtained. The selected ion is then fragmented using, e.g., blackbody irradiation, infrared multiphoton dissociation, or collisional activation. For example, ions generated by electrospray ionization (ESI) can be fragmented using IR multiphoton dissociation. This activation leads to dissociation of glycosidic bonds and the phosphate backbone, producing two series of fragment ions, called the w-series (having an intact 3' terminus and a 5' phosphate following internal cleavage) and the a-Base series (having an intact 5' terminus and a 3' furan).

The second stage of mass analysis is then used to detect and measure the mass of these resulting fragments of product ions. Such ion selection followed by fragmentation routines can be performed multiple times so as to essentially completely dissect the molecular sequence of a sample.

If there are two or more targets of similar molecular mass, or if a single amplification reaction results in a product which has the same mass as two or more reference standards, they can be distinguished by using mass-modifying "tags." In this embodiment of the invention, a nucleotide analog or "tag" is incorporated during amplification (e.g., a 5-(trifluoromethyl) deoxythymidine triphosphate) which has a different molecular weight than the unmodified base so as to improve distinction of masses. Such tags are described in, for example, PCT WO97/33000, which is incorporated herein by reference in its entirety. This further limits the number of possible base compositions consistent with any mass. For example, 5-(trifluoromethyl)deoxythymidine triphosphate can be used in place of dTTP in a separate nucleic acid amplification reaction. Measurement of the mass shift between a conventional amplification product and the tagged product is used to quantitate the number of thymidine nucleotides in each of the single strands. Because the strands are complementary, the number of adenosine nucleotides in each strand is also determined.

In another amplification reaction, the number of G and C residues in each strand is determined using, for example, the cytidine analog 5-methylcytosine (5-meC) or 5-prolynylcytosine. propyne C. The combination of the A/T reaction and G/C reaction, followed by molecular weight determination, provides a unique base composition. This method is summarized in FIG. 1 and Table 1.

TABLE 1

| Mass tag | Double strand sequence | Single strand Sequence | Total mass this strand | Base info this strand | Base info other strand | Total base comp. Top strand | Total base comp. Bottom strand |
|---|---|---|---|---|---|---|---|
| T* mass (T* − T) = x | T*ACGT*ACGT* AT*GCAT*GCA | T*ACGT*ACGT* | 3x | 3T | 3A | 3T 2A 2C 2G | 3A 2T 2G 2C |
| | | AT*GCAT*GCA | 2x | 2T | 2A | | |
| C* mass (C* − C) = y | TAC*GTAC*GT ATGC*ATGC*A | TAC*GTAC*GT | 2x | 2C | 2G | | |
| | | ATGC*ATGC*A | 2x | 2C | 2G | | |

Figure 2:
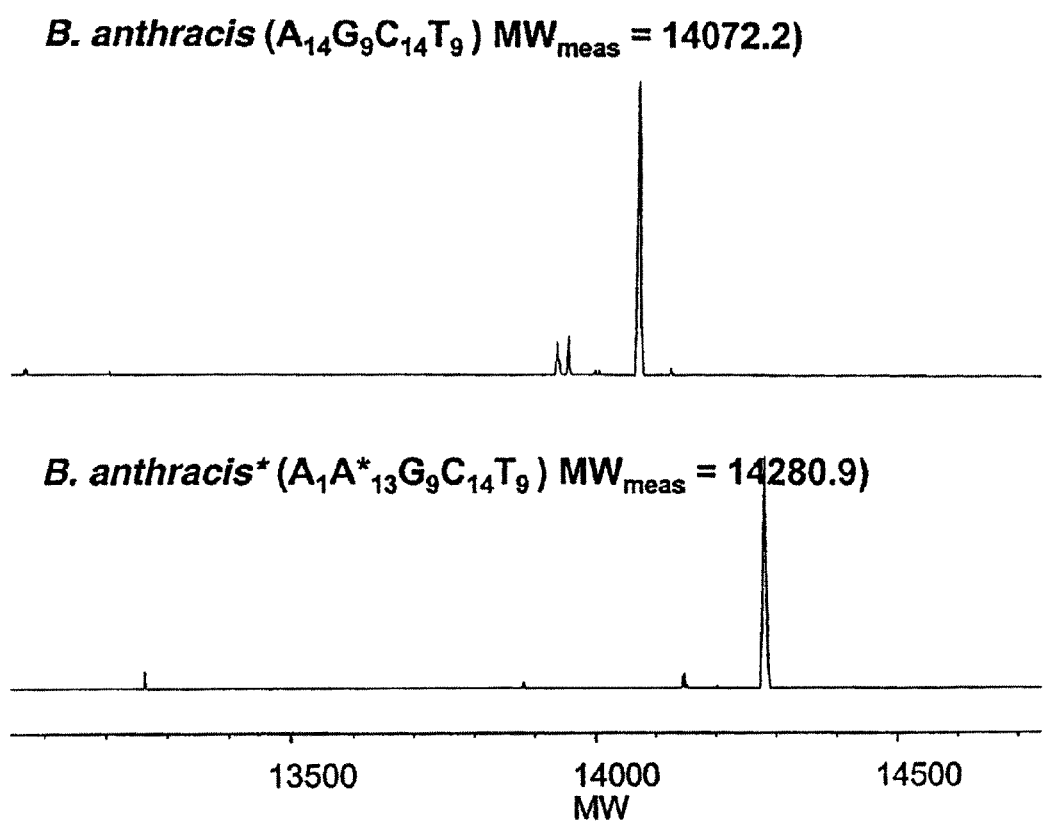
FIG. 2 shows the deconvoluted mass spectra of a *Bacillus anthracis* region with and without the mass tag phosphorothioate A (A*). The two spectra differ in that the measured molecular weight of the mass tag-containing sequence is greater than that of the unmodified sequence.

The mass tag phosphorothioate A (A*) was used to distinguish a *Bacillus anthracis* cluster. The *B. anthracis* ($A_{14}G_9Cl_4T_9$) had an average MW of 14072.26, and the *B. anthracis* ($A_1A*_{13}G_9C_{14}T_9$) had an average molecular weight of 14281.11 and the phosphorothioate A had an average molecular weight of +16.06 as determined by ESI-TOF MS. The deconvoluted spectra are shown in FIG. 2.

In another example, assume the measured molecular masses of each strand are 30,000.115 Da and 31,000.115 Da respectively, and the measured number of dT and dA residues are (30,28) and (28,30). If the molecular mass is accurate to 100 ppm, there are 7 possible combinations of dG+dC possible for each strand. However, if the measured molecular mass is accurate to 10 ppm, there are only 2 combinations of dG+dC, and at 1 ppm accuracy there is only one possible base composition for each strand.

Signals from the mass spectrometer may be input to a maximum-likelihood detection and classification algorithm such as is widely used in radar signal processing. Processing may end with a Bayesian classifier using log likelihood ratios developed from the observed signals and average background levels. Background signal strengths are estimated and used along with the matched filters to form signatures which are then subtracted. the maximum likelihood process is applied to this "cleaned up" data in a similar manner employing matched filters and a running-sum estimate of the noise-covariance for the cleaned up data.

In some embodiments, the mitochondrial DNA analyzed is human mitochondrial DNA obtained from human saliva, hair, blood, or nail. In other embodiments, the DNA analyzed can be obtained from an animal, a fungus, a parasite or a protozoan.

The present invention also comprises primer pairs which are designed to bind to highly conserved sequence regions mitochondrial DNA that flank an intervening variable region such as the variable sections found within regions HV1, HV2, R1, R2, R3, R4, R5, R6, R7, R8, R9, R10, R11 and R12 and yield amplification products which ideally provide enough variability to provide a forensic conclusion, and which are amenable to molecular mass analysis. By the term "highly conserved," it is meant that the sequence regions exhibit from about 80 to 100%, or from about 90 to 100%, or from about 95 to 100% identity, or from about 80 to 99%, or from about 90 to 99%, or from about 95 to 99% identity. The molecular mass of a given amplification product provides a means of drawing a forensic conclusion due to the variability of the variable region. Thus, design of primers involves selection of a variable section with optimal variability in the mtDNA of different individuals.

In some embodiments, each member of the pair has at least 70%, at least 80%, at least 90%, at least 95%, or at least 99% sequence identity with the sequence of the corresponding member of any one or more of the following primer pair sequences: SEQ ID NOs: 8:9, 10:11, 12:13, 12:14, 12:15, 16:17, 18:19, 20:21, 22:23, 24:25, 26:27, 28:29, 30:31, 32:33, 34:35, 36:37, 38:39, 40:41, 42:43, 44:45, 42:46, 47:48, 18:49, 50:51, 22:52, 53:54, 55:56, 57:29, 58:31, 59:60, 61:62, 63:39, 40:64, 65:66, 67:68, 69:70, 12:68, 12:70, 67:15, 71:70, 69:15, and 69:68.

In some embodiments, the region of mitochondrial DNA comprises HV1, each member of the primer pair has at least 70% sequence identity with the sequence of the corresponding member of any one of the following primer pair sequences: SEQ ID NOs: 12:13, 12:14, 12:15, 16:17, 42:43, 42:46, 67:68, 69:70, 12:68, 12:70, 67:15, 71:70, 69:15, or 69:68, and the restriction enzyme is RsaI.

In some embodiments, the region of mitochondrial DNA comprises HV2, each member of the primer pair has at least 70% sequence identity with the sequence of the corresponding member of any one of the following primer pair sequences: SEQ ID NOs: 8:9, 10:11, 16:17, or 65:66, and the at least one restriction enzyme is HaeIII, HpaII, MfeI, or SspI, or HpaII, HpyCH4IV, PacI, or EaeI.

In some embodiments, the region of mitochondrial DNA comprises region R1, each member of the primer pair has at least 70% sequence identity with the sequence of the corresponding member of any one of the following primer pair sequences: SEQ ID NOs: 18:19 and 18:49, at least one restriction enzyme is DdeI, MseI, HaeIII, or MboI.

In some embodiments, the region of mitochondrial DNA comprises region R2, each member of the primer pair has at least 70% sequence identity with the sequence of the corresponding member of any one of the following primer pair sequences: SEQ ID NOs: 20:21 and 50:51, and at least one restriction enzyme is DdeI, HaeIII, MboI, or MseI.

In some embodiments, the region of mitochondrial DNA comprises region R3, each member of the primer pair has at least 70% sequence identity with the sequence of the corresponding member of any one of the following primer pair sequences: SEQ ID NOs: 22:23 and 22:52, and at least one restriction enzyme is DdeI, MseI, MboI, or BanI.

In some embodiments, the region of mitochondrial DNA comprises region R4, each member of the primer pair has at least 70% sequence identity with the sequence of the corresponding member of any one of the following primer pair sequences: SEQ ID NOs: 24:25 and 53:54, and at least one restriction enzyme is DdeI, HpyCH4IV, MseI, or HaeIII.

In some embodiments, the region of mitochondrial DNA comprises region R5, each member of said primer pair has at least 70% sequence identity with the sequence of the corresponding member of any one of the following primer pair sequences: SEQ ID NOs: 26:27 and 55:56, and at least one restriction enzyme is AluI, BfaI, or MseI.

In some embodiments, the region of mitochondrial DNA comprises region R6, each member of the primer pair has at least 70% sequence identity with the sequence of the corresponding member of any one of the following primer pair sequences: SEQ ID NOs: 28:29 and 57:29, and at least one restriction enzyme is DdeI, HaeIII, MboI, MseI, or RsaI.

In some embodiments, the region of mitochondrial DNA comprises region R7, each member of said primer pair has at least 70% sequence identity with the sequence of the corresponding member of any one of the following primer pair sequences: SEQ ID NOs: 30:31 and 58:31, and at least one restriction enzyme is DdeI, HpaII, HaeIII, or MseI.

In some embodiments, the region of mitochondrial DNA comprises region R8, each member of the primer pair has at least 70% sequence identity with the sequence of the corresponding member of any one of the following primer pair sequences: SEQ ID NOs: 32:33 and 59:60, and at least one restriction enzyme is BfaI, DdeI, EcoRI, or MboI.

In some embodiments, the region of mitochondrial DNA comprises region R9, each member of the primer pair has at least 70% sequence identity with the sequence of the corresponding member of the following primer pair sequences: SEQ ID NOs: 34:35, and at least one restriction enzyme is BfaI, DdeI, HpaII, HpyCH4IV, or MboI.

In some embodiments, the region of mitochondrial DNA comprises region R10, each member of the primer pair has at least 70% sequence identity with the sequence of the corresponding member of the following primer pair sequences: SEQ ID NOs: 34:35, and at least one restriction enzyme is BfaI, HpaII, or MboI.

In some embodiments, the region of mitochondrial DNA comprises region R10, each member of the primer pair has at least 70% sequence identity with the sequence of the corresponding member of the following primer pair sequences: SEQ ID NOs: 36:37 and 61:62, and at least one restriction enzyme is BfaI, HpaII, or MboI.

In some embodiments, the region of mitochondrial DNA comprises region R11, each member of the primer pair has at least 70% sequence identity with the sequence of the corresponding member of the following primer pair sequences: SEQ ID NOs: 38:39 and 63:39, and at least one restriction enzyme is BfaI, DdeI, HpyCH4V, or MboI.

In some embodiments, the region of mitochondrial DNA comprises region R12, each member of the primer pair has at least 70% sequence identity with the sequence of the corresponding member of the following primer pair sequences: SEQ ID NOs: 40:41 and 40:64, and at least one restriction enzyme is BfaI, DdeI, or MseI.

Ideally, primer hybridization sites are highly conserved in order to facilitate the hybridization of the primer. In cases where primer hybridization is less efficient due to lower levels of conservation of sequence, the primers of the present invention can be chemically modified to improve the efficiency of hybridization. For example, because any variation (due to codon wobble in the $3^{rd}$ position) in these conserved regions among species is likely to occur in the third position of a DNA triplet, oligonucleotide primers can be designed such that the nucleotide corresponding to this position is a base which can bind to more than one nucleotide, referred to herein as a "universal base." For example, under this "wobble" pairing, inosine (I) binds to U, C or A; guanine (G) binds to U or C, and uridine (U) binds to U or C. Other examples of universal bases include nitroindoles such as 5-nitroindole or 3-nitropyrrole (Loakes et al., *Nucleosides and Nucleotides*, 1995, 14, 1001-1003), the degenerate nucleotides dP or dK (Hill et al.), an acyclic nucleoside analog containing 5-nitroindazole (Van Aerschot et al., *Nucleosides and Nucleotides*, 1995, 14, 1053-1056) or the purine analog 1-(2-deoxy-β-D-ribofuranosyl)-imidazole-4-carboxamide (Sala et al., *Nucl. Acids Res.*, 1996, 24, 3302-3306).

In another embodiment of the invention, to compensate for the somewhat weaker binding by the "wobble" base, the oligonucleotide primers are designed such that the first and second positions of each triplet are occupied by nucleotide analogs which bind with greater affinity than the unmodified nucleotide. Examples of these analogs include, but are not limited to, 2,6-diaminopurine which binds to thymine, propyne T (5-propynyluridine) which binds to adenine and propyne C (5-propynylcytidine) and phenoxazines, including G-clamp, which binds to G. Propynylated pyrimidines are described in U.S. Pat. Nos. 5,645,985, 5,830,653 and 5,484,908, each of which is commonly owned and incorporated herein by reference in its entirety. Propynylated primers are claimed in U.S. Ser. No. 10/294,203 which is also commonly owned and incorporated herein by reference in entirety. Phenoxazines are described in U.S. Pat. Nos. 5,502,177, 5,763,588, and 6,005,096, each of which is incorporated herein by reference in its entirety. G-clamps are described in U.S. Pat. Nos. 6,007,992 and 6,028,183, each of which is incorporated herein by reference in its entirety. Thus, In other embodiments, the primer pair has at least one modified nucleobase such as 5-propynylcytidine or 5-propynyluridine.

The present invention also comprises isolated mitochondrial DNA amplicons which are produced by the process of amplification of a sample of mitochondrial DNA with any of the above-mentioned primers.

While the present invention has been described with specificity in accordance with certain of its embodiments, the following examples serve only to illustrate the invention and are not intended to limit the same.

EXAMPLES

Example 1

Nucleic Acid Isolation and Amplification

General Genomic DNA Sample Prep Protocol: Raw samples were filtered using Supor-200 0.2 μm membrane syringe filters (VWR International). Samples were transferred to 1.5 ml eppendorf tubes pre-filled with 0.45 g of 0.7 mm Zirconia beads followed by the addition of 350 μl of ATL buffer (Qiagen, Valencia, Calif.). The samples were subjected to bead beating for 10 minutes at a frequency of 19 l/s in a Retsch Vibration Mill (Retsch). After centrifugation, samples were transferred to an S-block plate (Qiagen, Valencia, Calif.) and DNA isolation was completed with a BioRobot 8000 nucleic acid isolation robot (Qiagen, Valencia, Calif.).

Isolation of Blood DNA—Blood DNA was isolated using an MDx Biorobot according to according to the manufacturer's recommended procedure (Isolation of blood DNA on Qiagen QIAamp® DNA Blood BioRobot® MDx Kit, Qiagen, Valencia, Calif.)

Isolation of Buccal Swab DNA—Since the manufacturer does not support a full robotic swab protocol, the blood DNA isolation protocol was employed after each swab was first suspended in 400 ml PBS+400 ml Qiagen AL buffer+20 μl Qiagen Protease solution in 14 ml round-bottom falcon tubes, which were then loaded into the tube holders on the MDx robot.

Isolation of DNA from Nails and Hairs—The following procedure employs a Qiagen DNeasy® tissue kit and represents a modification of the manufacturer's suggested procedure: hairs or nails were cut into small segments with sterile scissors or razorblades and placed in a centrifuge tube to which was added 1 ml of sonication wash buffer (10 mM TRIS-Cl, pH 8.0+10 mM EDTA+0.5% Tween-20. The solution was sonicated for 20 minutes to dislodge debris and then washed 2× with 1 ml ultrapure double deionized water before addition of 100 µl of Buffer X1 (10 mM TRIS-Cl, ph 8.0+10 mM EDTA+100 mM NaCl+40 mM DTT+2% SDS+250:g/ml Qiagen proteinase K). The sample was then incubated at 55° C. for 1-2 hours, after which 200 µl of Qiagen AL buffer and 210 µl isopropanol were added and the solution was mixed by vortexing. The sample was then added to a Qiagen DNeasy mini spin column placed in a 2 ml collection tube and centrifuged for 1 min at 6000 g (8000 rpm). Collection tube and flow-through were discarded. The spin column was transferred to a new collection tube and 500 µl of buffer AW2 was added before centrifuging for 3 min. at 20,000 g (14,000 rpm) to dry the membrane. For elution, 50-100 µl of buffer AE was pipetted directly onto the DNeasy membrane and eluted by centrifugation (6000 g-8000 rpm) after incubation at room temperature for 1 min.

Amplification by PCR—An exemplary PCR procedure for amplification of mitochondrial DNA is the following: A 50 µl total volume reaction mixture contained 1× GenAmp® PCR buffer II (Applied Biosystems)—10 mM TRIS-Cl, pH 8.3 and 50 mM KCl, 1.5 mM MgCl$_2$, 400 mM betaine, 200 µM of each dNTP (Stratagene 200415), 250 nM of each primer, and 2.5-5 units of Pfu exo(−) polymerase Gold (Stratagene 600163) and at least 50 pg of template DNA. All PCR solution mixing was performed under a HEPA-filtered positive pressure PCR hood. An example of a programmable PCR cycling profile is as follows: 95° C. for 10 minutes, followed by 8 cycles of 95° C. for 20 sec, 62° C. for 20 sec, and 72° C. for 30 sec—wherein the 62° C. annealing step is decreased by 1° C. on each successive cycle of the 8 cycles, followed by 28 cycles of 95° C. for 20 sec, 55° C. for 20 sec, and 72° C. for 30 sec, followed by holding at 4° C. Development and optimization of PCR reactions is routine to one with ordinary skill in the art and can be accomplished without undue experimentation.

Example 2

Digestion of Amplicons with Restriction Enzymes

Reaction Conditions—The standard restriction digest reaction conditions outlined herein are applicable to all panels of restriction enzymes. The PCR reaction mixture is diluted into 2×NEB buffer 1+BSA and 1 µl of each enzyme per 50 µl of reaction mixture is added. The mixture is incubated at 37° C. for 1 hour followed by 72° C. for 15 minutes. Restriction digest enzyme panels for HV1, HV2 and twelve additional regions of mitochondrial DNA are indicated in Table 2.

TABLE 2 mtDNA Regions, Coordinates and Restriction Enzyme Digest Panels

| mtDNA REGION | COORDINATES RELATIVE TO THE ANDERSON SEQUENCE (SEQ ID NO: 72) | RESTRICTION ENZYME PANEL |
| --- | --- | --- |
| HV1 (highly variable control region 1) | 16050-16410 | RsaI |
| HV2 (highly variable control region 2) | 29-429 | HaeIII HpaII MfeI SspI HpaII, HpyCH4IV, PacI and EaeI |
| REGION R1 (COX2, Intergenic spacer, tRNA-Lys, ATP6) | 8162-8992 | DdeI MseI HaeIII MboI |
| REGION R2 (ND5) | 12438-13189 | DdeI HaeIII MboI MseI |
| REGION R3 (ND6 tRNA-Glu, CYTB) | 14629-15414 | DdeI MseI MboI BanI |
| REGION R4 (COX3, tRNA-Gly, ND3) | 9435-9461 | DdeI HpyCH4IV MseI HaeIII |
| REGION R5 (ND4L, ND4) | 10753-11500 | AluI BfaI MseI |
| REGION R6 (CYIB, tRNA-Thr, tRNA-Pro) | 15378-16006 | DdeI HaeIII MboI MseI RsaI |
| REGION R7 (ND5, ND6) | 13424-14206 | DdeI HpaII HaeIII MseI |
| REGION R8 (ND1) | 3452-4210 | BfaI DdeI EcoRI MboI |
| REGION R9 (COX2, Intergenic spacer, tRNA-Lys, ATP6) | 7734-8493 | BfaI DdeI HpaII HpyCH4IV MboI |
| REGION R10 (COX1) | 6309-7058 | BfaI HpaII MboI |
| REGION R11 (COX2, Intergenic spacer, tRNA-Lys, ATP6) | 7644-8371 | BfaI DdeI HpyCH4V MboI |
| REGION R12 (16S rRNA; ND1) | 2626-3377 | BfaI DdeI MseI |

Example 3

Nucleic Acid Purification

Procedure for Semi-automated Purification of a PCR mixture using Commercially Available ZipTips®—As described by Jiang and Hofstadler (Y. Jiang and S. A. Hofstadler *Anal. Biochem.* 2003, 316, 50-57) an amplified nucleic acid mixture can be purified by commercially available pipette tips containing anion exchange resin. For pre-treatment of ZipTips® AX (Millipore Corp. Bedford, Mass.), the following steps were programmed to be performed by an Evolution™ P3 liquid handler (Perkin Elmer) with fluids being drawn from stock solutions in individual wells of a 96-well plate (Marshall Bioscience): loading of a rack of ZipTips®AX; washing of ZipTips®AX with 15 µl of 10% NH$_4$OH/50% methanol; washing of ZipTips® AX with 15 µl of water 8 times; washing of ZipTips® AX with 15 µl of 100 mM NH$_4$OAc.

For purification of a PCR mixture, 20 µl of crude PCR product was transferred to individual wells of a MJ Research plate using a BioHit (Helsinki, Finland) multichannel pipette. Individual wells of a 96-well plate were filled with 300 µl of 40 mM NH$_4$HCO$_3$. Individual wells of a 96-well plate were filled with 300 µl of 20% methanol. An MJ research plate was filled with 10 µl of 4% NH₄OH. Two reservoirs were filled with deionized water. All plates and reservoirs were placed on the deck of the Evolution P3 (EP3) (Perkin-Elmer, Boston, Mass.) pipetting station in pre-arranged order. The following steps were programmed to be performed by an Evolution P3 pipetting station: aspiration of 20 µl of air into the EP3 P50 head; loading of a pre-treated rack of ZipTips® AX into the EP3 P50 head; dispensation of the 20 µl NH₄HCO₃ from the ZipTips® AX; loading of the PCR product into the ZipTips® AX by aspiration/dispensation of the PCR solution 18 times; washing of the ZipTips® AX containing bound nucleic acids with 15 µl of 40 mM NH₄ HCO₃ 8 times; washing of the ZipTips® AX containing bound nucleic acids with 15 µl of 20% methanol 24 times; elution of the purified nucleic acids from the ZipTips® AX by aspiration/dispensation with 15 µl of 4% NH₄OH 18 times. For final preparation for analysis by ESI-MS, each sample was diluted 1:1 by volume with 70% methanol containing 50 mM piperidine and 50 mM imidazole.

Procedure for Semi-Automated Purification of a PCR mixture with Solution Capture—The following procedure is disclosed in a U.S. patent application filed on May 12, 2004: for pre-treatment of ProPac® WAX weak anion exchange resin, the following steps were performed in bulk: sequential washing three times (10:1 volume ratio of buffer to resin) with each of the following solutions: (1) 1.0 M formic acid/50% methanol, (2) 20% methanol, (3) 10% NH₄OH, (4) 20% methanol, (5) 40 mM NH₄HCO₃, and (6) 100 mM NH₄OAc. The resin is stored in 20 mM NH₄OAc/50% methanol at 4° C.

Corning 384-well glass fiber filter plates were pre-treated with two rinses of 250 µl NH₄OH and two rinses of 100 µl NH₄HCO₃.

For binding of the PCR product nucleic acids to the resin, the following steps were programmed to be performed by the Evolution™ P3 liquid handler: addition of 0.05 to 10 µl of pre-treated ProPac® WAX weak anion exchange resin (30 µl of a 1:60 dilution) to a 50 µl PCR reaction mixture (80 µl total volume) in a 96-well plate; mixing of the solution by aspiration/dispensation for 2.5 minutes; and transfer of the solution to a pre-treated Corning 384-well glass fiber filter plate. This step was followed by centrifugation to remove liquid from the resin and is performed manually, or under the control of a robotic arm.

The resin containing nucleic acids was then washed by rinsing three times with 200 µl of 100 mM NH₄OAc, 200 µl of 40 mM NH₄HCO₃ with removal of buffer by centrifugation for about 15 seconds followed by rinsing three times with 20% methanol for about 15 seconds. The final rinse was followed by an extended centrifugation step (1-2 minutes).

Elution of the nucleic acids from the resin was accomplished by addition of 40 µl elution/electrospray buffer (25 mM piperidine/25 mM imidazole/35% methanol and 50 nM of an internal standard oligonucleotide for calibration of mass spectrometry signals) followed by elution from the 384-well filter plate into a 384-well catch plate by centrifugation. The eluted nucleic acids in this condition were amenable to analysis by ESI-MS. The time required for purification of samples in a single 96-well plate using a liquid handler is approximately five minutes.

Example 4

Mass Spectrometry

The mass spectrometer used is a Bruker Daltonics (Billerica, Mass.) Apex II 70e electrospray ionization Fourier transform ion cyclotron resonance mass spectrometer (ESI-FTICR-MS) that employs an actively shielded 7 Tesla superconducting magnet. All aspects of pulse sequence control and data acquisition were performed on a 1.1 GHz Pentium II data station running Bruker's Xmass software. 20 µL sample aliquots were extracted directly from 96-well microtiter plates using a CTC HTS PAL autosampler (LEAP Technologies, Carrboro, N.C.) triggered by the data station. Samples were injected directly into the ESI source at a flow rate of 75 µL/hr. Ions were formed via electrospray ionization in a modified Analytica (Branford, Conn.) source employing an off axis, grounded electrospray probe positioned ca. 1.5 cm from the metalized terminus of a glass desolvation capillary. The atmospheric pressure end of the glass capillary is biased at 6000 V relative to the ESI needle during data acquisition. A counter-current flow of dry $N_2/O_2$ was employed to assist in the desolvation process. Ions were accumulated in an external ion reservoir comprised of an rf-only hexapole, a skimmer cone, and an auxiliary gate electrode, prior to injection into the trapped ion cell where they were mass analyzed.

Spectral acquisition was performed in the continuous duty cycle mode whereby ions were accumulated in the hexapole ion reservoir simultaneously with ion detection in the trapped ion cell. Following a 1.2 ms transfer event, in which ions were transferred to the trapped ion cell, the ions were subjected to a 1.6 ms chirp excitation corresponding to 8000-500 m/z. Data was acquired over an m/z range of 500-5000 (IM data points over a 225K Hz bandwidth). Each spectrum was the result of co-adding 32 transients. Transients were zero-filled once prior to the magnitude mode Fourier transform and post calibration using the internal mass standard. The ICR-2LS software package (G. A. Anderson, J. E. Bruce (Pacific Northwest National Laboratory, Richland, Wash., 1995) was used to deconvolute the mass spectra and calculate the mass of the monoisotopic species using an "averaging" fitting routine (M. W. Senko, S. C. Beu, F. W. McLafferty, *J. Am. Soc. Mass Spectrom.* 1995, 6, 229) modified for DNA. Using this approach, monoisotopic molecular weights were calculated.

Example 5

Primer Pairs for Amplification of Informative Regions of Mitochondrial DNA

Conventional forensic mitochondrial DNA analysis typically involves amplification and sequencing of the two hypervariable regions within the non-coding control region known as HV1 and HV2. The present invention comprises primer pairs for amplification of informative regions within HV1 and HV2 (SEQ ID NOs: 8-17, 42-48 and 65-71 in Table 3). Additional individual discriminating power has been obtained by the selection for analysis of 12 additional non-control regions (Regions R1-R12) from which informative amplification products of approximately 630-840 bp each can be obtained using additional primer pairs (SEQ ID NOs: 18-41 and 49-70 in Table 3). The primers listed below in Table 3 are generally 10-50 nucleotides in length, 15-35 nucleotides in length, or 18-30 nucleotides in length.

By convention, human mtDNA sequences are described using the first complete and published mtDNA sequence as a reference (Anderson, S. et al., *Nature*, 1981, 290, 457-465). This sequence is commonly referred to as the Anderson sequence. Primer pair names on Table 3 indicate the mtDNA amplicon coordinates with reference to the Anderson mtDNA sequence: GenBank Accession No. NC_001807.3 (SEQ ID NO: 72). For example, primer pairs 8:9 produce an amplicon which corresponds to positions 76-353 of the Anderson sequence.

TABLE 3

Primer Pairs for Analysis of mtDNA

| PRIMER PAIR NAME | mtDNA REGION AMPLIFIED | FORWARD PRIMER SEQUENCE | FORWARD SEQ ID NO: | REVERSE PRIMER SEQUENCE | REVERSE SEQ ID NO: |
|---|---|---|---|---|---|
| HMTHV2_ANDRSN_76_353_TMOD | REGION HV2 | tcacgcgatagcattgag | 8 | tggtttggcagagatgtgtttaagt | 9 |
| HMTHV2_ANDRSN_29_429_TMOD | REGION HV2 | tctcacgggagctctccatgc | 10 | tctgttaaaagtgcataccgcca | 11 |
| HMTHV1_ANDRSN_16065_16410_TMOD | REGION HV1 | tgactcacccatcaacaaccgc | 12 | tgaggatggtggtcaagggac | 13 |
| HMTHV1_ANDRSN_16065_16354_TMOD | REGION HV1 | tgactcacccatcaacaaccgc | 12 | tggatttgactgtaatgtgcta | 14 |
| HMTHV1_ANDRSN_16064_16359 | REGION HV1 | tgactcacccatcaacaaccgc | 12 | tgaagggatttgactgtaatgtgctatg | 15 |
| HMT_ASN_16036_522 | REGION HV1 and REGION HV2 | gaagcagatttgggtaccacc | 16 | gtgtgtgtgctgggtaggatg | 17 |
| HMT_ASN_8162_8916 | REGION R1 (COX2, Intergenic spacer, tRNA-Lys, ATP6) | tacggtcaatgctctgaaatctgtgg | 18 | tggtaagaagtgggctagggcatt | 19 |
| HMT_ASN_12438_13189 | REGION R2 (ND5) | ttatgtaaaatccattgtcgcatccacc | 20 | tggtgatagcgcctaagcatagtg | 21 |
| HMT_ASN_14629_15353 | REGION R3 (ND6 tRNA-Glu, CYTB) | tcccattactaaacccacactcaacag | 22 | tttcgtgcaagaataggaggtggag | 23 |
| HMT_ASN_9435_10188 | REGION R4 (COX3, tRNA-Gly, ND3) | taaggccttcgatacgggataatccta | 24 | tagggtcgaagccgcactcg | 25 |
| HMT_ASN_10753_11500 | REGION R5 (ND4L, ND4) | tactaccaatgctaaaactaatcgtcccaac | 26 | tgtgaggcgtattataccatagccg | 27 |
| HMT_ASN_15369_16006 | REGION 6 (CYTB, tRNA-Thr, tRNA-Pro) | tcctaggaatcacctcccattccga | 28 | tagaatcttagctttgggtgctaatggtg | 29 |
| HMT_ASN_13461_14206 | REGION R7 (ND5, ND6) | tggcagcctagcattagcaggaata | 30 | tggctgaacattgtttgttggtgt | 31 |
| HMT_ASN_3452_4210 | REGION R8 (ND1) | tcgctgacgccataaaactcttcac | 32 | taagtaatgctagggtgagtggtaggaag | 33 |
| HMT_ASN_7734_8493 | REGION R9 (COX2, Intergenic spacer, tRNA-Lys, ATP6) | taactaatactaacatctcagacgctcagga | 34 | tttatgggctttggtgagggaggta | 35 |
| HMT_ASN_6309_7058 | REGION 10 (COX1) | tactcccaccctggagcctc | 36 | tgctcctattgataggacatagtggaagtg | 37 |
| HMT_ASN_7644_8371 | REGION R11 (COX2, Intergenic spacer, tRNA-Lys, ATP6) | ttatcacctttcatgatcacgccct | 38 | tggcatttcactgtaaagaggtgttg | 39 |
| HMT_ASN_2626_3377 | REGION R12 (16S rRna; ND1) | tgtatgaatggctccacgagggt | 40 | tcggtaagcattaggaatgccattgc | 41 |
| HMTHV1_ANDRSN_16065_16410 | REGION HV1 | gactcacccatcaacaaccgc | 42 | gaggatggtggtcaagggac | 43 |
| HMTHV2_ANDRSN_29_429 | REGION HV2 | ctcacgggagctctccatgc | 44 | ctgttaaaagtgcataccgcca | 45 |
| HMTHV1_ANDRSN_16065_16354 | REGION HV1 | gactcacccatcaacaaccgc | 42 | ggatttgactgtaatgtgcta | 46 |
| HMTHV2_ANDRSN_76_353 | REGION HV2 | cacgcgatagcattgcg | 47 | ggtttggcagagatgtgtttaagt | 48 |

TABLE 3-continued

Primer Pairs for Analysis of mtDNA

| PRIMER PAIR NAME | mtDNA REGION AMPLIFIED | FORWARD PRIMER SEQUENCE | FORWARD SEQ ID NO: | REVERSE PRIMER SEQUENCE | REVERSE SEQ ID NO: |
|---|---|---|---|---|---|
| HMT_ASN_8162_8992 | REGION R1 (COX2, Intergenic spacer, tRNA-Lys, ATP6) | tacggtcaatgctct gaaatctgtgg | 18 | tggctattggttg aatgagtaggctg | 49 |
| HMT_ASN_12432_13262 | REGION R2 (ND5) | tccccattatgtaaa atccattgtcgc | 50 | tgacttgaagtgg agaaggctacg | 51 |
| HMT_ASN_14629_15414 | REGION R3 (ND6 tRNA-Glu, CYTB) | tcccattactaaacc cacactcaacag | 22 | taaggtggaagg tgattttatcgga a | 52 |
| HMT_ASN_9411_10190 | REGION R4 (COX3, tRNA-GLY, ND3) | tgccaccacacacca cctg | 53 | tatagggtcgaag ccgcactc | 54 |
| HMT_ASN_10751_11514 | REGION R5 (ND4L, ND4) | tctactccaatgcta aaactaatcgtccc | 55 | tggttgagaatga gtgtgaggcg | 56 |
| HMT_ASN_15378_16006 | REGION R6 (CYTB, tRNA-Thr, tRna-Pro) | tcacctcccattccg ataaaatcacct | 57 | tagaatcttagct ttgggtgctaatg gtg | 29 |
| HMT_ASN_13424_14206 | REGION R7 (ND5, ND6) | tcaaaaccatacctc tcacttcaacctc | 58 | tggctgaacattg tttgttggtgt | 31 |
| HMT_ASN_3443_4210_2 | REGION R8 (ND1) | tacaacccttcgctg acgccat | 59 | taagtaatgctag ggtgagtggtagg aa | 60 |
| HMT_ASN_6278_7006 | REGION R10 (COX1) | ttgaacagtctaccc tcccttagc | 61 | tgtagtcgatgt ctagtgatgagtt tgc | 62 |
| HMT_ASN_7688_8371 | REGION R11 (COX2, Intergenic spacer, tRNA-Lys, ATP6) | tgcttcctagtcctg tatgccctttttcc | 63 | tggcatttcactg taaagaggtgttg g | 39 |
| HMT_ASN_2626_3463 | REGION R12 (16S rRNA; ND1) | tgtatgaatggctcc acgaggt | 40 | tggcgtcagcgaa gggttgta | 64 |
| HMTHV2_ASN_72_357 | REGION HV2 | tgtgcacgcgatagc attgcg | 65 | tggggtttggcag agatgtgtttaag t | 66 |
| HMTHV1_ASN_16056_16362 | REGION HV1 | tcaagtattgactca cccatcaacaacc | 67 | tcgagaagggatt tgactgtaatgtg cta | 68 |
| HMTHV1_ASN_16050_16370 | REGION HV1 | taccacccaagtatt gactcacccatc | 69 | tcatggggacgag aagggatttgac | 70 |
| HMTHV1_ASN_16064_16362 | REGION HV1 | tgactcacccatcaa caaccgc | 12 | tcgagaagggatt tgactgtaatgtg cta | 68 |
| HMTHV1_ASN_16064_16370 | REGION HV1 | tgactcacccatcaa caaccgc | 12 | tcatggggacgag aagggatttgac | 70 |
| HMTHV1_ASN_16056_16359 | REGION HV1 | tcaagtattgactca cccatcaacaacc | 67 | tgaagggatttga ctgtaatgtgcta tg | 15 |
| HMTHV1_ASN_16056_16370 | REGION HV1 | tcaagtattgactca cccatcaacaacc | 71 | tcatggggacgag aagggatttgac | 70 |
| HMTHV1_ASN_16050_16359 | REGION HV1 | taccacccaagtatt gactcacccatc | 69 | tgaagggatttga ctgtaatgtgcta tg | 15 |
| HMTHV1_ASN_16050_16362 | REGION HV1 | taccacccaagtatt gactcacccatc | 69 | tcgagaagggatt tgactgtaatgtg cta | 68 |

Example 6

Analysis of 10 Blinded DNA Samples

Figure 3:
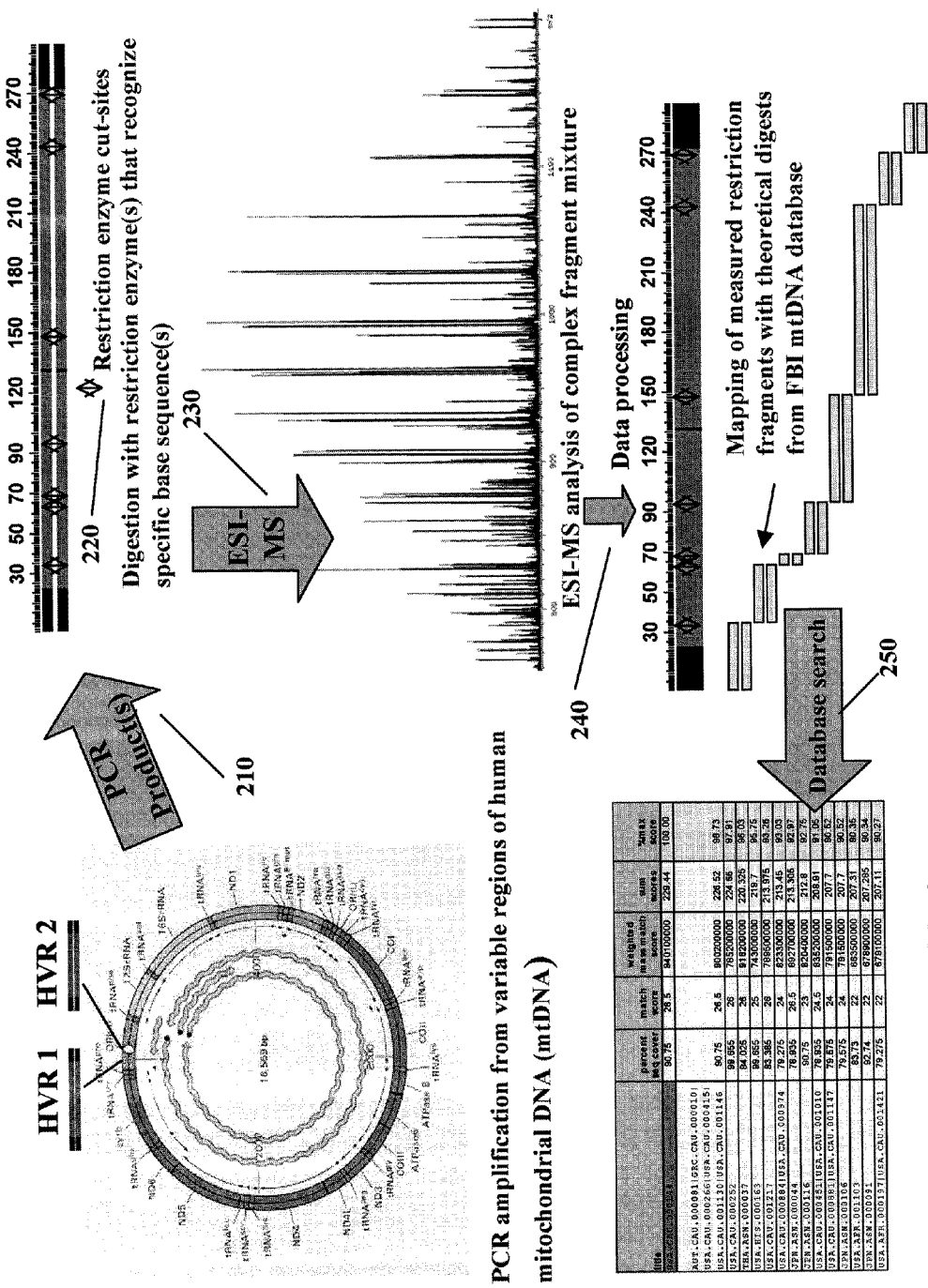
FIG. 3 indicates the process of mtDNA analysis. After amplification by PCR (210), the PCR products were subjected to restriction digests (220) with RsaI for HV1 and a combination of HpaII, HpyCH4IV, PacI and EaeI for HV2 in order to obtain amplicon segments suitable for analysis by FTICR-MS (240). The data were processed to obtain mass data for each amplicon segment (250) which were then compared to the masses calculated for theoretical digests from the FBI mtDNA database by a scoring scheme (260).

Ten different blinded samples of human DNA provided by the FBI were subjected to rapid mtDNA analysis by the method of the present invention according to the process illustrated in FIG. 3. After amplification of human mtDNA by PCR (210), the PCR products were subjected to restriction digestion (220) with RsaI for HV1 and a combination of HpaII, HpyCH4IV, PacI and EaeI for HV2 in order to obtain amplicon segments suitable for analysis by mass spectrometry (230). The data were processed to obtain mass data for each amplicon fragment (240) from which a "fragment coverage map" was generated (an example of a fragment coverage map is shown in FIG. 3—represented as a series of horizontal bars beneath the mass spectrum). The fragment coverage map was then compared, using a scoring scheme to fragment coverage maps calculated for theoretical digests from mtDNA sequences in the FBI mtDNA database (250).

A group of 10 blinded DNA samples was provided by the FBI. HV1 and HV2 primer pairs were selected from a sequence alignment created by translating the FBI's forensic mtDNA database back into full sequences via comparison to the Anderson reference, then selecting primers within the full representation core of the alignment and restriction enzymes that will cleave the 280 and 292 bp PCR products into mass spectrometry-compatible fragments. Primer pairs selected for amplification of HV1 segments were SEQ ID NOs: 12:14 and 42:43. Primer pairs selected for amplification of HV2 segments were SEQ ID NOs: 8:9 and 44:45 (Table 3). PCR amplification was carried out as indicated in Example 1, with the exception that 2 mM $MgCl_2$ was included instead of 1.5 mM $MgCl_2$, and that 4 units of Amplitaq Gold® polymerase (Applied Biosystems) was included instead of 2.5 units of Pfu exo(−) polymerase. 3 µl of FBI DNA sample were included in the reaction. Thermal cycler parameters were as follows: 96° C. for 10 min., followed by 45 cycles of the following: 96° C. for 30 sec, 54° C. for 30 sec., and 72° C. for 30 sec., after which the reaction was kept at 72° C. for 5 minutes.

Theoretical digestions of the 2754 unambiguous unique sequences contained within the 4840 FBI sequence entries (there are 399 sequences in the FBI database which contain at least one ambiguous base call within the amplified regions, leading to 4441 unambiguous sequences, 2754 of which are unique), with all possible products resulting from incomplete digestion, were performed and fragment start and end coordinates, base composition, mass, and end chemistry were stored in a data structure for subsequent fragment pattern reconstruction. A deconvolved list of monoisotopic exact mass determinations from ICR-2LS$_1$ was determined for each restriction digestion for each blinded sample. For each sample, expected digestion fragment masses were matched to observed masses with a threshold of ±4 ppm for each database entry (1 ppm match error is defined as a difference between observed and expected mass equal to one millionth of the expected mass).

To evaluate the ability of a single-pass MS-based assay to exclude known database entries as having base compositions that are different than that of an unknown sample, a scoring system was devised that, for a given input sample, assigns each database sequence a score relative to the highest scoring sequence. To evaluate whether base composition of mtDNA fragments can achieve a discrimination power approaching that of sequencing, the ten blinded samples of human DNA from the FBI were analyzed. The overall consistency of the observed digestion products with the expected fragment pattern for each of the 4840 database entries was scored using the sum of four values: 1.) The total number of observed masses accounted for in the expected fragment list, 2.) The percentage of expected fragments observed for a complete digestion 3.) A "floating percentage" of expected fragments matched, where matches to incomplete digestion fragments were scored ½ percentage point and the total number of expected fragments was incremented by ½ for each observed incomplete digestion fragment, and 4.) The percentage of sequence positions accounted for by matches with observed masses. Scores for the HV1 and HV2 regions were summed to produce a total score for each entry. Database entries were sorted by high score and assigned a final score as a percentage of the top score. An arbitrary (but conservative) scoring threshold of 80% of the top score was set to produce a very conservative lower bound on the percentage of database entries that could be excluded as consistent with each sample.

Without knowing the true sequence of the initial ten samples and allowing for slight experimental variations in restriction digestions and mass spectrometry, comparison to a large collection of database entries enabled exclusion of a vast majority of entries in the database. Table 4 shows an example of the scoring output for one sample (sample 4) and summarizes the exclusion percentages for each of the blinded samples for a set of reactions run side-by-side on a single day. The HV1 and HV2 regions of each sample were sequenced following the analysis described in this work for final verification. Table 4 summaries the overall results of this exercise for this preliminary data analysis.

TABLE 4

Scoring of FBI Sample 3 Against the FBI Mitochondrial DNA Database

| Row | Database Entry Title | Number of Sequences Represented | % of Sequence Covered | % of Fragment Covered | Floating Fragment Covered | Match Score | Cumulative Score | % Match Score |
|---|---|---|---|---|---|---|---|---|
| 1 | AUT.CAU.000066\|<br>USA.CAU.000389\|<br>USA.CAU.000572\|<br>USA.CAU.000841\|<br>USA.CAU.001074\|<br>USA.CAU.00121\| | 6 | 99.655 | 51.04 | 63.18 | 32.5 | 333.89 | 100 |
| 2 | USA.CAU.000101 | 1 | 90.92 | 47.02 | 57.005 | 24.5 | 300.38 | 89.9638 |
| 3 | USA.CAU.000783 | 1 | 90.75 | 44.79 | 56.37 | 27 | 298.08 | 89.2749 |
| 4 | USA.CAU.000130 | 1 | 88.18 | 46.53 | 56.68 | 27.5 | 296.92 | 88.9275 |
| 5 | USA.CAU.000142 | 1 | 88.18 | 46.53 | 56.68 | 27.5 | 296.92 | 88.9275 |

TABLE 4-continued

Scoring of FBI Sample 3 Against the FBI Mitochondrial DNA Database

| Row | Database Entry Title | Number of Sequences Represented | % of Sequence Covered | % of Fragment Covered | Floating Fragment Covered | Match Score | Cumulative Score | % Match Score |
|---|---|---|---|---|---|---|---|---|
| 6 | FRA.CAU.000087\|GRC.CAU.000032\|USA.CAU.000425\|USA.CAU.000483\|USA.CAU.000772\|USA.CAU.001067\|USA.CAU.001168 | 7 | 92.765 | 42.71 | 51.86 | 25 | 295.95 | 88.637 |
| 44 | USA.HIS.000672 | 1 | 84.52 | 40.555 | 46.43 | 18 | 268.15 | 80.3109 |
| 45 | FRA.CAU.000108\|USA.CAU.000890 | 2 | 92.055 | 33.035 | 42.22 | 17.5 | 267.68 | 80.1701 |
| 46 | USA.CAU.000361\|USA.CAU.001184 | 2 | 92.055 | 33.035 | 42.22 | 17.5 | 267.68 | 80.1701 |
| 47 | USA.CAU.001378\|USA.CAU.001382 | 2 | 92.055 | 33.035 | 42.22 | 17.5 | 267.68 | 80.1701 |
| 48 | CHN.ASN.000443 | 1 | 88.525 | 34.03 | 43.135 | 22 | 267.11 | 79.9994 |
| 49 | USA.CAU.000548 | 1 | 83.385 | 39.58 | 47.795 | 21 | 266.93 | 79.9455 |
| 50 | USA.CAU.000814 | 1 | 83.385 | 39.58 | 47.795 | 21 | 266.93 | 79.9455 |
| 51 | USA.CAU.000338\|USA.CAU.000580\|USA.CAU.001139 | 3 | 99.655 | 24.7 | 36.37 | 17 | 265.71 | 79.5801 |
| 2750 | USA.AFR.000947 | 1 | 20.205 | 0 | 4.285 | 3 | 43.41 | 13.0013 |
| 2751 | USA.AFR.000558 | 1 | 8.735 | 5.555 | 10 | 6 | 34.58 | 10.3567 |
| 2752 | SKE.AFR.000107 | 1 | 5.495 | 8.335 | 8.335 | 2 | 29.66 | 8.88317 |
| 2753 | USA.AFR.000440 | 1 | 5.495 | 8.335 | 8.335 | 2 | 29.66 | 8.88317 |
| 2754 | EGY.AFR.000021 | 1 | 11.475 | 0 | 1.515 | 1 | 23.95 | 7.17302 |

Table 4 illustrates the example of scoring sample 3 against the mtDNA database of 4441 entries (4840 original FBI mtDNA entries minus the 399 sequences containing ambiguous base calls). The total combined score for the HV1 and HV2 regions is shown in the column entitled "cumulative score". All entries are given a score relative to the highest cumulative score in the column "% max score". Database entry titles are in the column "DB entries." Sequences whose HV1 and HV2 PCR products are identical are grouped into bins, with entry titles separated by vertical lines. The cut-off point for this exercise was defined as 80% of the top cumulative score. The two bins that define this boundary are rows 47 and 48. The total number of database entries that fall below this threshold is 4347, or 97.9%.

Identification codes used in Table 4 are from the mtDNA population database (Miller K W, Budowle B. *Croat. Med. J.* 2001, 42(3), 315-27). AFR: African; CAU: Caucasian; ASN: Asian; CHN: Chinese; HIS: Hispanic; AUT: Austrian; EGY: Egypt; FRA: France; GRC: Greece; SKE: Sierra Leone.

Example 7

Optimization of Amplification Conditions and Reagents for Efficient Data Processing and Pattern Matching Forensic analysis of human mtDNA by mass spectrometry presents a number of challenges. First, PCR amplification reactions may result in non-templated additions of adenosine to the 3'-end of the template. When this occurs, mass spectrum signals become mixed and detection sensitivity is lowered. Second, the process of carrying out several purification steps to convert a PCR amplification mixture to appropriate specific buffer conditions required for specific restriction digests results in significant sample loss. Lastly, a significant subset of useful restriction endonuclease enzymes yield double-stranded digest products with staggered ends. This occurrence has the effect of complicating the process of restriction pattern analysis and limits the choice of restriction endonucleases to those that only generate blunt-ended digestion products.

Figure 4:
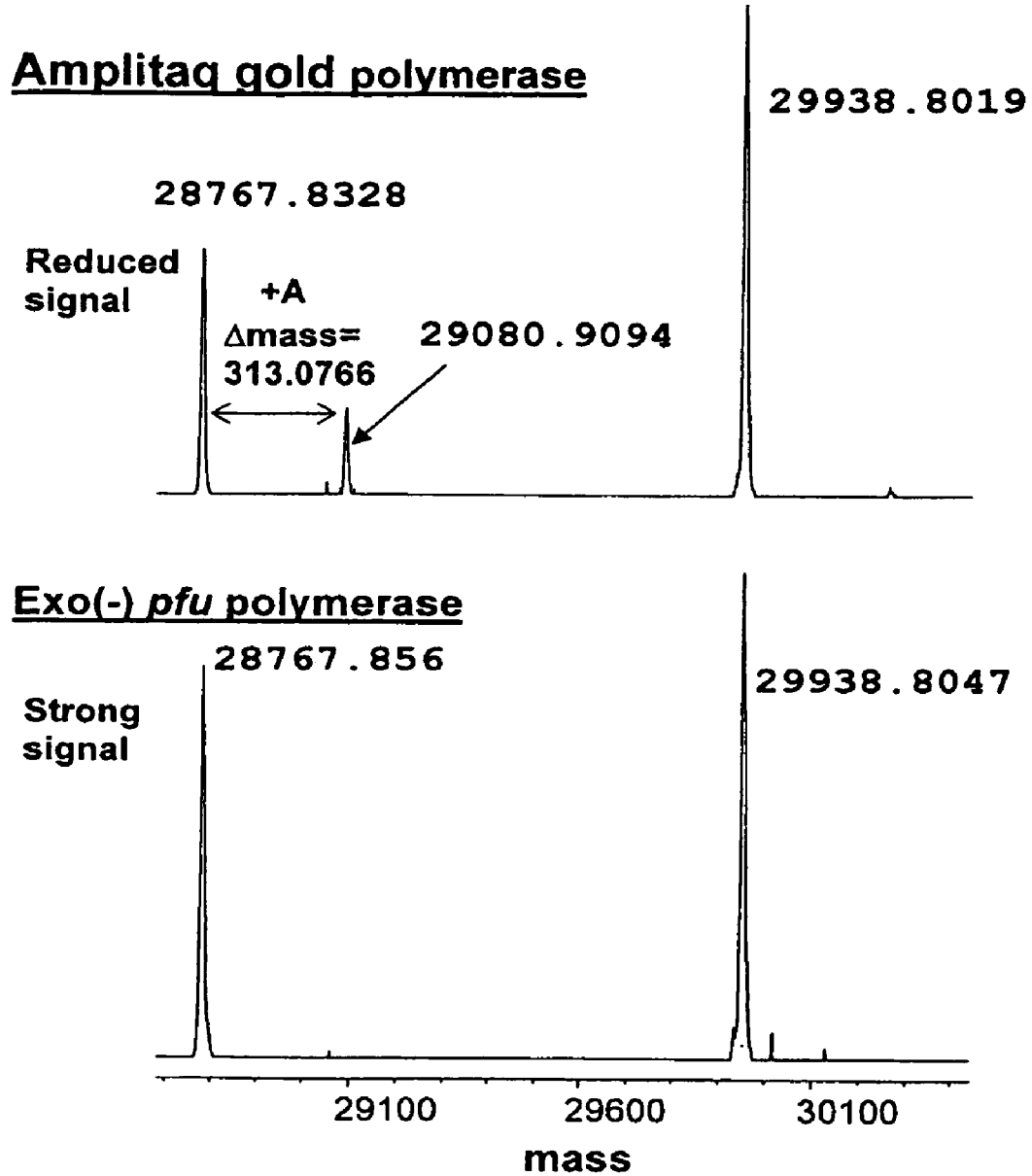
FIG. 4 is a comparison of two mass spectra which indicates that the use of exo(−) pfu polymerase prevents addition of non-templated adenosine residues and results in a strong signal, relative to the use of the commonly used Amplitaq™ gold polymerase.

These complications have been solved by the use of exo(−) Pfu polymerase (Stratagene, La Jolla, Calif.), a 3'-5' exonuclease-deleted Pfu polymerase. The mass spectra of FIG. 4 indicate that the use of exo(−) Pfu polymerase prevents the addition of non-templated adenosine residues and 3'-end deletions which are normally observed when standard pfu polymerases are used. The resulting product exhibited a strong signal in the mass spectrum. On the other hand, use of the commonly used Amplitaq gold polymerase (Applied Biosystems) did not circumvent this problem (FIG. 4). An additional advantage obtained through the use of exo(−) Pfu polymerase is that there is no need for purification of the PCR product. The PCR product mixture can be easily modified with appropriate restriction enzyme activating buffer which is also compatible with the exo(−) Pfu polymerase.

A further additional advantage obtained from the avoidance of a purification procedure is that exo(−) Pfu polymerase remains viable throughout the subsequent restriction digest process and this remaining polymerase activity can be used to add leftover dNTPs to convert staggered restriction products to blunt-ended products by filling in the "missing" nucleotide residues.

Figure 5:
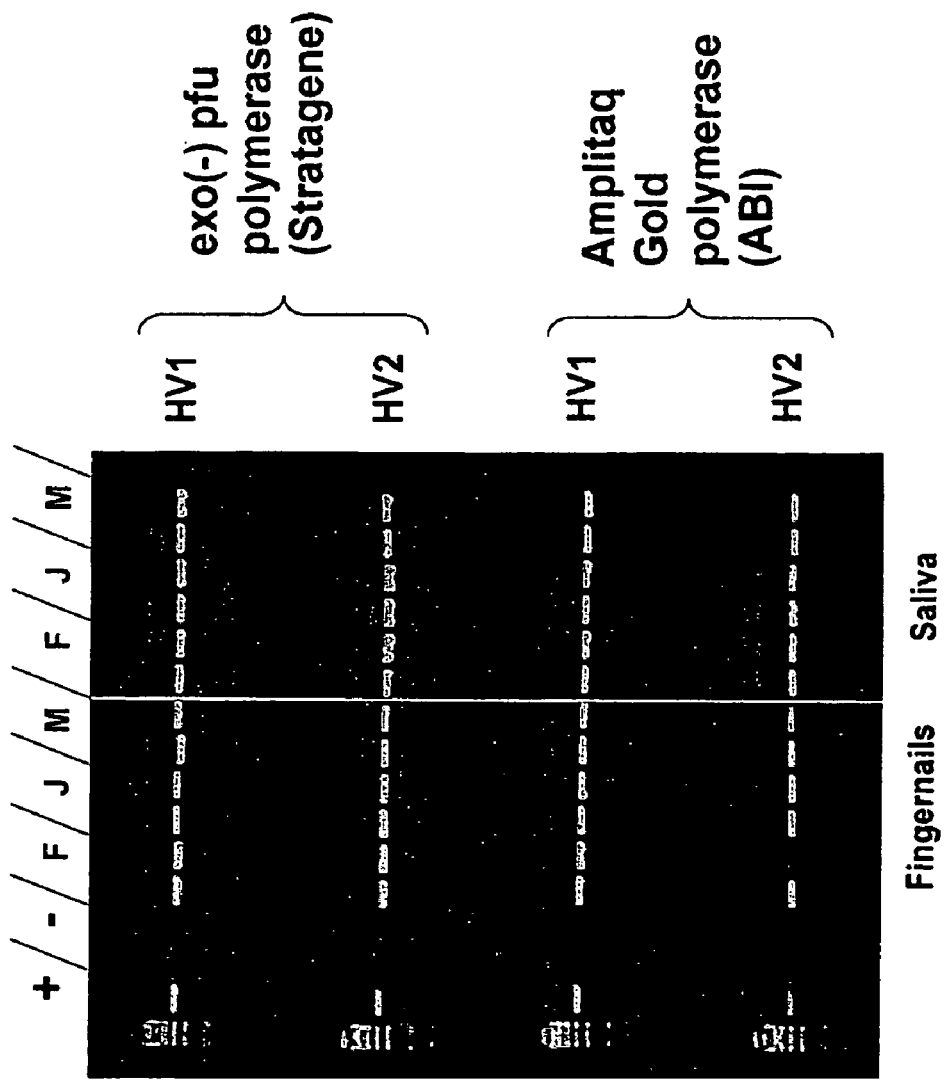
FIG. 5 indicates that gel electrophoresis confirms that exo (−) pfu polymerase is equally effective as a standard polymerase in amplification of mtDNA obtained from blood, fingernail and saliva samples.

Thus, crude PCR products are directly subjected to the restriction digestion process, minimizing time, sample handling and potential contamination. FIG. 5 indicates that exo (−) Pfu polymerase is effective for consistent amplification of mtDNA obtained from blood, fingernail and saliva samples. PCR conditions for this experiment were as follows: A 50 μl reaction volume contained the following: 10 mM TRIS-HCl, 50 mM KCl, $MgCl_2$, 200 μM deoxynucleotide triphosphates, 400 mM betaine, 200 nM primers, 4 units of Amplitaq Gold™ or 5 units exo(−) Pfu polymerase and mtDNA template and was subjected to incubation at 95° C. for 10 minutes first, then 35 cycles of the following thermal sequence: 95° C. for 20 seconds, 52° C. for 20 seconds, 72° C. for 30 seconds. Following the 35 cycles, the reaction was incubated at 72° C. for 4 minutes.

To take advantage of the modified function of the exo(−) Pfu polymerase, the experimental method was modified as follows: upon completion of amplification of mtDNA, restriction endonucleases were added to the amplification mixture which was then incubated for 1 hour at 37° C. The temperature of the mixture was then raised to 37° C. for 15 minutes to activate the exo(−) Pfu polymerase and enable the addition of nucleotides to staggered ends to produce the blunt ends which facilitate pattern analysis.

Figure 6:
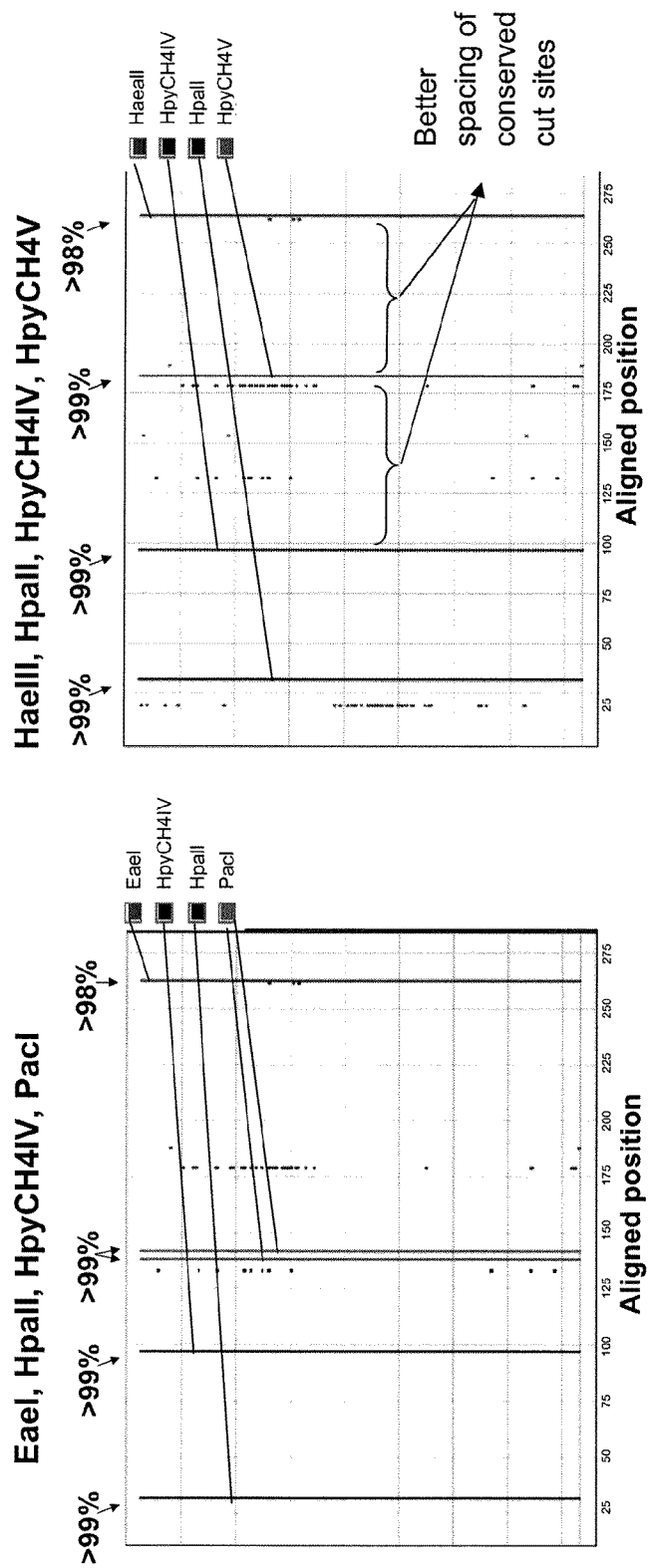
FIG. 6 exhibits two plots that indicate positions of cleavage of human mtDNA obtained with different panels of restriction endonucleases. The modified panel wherein EaeI and PacI are replaced with HaeIII and HpyCH4V respectively, results in better spacing of conserved restriction sites.
Figure 7:
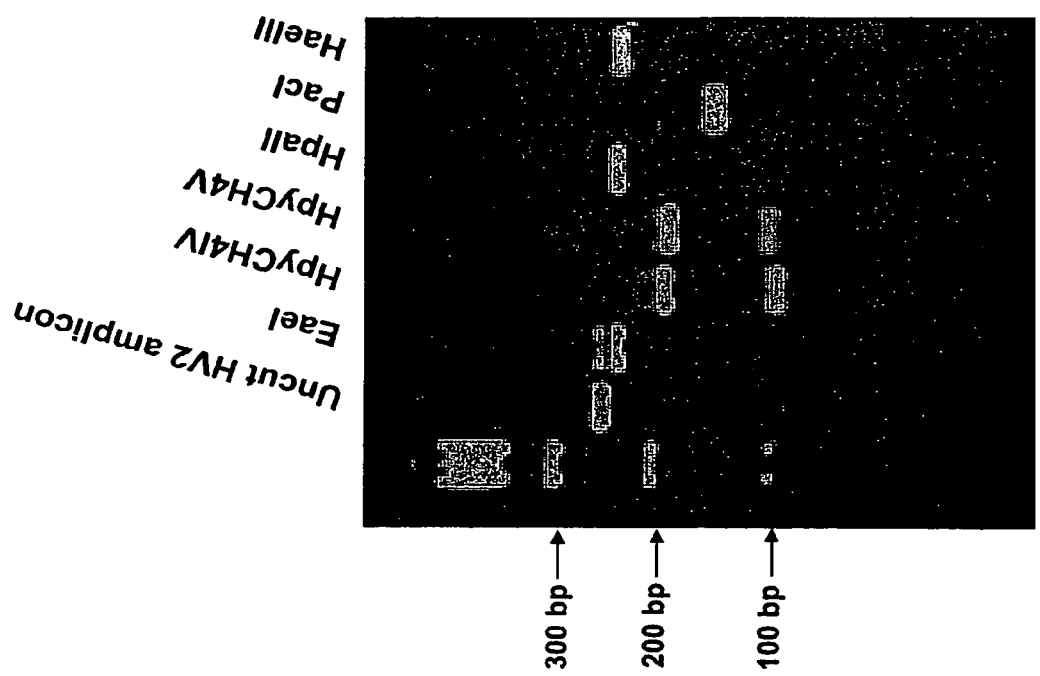
FIG. 7 is an agarose gel electrophoresis photo confirming the activity of restriction endonucleases: EaeI, HpyCH4IV, HpyCH4IV, HpaII, PacI and HaeIII on HV2 amplicon from a mtDNA preparation obtained from a blood sample (Seracare N31773).

As discussed above, the ability of exo(−) Pfu polymerase provides the means of expanding the number of restriction endonucleases that are compatible with the present method and simplifying data processing by simplifying restriction digest patterns. Shown in FIG. 6 is the result of a comparison of digest patterns obtained when the originally chosen restriction enzymes EaeI and PacI are replaced with HaeIII and HpyCH4V. The pattern obtained using the newly chosen enzymes clearly results in a restriction digest pattern with better spacing of conserved restriction sites which facilitates analysis. Shown in FIG. 7 is the result of a gel electrophoresis analysis of the products of restriction digests. In this experiment a HV2 amplicon from a human mtDNA sample designated Seracare N31773. The mtDNA sample was amplified with Amplitaq Gold in 50 μl reaction volumes where 25 μl of PCR reaction was diluted up to 50 μl in: 1× NEB restriction buffer #1, 10 mM Bis-TRIS Propane-HCl, 10 mM $MgCl_2$, 1 mM DTT pH 7.0 (at 25° C.), 1×NEB BSA and (separately) 100 mg/μl in 1 μl volumes of each enzyme as follows: EaeI: 3 units; HpyCH4IV: 10 units; HpyCH4V: 5 units; HpaII: 10 units; PacI: 10 units; and HaeIII: 10 units. The mixtures were incubated for 1 hour at 37° C. before analysis in 4% agarose gel.

Restriction endonucleases MfeI and SspI are both useful alternatives to HpyCH4V and HpyCH4IV respectively, because they cleave at similar positions and cost significantly less than HpyCH4V and HpyCH4IV.

Example 8

Validation of Mitochondrial DNA Analysis Method: Analysis of Human Cheek Swab mtDNA Samples and Comparison with the mtDNA Population Database Cheek swabs were obtained from 16 volunteer donors. Genomic DNA was isolated from the cheek swabs on a Qiagen MDx robot according to procedures outlined in Example 1. Final elution volumes were 160 μl for each well. 2 μl template was used in each PCR reaction which was run according to Example 1 except that the following cycling parameters were used: 95° C. for 10 minutes followed by 45 cycles of 95° C. for 20 sec, 52° C. for 20 sec and 72° C. for 30 sec, followed by holding at 72° C. for 4 minutes. Primer pairs used for HV1 were SEQ ID NOs: 12:15 and for HV2, SEQ ID NOs: 8:9.

PCR products (not shown) were digested with RsaI (HV1) or HaeIII, HpaII, HpyCH4IV, and HpyCH4V (HV2) according to the procedure outlined in Example 2.

Restriction digests were performed in duplicate with each duplicate swab, followed by mass determination of the amplicon fragments by mass spectrometry as described in Example 3. Samples were qualitatively scored for HV1 and HV2 against each unique database entry by the sum of:

a) the percentage of expected fragments observed in the mass spectrum;

b) the percentage of sequence positions covered by matched masses; and c) the total number of observed mass peaks accounted for by matches to theoretical digest fragments.

Table 5 shows that, for the majority of the 16 samples, the ethnic designation of the majority of top-scoring entries from the FBI database coincide with the ethnic background of the donor. In general, mtDNA sequence data cannot be used to reliably associate a sample to the ethnic background of the donor, because the mitochondria follow the maternal line exclusively and ethnic mixing in populations increases as the general population becomes increasingly genetically integrated. However, as an overall assessment of the preliminary matching and scoring system, this association served well, because at the time of this evaluation, mtDNA samples had not been sequenced. Two outliers in the association of donor ethnic background and major ethnic backgrounds of top database scores were samples 2 and 16. Sample 2 was an African-American male with top database scores all designated "USA.CAU.xxx". Upon inquiry, it was learned that this donor has a Caucasian mother. Because mtDNA is inherited maternally, the result appears valid.

TABLE 5

Results of Cheek Swab Comparison to the mtDNA Population Database

| Donor | Full pattern match in mtDNA database | Number of DB entries with highest score | % of database below highest score | % of database below 95% of highest score | % of database below 90% of highest score | % of database below 85% of highest score | % of database below 80% of highest score | Ethnicity closest match | Donor Ethnicity |
|---|---|---|---|---|---|---|---|---|---|
| 1 | USA.AFR.000975 | 1 | 99.979 | 99.979 | 99.959 | 99.917 | 99.917 | AFR | Af. Amer. |
| 2 | USA.CAU.000191 USA.CAU.001303 USA.CAU.001041 | 3 | 99.938 | 99.731 | 99.153 | 96.054 | 92.169 | CAU | Af. Amer. With Cauc. Mother |
| 3 | None | 1 | 99.979 | 99.938 | 99.917 | 99.566 | 98.905 | CHN | Chinese |
| 4 | AUT.CAU.000080 AUT.CAU.000090 AUT.CAU.000099 FRA.CAU.000041 18 more . . . | 22 | 99.545 | 98.12 | 96.777 | 89.628 | 83.657 | 17 CAU 4 HIS 2 AFR | Caucasian |
| 5 | None | 13 | 99.731 | 99.731 | 99.587 | 98.678 | 97.417 | 12 CAU 1 AFR | Caucasian |
| 6 | None | 1 | 99.979 | 99.793 | 99.442 | 97.438 | 94.38 | CAU | Caucasian |
| 7 | None | 1 | 99.979 | 99.959 | 99.628 | 96.529 | 94.587 | ASN | Chinese |
| 8 | None | 1 | 99.979 | 99.876 | 99.793 | 98.244 | 96.157 | CAU | Caucasian |
| 9 | USA.CAU.000031 | 1 | 99.979 | 99.979 | 99.979 | 99.256 | 98.574 | CAU | Caucasian |

TABLE 5-continued

Results of Cheek Swab Comparison to the mtDNA Population Database

| Donor | Full pattern match in mtDNA database | Number of DB entries with highest score | % of database below highest score | % of database below 95% of highest score | % of database below 90% of highest score | % of database below 85% of highest score | % of database below 80% of highest score | Ethnicity closest match | Donor Ethnicity |
|---|---|---|---|---|---|---|---|---|---|
| 10 | USA.CAU.000303 USA.CAU.000969 | 2 | 99.959 | 98.285 | 96.364 | 87.934 | 78.616 | CAU | Caucasian |
| 11 | None | 2 | 99.959 | 99.959 | 99.835 | 99.814 | 99.36 | ASN | Chinese |
| 12 | USA.CAU.000113 | 1 | 99.979 | 99.897 | 99.07 | 98.099 | 92.149 | CAU | Caucasian |
| 13 | CHN.ASN.000374 CHN.ASN.000411 USA.335.000122 GRC.CAU.000007 9 others . . . | 12 | 99.752 | 99.442 | 98.243 | 89.917 | 84.091 | 5 CAU 3 ASN 3 AFR 1 335 | Caucasian |
| 14 | USA.CAU.000297 | 1 | 99.979 | 99.979 | 99.917 | 99.649 | 95.806 | CAU | Caucasian |
| 15 | None | 1 | 99.979 | 99.959 | 98.037 | 92.417 | 86.59 | ASN | Indian (India) |
| 16 | AUT.CAU.000096 AUT.CAU.000100 GRC.CAU.000011 USA.CAU.000604 4 others . . . | 12 | 99.752 | 99.669 | 98.863 | 95.971 | 84.7737 | CAU | Indian (India) |

Identification codes used in Table 5 are from the mtDNA population database (Miller K W, Budowle B. *Croat. Med. J.* 2001, 42(3), 315-27). AFR: African; CAU: Caucasian; ASN: Asian; CHN: Chinese; HIS: Hispanic; AUT: Austrian; GRC: Greece. Code 335 (USA.335) in the donor 13 entry refers to the U.S. territory of Guam.

Example 9

Expanding Discriminating Power of the Mitochondrial DNA Analysis by Examination of Regions Outside of HV1 and HV2

Twelve regions of human mtDNA (referred to as R1-R12) were selected for investigation based upon a relatively large number of differences between individual entries in 524 non-control-region human mitochondrial sequences obtained from Mitokor, Inc. (San Diego, Calif.). The initial twelve primer pairs (see Table 3—SEQ ID NOs: 18:19, 20:21, 22:23, 24:25, 26:27, 28:29, 30:31, 32:33, 34:35, 36:37, 38:39, and 40:41) were tested upon ~1.6 ng of human blood-derived DNA (Seracare blood sample N31773) which was isolated as indicated in Example 1.

Figure 8:
FIG. 8 is an agarose gel electrophoresis photo confirming that the primers designed to amplify the 12 non-control regions (Regions R1-R12) produce amplicons of the expected sizes.

The PCR protocol and cycling conditions are as described in Example 1 with the exception that 4 U of Amplitaq Gold polymerase (Applied Biosystems, Foster City, Calif.) was used. The results of the reactions are shown in FIG. 8 which indicates that reproducible amplicons were obtained for all twelve non-control regions investigated.

Initial digestions with enzyme panels outlined in Example 2 were employed, and coverage maps were assembled by matching observed masses at +4 ppm error to all sequences existing in the database as of Sep. 8, 2003-524 Mitokor-obtained sequences and 444 mtDNA genomes from GenBank.

The total number of unique sequences found within 968 predicted amplicon sequences from Mitokor and GenBank for each of the 12 non-control region primer pairs shows that the greatest number of different sequences is found within regions R1, R3, R6, R7 and R9 (Table 6). When amplicon sequences are concatenated together as collinear sequences, the combination of R1, R3, R6 and R7 comes out on top, with 508 unique base count signatures out of 968 sequences predicted for the combination R1+R3+R6+R7 compared to 475 unique signatures predicted for the combination R1+R3+R9+R7. It was thus decided that regions R1, R3, R6 and R7 provide the best discriminating power. The numbers of unique sequences for each of these regions are denoted by an asterisk in Table 6.

TABLE 6

Final Choices of Primers Optimized for Characterization of Non-Control Mitochondrial DNA Regions

| REGION | mtDNA REGION AMPLIFIED | RESTRICTION ENZYME PANEL | FORWARD SEQ ID NO: | REVERSE SEQ ID NO: | NO. OF UNIQUE BASE COMPOSITIONS | NO. OF UNIQUE SEQUENCES |
|---|---|---|---|---|---|---|
| R1 | COX2; Intergenic spacer; tRNA-Lys; ATP6 | DdeI MseI HaeIII MboI | 18 | 49 | 182 | 204* |
| R2 | ND5 | DdeI HaeIII MboI MseI | 20 | 21 | 106 | 132 |
| R3 | ND6, tRNA-Glu; CYTB | DdeI MseI MboI BanI | 22 | 52 | 135 | 170* |

TABLE 6-continued

Final Choices of Primers Optimized for Characterization of Non-Control Mitochondrial DNA Regions

| REGION | mtDNA REGION AMPLIFIED | RESTRICTION ENZYME PANEL | FORWARD SEQ ID NO: | REVERSE SEQ ID NO: | NO. OF UNIQUE BASE COMPOSITIONS | NO. OF UNIQUE SEQUENCES |
|---|---|---|---|---|---|---|
| R4 | COX3; tRNA-Gly; ND3 | DdeI HpyCH4IV MseI HaeIII | 24 | 25 | 94 | 132 |
| R5 | ND4L; ND4 | AluI BfaI MseI | 26 | 27 | 107 | 130 |
| R6 | CYTB; tRNA-Thr; tRNA-Pro | DdeI HaeIII MboI MseI RsaI | 57 | 29 | 118 | 143* |
| R7 | ND5; ND6 | DdeI HpaII HaeIII MseI | 58 | 31 | 137 | 174* |
| R8 | ND1 | BfaI DdeI EcoRI MboI | 32 | 33 | 88 | 122 |
| R9 | COX2; Intergenic spacer; tRNA-Lys; ATP6 | BfaI DdeI HpaII HpyCH4IV MboI | 34 | 35 | 118 | 145 |
| R10 | COX1 | BfaI HpaII MboI | 36 | 37 | 81 | 109 |
| R11 | COX2; Intergenic spacer; tRNA-Lys; ATP6 | BfaI DdeI HpyCH4V MboI | 38 | 39 | 113 | 136 |
| R12 | 16S rRNA; ND1 | BfaI DdeI MseI | 40 | 43 | 65 | 79 |

The 12 regions were evaluated informatically by considering the total number of unique sequences in each region out of a database of 968 sequences, 524 of which were obtained from Mitokor, Inc, and 444 of which are human mitochondrial genomes obtained from GenBank. Coordinates are given in terms of the Anderson sequence (SEQ ID NO: 72). The number of unique base count signatures was determined by theoretical digestion of each of the 968 database sequences with the indicated enzymes.

Example 10

Sensitivity Assessed with Quantified Human Blood DNA

To measure sensitivity against total human genomic DNA, a preparation of DNA derived from whole human blood (Seracare blood sample N31774) was obtained using the procedure of Example 1. A stock of blood-derived DNA was quantitated to 1.6+0.06 ng/µl using the average of five independent concentration measurements taken with the Molecular Probes PicoGreen® Assay P-7589. 10-fold serial dilutions of human DNA were tested in PCR reactions according to Example 1 using the primer pairs of SEQ ID NOs: 12:15 (HV1) and SEQ ID NOs: 65:66 (HV2), starting with 1.6 ng/reaction and diluting to extinction (as a set of stock dilutions in double deionized $H_2O$) down to a calculated concentration of 160 zg/reaction (10 orders of magnitude dilution). No carrier DNA was used in these reactions.

FIG. 9 shows clear PCR product detection down to 1.6 pg/reaction for both HV1 and HV2 primer pairs, with possible stochastic detection of a faint product at 160 fg input template. It is typically estimated that a single human cell has approximately 3.3 billion base pairs–48, or 6.6 billion total bases, which corresponds roughly to approximately 6-7 pg total DNA per cell. This suggests PCR detection of mtDNA targets down to single-cell or sub cellular levels.

After digesting HV1 amplicons with RsaI, and HV2 amplicons with HaeIII, HpaII, HpyCH4IV and HpyCH4V, a full profile was recovered for HV2 with 16 pg input template, and for HV1 with 160 pg input template. Subsequent experiments have demonstrated full profile recovery for HV1 down to at about 50 pg input template concentration with human DNA from the same source. This represents an estimated 8 to 10 cells worth of DNA.

Example 11

Characterization of Mitochondrial DNA From Human Hair and Specificity of HV1 and HV1 Primer Pairs in the Presence of Non-Human DNA To test our ability to detect mitochondrial DNA from human hair shafts, and the specificity of our control-region primer targets in the presence of non-human mammalian DNA, DNA was extracted from washed human hair shafts (8, 4, 2, 1 and ½ cm), washed hamster, dog, and cat hair (4-6 cm) and washed human (2-3 cm) plus hamster, dog or cat hair (4-6 cm) present together in the same tube, according to the protocol outlined in Example 1. Hairs were taken by cutting with scissors, rather than pulling to avoid including a hair root in the reactions. PCR reactions were carried out using the primer pairs of SEQ ID NOs: 12:15 (HV1) and SEQ ID NOs: 65:66 (HV2) with PCR conditions as outlined in Example 1. Duplicate PCR reactions, demonstrated the presence of a PCR product of the expected size in the presence of human hair-derived DNA, but not in the negative controls (identical reactions, but with double deionized $H_2O$ substituted for template) or with hamster, dog, or cat hair alone.

When these PCR were digested with RsaI (HV1) and HaeIII, HpaII, HpyCH4IV, and HpyCH4V (HV2) as described in Example 2, a profile of base compositions matching Ibis internal blinded sample CS0022 was found for products amplified in the presence of animal hair and for human hair alone down to 2 cm.

Example 12

Characterization of Mitochondrial DNA Isolated Four Non-Invasive Tissues (Cheek Swab, Hair, Fingernail and Saliva) from Three Independent Donors: Analysis for Consistency in Processed Mass Spectrometry Data In this experiment, DNA was isolated from 3 pooled hairs of ~2-3 cm length each from 3 donors (designated "F", "M" and "J") according to procedures outlined in Example 1. DNA from Several (3-5) pooled small fingernail clippings was isolated from the same three donor according to Example 1 with the exception that there was no sonication step prior to DNA isolation, as this step was added at a later time. DNA from ~0.5 ml saliva was isolated from the same three donors according to Example 1. These three donors were also part of the 16-donor cheek swab panel described in Example 8, and processed data from cheek swabs representing these donors existed before this experiment and was used for comparison to the three new tissue samplings.

PCR reactions were performed using 1 μl of template from each of the four sample preparations for each of the three donors according to Example 1 using primer pair SEQ ID NOs: 12:15 (HV1) and SEQ ID NOs: 8:9 (HV2). Restriction digestions were performed according to Example 2. To determine a truth base for each sample for this experiment, PCR reactions performed with primer pair SEQ ID NOs: 12:15 (HV1) and SEQ ID NOs: 8:9 (HV2) were purified with a QIAQuick PCR purification kit (according to Qiagen kit recommendations) and sequenced at Retrogen (San Diego).

Digestion results for the original cheek swab-derived products were first compared to the sequences determined for cheek-swab-derived amplicons for consistency. After confirming consistency between the determined sequence and the mass spectrometry derived fragment profile, the ability to qualitatively exclude each of the samples from the other two was evaluated by matching the processed mass data for the cheek swab-derived samples from each of the donors to theoretical digestions from the PCR-derived sequences corresponding to the other two donors.

Processed mass spectrometry data for samples derived from the four different tissue sources were then compared to the cheek-swab-derived sequence for each donor individually and found to be consistent across the four tissue types, with the exception that the HV2 length heteroplasmy observed in HV2 of both sample "M" and sample "J" was observed in only three of the four tissue samples. The length heteroplasmy was not observed in the hair-derived sample for either "M" or "J".

Example 13

Figure 10:
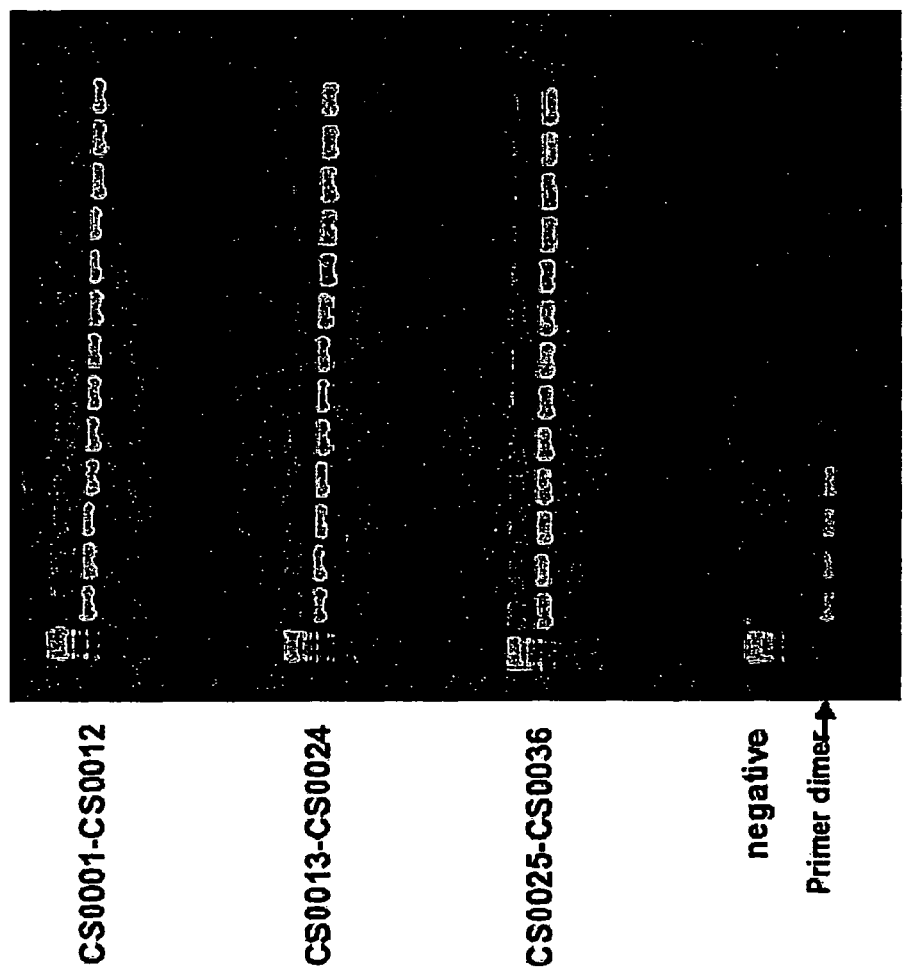
FIG. 10 is an agarose gel electrophoresis photo indicating that PCR products are obtained for each of the 36 samples described in Example 13 when amplified with HV1 primers.

Validation of Mitochondrial DNA Analysis Process on Saliva Samples from 36 Volunteer Donors In this validation experiment, 1 μl of each of the 36 Ibis samples (CS0001-CS0036) was PCR amplified in duplicate using each of the final primer pairs shown in Table 6 on two different days (four reactions were performed on each sample) using the cycling parameters in indicated in Example 1. FIG. 10 shows one set of the 36 sample PCR reactions for the HV1 region. After PCR, 25 μl of each reaction were digested in 50 μl restriction digestion reactions as described in Example 2. Samples from each of the 12 PCR plates were then subjected to mass spectrometry and processed with the ICR-2LS software to produce monoisotopic neutral masses. Each set of mass data was scanned against the database individually at +4 ppm matching threshold, allowing for the possibility of a 1-dalton error on each mass determination.

One potential issue with the deconvolution from raw mass spectrometry data to exact mass determination is the potential for the algorithm that fits a theoretical isotopic distribution to an observed distribution can occasionally predict the best fit with the distribution shifted by exactly one Dalton to the right or to the left of the true distribution, resulting in a mass determination that is exactly one Dalton off. This is not a serious issue when using mass data to verify consistency with a known sequence, because the expected base composition is known and two independent measurements are made on each double stranded fragment where each strand (top and bottom) is linked to the other in a highly constrained manner because of base complementarity. When using deconvolved numerical masses to make de novo base composition predictions, however, this must be dealt with properly to ensure a proper interpretation of match data. For example, the mass difference between an internal 'C' and an internal 'T' in a DNA sequence is −14.9997 Daltons. The mass difference between an internal 'G' and an internal 'A' is 15.9949 Daltons. Because of this, the mass difference between two strands of DNA that differ exactly by C T+G A is 0.9952 Daltons. Likewise, the reverse, T C+A G is a difference of −0.9952 Daltons.

For this reason, all of the matching to the database is performed assuming this as a possibility on every strand. However, when two masses match perfectly to two complementary base compositions at <10 ppm error (we generally use a threshold of 5 ppm or less) both masses would simultaneously require a 1-dalton error, and both would be required to have the error shifted in the same direction, to match a base composition fitting the above scenario. To avoid the rare occurrence of this situation, replicate reactions are required to ensure reproducible results for a profile analysis.

After scanning the database to generate a list of all possible fragment matches for each mass at +4 ppm threshold and allowing a precise +1 Dalton error on every mass, an automatic filter was applied that assumes that a pair of perfect matches to a complementary pair of base compositions overrides a match requiring a 1-dalton shift in the same direction on both strands (as described in the above paragraph). A second filter was applied to completely filter out ambiguous fragments where one mass actually did exhibit a one-Dalton shift error. This is easily spotted in an automated fashion, because two masses will only match a complementary set of base compositions with high precision if one of them is shifted by exactly 1 Dalton under this scenario. This can present ambiguity, however, because there is no de novo way to tell which mass has the error. Replicate reactions are relied upon to resolve this type of ambiguity (alternatively, a profile can be scanned with ambiguity in an "either-or" mode with little or no effect on the actual match result if enough fragments are present in a profile, much like using an 'R' to represent 'A' or 'G', or an 'N' to represent any nucleotide).

The last step is to create a composite profile from the combination of pre-filtered matches in each reaction scenario. To do this, all of the unfiltered masses from each of the replicates in each reaction scenario (e.g., one reaction scenario would be HV1 PCR product digested with RsaI) were combined into one data set and used again against the entire database to regenerate a single composite profile. This operation provides the benefit of increasing sensitivity in that a fragment lost in one reaction can be picked up in another, and can help prevent ambiguous base composition assignments. The final step is to filter any ambiguous assignments from the composite profile before comparing profiles or scanning the database with a profile. Even in the very unlikely case that masses representing both strands of a fragment were Dalton-shifted in the same direction, the same fragment in a replicate reaction should disagree, which is the precautionary purpose of the final filtering step.

Table 7 summarizes the results of the database scans using the six-region profiles. It should be noted here that there was considerably more noise in the larger non-control-region spectra than the spectra for the HV1 and HV2 regions. Although it did not detract from the ability to match the proper donor signature, it did produce more than desired ambiguity in data processing. The level of noise in this data set also did not cause a problem in the ability to differentiate samples from each other by at least one SNP, with the exception of samples CS0004, CS0025 and CS0032. Interestingly, one SNP in R1 differentiates CS0004 and CS0025 (which appear to a very common mtDNA type when HV1 and HV2 are matched to the database), which was detected only in the CS0025 profile. Therefore, CS0004 and CS0025 could not be resolved from each other by direct comparison (see next section), CS0004 hits equally to CS0004 and CS0025 in the database scan, and CS0025 appears to differentiate from CS0004 in a database scan (due to the fact that the profile is being compared to the known CS0004 sequence in the latter case, rather than the experimentally determined base composition profile that has a missing fragment). Two incorrect base compositions were predicted in CS0018 that were corrected by analysis of a duplicate set of restriction digestions. One incorrect base composition was predicted in each of samples CS0006, CS0011 and CS0026, each of which was likewise corrected by analysis of a duplicate set of restriction digestions. This did not change the top database hit (Table 7), nor does it change the ability of CS0001-CS0036 to be differentiated from CS0018, CS0006, CS0011, or CS0026.

TABLE 7

Overview of Validation Results

| SAMPLE | BEST DATABASE MATCH | % FRAGMENTS MATCH | NO. OF MATCHING HIGHEST % | NO. OF MATCHED REFERENCE POSITIONS | SECOND BEST % FRAGMENTS MATCHED | NO. OF ID WITH SECOND BEST FRAGMENTS MATCHED |
|---|---|---|---|---|---|---|
| CS0001 | CS0001 | 100 | 1 | 2942 | 90 | 2 |
| CS0002 | CS0002 | 100 | 1 | 3356 | 95.3 | 2 |
| CS0003 | CS0003 | 100 | 1 | 3294 | 90.7 | 2 |
| CS0004 | CS0004 CS0025 CS0032 gi\|17985669 gi\|13272808 gi\|7985543 | 100 | 6 | 2879 | 97.3 | 14 |
| CS0005 | CS0005 | 100 | 1 | 3190 | 95.1 | 12 |
| CS0006 | CS0006 | 97.5 | 1 | 3088 | 92.5 | 2 |
| CS0006 Re-anal. | CS0006 | 100 | 1 | 3198 | 95 | 2 |
| CS0007 | CS0007 | 100 | 1 | 2940 | 87.2 | 11 |
| CS0008 | CS0008 | 100 | 1 | 3251 | 95.2 | 2 |
| CS0009 | CS0009 | 100 | 1 | 2617 | 89.2 | 6 |
| CS0010 | CS0010 gi\|32692659 | 100 | 2 | 3205 | 97.6 | 8 |
| CS0011 | CS0011 | 97.7 | 1 | 3086 | 90.7 | 5 |
| CS0011 Re-anal. | CS0011 | 100 | 1 | 3028 | 92.7 | 5 |
| CS0012 | CS0012 | 100 | 1 | 3193 | 92.7 | 2 |
| CS0013 | CS0013 | 100 | 1 | 3016 | 87.5 | 4 |
| CS0014 | CS0014 | 100 | 1 | 3017 | 92.5 | 1 |
| CS0015 | CS0015 | 100 | 1 | 3378 | 95.3 | 1 |
| CS0016 | CS0016 | 100 | 1 | 2915 | 94.7 | 1 |
| CS0017 | CS0017 | 100 | 1 | 3229 | 92.9 | 3 |
| CS0018 | CS0018 | 94.9 | 1 | 2629 | 89.7 | 1 |
| CS0018 Re-anal. | CS0018 | 100 | 1 | 2691 | 94.4 | 1 |
| CS0019 | CS0019 | 100 | 1 | 2794 | 92.3 | 1 |
| CS0020 | CS0020 | 100 | 1 | 3231 | 92.9 | 8 |
| CS0021 | CS0021 | 100 | 1 | 2902 | 97.5 | 3 |
| CS0022 | CS0022 | 100 | 1 | 3314 | 95.3 | 10 |
| CS0023 | CS0023 | 100 | 1 | 2953 | 84.6 | 3 |
| CS0024 | CS0024 | 100 | 1 | 3224 | 87.8 | 1 |
| CS0025 | CS0025 gi\|3272808 gi\|7985669 | 100 | | 3080 | 97.6 | 11 |
| CS0026 | CS0026 | 97.6 | 1 | 2787 | 90.2 | 1 |
| CS0026 Re-anal. | CS0026 | 100 | | 2787 | 92.5 | 1 |
| CS0027 | CS0027 | 100 | 1 | 2940 | 94.9 | 4 |
| CS0028 | CS0028 | 100 | 1 | 2975 | 97.5 | 8 |
| CS0029 | CS0029 | 100 | 1 | 3002 | 92.7 | 4 |
| CS0030 | CS0030 | 100 | 1 | 3066 | 97.6 | 1 |
| CS0031 | CS0031 | 100 | 1 | 3409 | 86.4 | 7 |
| CS0032 | CS0032 gi\|17985543 | 100 | 2 | 3288 | 97.6 | 3 |
| CS0033 | CS0033 | 100 | 1 | 3098 | 92.7 | 2 |
| CS0034 | CS0034 | 100 | 1 | 3100 | 85.4 | 2 |

TABLE 7-continued

Overview of Validation Results

| SAMPLE | BEST DATABASE MATCH | % FRAGMENTS MATCH | NO. OF MATCHING HIGHEST % | NO. OF MATCHED REFERENCE POSITIONS | SECOND BEST % FRAGMENTS MATCHED | NO. OF ID WITH SECOND BEST FRAGMENTS MATCHED |
|---|---|---|---|---|---|---|
| CS0035 | CS0035 gi\|32892351 gi\|32892449 | 100 | 3 | 2971 | 97.5 | 3 |
| CS0036 | CS0036 | 100 | 1 | 2703 | 91.9 | 3 |

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A method of forensic analysis of a sample comprising mitochondrial DNA comprising:
   selecting a region of mitochondrial DNA comprising at least one restriction site whereat a restriction enzyme cleaves said mitochondrial DNA to produce a plurality of restriction fragments;
   populating a relational database of known mitochondrial DNA sequences with base compositions which correspond to theoretical restriction fragments obtained from theoretical digestion of each member of said database at said at least one restriction site;
   selecting a primer pair with which to amplify said region of mitochondrial DNA in said sample;
   amplifying said region of mitochondrial DNA in said sample to produce an amplification product;
   digesting said amplification product with at least one restriction enzyme to produce a plurality of restriction fragments;
   experimentally determining the base compositions of each member of said plurality of restriction fragments, wherein said base composition is determined without sequencing said restriction fragments; and
   comparing said experimentally determined base compositions with the base compositions of said theoretical digestion of each member of said database, wherein at least one match or lack of a match provides a forensic conclusion.

2. The method of claim 1 wherein said region of mitochondrial DNA comprises HV1.

3. The method of claim 2 wherein each member of said primer pair has at least 70% sequence identity with the sequence of the corresponding member of any one of the following primer pair sequences: SEQ ID NOs: 12:13, 12:14, 12:15, 16:17, 42:43, 42:46, 67:68, 69:70, 12:68, 12:70, 67:15, 71:70, 69:15 and 69:68.

4. The method of claim 2 wherein said at least one restriction enzyme is RsaI.

5. The method of claim 1 wherein said region of mitochondrial DNA comprises HV2.

6. The method of claim 5 wherein each member of said primer pair has at least 70% sequence identity with the sequence of the corresponding member of any one of the following primer pair sequences: SEQ ID NOs: 8:9, 10:11, 16:17 and 65:66.

7. The method of claim 5 wherein said at least one restriction enzyme is HaeIII, HpaII, MfeI, or SspI.

8. The method of claim 5 wherein said at least one restriction enzyme is HpaII, HpyCH4IV, PacI, or EaeI.

9. The method of claim 1 wherein said region of mitochondrial DNA comprises region R1.

10. The method of claim 9 wherein each member of said primer pair has at least 70% sequence identity with the sequence of the corresponding member of any one of the following primer pair sequences: SEQ ID NOs: 18:19 and 18:49.

11. The method of claim 9 wherein said at least one restriction enzyme is DdeI, MseI, HaeIII, or MboI.

12. The method of claim 1 wherein said region of mitochondrial DNA comprises region R2.

13. The method of claim 12 wherein each member of said primer pair has at least 70% sequence identity with the sequence of the corresponding member of any one of the following primer pair sequences: SEQ ID NOs: 20:21 and 50:51.

14. The method of claim 12 wherein said at least one restriction enzyme is DdeI, HaeIII, MboI, or MseI.

15. The method of claim 1 wherein said region of mitochondrial DNA comprises region R3.

16. The method of claim 15 wherein each member of said primer pair has at least 70% sequence identity with the sequence of the corresponding member of any one of the following primer pair sequences: SEQ ID NOs: 22:23 and 22:52.

17. The method of claim 15 wherein said at least one restriction enzyme is DdeI, MseI, MboI, or BanI.

18. The method of claim 1 wherein said region of mitochondrial DNA comprises region R4.

19. The method of claim 18 wherein each member of said primer pair has at least 70% sequence identity with the sequence of the corresponding member of any one of the following primer pair sequences: SEQ ID NOs: 24:25 and 53:54.

20. The method of claim 18 wherein said at least one restriction enzyme is DdeI, HpyCH4IV, MseI, or HaeIII.

21. The method of claim 1 wherein said region of mitochondrial DNA comprises region R5.

22. The method of claim 21 wherein each member of said primer pair has at least 70% sequence identity with the sequence of the corresponding member of any one of the following primer pair sequences: SEQ ID NOs: 26:27 and 55:56.

23. The method of claim 21 wherein said at least one restriction enzyme is AluI, BfaI, or MseI.

24. The method of claim 1 wherein said region of mitochondrial DNA comprises region R6.

25. The method of claim 24 wherein each member of said primer pair has at least 70% sequence identity with the sequence of the corresponding member of any one of the following primer pair sequences: SEQ ID NOs: 28:29 and 57:29.

26. The method of claim 24 wherein said at least one restriction enzyme is DdeI, HaeIII, MboI, MseI, or RsaI.

27. The method of claim 1 wherein said region of mitochondrial DNA comprises region R7.

28. The method of claim 27 wherein each member of said primer pair has at least 70% sequence identity with the sequence of the corresponding member of any one of the following primer pair sequences: SEQ ID NOs: 30:31 and 58:31.

29. The method of claim 27 wherein said at least one restriction enzyme is DdeI, HpaII, HaeIII, or MseI.

30. The method of claim 1 wherein said region of mitochondrial DNA comprises region R8.

31. The method of claim 30 wherein each member of said primer pair has at least 70% sequence identity with the sequence of the corresponding member of any one of the following primer pair sequences: SEQ ID NOs: 32:33 and 59:60.

32. The method of claim 30 wherein said at least one restriction enzyme is BfaI, DdeI, EcoRI, or MboI.

33. The method of claim 1 wherein said region of mitochondrial DNA comprises region R9.

34. The method of claim 33 wherein each member of said primer pair has at least 70% sequence identity with the sequence of the corresponding member of the following primer pair sequences: SEQ ID NOs: 34:35.

35. The method of claim 33 wherein said at least one restriction enzyme is BfaI, DdeI, HpaII, HpyCH4IV, or MboI.

36. The method of claim 1 wherein said region of mitochondrial DNA comprises region R10.

37. The method of claim 36 wherein each member of said primer pair has at least 70% sequence identity with the sequence of the corresponding member of the following primer pair sequences: SEQ ID NOs: 34:35.

38. The method of claim 36 wherein said at least one restriction enzyme is BfaI, HpaII, or MboI.

39. The method of claim 1 wherein said region of mitochondrial DNA comprises region R10.

40. The method of claim 39 wherein each member of said primer pair has at least 70% sequence identity with the sequence of the corresponding member of the following primer pair sequences: SEQ ID NOs: 36:37 and 61:62.

41. The method of claim 39 wherein said at least one restriction enzyme is BfaI, HpaII, or MboI.

42. The method of claim 1 wherein said region of mitochondrial DNA comprises region R11.

43. The method of claim 42 wherein each member of said primer pair has at least 70% sequence identity with the sequence of the corresponding member of the following primer pair sequences: SEQ ID NOs: 38:39 and 63:39.

44. The method of claim 42 wherein said at least one restriction enzyme is BfaI, DdeI, HpyCH4V, or MboI.

45. The method of claim 1 wherein said region of mitochondrial DNA comprises region R12.

46. The method of claim 45 wherein each member of said primer pair has at least 70% sequence identity with the sequence of the corresponding member of the following primer pair sequences: SEQ ID NOs: 40:41 and 40:64.

47. The method of claim 45 wherein said at least one restriction enzyme is BfaI, DdeI, or MseI.

48. The method of claim 1 wherein said base compositions of said restriction fragments are determined from molecular masses.

49. The method of claim 1 wherein said amplifying step comprises polymerase chain reaction.

50. The method of claim 49 wherein said polymerase chain reaction is catalyzed by a polymerase enzyme whose function is modified relative to a native polymerase.

51. The method of claim 50 wherein said modified polymerase enzyme is exo(−) Pfu polymerase.

52. The method of claim 50 wherein said modified polymerase catalyzes the addition of nucleotide residues to staggered restriction digest products to convert said staggered digest products to blunt-ended digest products.

53. The method of claim 1 wherein said amplifying step comprises ligase chain reaction or strand displacement amplification.

54. The method of claim 1 wherein said database is a human mtDNA population database.

55. The method of claim 48 wherein said molecular masses are determined by ESI-FTICR mass spectrometry.

56. The method of claim 48 wherein said molecular masses are determined by ESI-TOF mass spectrometry.

57. The method of claim 1 further comprising repeating all steps of the method for at least one additional region of mitochondrial DNA.

58. The method of claim 57 wherein said at least one additional region is from HV1, HV2, R1, R2, R3, R4, R5, R6, R7, R8, R9, R10, R11, or R12.

59. The method of claim 1 wherein said mitochondrial DNA is human mitochondrial DNA.

60. The method of claim 1 wherein said mitochondrial DNA is animal mitochondrial DNA.

61. The method of claim 1 wherein said mitochondrial DNA is fungal, parasitic, or protozoan DNA.

62. The method of claim 1 wherein said amplified DNA is digested directly without purification.

63. The method of claim 1 wherein said sample of mitochondrial DNA is obtained from saliva, hair, blood, or nail.

64. The method of claim 1 wherein said plurality of restriction fragments are up to about 150 base pairs in length.

65. The method of claim 1, wherein said forensic conclusion comprises the identity of a source of said sample.

66. The method of claim 48, wherein said forensic conclusion comprises the identity of a source of said sample.

* * * * *

SEQUENCE LISTING

<160> NUMBER OF SEQ ID NOS: 72

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8
<211> LENGTH: 18
<212> TYPE: DNA
<213> ORGANISM: Artificial Sequence
<220> FEATURE:

<223> OTHER INFORMATION: PCR Primer

<400> SEQUENCE: 8
tcacgcgata gcattgcg                                            18

<210> SEQ ID NO 9
<211> LENGTH: 25
<212> TYPE: DNA
<213> ORGANISM: Artificial Sequence
<220> FEATURE:
<223> OTHER INFORMATION: PCR Primer

<400> SEQUENCE: 9
tggtttggca gagatgtgtt taagt                                    25

<210> SEQ ID NO 10
<211> LENGTH: 21
<212> TYPE: DNA
<213> ORGANISM: Artificial Sequence
<220> FEATURE:
<223> OTHER INFORMATION: PCR Primer

<400> SEQUENCE: 10
tctcacggga gctctccatg c                                        21

<210> SEQ ID NO 11
<211> LENGTH: 23
<212> TYPE: DNA
<213> ORGANISM: Artificial Sequence
<220> FEATURE:
<223> OTHER INFORMATION: PCR Primer

<400> SEQUENCE: 11
tctgttaaaa gtgcataccg cca                                      23

<210> SEQ ID NO 12
<211> LENGTH: 22
<212> TYPE: DNA
<213> ORGANISM: Artificial Sequence
<220> FEATURE:
<223> OTHER INFORMATION: PCR Primer

<400> SEQUENCE: 12
tgactcaccc atcaacaacc gc                                       22

<210> SEQ ID NO 13
<211> LENGTH: 21
<212> TYPE: DNA
<213> ORGANISM: Artificial Sequence
<220> FEATURE:
<223> OTHER INFORMATION: PCR Primer

<400> SEQUENCE: 13
tgaggatggt ggtcaaggga c                                        21

<210> SEQ ID NO 14
<211> LENGTH: 22
<212> TYPE: DNA
<213> ORGANISM: Artificial Sequence
<220> FEATURE:
<223> OTHER INFORMATION: PCR Primer

<400> SEQUENCE: 14
tggatttgac tgtaatgtgc ta                                       22

<210> SEQ ID NO 15

```
<211> LENGTH: 28
<212> TYPE: DNA
<213> ORGANISM: Artificial Sequence
<220> FEATURE:
<223> OTHER INFORMATION: PCR Primer

<400> SEQUENCE: 15
tgaagggatt tgactgtaat gtgctatg                                       28

<210> SEQ ID NO 16
<211> LENGTH: 21
<212> TYPE: DNA
<213> ORGANISM: Artificial Sequence
<220> FEATURE:
<223> OTHER INFORMATION: PCR Primer

<400> SEQUENCE: 16
gaagcagatt tgggtaccac c                                              21

<210> SEQ ID NO 17
<211> LENGTH: 21
<212> TYPE: DNA
<213> ORGANISM: Artificial Sequence
<220> FEATURE:
<223> OTHER INFORMATION: PCR Primer

<400> SEQUENCE: 17
gtgtgtgtgc tgggtaggat g                                              21

<210> SEQ ID NO 18
<211> LENGTH: 26
<212> TYPE: DNA
<213> ORGANISM: Artificial Sequence
<220> FEATURE:
<223> OTHER INFORMATION: PCR Primer

<400> SEQUENCE: 18
tacggtcaat gctctgaaat ctgtgg                                         26

<210> SEQ ID NO 19
<211> LENGTH: 24
<212> TYPE: DNA
<213> ORGANISM: Artificial Sequence
<220> FEATURE:
<223> OTHER INFORMATION: PCR Primer

<400> SEQUENCE: 19
tggtaagaag tgggctaggg catt                                           24

<210> SEQ ID NO 20
<211> LENGTH: 28
<212> TYPE: DNA
<213> ORGANISM: Artificial Sequence
<220> FEATURE:
<223> OTHER INFORMATION: PCR Primer

<400> SEQUENCE: 20
ttatgtaaaa tccattgtcg catccacc                                       28

<210> SEQ ID NO 21
<211> LENGTH: 24
<212> TYPE: DNA
<213> ORGANISM: Artificial Sequence
<220> FEATURE:
<223> OTHER INFORMATION: PCR Primer

<400> SEQUENCE: 21
```

```
tggtgatagc gcctaagcat agtg                                          24
```

<210> SEQ ID NO 22
<211> LENGTH: 27
<212> TYPE: DNA
<213> ORGANISM: Artificial Sequence
<220> FEATURE:
<223> OTHER INFORMATION: PCR Primer

<400> SEQUENCE: 22

```
tcccattact aaacccacac tcaacag                                       27
```

<210> SEQ ID NO 23
<211> LENGTH: 25
<212> TYPE: DNA
<213> ORGANISM: Artificial Sequence
<220> FEATURE:
<223> OTHER INFORMATION: PCR Primer

<400> SEQUENCE: 23

```
tttcgtgcaa gaataggagg tggag                                         25
```

<210> SEQ ID NO 24
<211> LENGTH: 27
<212> TYPE: DNA
<213> ORGANISM: Artificial Sequence
<220> FEATURE:
<223> OTHER INFORMATION: PCR Primer

<400> SEQUENCE: 24

```
taaggccttc gatacgggat aatccta                                       27
```

<210> SEQ ID NO 25
<211> LENGTH: 20
<212> TYPE: DNA
<213> ORGANISM: Artificial Sequence
<220> FEATURE:
<223> OTHER INFORMATION: PCR Primer

<400> SEQUENCE: 25

```
tagggtcgaa gccgcactcg                                               20
```

<210> SEQ ID NO 26
<211> LENGTH: 30
<212> TYPE: DNA
<213> ORGANISM: Artificial Sequence
<220> FEATURE:
<223> OTHER INFORMATION: PCR Primer

<400> SEQUENCE: 26

```
tactccaatg ctaaaactaa tcgtcccaac                                    30
```

<210> SEQ ID NO 27
<211> LENGTH: 25
<212> TYPE: DNA
<213> ORGANISM: Artificial Sequence
<220> FEATURE:
<223> OTHER INFORMATION: PCR Primer

<400> SEQUENCE: 27

```
tgtgaggcgt attataccat agccg                                         25
```

<210> SEQ ID NO 28
<211> LENGTH: 25
<212> TYPE: DNA
<213> ORGANISM: Artificial Sequence
<220> FEATURE:

<223> OTHER INFORMATION: PCR Primer

<400> SEQUENCE: 28
tcctaggaat cacctcccat tccga                                    25

<210> SEQ ID NO 29
<211> LENGTH: 29
<212> TYPE: DNA
<213> ORGANISM: Artificial Sequence
<220> FEATURE:
<223> OTHER INFORMATION: PCR Primer

<400> SEQUENCE: 29
tagaatctta gctttgggtg ctaatggtg                                29

<210> SEQ ID NO 30
<211> LENGTH: 25
<212> TYPE: DNA
<213> ORGANISM: Artificial Sequence
<220> FEATURE:
<223> OTHER INFORMATION: PCR Primer

<400> SEQUENCE: 30
tggcagccta gcattagcag gaata                                    25

<210> SEQ ID NO 31
<211> LENGTH: 24
<212> TYPE: DNA
<213> ORGANISM: Artificial Sequence
<220> FEATURE:
<223> OTHER INFORMATION: PCR Primer

<400> SEQUENCE: 31
tggctgaaca ttgtttgttg gtgt                                     24

<210> SEQ ID NO 32
<211> LENGTH: 25
<212> TYPE: DNA
<213> ORGANISM: Artificial Sequence
<220> FEATURE:
<223> OTHER INFORMATION: PCR Primer

<400> SEQUENCE: 32
tcgctgacgc cataaaactc ttcac                                    25

<210> SEQ ID NO 33
<211> LENGTH: 29
<212> TYPE: DNA
<213> ORGANISM: Artificial Sequence
<220> FEATURE:
<223> OTHER INFORMATION: PCR Primer

<400> SEQUENCE: 33
taagtaatgc tagggtgagt ggtaggaag                                29

<210> SEQ ID NO 34
<211> LENGTH: 31
<212> TYPE: DNA
<213> ORGANISM: Artificial Sequence
<220> FEATURE:
<223> OTHER INFORMATION: PCR Primer

<400> SEQUENCE: 34
taactaatac taacatctca gacgctcagg a                             31

<210> SEQ ID NO 35

```
<211> LENGTH: 25
<212> TYPE: DNA
<213> ORGANISM: Artificial Sequence
<220> FEATURE:
<223> OTHER INFORMATION: PCR Primer

<400> SEQUENCE: 35
tttatgggct tggtgaggg aggta                                          25

<210> SEQ ID NO 36
<211> LENGTH: 20
<212> TYPE: DNA
<213> ORGANISM: Artificial Sequence
<220> FEATURE:
<223> OTHER INFORMATION: PCR Primer

<400> SEQUENCE: 36
tactcccacc ctggagcctc                                               20

<210> SEQ ID NO 37
<211> LENGTH: 30
<212> TYPE: DNA
<213> ORGANISM: Artificial Sequence
<220> FEATURE:
<223> OTHER INFORMATION: PCR Primer

<400> SEQUENCE: 37
tgctcctatt gataggacat agtggaagtg                                    30

<210> SEQ ID NO 38
<211> LENGTH: 25
<212> TYPE: DNA
<213> ORGANISM: Artificial Sequence
<220> FEATURE:
<223> OTHER INFORMATION: PCR Primer

<400> SEQUENCE: 38
ttatcacctt tcatgatcac gccct                                         25

<210> SEQ ID NO 39
<211> LENGTH: 27
<212> TYPE: DNA
<213> ORGANISM: Artificial Sequence
<220> FEATURE:
<223> OTHER INFORMATION: PCR Primer

<400> SEQUENCE: 39
tggcatttca ctgtaaagag gtgttgg                                       27

<210> SEQ ID NO 40
<211> LENGTH: 23
<212> TYPE: DNA
<213> ORGANISM: Artificial Sequence
<220> FEATURE:
<223> OTHER INFORMATION: PCR Primer

<400> SEQUENCE: 40
tgtatgaatg gctccacgag ggt                                           23

<210> SEQ ID NO 41
<211> LENGTH: 26
<212> TYPE: DNA
<213> ORGANISM: Artificial Sequence
<220> FEATURE:
<223> OTHER INFORMATION: PCR Primer

<400> SEQUENCE: 41
```
tcggtaagca ttaggaatgc cattgc    26

<210> SEQ ID NO 42
<211> LENGTH: 21
<212> TYPE: DNA
<213> ORGANISM: Artificial Sequence
<220> FEATURE:
<223> OTHER INFORMATION: PCR Primer

<400> SEQUENCE: 42
gactcaccca tcaacaaccg c    21

<210> SEQ ID NO 43
<211> LENGTH: 20
<212> TYPE: DNA
<213> ORGANISM: Artificial Sequence
<220> FEATURE:
<223> OTHER INFORMATION: PCR Primer

<400> SEQUENCE: 43
gaggatggtg gtcaagggac    20

<210> SEQ ID NO 44
<211> LENGTH: 20
<212> TYPE: DNA
<213> ORGANISM: Artificial Sequence
<220> FEATURE:
<223> OTHER INFORMATION: PCR Primer

<400> SEQUENCE: 44
ctcacgggag ctctccatgc    20

<210> SEQ ID NO 45
<211> LENGTH: 22
<212> TYPE: DNA
<213> ORGANISM: Artificial Sequence
<220> FEATURE:
<223> OTHER INFORMATION: PCR Primer

<400> SEQUENCE: 45
ctgttaaaag tgcataccgc ca    22

<210> SEQ ID NO 46
<211> LENGTH: 21
<212> TYPE: DNA
<213> ORGANISM: Artificial Sequence
<220> FEATURE:
<223> OTHER INFORMATION: PCR Primer

<400> SEQUENCE: 46
ggatttgact gtaatgtgct a    21

<210> SEQ ID NO 47
<211> LENGTH: 17
<212> TYPE: DNA
<213> ORGANISM: Artificial Sequence
<220> FEATURE:
<223> OTHER INFORMATION: PCR Primer

<400> SEQUENCE: 47
cacgcgatag cattgcg    17

<210> SEQ ID NO 48
<211> LENGTH: 24
<212> TYPE: DNA
<213> ORGANISM: Artificial Sequence
<220> FEATURE:

<223> OTHER INFORMATION: PCR Primer

<400> SEQUENCE: 48
ggtttggcag agatgtgttt aagt                                    24

<210> SEQ ID NO 49
<211> LENGTH: 26
<212> TYPE: DNA
<213> ORGANISM: Artificial Sequence
<220> FEATURE:
<223> OTHER INFORMATION: PCR Primer

<400> SEQUENCE: 49
tggctattgg ttgaatgagt aggctg                                  26

<210> SEQ ID NO 50
<211> LENGTH: 27
<212> TYPE: DNA
<213> ORGANISM: Artificial Sequence
<220> FEATURE:
<223> OTHER INFORMATION: PCR Primer

<400> SEQUENCE: 50
tccccattat gtaaaatcca ttgtcgc                                 27

<210> SEQ ID NO 51
<211> LENGTH: 24
<212> TYPE: DNA
<213> ORGANISM: Artificial Sequence
<220> FEATURE:
<223> OTHER INFORMATION: PCR Primer

<400> SEQUENCE: 51
tgacttgaag tggagaaggc tacg                                    24

<210> SEQ ID NO 52
<211> LENGTH: 27
<212> TYPE: DNA
<213> ORGANISM: Artificial Sequence
<220> FEATURE:
<223> OTHER INFORMATION: PCR Primer

<400> SEQUENCE: 52
taagggtgga aggtgatttt atcggaa                                 27

<210> SEQ ID NO 53
<211> LENGTH: 19
<212> TYPE: DNA
<213> ORGANISM: Artificial Sequence
<220> FEATURE:
<223> OTHER INFORMATION: PCR Primer

<400> SEQUENCE: 53
tgccaccaca caccacctg                                          19

<210> SEQ ID NO 54
<211> LENGTH: 21
<212> TYPE: DNA
<213> ORGANISM: Artificial Sequence
<220> FEATURE:
<223> OTHER INFORMATION: PCR Primer

<400> SEQUENCE: 54
tatagggtcg aagccgcact c                                       21

<210> SEQ ID NO 55

```
<211> LENGTH: 29
<212> TYPE: DNA
<213> ORGANISM: Artificial Sequence
<220> FEATURE:
<223> OTHER INFORMATION: PCR Primer

<400> SEQUENCE: 55
tctactccaa tgctaaaact aatcgtccc                                          29

<210> SEQ ID NO 56
<211> LENGTH: 23
<212> TYPE: DNA
<213> ORGANISM: Artificial Sequence
<220> FEATURE:
<223> OTHER INFORMATION: PCR Primer

<400> SEQUENCE: 56
tggttgagaa tgagtgtgag gcg                                                23

<210> SEQ ID NO 57
<211> LENGTH: 27
<212> TYPE: DNA
<213> ORGANISM: Artificial Sequence
<220> FEATURE:
<223> OTHER INFORMATION: PCR Primer

<400> SEQUENCE: 57
tcacctccca ttccgataaa atcacct                                            27

<210> SEQ ID NO 58
<211> LENGTH: 28
<212> TYPE: DNA
<213> ORGANISM: Artificial Sequence
<220> FEATURE:
<223> OTHER INFORMATION: PCR Primer

<400> SEQUENCE: 58
tcaaaaccat acctctcact tcaacctc                                           28

<210> SEQ ID NO 59
<211> LENGTH: 22
<212> TYPE: DNA
<213> ORGANISM: Artificial Sequence
<220> FEATURE:
<223> OTHER INFORMATION: PCR Primer

<400> SEQUENCE: 59
tacaaccctt cgctgacgcc at                                                 22

<210> SEQ ID NO 60
<211> LENGTH: 28
<212> TYPE: DNA
<213> ORGANISM: Artificial Sequence
<220> FEATURE:
<223> OTHER INFORMATION: PCR Primer

<400> SEQUENCE: 60
taagtaatgc tagggtgagt ggtaggaa                                           28

<210> SEQ ID NO 61
<211> LENGTH: 24
<212> TYPE: DNA
<213> ORGANISM: Artificial Sequence
<220> FEATURE:
<223> OTHER INFORMATION: PCR Primer

<400> SEQUENCE: 61
```

-continued ttgaacagtc taccctccct tagc                                          24

<210> SEQ ID NO 62
<211> LENGTH: 29
<212> TYPE: DNA
<213> ORGANISM: Artificial Sequence
<220> FEATURE:
<223> OTHER INFORMATION: PCR Primer

<400> SEQUENCE: 62
tgtagtacga tgtctagtga tgagtttgc                                     29

<210> SEQ ID NO 63
<211> LENGTH: 28
<212> TYPE: DNA
<213> ORGANISM: Artificial Sequence
<220> FEATURE:
<223> OTHER INFORMATION: PCR Primer

<400> SEQUENCE: 63
tgcttcctag tcctgtatgc ccttttcc                                      28

<210> SEQ ID NO 64
<211> LENGTH: 21
<212> TYPE: DNA
<213> ORGANISM: Artificial Sequence
<220> FEATURE:
<223> OTHER INFORMATION: PCR Primer

<400> SEQUENCE: 64
tggcgtcagc gaagggttgt a                                             21

<210> SEQ ID NO 65
<211> LENGTH: 21
<212> TYPE: DNA
<213> ORGANISM: Artificial Sequence
<220> FEATURE:
<223> OTHER INFORMATION: PCR Primer

<400> SEQUENCE: 65
tgtgcacgcg atagcattgc g                                             21

<210> SEQ ID NO 66
<211> LENGTH: 27
<212> TYPE: DNA
<213> ORGANISM: Artificial Sequence
<220> FEATURE:
<223> OTHER INFORMATION: PCR Primer

<400> SEQUENCE: 66
tggggtttgg cagagatgtg tttaagt                                       27

<210> SEQ ID NO 67
<211> LENGTH: 28
<212> TYPE: DNA
<213> ORGANISM: Artificial Sequence
<220> FEATURE:
<223> OTHER INFORMATION: PCR Primer

<400> SEQUENCE: 67
tcaagtattg actcacccat caacaacc                                      28

<210> SEQ ID NO 68
<211> LENGTH: 29
<212> TYPE: DNA
<213> ORGANISM: Artificial Sequence
<220> FEATURE:

<223> OTHER INFORMATION: PCR Primer

<400> SEQUENCE: 68
tcgagaaggg atttgactgt aatgtgcta                                          29

<210> SEQ ID NO 69
<211> LENGTH: 27
<212> TYPE: DNA
<213> ORGANISM: Artificial Sequence
<220> FEATURE:
<223> OTHER INFORMATION: PCR Primer

<400> SEQUENCE: 69
taccacccaa gtattgactc acccatc                                            27

<210> SEQ ID NO 70
<211> LENGTH: 25
<212> TYPE: DNA
<213> ORGANISM: Artificial Sequence
<220> FEATURE:
<223> OTHER INFORMATION: PCR Primer

<400> SEQUENCE: 70
tcatggggac gagaagggat ttgac                                              25

<210> SEQ ID NO 71
<211> LENGTH: 28
<212> TYPE: DNA
<213> ORGANISM: Artificial Sequence
<220> FEATURE:
<223> OTHER INFORMATION: PCR Primer

<400> SEQUENCE: 71
tcaagtattg actcacccat caacaacc                                           28

<210> SEQ ID NO 72
<211> LENGTH: 16568
<212> TYPE: DNA
<213> ORGANISM: Artificial Sequence
<220> FEATURE:
<223> OTHER INFORMATION: PCR Primer

<400> SEQUENCE: 72
gatcacaggt ctatcaccct attaaccact cacgggagct ctccatgcat ttggtatttt         60
cgtctggggg gtatgcacgc gatagcattg cgagacgctg gagccggagc accctatgtc       120
gcagtatctg tctttgattc ctgcctcatc ctattattta tcgcacctac gttcaatatt       180
acaggcgaac atacttacta aagtgtgtta attaattaat gcttgtagga cataataata       240
acaattgaat gtctgcacag ccactttcca cacagacatc ataacaaaaa atttccacca       300
aaccccccct cccccgcttc tggccacagc acttaaacac atctctgcca aaccccaaaa       360
acaaagaacc ctaacaccag cctaaccaga tttcaaattt tatctttttgg cggtatgcac       420 ttttaacagt cacccccaa ctaacacatt attttccct cccactccca tactactaat         480
ctcatcaata caaccccgc ccatcctacc cagcacacac acaccgctgc taaccccata        540
ccccgaacca accaaacccc aaagacaccc ccacagtttt atgtagctta cctcctcaaa       600
gcaatacact gaaaatgttt agacgggctc acatcaccc ataaacaaat aggtttggtc        660
ctagcctttc tattagctct tagtaagatt acacatgcaa gcatcccgt tccagtgagt        720 tcaccctcta atcaccacg atcaaaaggg acaagcatca agcacgcagc aatgcagctc       780
aaaacgctta gcctagccac accccacgg gaaacagcag tgattaacct ttagcaataa       840

```
acgaaagttt aactaagcta tactaacccc agggttggtc aatttcgtgc cagccaccgc      900
ggtcacacga ttaacccaag tcaatagaag ccggcgtaaa gagtgtttta gatcaccccc      960
tccccaataa agctaaaact cacctgagtt gtaaaaaact ccagttgaca caaaatagac     1020
tacgaaagtg gctttaacat atctgaacac acaatagcta agacccaaac tgggattaga     1080
taccccacta tgcttagccc taaacctcaa cagttaaatc aacaaaactg ctcgccagaa     1140
cactacgagc cacagcttaa aactcaaagg acctggcggt gcttcatatc cctctagagg     1200
agcctgttct gtaatcgata aaccccgatc aacctcacca cctcttgctc agcctatata     1260
ccgccatctt cagcaaaccc tgatgaaggc tacaaagtaa gcgcaagtac ccacgtaaag     1320
acgttaggtc aaggtgtagc ccatgaggtg gcaagaaatg ggctacattt tctaccccag     1380
aaaactacga tagcccttat gaaacttaag ggtcgaaggt ggatttagca gtaaactaag     1440
agtagagtgc ttagttgaac agggccctga agcgcgtaca caccgcccgt caccctcctc     1500
aagtatactt caaaggacat ttaactaaaa cccctacgca tttatataga ggagacaagt     1560
cgtaacatgg taagtgtact ggaaagtgca cttggacgaa ccagagtgta gcttaacaca     1620
aagcacccaa cttacactta ggagatttca acttaacttg accgctctga gctaaaccta     1680
gccccaaacc cactccacct tactaccaga caaccttagc caaaccattt acccaaataa     1740
agtataggcg atagaaattg aaacctggcg caatagatat agtaccgcaa gggaaagatg     1800
aaaaattata accaagcata atatagcaag gactaacccc tataccttct gcataatgaa     1860
ttaactagaa ataactttgc aaggagagcc aaagctaaga cccccgaaac cagacgagct     1920
acctaagaac agctaaaaga gcacacccgt ctatgtagca aaatagtggg aagatttata     1980
ggtagaggcg acaaacctac cgagcctggt gatagctggt tgtccaagat agaatcttag     2040
ttcaacttta aatttgccca cagaaccctc taaatcccct tgtaaattta actgttagtc     2100
caaagaggaa cagctctttg gacactagga aaaaaccttg tagagagagt aaaaaattta     2160
acacccatag taggcctaaa agcagccacc aattaagaaa gcgttcaagc tcaacaccca     2220
ctacctaaaa atcccaaac atataactga actcctcaca cccaattgga ccaatctatc     2280
accctataga agaactaatg ttagtataag taacatgaaa acattctcct ccgcataagc     2340
ctgcgtcaga ttaaaacact gaactgacaa ttaacagccc aatatctaca atcaaccaac     2400
aagtcattat taccctcact gtcaacccaa cacaggcatg ctcataagga aaggttaaaa     2460
aaagtaaaag gaactcggca atcttaccc cgcctgttta ccaaaaacat cacctctagc     2520
atcaccagta ttagaggcac cgcctgccca gtgacacatg tttaacggcc gcggtacccct     2580 aaccgtgcaa aggtagcata atcacttgtt ccttaaatag ggacctgtat gaatggctcc     2640
acgagggttc agctgtctct tactttttaac cagtgaaatt gacctgcccg tgaagaggcg     2700
ggcataacac agcaagacga aagaccccta tggagcttta atttattaat gcaaacagta     2760
cctaacaaac ccacaggtcc taaactacca aacctgcatt aaaaatttcg gttgggcga     2820 cctcggagca gaacccaacc tccgagcagt acatgctaag acttcaccag tcaaagcgaa     2880
ctactatact caattgatcc aataacttga ccaacggaac aagttaccct agggataaca     2940
gcgcaatcct attctagagt ccatatcaac aatagggttt acgacctcga tgttggatca     3000
ggacatcccg atggtgcagc cgctattaaa ggttcgtttg ttcaacgatt aaagtcctac     3060
gtgatctgag ttcagaccgg agtaatccag gtcggtttct atctacttca aattcctccc     3120
tgtacgaaag gacaagagaa ataaggccta cttcacaaag cgccttcccc cgtaaatgat     3180
atcatctcaa cttagtatta tacccacacc cacccaagaa cagggtttgt taagatggca     3240
```

```
gagcccggta atcgcataaa acttaaaact ttacagtcag aggttcaatt cctcttctta    3300
acaacatacc catggccaac ctcctactcc tcattgtacc cattctaatc gcaatggcat    3360
tcctaatgct taccgaacga aaaattctag gctatataca actacgcaaa ggccccaacg    3420
ttgtaggccc ctacgggcta ctacaaccct tcgctgacgc cataaaactc ttcaccaaag    3480
agcccctaaa acccgccaca tctaccatca ccctctacat caccgccccg accttagctc    3540
tcaccatcgc tcttctacta tgaaccccct ccccatacc caaccccctg gtcaacctca    3600
acctaggcct cctatttatt ctagccacct ctagcctagc cgtttactca atcctctgat    3660
cagggtgagc atcaaactca aactacgccc tgatcggcgc actgcgagca gtagcccaaa    3720
caatctcata tgaagtcacc ctagccatca ttctactatc aacattacta ataagtggct    3780
cctttaacct ctccaccctt atcacaacac aagaacacct ctgattactc ctgccatcat    3840
gacccttggc cataatatga tttatctcca cactagcaga gaccaaccga ccccccttcg    3900
accttgccga aggggagtcc gaactagtct caggcttcaa catcgaatac gccgcaggcc    3960
ccttcgccct attcttcata gccgaataca caaacattat tataataaac accctcacca    4020
ctacaatctt cctaggaaca acatatgacg cactctcccc tgaactctac acaacatatt    4080
ttgtcaccaa gaccctactt ctaacctccc tgttcttatg aattcgaaca gcatacccc    4140 gattccgcta cgaccaactc atacacctcc tatgaaaaaa cttcctacca ctcaccctag    4200
cattacttat atgatatgtc tccataccca ttacaatctc cagcattccc cctcaaacct    4260
aagaaatatg tctgataaaa gagttacttt gatagagtaa ataataggag cttaaacccc    4320
cttatttcta ggactatgag aatcgaaccc atccctgaga tccaaaattc tccgtgcca    4380 cctatcacac cccatcctaa agtaaggtca gctaaataag ctatcgggcc catacccga    4440 aaatgttggt tataccccttc ccgtactaat taatcccctg gcccaacccg tcatctactc    4500
taccatcttt gcaggcacac tcatcacagc gctaagctcg cactgatttt ttacctgagt    4560
aggcctagaa ataaacatgc tagctttat tccagttcta accaaaaaaa taaaccctcg    4620
ttccacagaa gctgccatca agtatttcct cacgcaagca accgcatcca taatccttct    4680
aatagctatc ctcttcaaca atatactctc cggacaatga accataacca atactaccaa    4740
tcaatactca tcattaataa tcataatagc tatagcaata aaactaggaa tagccccctt    4800
tcacttctga gtcccagagg ttacccaagg caccccctctg acatccggcc tgcttcttct    4860
cacatgacaa aaactagccc ccatctcaat catataccaa atctctccct cactaaacgt    4920
aagccttctc ctcactctct caatcttatc catcatagca ggcagttgag gtggattaaa    4980
ccaaacccag ctacgcaaaa tcttagcata ctcctcaatt acccacatag gatgaataat    5040
agcagttcta ccgtacaacc ctaacataac cattcttaat ttaactattt atattatcct    5100
aactactacc gcattcctac tactcaactt aaactccagc accacgaccc tactactatc    5160
tcgcacctga aacaagctaa catgactaac accccttaatt ccatccaccc tcctctcct    5220 aggaggcctg cccccgctaa ccggcttttt gcccaaatgg gccattatcg aagaattcac    5280
aaaaaacaat agcctcatca tccccaccat catagccacc atcaccctcc ttaacctcta    5340
cttctaccta cgcctaatct actccaccte aatcacacta ctccccatat ctaacaacgt    5400
aaaaataaaa tgacagtttg aacatacaaa acccacccca ttcctcccca cactcatcgc    5460
ccttaccacg ctactcctac ctatctcccc ttttatacta ataatcttat agaaatttag    5520
gttaaataca gaccaagagc cttcaaagcc ctcagtaagt tgcaatactt aatttctgta    5580
acagctaagg actgcaaaac cccactctgc atcaactgaa cgcaaatcag ccactttaat    5640
```

```
taagctaagc ccttactaga ccaatgggac ttaaacccac aaacacttag ttaacagcta    5700
agcaccctaa tcaactggct tcaatctact tctcccgccg ccgggaaaaa aggcgggaga    5760
agccccggca ggtttgaagc tgcttcttcg aatttgcaat tcaatatgaa aatcacctcg    5820
gagctggtaa aaagaggcct aacccctgtc tttagattta cagtccaatg cttcactcag    5880
ccattttacc tcaccccccac tgatgttcgc cgaccgttga ctattctcta caaaccacaa    5940
agacattgga acactatacc tattattcgg cgcatgagct ggagtcctag cacagctct     6000
aagcctcctt attcgagccg agctgggcca gccaggcaac cttctaggta acgaccacat    6060
ctacaacgtt atcgtcacag cccatgcatt tgtaataatc ttcttcatag taatacccat    6120
cataatcgga ggctttggca actgactagt tccccctaata atcggtgccc ccgatatggc    6180
gtttccccgc ataaacaaca taagcttctg actcttaccct ccctctctcc tactcctgct    6240
cgcatctgct atagtggagg ccggagcagg aacaggttga acagtctacc ctcccttagc    6300
agggaactac tcccaccctg gagcctccgt agacctaacc atcttctcct tacacctagc    6360
aggtgtctcc tctatcttag gggccatcaa tttcatcaca acaattatca atataaaacc    6420
ccctgccata acccaatacc aaacgcccct cttcgtctga tccgtcctaa tcacagcagt    6480
cctacttctc ctatctctcc cagtcctagc tgctggcatc actatactac taacagaccg    6540
caacctcaac accaccttct tcgacccccgc cggaggagga gacccccattc tataccaaca    6600
cctattctga ttttcggtc accctgaagt ttatattctt atcctaccag gcttcggaat    6660
aatctcccat attgtaactt actactccgg aaaaaaagaa ccatttggat acataggtat    6720
ggtctgagct atgatatcaa ttggcttcct agggtttatc gtgtgagcac accatatatt    6780
tacagtagga atagacgtag acacacgagc atatttcacc tccgctacca taatcatcgc    6840
tatccccacc ggcgtcaaag tatttagctg actcgccaca ctccacggaa gcaatatgaa    6900
atgatctgct gcagtgctct gagccctagg attcatcttt cttttcaccg taggtggcct    6960
gactggcatt gtattagcaa actcatcact agacatcgta ctacacgaca cgtactacgt    7020
tgtagcccac ttccactatg tcctatcaat aggagctgta tttgccatca taggaggctt    7080
cattcactga tttcccctat tctcaggcta cacccctagac caaacctacg ccaaaatcca    7140
tttcactatc atattcatcg gcgtaaatct aactttcttc ccacaacact ttctcggcct    7200
atccggaatg ccccgacgtt actcggacta ccccgatgca tacaccacat gaaacatcct    7260
atcatctgta ggctcattca tttctctaac agcagtaata ttaataattt tcatgatttg    7320
agaagccttc gcttcgaagc gaaaagtcct aatagtagaa gaaccctcca taaacctgga    7380
gtgactatat ggatgccccc caccctacca cacattcgaa gaacccgtat acataaaatc    7440
tagacaaaaa aggaaggaat cgaaccccc aaagctggtt tcaagccaac cccatggcct    7500
ccatgacttt ttcaaaaagg tattagaaaa accatttcat aactttgtca agttaaatt     7560
ataggctaaa tcctatatat cttaatggca catgcagcgc aagtaggtct acaagacgct    7620
acttccccta tcatagaaga gcttatcacc tttcatgatc acgccctcat aatcattttc    7680
cttatctgct tcctagtcct gtatgccctt ttcctaacac tcacaacaaa actaactaat    7740
actaacatct cagacgctca ggaaatagaa accgtctgaa ctatcctgcc cgccatcatc    7800
ctagtcctca tcgccctccc atccctacgc atcctttaca taacagacga ggtcaacgat    7860
ccctccctta ccatcaaatc aattggccac caatggtact gaacctacga gtacaccgac    7920
tacggcggac taatcttcaa ctcctacata cttcccccat tattcctaga accaggcgac    7980
ctgcgactcc ttgacgttga caatcgagta gtactcccga ttgaagcccc cattcgtata    8040
```

```
ataattacat cacaagacgt cttgcactca tgagctgtcc ccacattagg cttaaaaaca    8100
gatgcaattc ccggacgtct aaaccaaacc actttcaccg ctacacgacc gggggtatac    8160
tacggtcaat gctctgaaat ctgtggagca aaccacagtt tcatgcccat cgtcctagaa    8220
ttaattcccc taaaaatctt tgaaataggg cccgtattta ccctatagca cccctctac     8280 cccctctaga gcccactgta aagctaactt agcattaacc ttttaagtta aagattaaga    8340
gaaccaacac ctctttacag tgaaatgccc caactaaata ctaccgtatg gccaccata     8400 attacccca tactccttac actattcctc atcacccaac taaaaatatt aaacacaaac     8460
taccacctac ctccctcacc aaagcccata aaaataaaaa attataacaa accctgagaa    8520
ccaaaatgaa cgaaaatctg ttcgcttcat tcattgcccc cacaatccta ggcctacccg    8580
ccgcagtact gatcattcta tttcccctc tattgatccc cacctccaaa tatctcatca     8640
acaaccgact aatcaccacc caacaatgac taatcaaact aacctcaaaa caaatgataa    8700
ccatacacaa cactaaagga cgaacctgat ctcttatact agtatcctta atcattttta    8760
ttgccacaac taacctcctc ggactcctgc ctcactcatt tacaccaacc acccaactat    8820
ctataaacct agccatggcc atcccctat gagcgggcac agtgattata ggctttcgct      8880
ctaagattaa aaatgcccta gcccacttct taccacaagg cacacctaca ccccttatcc    8940
ccatactagt tattatcgaa accatcagcc tactcattca accaatagcc ctggccgtac    9000
gcctaaccgc taacattact gcaggccacc tactcatgca cctaattgga agcgccaccc    9060
tagcaatatc aaccattaac cttccctcta cacttatcat cttcacaatt ctaattctac    9120
tgactatcct agaaatcgct gtcgccttaa tccaagccta cgttttcaca cttctagtaa    9180
gcctctacct gcacgacaac acataatgac ccaccaatca catgcctatc atatagtaaa    9240
acccagccca tgaccccctaa caggggccct ctcagccctc ctaatgacct ccggcctagc    9300
catgtgattt cacttccact ccataacgct cctcatacta ggcctactaa ccaacacact    9360
aaccatatac caatgatggc gcgatgtaac acgagaaagc ataccaag gccaccacac     9420 accacctgtc caaaaaggcc ttcgatacgg gataatccta tttattacct cagaagtttt    9480
tttcttcgca ggatttttct gagccttta ccactccagc ctagcccta cccccaatt      9540 aggagggcac tggccccaa caggcatcac ccgctaaat cccctagaag tcccactcct     9600
aaacacatcc gtattactcg catcaggagt atcaatcacc tgagctcacc atagtctaat    9660
agaaaacaac cgaaaccaaa taattcaagc actgcttatt acaattttac tgggtctcta    9720
ttttaccctc ctacaagcct cagagtactc cgagtctccc ttcaccattt ccgacggcat    9780
ctacggctca acatttttg tagccacagg cttccacgga cttcacgtca ttattggctc     9840
aactttcctc actatctgct tcatccgcca actaatattt cactttacat ccaaacatca    9900
ctttggcttc gaagccgccg cctgatactg gcattttgta gatgtggttt gactatttct    9960
gtatgtctcc atctattgat gagggtctta ctcttttagt ataaatagta ccgttaactt    10020
ccaattaact agttttgaca acattcaaaa aagagtaata aacttcgcct aattttaat    10080 aatcaacacc ctcctagcct tactactaat aattattaca ttttgactac cacaactcaa    10140
cggctacata gaaaaatcca ccccttacga gtgcggcttc gaccctatat ccccgcccg    10200 cgtccctttc tccataaaat tcttcttagt agctattacc ttcttattat tgatctaga    10260 aattgccctc cttttacccc taccatgagc cctacaaaca actaacctgc cactaatagt    10320
tatgtcatcc ctcttattaa tcatcatcct agccctaagt ctggcctatg agtgactaca    10380
aaaaggatta gactgaaccg aattggtata tagtttaaac aaaacgaatg atttcgactc    10440
```

```
attaaattat gataatcata tttaccaaat gcccctcatt tacataaata ttatactagc    10500
atttaccatc tcacttctag gaatactagt atatcgctca cacctcatat cctccctact    10560
atgcctagaa ggaataatac tatcgctgtt cattatagct actctcataa ccctcaacac    10620
ccactccctc ttagccaata ttgtgcctat tgccatacta gtctttgccg cctgcgaagc    10680
agcggtgggc ctagccctac tagtctcaat ctccaacaca tatggcctag actacgtaca    10740
taacctaaac ctactccaat gctaaaacta atcgtcccaa caattatatt actaccactg    10800
acatgacttt ccaaaaaaca cataatttga atcaacacaa ccacccacag cctaattatt    10860
agcatcatcc ctctactatt ttttaaccaa atcaacaaca acctatttag ctgttcccca    10920
accttttcct ccgaccccct aacaaccccc ctcctaatac taactacctg actcctaccc    10980
ctcacaatca tggcaagcca acgccactta tccagtgaac cactatcacg aaaaaaactc    11040
tacctctcta tactaatctc cctacaaatc tccttaatta taacattcac agccacagaa    11100
ctaatcatat tttatatctt cttcgaaacc acacttatcc ccaccttggc tatcatcacc    11160
cgatgaggca accagccaga acgcctgaac gcaggcacat acttcctatt ctacacccta    11220
gtaggctccc ttcccctact catcgcacta atttacactc acaacaccct aggctcacta    11280
aacattctac tactcactct cactgcccaa gaactatcaa actcctgagc caacaactta    11340
atatgactag cttacacaat agcttttata gtaaagatac ctctttacgg actccactta    11400
tgactcccta aagcccatgt cgaagccccc atcgctgggt caatagtact tgccgcagta    11460
ctcttaaaac taggcggcta tggtataata cgcctcacac tcattctcaa ccccctgaca    11520
aaacacatag cctacccctt ccttgtacta tccctatgag gcataattat aacaagctcc    11580
atctgcctac gacaaacaga cctaaaatcg ctcattgcat actcttcaat cagccacata    11640
gccctcgtag taacagccat tctcatccaa accccctgaa gcttcaccgg cgcagtcatt    11700
ctcataatcg cccacgggct tacatcctca ttactattct gcctagcaaa ctcaaactac    11760
gaacgcactc acagtcgcat cataatcctc tctcaaggac ttcaaactct actcccacta    11820
atagcttttt gatgacttct agcaagcctc gctaacctcg ccttaccccc cactattaac    11880
ctactgggag aactctctgt gctagtaacc acgttctcct gatcaaatat cactctccta    11940
cttacaggac tcaacatact agtcacagcc ctatactccc tctacatatt taccacaaca    12000
caatggggct cactcaccca ccacattaac aacataaaac cctcattcac acgagaaaac    12060
accctcatgt tcatacacct atccccccatt ctcctcctat ccctcaaccc cgacatcatt    12120
accgggtttt cctcttgtaa atatagttta accaaaacat cagattgtga atctgacaac    12180
agaggcttac gaccccttat ttaccgagaa agctcacaag aactgctaac tcatgccccc    12240
atgtctaaca acatggcttt ctcaactttt aaaggataac agctatccat tggtcttagg    12300
ccccaaaaat tttggtgcaa ctccaaataa agtaataaac catgcacact actataacca    12360
ccctaaccct gacttcccta attccccca tccttaccac cctcgttaac cctaacaaaa    12420
aaaactcata cccccattat gtaaaatcca ttgtcgcatc caccttttatt atcagtctct    12480 tccccacaac aatattcatg tgcctagacc aagaagttat tatctcgaac tgacactgag    12540
ccacaaccca acaacccag ctctccctaa gcttcaaact agactacttc tccataatat    12600
tcatccctgt agcattgttc gttacatggt ccatcataga attctcactg tgatatataa    12660
actcagaccc aaacattaat cagttcttca aatatctact catcttccta attaccatac    12720
taatcttagt taccgctaac aacctattcc aactgttcat cggctgagag ggcgtaggaa    12780
ttatatcctt cttgctcatc agttgatgat acgcccgagc agatgccaac acagcagcca    12840
```

```
ttcaagcaat cctatacaac cgtatcggcg atatcggttt catcctcgcc ttagcatgat   12900
ttatcctaca ctccaactca tgagaccac aacaaatagc ccttctaaac gctaatccaa    12960
gcctcacccc actactaggc ctcctcctag cagcagcagg caaatcagcc caattaggtc   13020
tccacccctg actcccctca gccatagaag gccccacccc agtctcagcc ctactccact   13080
caagcactat agttgtagca ggaatcttct tactcatccg cttccacccc ctagcagaaa   13140
atagcccact aatccaaact ctaacactat gcttaggcgc tatcaccact ctgttcgcag   13200
cagtctgcgc ccttacacaa atgacatca aaaaaatcgt agccttctcc acttcaagtc    13260
aactaggact cataatagtt acaatcggca tcaaccaacc acacctagca ttcctgcaca   13320
tctgtaccca cgccttcttc aaagccatac tatttatgtg ctccgggtcc atcatccaca   13380
accttaacaa tgaacaagat attcgaaaaa taggaggact actcaaaacc atacctctca    13440
cttcaacctc cctcaccatt ggcagcctag cattagcagg aatacctttc ctcacaggtt    13500
tctactccaa agaccacatc atcgaaaccg caaacatatc atacacaaac gcctgagccc    13560
tatctattac tctcatcgct acctccctga caagcgccta tagcactcga ataattcttc    13620
tcaccctaac aggtcaacct cgcttcccca cccttactaa cattaacgaa ataaccccca    13680
ccctactaaa ccccattaaa cgcctggcag ccggaagcct attcgcagga tttctcatta    13740
ctaacaacat ttcccccgca tcccccttcc aaacaacaat cccctctac ctaaaactca     13800 cagccctcgc tgtcactttc ctaggacttc taacagccct agacctcaac tacctaacca    13860
acaaacttaa aataaaatcc ccactatgca catttattt ctccaacata ctcggattct     13920
accctagcat cacacaccgc acaatccct atctaggcct tcttacgagc caaaacctgc     13980
ccctactcct cctagaccta acctgactag aaaagctatt acctaaaaca atttcacagc    14040
accaaatctc cacctccatc atcacctcaa cccaaaaagg cataattaaa ctttacttcc    14100
tctctttctt cttcccactc atcctaaccc tactcctaat cacataacct attccccga     14160 gcaatctcaa ttacaatata tacaccaaca aacaatgttc aaccagtaac tactactaat    14220
caacgcccat aatcatacaa agccccgca ccaataggat cctccgaat caaccctgac      14280 ccctctcctt cataaattat tcagcttcct acactattaa agtttaccac aaccaccacc    14340
ccatcatact ctttcacccca cagcaccaat cctacctcca tcgctaaccc cactaaaaca   14400
ctcaccaaga cctcaaccc tgaccccat gcctcaggat actcctcaat agccatcgct      14460
gtagtatatc caaagacaac catcattccc cctaaataaa ttaaaaaac tattaaaccc     14520 atataacctc ccccaaaatt cagaataata acacacccga ccacccgct aacaatcaat     14580 actaaacccc cataaatagg agaaggctta gaagaaaacc ccacaaaccc cattactaaa    14640
cccacactca acagaaacaa agcatacatc attattctcg cacggactac aaccacgacc    14700
aatgatatga aaaccatcg ttgtatttca actacaagaa caccaatgac cccaatacgc     14760
aaaactaacc ccctaataaa attaattaac cactcattca tcgacctccc caccccatcc    14820
aacatctccg catgatgaaa cttcggctca ctccttggcg cctgcctgat cctccaaatc    14880
accacaggac tattcctagc catgcactac tcaccagacg cctcaaccgc cttttcatca    14940
atcgcccaca tcactcgaga cgtaaattat ggctgaatca tccgctacct tcacgccaat    15000
ggcgcctcaa tattctttat ctgcctcttc ctacacatcg gccgaggcct atattacgga    15060
tcatttctct actcagaaac ctgaaacatc ggcattatcc tcctgcttgc aactatagca    15120
acagccttca taggctatgt cctcccgtga ggccaaatat cattctgagg ggccacagta    15180 attacaaaact tactatccgc catccctac attgggacag acctagttca atgaatctga    15240
```

-continued

```
ggaggctact cagtagacag tcccaccctc acacgattct ttacctttca cttcatcttg   15300
cccttcatta ttgcagccct agcaacactc cacctcctat tcttgcacga aacgggatca   15360
aacaaccccc taggaatcac ctcccattcc gataaaatca ccttccaccc ttactacaca   15420
atcaaagacg ccctcggctt acttctcttc cttctctcct taatgacatt aacactattc   15480
tcaccagacc tcctaggcga cccagacaat tataccctag ccaacccctt aaacacccct   15540
ccccacatca agcccgaatg atatttccta ttcgcctaca caattctccg atccgtccct   15600
aacaaactag gaggcgtcct tgccctatta ctatccatcc tcatcctagc aataatcccc   15660
atcctccata tatccaaaca acaaagcata atatttcgcc cactaagcca atcactttat   15720
tgactcctag ccgcagacct cctcattcta acctgaatcg gaggacaacc agtaagctac   15780
ccttttacca tcattggaca agtagcatcc gtactatact tcacaacaat cctaatccta   15840
ataccaacta tctccctaat tgaaaacaaa atactcaaat gggcctgtcc ttgtagtata   15900
aactaataca ccagtcttgt aaaccggaga tgaaaacctt tttccaagga caaatcagag   15960
aaaaagtctt taactccacc attagcaccc aaagctaaga ttctaattta aactattctc   16020
tgttctttca tggggaagca gatttgggta ccacccaagt attgactcac ccatcaacaa   16080
ccgctatgta tttcgtacat tactgccagc caccatgaat attgtacggt accataaata   16140
cttgaccacc tgtagtacat aaaaacccaa tccacatcaa aacccctcc ccatgcttac    16200
aagcaagtac agcaatcaac cctcaactat cacacatcaa ctgcaactcc aaagccaccc   16260
ctcacccact aggataccaa caaacctacc cacccttaac agtacatagt acataaagcc   16320
atttaccgta catagcacat tacagtcaaa tcccttctcg tccccatgga tgacccccct   16380
cagatagggg tcccttgacc accatcctcc gtgaaatcaa tatcccgcac aagagtgcta   16440
ctctcctcgc tccgggccca taacacttgg gggtagctaa agtgaactgt atccgacatc   16500
tggttcctac ttcagggtca taaagcctaa atagcccaca cgttcccctt aaataagaca   16560
tcacgatg                                                            16568
```